US010729703B2

(12) United States Patent
Zavoronkovs et al.

(10) Patent No.: US 10,729,703 B2
(45) Date of Patent: Aug. 4, 2020

(54) WITHAFERIN COMPOSITIONS FOR PREVENTION OF AGING

(71) Applicant: Insilico Medicine, Inc., Baltimore, MD (US)

(72) Inventors: Aleksandrs Zavoronkovs, London (GB); Alexander Aliper, Ramenskoye (RU); Polina Mamoshina, Moscow (RU); Artem Artemov, Moscow (RU); Ivan Ozerov, Shchelkovo (RU)

(73) Assignee: Insilico Medicine IP Limited, Hong Kong (HK)

( * ) Notice: Subject to any disclaimer, the term of this patent is extended or adjusted under 35 U.S.C. 154(b) by 0 days.

(21) Appl. No.: 15/717,985

(22) Filed: Sep. 28, 2017

(65) Prior Publication Data

US 2018/0125865 A1 May 10, 2018

Related U.S. Application Data

(60) Provisional application No. 62/401,789, filed on Sep. 29, 2016.

(51) Int. Cl.
| | | |
|---|---|---|
| *A61K 31/585* | (2006.01) | |
| *A61K 31/366* | (2006.01) | |
| *A61K 31/704* | (2006.01) | |
| *A61K 31/4709* | (2006.01) | |
| *A61K 31/357* | (2006.01) | |
| *A61P 25/28* | (2006.01) | |
| *A61K 31/385* | (2006.01) | |
| *A61K 31/352* | (2006.01) | |
| *A61P 1/16* | (2006.01) | |
| *A61P 17/00* | (2006.01) | |
| *A61K 31/12* | (2006.01) | |

(52) U.S. Cl.
CPC ............ *A61K 31/585* (2013.01); *A61K 31/12* (2013.01); *A61K 31/352* (2013.01); *A61K 31/357* (2013.01); *A61K 31/366* (2013.01); *A61K 31/385* (2013.01); *A61K 31/4709* (2013.01); *A61K 31/704* (2013.01); *A61P 1/16* (2018.01); *A61P 17/00* (2018.01); *A61P 25/28* (2018.01)

(58) Field of Classification Search
None
See application file for complete search history.

(56) References Cited

U.S. PATENT DOCUMENTS

2006/0188866 A1* 8/2006 Atamna .................. A61K 8/49
   435/2
2016/0279161 A1* 9/2016 Wu ....................... A61K 31/352

FOREIGN PATENT DOCUMENTS

WO   WO-2005082392 A1 * 9/2005 ............. C07J 71/00

OTHER PUBLICATIONS

Thring, T. S., Hili, P., & Naughton, D. P. (2009). Anti-collagenase, anti-elastase and anti-oxidant activities of extracts from 21 plants. BMC complementary and alternative medicine, 9(1), 27. (Year: 2009).*
Chandra, P., Pandey, R., Srivastva, M., & Kumar, B. (2015). Quality control assessment of polyherbal formulation based on a quantitative determination multimarker approach . . . Journal of separation science, 38(18), 3183-3191. (Year: 2015).*
Bhondave, P. D., Devarshi, P. P., Mahadik, K. R., & Harsulkar, A. M. (2014). 'Ashvagandharishta'prepared using yeast consortium from Woodfordia fruticosa flowers exhibit hepatoprotective effect on CCl4 induced liver damage in Wistar rats. Journal of ethnopharmacology, 151(1), 183-190. (Year: 2014).*
Binic, I., Lazarevic, V., Ljubenovic, M., Mojsa, J., & Sokolovic, D. (2013). Skin ageing: natural weapons and strategies. Evidence-Based Complementary and Alternative Medicine, 2013. (Year: 2013).*
Aliper, A., Mamoshina, P., Artemov, A., Moskalev, A., Buzdin, A., Schastnaya, E., & Zhavoronkov, A. (2015) Using Signaling Pathway Activation Analysis to Identify Prospective Drugs that May Slow Down or Reverse the Effects of Skin Aging and Photoaging. BASEL Life Science Week. (Year: 2015).*
Tiwari, R., Chakraborty, S., Saminathan, M., Dhama, K., & Singh, S. V. (2014). Ashwagandha (*Withania somnifera*): Role in safeguarding health, immunomodulatory effects, combating infections and therapeutic applications: A review. J Biol Sci, 14(2), 77-94. (Year: 2014).*

* cited by examiner

*Primary Examiner* — Dale R Miller
(74) *Attorney, Agent, or Firm* — Maschoff Brennan; Jonathan M. Benns

(57) ABSTRACT

The present invention provides gero-protective pharmaceutical compositions and methods, the compositions being adapted to enhance at least one of cell survival and cell metabolism in a mammalian subject, the pharmaceutical compositions include at least two of Withaferin a or its structural analogs, coumestrol, ginsenoside, quinidine, silymarin, licochalcone a, lipoic acid and apigenin, in a pharmaceutically effective amount.

9 Claims, No Drawings

WITHAFERIN COMPOSITIONS FOR PREVENTION OF AGING

FIELD OF THE INVENTION

The present invention relates generally to pharmaceutical compositions, and more specifically to methods and compositions for preventing ageing.

BACKGROUND OF THE INVENTION

The population of the world is growing and the average age is increasing, leading to an aging population.

Cellular senescence combined with an inability of immune system to effectively eliminate senescent cells leads to persistent accumulation of senescent cells in an aging organism. On the other hand senescent cells represent a constant danger to the cell population as far as they partly lose their functions and induce malfunctioning of surrounding cells (Campisi & d'Adda di Fagagna 2007).

Albeit the portion of senescent cells is rather low even in aged tissues and reaches no more than 15% in tissues of old primates, senescent cells can produce and secrete cytokines, chemokines and extracellular proteases, which can potentially lead to detrimental changes in the entire cell population (Herbig et al. 2006; Kuilman et al. 2008). Therefore a specific state of the cell population is formed, that can be classified as senescence-associated secretory phenotype (SASP) (Coppé et al. 2008).

As senescent cells accumulate in even greater numbers over the years, the whole tissues gradually lose their specific properties. Such process results in developing of aging phenotype and encourages the risk of malignant transformation in the affected cells (Chen et al. 2005; Rodier & Campisi 2011). Hence therapies aimed to selectively eliminate senescent cells have a potential to slow down age-related changes in tissues and body in whole as well as to reduce the risks of cancer generation (Velarde & Demaria 2016; Oh et al. 2014; Naylor et al. 2013).

As reported previously, senescent cells demonstrate high resistance to apoptosis along with upregulated pro-survival signalling axes (Childs et al. 2014; Hampel et al. 2004). Several signalling axes including PI3K, BCL2 and p21 pathways are shown to be involved in senescent phenotype formation (Datta et al. 1999; Osaki et al. 2004; Minn et al. 1999; Yosef et al. 2016).

The further investigation using siRNA for silencing the key anti-apoptotic players of these networks showed the ability of such approach to specifically eliminate senescent cells from the population while preserving the rest of the population (Zhu et al. 2015). Consequently, the very same effect can be achieved when low molecular compounds are used for downregulation of senescence associated anti-apoptotic signaling networks.

Recently several low-molecular compounds which demonstrate an ability to selectively eliminate senescent cells in various tissues were proposed. This novel class of prospective drugs is referred to as senolytics. The newly identified senolytic compounds include anti-cancer agents dasatinib and navitoclax along with natural phytochemicals quercetin and tocotrienols (Zhu et al. 2015; Zhu et al. 2016; Chang et al. 2016; Malavolta et al. 2016). However, the listed compounds demonstrated diverse ability to clear senescent cells in various tissues. Dasatinib was shown to be the most effective in adipocyte progenitor cells, while Navitoclax can efficiently eliminate senescent cells in hematopoietic stem cells and muscle stem cells in mice, human umbilical vein epithelial cells, IMR90 human lung fibroblasts, and murine embryonic fibroblasts.

Quercetin and tocotrienols were more effective against senescent human endothelial cells and mouse bone marrow mesenchymal stem cells. These substantial differences in tissue specificity can be explained by the mechanism of action of these compounds. Dasatinib is multiple tyrosine kinase inhibitor, navitoclax is a BCL-family inhibitor, while quercetin and tocotrienols may affect various anti-apoptotic members of PI3K, mTOR and other signalling pathways (Montero et al. 2011; Olave et al. 2010; Bruning 2013; Gandhi et al. 2011).

Therefore thorough analysis of tissue specific signalling networks involved in survival of senescent cells may lead to bringing out novel compounds with senolytic properties specifically effective in particular tissues.

U.S. Pat. No. 7,318,938B2 discloses a composition of the plant Withania Somnifera, and, more particularly to a high purity extract composition with advantageous levels of withanolide glycosides and oligosaccharides, a minimum of polysaccharides, and substantially low levels of free withaferin A and equivalents (withanolide aglycones), which composition provides enhanced cognition-enhancing effects for the user, and an extraction process for obtaining such composition, as well as pharmaceutical, nutritional and personal care use products thereof.

There is a need to provide methods and compositions for preventing ageing.

SUMMARY OF THE INVENTION

It is an object of some aspects of the present invention to provide methods and compositions for preventing ageing.

In preferred embodiments of the present invention, improved methods and compositions are provided for alleviating some aspects of ageing.

The present invention provides gero-protective pharmaceutical compositions and methods, the compositions being adapted to enhance at least one of cell survival and cell metabolism in a mammalian subject, the pharmaceutical compositions include at least two of Withaferin a or its structural analogs, coumestrol, ginsenoside, quinidine, silymarin, licochalcone a, lipoic acid and apigenin, in a pharmaceutically effective amount.

There is thus provided, according to an embodiment of the present invention, a gero-protective pharmaceutical composition adapted to enhance at least one of cell survival and cell metabolism in a mammalian subject, the pharmaceutical composition including at least two of Withaferin a or its structural analogs, coumestrol, ginsenoside, quinidine, silymarin, licochalcone a, lipoic acid and apigenin, in a pharmaceutically effective amount.

Additionally, according to an embodiment of the present invention, the gero-protective pharmaceutical composition includes at least three of withaferin a or its structural analogs, coumestrol, ginsenoside, quinidine, silymarin, licochalcone a, lipoic acid and apigenin.

Furthermore, according to an embodiment of the present invention, the gero-protective pharmaceutical composition includes at least four of withaferin a or its structural analogs, coumestrol, ginsenoside, quinidine, silymarin, licochalcone a, lipoic acid and apigenin.

Further, according to an embodiment of the present invention, the gero-protective pharmaceutical composition includes withaferin a or its structural analogs, coumestrol, ginsenoside, silymarin, lipoic acid and apigenin.

Yet further, according to an embodiment of the present invention, the gero-protective pharmaceutical composition includes withaferin a or its structural analogs, ginsenoside, silymarin, licochalcone a, lipoic acid and apigenin.

Moreover, according to an embodiment of the present invention, the gero-protective pharmaceutical composition includes withaferin a or its structural analogs, ginsenoside and apigenin.

Additionally or alternatively, according to an embodiment of the present invention, the gero-protective pharmaceutical composition includes withaferin a and its structural analogs, coumestrol, ginsenoside, silymarin, lipoic acid and apigenin.

Additionally, according to an embodiment of the present invention, the gero-protective pharmaceutical composition includes a pharmaceutical carrier.

There is thus provided, according to another embodiment of the present invention, a use of a gero-protective pharmaceutical composition, as described herein, in the preparation of a medicament for protecting an elderly subject from aging.

There is thus provided, according to an additional embodiment of the present invention, a use of a gero-protective pharmaceutical composition, as described herein, in the preparation of a medicament for protecting human skin from aging associated changes.

There is thus provided, according to an additional embodiment of the present invention, a use of a gero-protective pharmaceutical composition, as described herein, in the preparation of a medicament for protecting human neural tissue from aging associated changes.

There is further provided, according to an embodiment of the present invention, a use of a gero-protective pharmaceutical composition, as described herein, in the preparation of a medicament for mimicking metformin-associated response and blood glucose lowering.

There is thus provided, according to another embodiment of the present invention, a method for protecting an elderly subject from aging including administering a gero-protective pharmaceutical composition, as described herein, to the subject in a pharmaceutically effective dosage.

Additionally, according to another embodiment of the present invention, the gero-protective pharmaceutical composition is adapted to vitalize cells in the subject.

There is thus provided, according to another embodiment of the present invention, a method for protecting an elderly subject from aging including administering a pharmaceutical composition, as described herein, to the subject in a pharmaceutically effective dosage.

A recently-developed approach to large-scale transcriptomic data analysis, called in silico Pathway Activation Network Decomposition Analysis (iPANDA) has been applied to identify pathway signatures of senescent cells in various tissues and pathway signatures of known senolytic drugs.

The iPANDA algorithm is specifically designed to obtain robust results when analysing transcriptomic data from multiple sources. Thus the common tissue-independent features of senescent cells were extracted, including downregulated anti-apoptosis signaling networks, as well as several tissue-specific features of cellular senescence. In order to find novel compounds with senolytic properties, this information was utilized for obtaining a list of prospective protein targets. A list of about 100 low-molecular senolytic candidates was derived partly from the pharmacophore-based scanning of proposed protein targets and partly from a list of known drugs which selectively affect the identified pathways involved in cellular senescence.

The natural compound withaferin a was identified as the most promising prospective senolytic agent applicable to skin and neural tissue treatment. It affects a high number of age-related signaling networks which also supports the hypothesis that withaferin a can be considered as a potential geroprotector.

In order to identify novel senolytic compounds which can specifically eliminate senescent cells in the population and/or mimic metformin-associated effects in human, several in silico approaches were applied including:

1) drug-target interactions analysis (ability of novel compounds to bind targets of previously identified senolytic compounds and targets identified using transcriptomic data on gene knockdowns in cell lines), 2) structural similarity to known senolytics (QSAR descriptors, pharmacophore search), 3) transcriptomic response profile similarity to known senolytics, 4) transcriptomic response profile scoring of various aging tissue datasets and metformin perturbations, 5) deep neural network (DNN)-based model for data integration, and 6) structural analogs search for top candidates.

Using listed methods, compound Withaferin a and its structural analogs (as shown in Tables 1 and 2, hereinbelow), coumestrol, ginsenoside, quinidine, silymarin, licochalcone a, lipoic acid and apigenin were identified as prospective geroprotectors, senolytics, metformin-mimetics and senolytic compounds in skin, neural tissue, liver, adipocytes, mesenchymal stem cells. Withaferin A is a steroidal lactone, derived from Acnistus *arborescens*, Withania somnifera (Indian Winter cherry or Ashwagandha in Sanskrit) and other members of Solanaceae family (Kupchan et al. 1969; Mohan et al. 2004).

This compound is known for its anti-inflammatory properties and it was shown to inhibit prosurvival networks including NF-kB (Lee et al. 2012; Kaileh et al. 2007; Kumar et al. 2009). We also found that withaferin a effects strongly resembles metformin associated response. Along with withaferin a we also discovered that coumestrol, ginsenoside, quinidine, silymarin, licochalcone a, lipoic acid and apigenin are also similar to metformin in and possess strong geroprotective effects and senolytic effects. Pathway analysis indicates the probable synergy between various combinations of abovementioned compound, therefore we suggest here highly perspective combinatorial treatment options.

DETAILED DESCRIPTION OF THE EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

The general design of the computational procedures which led to Withaferin a identification is described below. It included four sequential steps: 1) transcriptomic similarity search, 2) protein target based search, 3) structural similarity based search 4) transcriptomic signature screening and 5) deep neural network based search.

1) In silico Pathway Activation Network Decomposition Analysis (iPANDA) was applied to transcriptomic tissue-specific aging datasets obtained from Gene Expression Omnibus (GEO) with total number of samples not less than 250 for each tissue. Five tissues were considered including skin, muscles, temporal cortex, mesenchymal stem cells (MSC) and adipose tissue. Tissue-specific cellular senescence pathway marker sets were identified. Cellular senescence signature common for all tissues was also obtained. Only pathways considerably perturbed in senescent cells (pathways with iPANDA-generated p-values less than 0.05 were considered as pathway markers). iPANDA scores were precalculated for Broad Institute LINCS Project data and were utilized for calculating transcriptomic compound similarity. Euclidian similarity between vectors of iPANDA scores for known senolytics (dasatinib (D), quercetin (Q) and navitoclax (N)) and all other compounds was calculated using data on primary and cancer cell lines for corresponding tissue. Only previously identified tissue-specific pathway markers were used for similarity calculation.

2) Using LINCS Project data on knockdown cell lines the same procedure was performed to identify key target genes involved in the action of previously identified senolytic compounds D, N and Q. The list of target genes was enriched by proteins likely to interact with these compounds using STITCH human drug-target interaction database. Pharmacophore-based search and publicly available docking algorithms were applied to identify the compounds which specifically bind the identified targets with highest affinity.

3) Structural similarity search was performed for three compounds already known to have senolytic properties (D,N,Q). Using publicly available molecular docking algorithms the importance weights for chemical groups were defined. This information was utilized for QSAR-based structure generation and filtering. Compounds from pubchem database were also screened during the similar procedure in order to find structural analogues of D, N and Q.

4) To investigate potential geroprotective effects and metformin related effects of natural compounds without known molecular targets GEO and LINCS Project gene expression data were used. In both databases, datasets were examined, consisting of transcriptomes of cell lines before and after treatment with multiple different chemical compounds. For aging datasets scoring exactly the same GEO datasets GSE66236, GSE69391, GSE18876, GSE21779, GSE38718, GSE59980, GSE52699, GSE48662 were used. It was assumed that an anti-aging compound would affect an aged transcriptome to turn it into "younger" state. Mechanistically, this reflected a fact that if a certain regulatory pathway is increased (or decreased) with aging, its end targets would increase (or decrease) expression with aging. By searching for compounds which decrease (or increase) the expression of those end targets, the drugs which target these aging-associated pathways (some of its master regulators) could be discovered.

First, differentially expressed genes associated with aging were found, as well as differentially expressed genes after drug treatment. For microarray-based transcriptome data, a limma test of differential gene expression was used. Each set of differentially expressed genes was ordered accordingly to the following measure which takes into account both magnitude and statistical significance of the effect: $FC*\max(0, -\log(pvalue))$, where FC is fold-change of gene expression between groups and pvalue represents the result of limma test.

A statistically motivated score estimating anti-aging abilities of a compound was designed. A significantly up- or down-regulated gene were defined as the ones with $FDR<0.01$ (after multiple-testing correction). A Fisher exact test was performed which measured the association of two characteristics of each gene: being significantly downregulated after the drug treatment and being significantly upregulated during aging. Vice versa, the same test was performed for significantly upregulated genes after the drug treatment versus significantly downregulated genes during aging. The best of p-values of those two tests was taken as a score for the given drug against aging. A multiple testing correction of the obtained p-values for the amount of compound under study was performed.

The same methodology was applied for screening natural compounds within LINCS transcriptomic database that are similar to the effect of metformin.

5) The deep neural network based classifier of compound pharmacological class was trained on more than 100000 compounds. Training data included structural data (QSAR, SMILES), transcriptomic response LINCS Project data on gene-level and pathway level (iPANDA) and drug-target interaction network from STITCH database. The specific class of prospective senolytic compounds was declared during training. This class included compounds identified on the steps 1, 2, 3 of the study. Established classifier accuracy was equal to 0.635 after the class-balancing of the test set. A list of senolytic compounds after scanning the database of 300000+ compounds was obtained for further analysis.

Top ranking compounds were obtained on each of the steps and intersection was found for each tissue independently. As a result withaferin a compound was identified as the most promising compound with senolytic properties in skin and neural tissue. A set of structural analogues of withaferin a according to the procedure in step 3 was obtained, which possess the similar molecular properties, and are claimed to have senolytic properties.

6) Finding structural analogs of withaferin A molecules. At this part of research, the aim is to find structural analogs of molecule of interest for protein-ligand interaction. This approach is highly efficient for increasing the specificity of binding with targets (proteins).

Withaferin A is a steroidal lactone molecule which means it can be delivered not only in the cell cytoplasm but also directly inside the nucleus and controls the gene expression, cell cycle and proliferative activity of the cell.

At the first step we provide an analysis of possible targets for natural withaferin A compound. This can be done in two ways: 1) using specific programs for searching in databases for different interactions of molecules of interest with proteins/genes (e.g. STITCH); 2) article analysis of an experimental data. In the case of withaferin A molecule we've chosen the second way as it helps to select the best variants of experimentally approved protein-ligand interactions. From literature analysis 3 targets were chosen according to parameters: 1) specific binding of target with withaferin A; 2) the lowest IC50; 3) the presence of the structure in protein data bank. The targets were:

1) NF-kB (PDB ID 1SVC), controls transcription of DNA, cytokine production and cell survival (Baudy et al, 2009; Oh and Kwon, 2009);

2) AP-1 (PDB ID 1FOS), controls a number of cellular processes including differentiation, proliferation, and apoptosis (Singh et al, 2007);

3) HSP90 (PDB ID 5FWL), assists other proteins to fold properly, stabilizes proteins against heat stress, and aids in protein degradation, stabilizes a number of proteins required for tumor growth (Yu et al, 2010).

After that for all of the structures we applied docking for all possible active sites and additional pockets of binding. The best positions of withaferin A in target were chosen and after an additional docking was done with the usage of algorithm of flexible chains.

Then all the structures of withaferin A-target were analyzed according to algorithm: 1) amount of hydrogen bonds 2) hydrophobic/hydrophilic interactions 3) number π-π interactions. This information were used further to understand the key principles by which molecule can bind into the specific site of the target. According to such analysis one can find the rules for the Withaferin A molecule to be modified in "right way" for better binding properties with specific target.

With the usage of the software the analogs were found according to the rules for the Withaferin A molecule. After that toxicology in silico test was provided with choosing non-toxic analogs. These new non-toxic analogs were again docked into the binding site of the target for interactions analysis and those which showed the best score results were selected as most promising and perspective ones. Final list of discovered structural analogs of Withaferin A after target-based screening can be found in Table 1.

Other structural analogs and conformers were extracted from the Pubchem database and present in Table 2.

REFERENCES

Baudy, A. R., Saxena, N., Gordish, H., Hoffman, E. P. and Nagaraju, K., 2009. A robust in vitro screening assay to identify NF-κB inhibitors for inflammatory muscle diseases. International immunopharmacology, 9(10), pp. 1209-1214.

Bruning, A., 2013. Inhibition of mTOR signaling by quercetin in cancer treatment and prevention. Anti-cancer agents in medicinal chemistry, 13(7), pp. 1025-1031.

Campisi, J. & d'Adda di Fagagna, F., 2007. Cellular senescence: when bad things happen to good cells. Nature reviews. Molecular cell biology, 8(9), pp. 729-740.

Chang, J. et al., 2016. Clearance of senescent cells by ABT263 rejuvenates aged hematopoietic stem cells in mice. Nature medicine, 22(1), pp. 78-83.

Chen, Z. et al., 2005. Crucial role of p53-dependent cellular senescence in suppression of Pten-deficient tumorigenesis. Nature, 436(7051), pp. 725-730.

Childs, B. G. et al., 2014. Senescence and apoptosis: dueling or complementary cell fates? EMBO reports, 15(11), pp. 1139-1153.

Coppé, J.-P. et al., 2008. Senescence-associated secretory phenotypes reveal cell-nonautonomous functions of oncogenic RAS and the p53 tumor suppressor. PLoS biology, 6(12), pp. 2853-2868.

Datta, S. R., Brunet, A. & Greenberg, M. E., 1999. Cellular survival: a play in three Akts. Genes & development, 13(22), pp. 2905-2927.

Gandhi, L. et al., 2011. Phase I study of Navitoclax (ABT-263), a novel Bcl-2 family inhibitor, in patients with small-cell lung cancer and other solid tumors. Journal of clinical oncology: official journal of the American Society of Clinical Oncology, 29(7), pp. 909-916.

Hampel, B. et al., 2004. Differential regulation of apoptotic cell death in senescent human cells. Experimental gerontology, 39(11-12), pp. 1713-1721.

Herbig, U. et al., 2006. Cellular senescence in aging primates. Science, 311(5765), p. 1257.

Kaileh, M. et al., 2007. Withaferin a strongly elicits IkappaB kinase beta hyperphosphorylation concomitant with potent inhibition of its kinase activity. The Journal of biological chemistry, 282(7), pp. 4253-4264.

Kuilman, T. et al., 2008. Oncogene-induced senescence relayed by an interleukin-dependent inflammatory network. Cell, 133(6), pp. 1019-1031.

Kumar, P., Shilpa, P. & Salimath, B. P., 2009. Withaferin A suppresses the expression of vascular endothelial growth factor in Ehrlich ascites tumor cells via Sp1 transcription factor. Current Trends in Biotechnology. Available at: http://abap.co.in/files/CTBP_3_2_2009.pdf#page=32.

Kupchan, S. M. et al., 1969. Tumor inhibitors. XXXIX. Active principles of Acnistus arborescens. Isolation and structural and spectral studies of withaferin A and withacnistin. The Journal of organic chemistry, 34(12), pp. 3858-3866.

Lee, W. et al., 2012. Barrier protective effects of withaferin A in HMGB1-induced inflammatory responses in both cellular and animal models. Toxicology and applied pharmacology, 262(1), pp. 91-98.

Malavolta, M. et al., 2016. Pleiotropic Effects of Tocotrienols and Quercetin on Cellular Senescence: Introducing the Perspective of Senolytic Effects of Phytochemicals. Current drug targets, 17(4), pp. 447-459.

Minn, A. J. et al., 1999. Bcl-xL regulates apoptosis by heterodimerization-dependent and -independent mechanisms. The EMBO journal, 18(3), pp. 632-643.

Mohan, R. et al., 2004. Withaferin A is a potent inhibitor of angiogenesis. Angiogenesis, 7(2), pp. 115-122.

Montero, J. C. et al., 2011. Inhibition of SRC family kinases and receptor tyrosine kinases by dasatinib: possible combinations in solid tumors. Clinical cancer research: an official journal of the American Association for Cancer Research, 17(17), pp. 5546-5552.

Naylor, R. M., Baker, D. J. & van Deursen, J. M., 2013. Senescent cells: a novel therapeutic target for aging and age-related diseases. Clinical pharmacology and therapeutics, 93(1), pp. 105-116.

Oh, J. H. and Kwon, T. K., 2009. Withaferin A inhibits tumor necrosis factor-α-induced expression of cell adhesion molecules by inactivation of Akt and NF-κB in human pulmonary epithelial cells. International immunopharmacology, 9(5), pp. 614-619.

Oh, J., Lee, Y. D. & Wagers, A. J., 2014. Stem cell aging: mechanisms, regulators and therapeutic opportunities. Nature medicine, 20(8), pp. 870-880.

Olave, N.C. et al., 2010. Upstream stimulatory factor-2 mediates quercetin-induced suppression of PAI-1 gene expression in human endothelial cells. Journal of cellular biochemistry, 111(3), pp. 720-726.

Osaki, M., Oshimura, M. & Ito, H., 2004. PI3K-Akt pathway: its functions and alterations in human cancer. Apoptosis: an international journal on programmed cell death, 9(6), pp. 667-676.

Rodier, F. & Campisi, J., 2011. Four faces of cellular senescence. The Journal of cell biology, 192(4), pp. 547-556.

Singh, D., Aggarwal, A., Maurya, R. and Naik, S., 2007. Withania somnifera inhibits NF κB and AP 1 transcription factors in human peripheral blood and synovial fluid mononuclear cells. Phytotherapy Research, 21(10), pp. 905-913.

Velarde, M. C. & Demaria, M., 2016. Targeting Senescent Cells: Possible Implications for Delaying Skin Aging: A Mini-Review. Gerontology, 62(5), pp. 513-518.

Yosef, R. et al., 2016. Directed elimination of senescent cells by inhibition of BCL-W and BCL-XL. Nature communications, 7, p. 11190.

Yu, Y., Hamza, A., Zhang, T., Gu, M., Zou, P., Newman, B., Li, Y., Gunatilaka, A. L., Zhan, C. G. and Sun, D., 2010. Withaferin A targets heat shock protein 90 in pancreatic cancer cells. Biochemical pharmacology, 79(4), pp. 542-551.

Zhu, Y. et al., 2016. Identification of a novel senolytic agent, navitoclax, targeting the Bcl-2 family of anti-apoptotic factors. Aging cell, 15(3), pp. 428-435.

Zhu, Y. et al., 2015. The Achilles' heel of senescent cells: from transcriptome to senolytic drugs. Aging cell, 14(4), pp. 644-658.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

TABLE 1

LIST OF WITHAFERIN A ANALOGS AND DERIVATIVES BASED ON TARGET-WISE SCREENING

| SMILES | Molecular target | IUPAC name |
|---|---|---|
| COC1=CC(=CC=C1OCC(N)=O)C=CC(=O)N(C)C(C)C2=CC=C(C=C2)S(N)(=O)=O | NF-kB | (2E)-3-[4-(carbamoylmethoxy)-3-hydroxyphenyl]-N-methyl-N-[1-(4-sulfamoylphenyl)ethyl]prop-2-enamide |
| CC1=C(CCC(=O)NCCCCCC2=N[NH]C(=C2C#N)C(=O)N=C(S)N1 | NF-kB | N-[5-amino-4-cyano-1H-pyrazol-3-yl)pentyl]-3-(6-methyl-4-oxo-2-sulfanyl-1,4-dihydropyrimidin-5-yl)propanamide |
| CN1C(=O)N=C(O)C2=C1N=C(SCC(=O)N/N=C/C3=C(O)C=C(O)C=C3)[N]2CCC4=CC=CC=C4 | NF-kB | N'-[(1E)-(2,4-dihydroxyphenyl)methylidene]-2-{[6-hydroxy-3-methyl-2-oxo-7-(2-phenylethyl)-3,7-dihydro-2H-purin-8-yl]sulfanyl}-acetohydrazide |
| N[S](=O)(=O)C1=CC=C(NC(=O)C2CCN(CC2)C(=O)C3=CC=CC=C3)NC(=O)C4CC4)C=C1 | NF-kB | 1-(3-cyclopropaneamidobenzoyl)-N-(4-sulfamoylphenyl)piperidine-4-carboxamide |
| CC(=O)C1=C(O)C=C(O)C2=C1OC3=CC(=O)C(=C(O)NCCSCCO)C(=O)C23C | NF-kB | (4E)-10-acetyl-11,13-dihydroxy-4-[1-({2-[(2-hydroxyethyl)sulfanyl]ethyl}amino)ethylidene]-2,12-dimethyl-8-oxatricyclo[7.4.0.0²,⁷]trideca-1(9),6,10,12-tetraene-3,5-dione |
| N[S](=O)(=O)C1=CC=C(CCNC(=O)C2=CC=CC(=O)NC4=CC=CC=C34)C=C1 | NF-kB | 2-oxo-N-(3-[2-(4-sulfamoylphenyl)ethyl]carbamoyl}phenyl)-1,2-dihydroquinoline-4-carboxamide |
| C[C@H]1[C@H]CC(=O)C(=O)[C@H]1CC(=O)[C@H]3[C@@H]SO[C@]56[C@@H](O)C=CC(=O)[C@]6(C)[C@H]4CC[C@]23C | NF-kB | (1S,2R,6S,7R,9R,11S,12S,15R,16R)-6- |

TABLE 1-continued

LIST OF WITHAFERIN A ANALOGS AND DERIVATIVES BASED ON TARGET-WISE SCREENING

| SMILES | Molecular target | IUPAC name |
|---|---|---|
| CC1C[C@H]CC(=C1CO)C[C@@H]C[C@H]4O[C@]45C(O)C=CC(=O)[C@]3SC[C@@H]1CC[C@@H]2[C@H]O[C@H]6CC=C(CO)C(=O)O)O | | hydroxy-15-[(1R)-1-[(1R,6R)-4-(hydroxymethyl)-3,6-dimethyl-5-oxocyclohex-3-en-1-yl]ethyl]-2,16-dimethyl-8-oxapentacyclo [9.7.0.0$^{2,7}$.0$^{7,9}$.0$^{12,16}$]octadec-4-en-3-one |
| CC1C[C@H]CC(=C1CO)C[C@@H](C)[C@H]2CC[C@H]3[C@@H]4C[C@H]5O[C@]56C(O)C=CC(=O)[C@]6(C)[C@H]4CC[C@]23C | NF-kB | (1S,2R,7R,9R,11S,12S,15R,16R)-6-hydroxy-15-[(1R)-4-(hydroxymethyl)-3,5-dimethylcyclohex-3-en-1-yl]ethyl]-2,16-dimethyl-8-oxapentacyclo [9.7.0.0$^{2,7}$.0$^{7,9}$.0$^{12,16}$]octadec-4-en-3-one |
| C[C@@]12CC[C@H]3[C@@H]C[C@H]4O[C@]45C(O)C=CC(=O)[C@]35C[C@@H]1CC[C@@H]2[C@H]O[C@H]6CC=C(CO)C(=O)O)O | NF-kB | (1S,2R,7R,9R,11S,12S,15S,16S)-6-hydroxy-15-[(S)-hydroxy[(2R)-4-hydroxy-5-(hydroxymethyl)-6-oxo-3,6-dihydro-2H-pyran-2-yl]methyl]-2,16-dimethyl-8-oxapentacyclo [9.7.0.0$^{2,7}$.0$^{7,9}$.0$^{12,16}$]octadec-4-en-3-one |
| CC[C@H]1C=CC(=O)[C@]2(C)[C@H]3CC[C@]4(C)[C@H]CC[C@H]4[C@@H]3C[C@H]CC[C@@H]3C[C@H]SO[C@@]125[C@H](C)[C@H]6CC=C(CO)C(=O)O6)C | NF-kB | (1S,2R,6S,7S,9R,11S,12S,15R,16S)-6-ethyl-15-[(1S)-1-[(2R)-5-(hydroxymethyl)-4-methyl-6-oxo-3,6-dihydro-2H-pyran-2-yl]ethyl]-2,16-dimethyl-8-oxapentacyclo [9.7.0.0$^{2,7}$.0$^{7,9}$.0$^{12,16}$]octadec-4-en-3-one |

TABLE 1-continued

LIST OF WITHAFERIN A ANALOGS AND DERIVATIVES BASED ON TARGET-WISE SCREENING

| SMILES | Molecular target | IUPAC name |
| --- | --- | --- |
| CC[C@@]1(C)C=CC(=O)[C@]2(C)[C@H]3CC[C@@]4C)[C@H](CC[C@H]5C[C@@]125)[C@H](C)[C@H]6CC=C(CO)C(=O)O6C | NF-kB | (6R)-6-[(1S)-1-[(1S,2R,6S,7R,9S,11S,12S,15R,16S)-6-ethyl-2,6,16-trimethyl-3-oxopentacyclo[9.7.0.0²,⁷.0⁷,⁹.0¹²,¹⁶]octadec-4-en-15-yl]ethyl]-3-(hydroxymethyl)-4-methyl-5,6-dihydro-2H-pyran-2-one |
| CC(O)CNC(=O)CCCNC(=O)CCOC1=CC=C2C3=C(CCCC3)C(=O)OC2=C1C(O)=O | HSP90 | 3-methyl-2-{4-[2-({4-methyl-6-oxo-6H,7H,8H,9H,10H-cyclohexa[c]chromen-3-yl}oxy)acetamido]butanamido}butanoic acid |
| CC1(O)CCCC2CCC4=C/C(CCC(CC3CCC12C)=N)OCC(=O)NCC5=NC=CC=C5 | HSP90 | 2-({[(7E)-1-hydroxy-1,9a,11a-trimethyl-1H,2H,3H,3aH,3bH,4H,5H,7H,8H,9H,9aH,9bH,10H,11H,11aH-cyclopenta[a]phenanthren-7-ylidene]amino}oxy)-N-[(pyridin-2-yl)methyl]acetamide |
| CC(CCC=C(/C(O)C(O)=O)C1CCCC2(C)C3CCC4C(C)(C)C=C(=O)CCC45CC35CCC12C | HSP90 | (2E)-2-(hydroxymethyl)-6-{7,7,12,16-tetramethyl-6-oxopentacyclo[9.7.0.0¹,³.0³,⁸.0¹²,¹⁶]octadecan-15-yl}hept-2-enoicacid |
| COC(=O)C1CCCN1C(=O)CO/N=C2/CCC3(C)C4CCC5(C)C(CCC5(O)C#C)C4CCC3=C2 | HSP90 | methyl 1-[2-({[(7Z)-1-ethynyl-1-hydroxy-9a,11a-dimethyl-1H,2H,3H,3aH,3bH,4H,5H,7H,8H,9H,9aH,9bH,10H,11H,11aH-cyclopenta[a]phenanthren-7- |

TABLE 1-continued

LIST OF WITHAFERIN A ANALOGS AND DERIVATIVES BASED ON TARGET-WISE SCREENING

| SMILES | Molecular target | IUPAC name |
| --- | --- | --- |
| CC(C)C(=C(/C)C(O)=O)C1CCC2(C)C3=CCC4C(C)C(O)C(O)CCC4(C)C3=CCC12C | HSP90 | ylidene[amino}oxy)acetyl]pyrrolidine-2-carboxylate (2E)-6-{7-hydroxy-3a,6,6,9a,11a-pentamethyl-1H,2H,3H,3aH,5H,5aH,6H,7H,8H,9H,9aH,11H,11aH-cyclopenta[a]phenanthren-1-yl}-2-methylhept-2-enoic acid |
| CCOC1=CC(=C(=O)C(=COC2=C1)C3=CC=C(OC4OC(CO)C(O)C(O)C4O)C=C3)O | AP-1 | 7-ethoxy-5-hydroxy-3-(4-{[3,4,5-trihydroxy-6-(hydroxymethyl)oxan-2-yl]oxy}phenyl)-4H-chromen-4-one |
| OC1=CC=C(C(=C1)C=N\NC(=O)CCCCCCCCCC(=O)N\N=C/C2=C(O)C=C(O)C=C2)O | AP-1 | N'1,N'12-bis[(1E)-(2,4-dihydroxyphenyl)methylidene]dodecanedihydrazide |

TABLE 2

LIST OF WITHAFERIN A ANALOGS AND DERIVATIVES BASED ON SIMILARITY

| Pubchem CID | SMILES |
|---|---|
| 56928031 | O=C(c1ccccc1)NC1=C(N2CCN(CC2)c2ccccc2)C(=O)c2c(C1=O)cccc2 |
| 50904531 | O=C(n1nnc(c1)C(c1ccccc1)(c1ccccc1)O)N1CCc2c(C1)cccc2 |
| 16293465 | O=C(c1cccc(c1)NC(=O)c1cc(=O)[nH]c2c1cccc2)NCCc1ccc(cc1)S(=O)(=O)N |
| 135584558 | Cc1ccccc1Cn1nnc2c(O)nc(nc12)C1CCCN(C1)C(=O)c1ccccc1Cl |
| 119045958 | OC(Cn1cnc2c(c1=O)ccnc2)CC1CCCC1 |
| 45918956 | CC(Oc1ccc(cc1)NS(=O)(=O)c1cnc([nH]c1=O)O)C |
| 47610414 | CNC(=O)COc1ccc(cc1OC)CNC1CCC(CC1)O |
| 40957584 | COc1cc(OC)ccc1S(=O)(=O)Nc1ccc2c(c1)OCC(C(=O)N2CCC(C)(C)C)C |
| 45597893 | COc1cc(OC)ccc1CNC(=O)CCC1CCCN(C1)C1CCSCC1 |
| 39336661 | COc1cc(F)ccc1c1ccnc2n1ncc2C(=O)N |
| 7161251 | Oc1ncc(c(=O)[nH]1)S(=O)(=O)Nc1ccc(cc1)Oc1ccccc1 |
| 45194095 | COc1cc(CNCc2cccc(c2)C)ccc1OCC(CN1CCC(CC1)O)O |
| 53024242 | COc1cc(OC)ccc1CNC(=O)CCn1cnc2c(c1=O)c(C)c(o2)C |
| 71702747 | COC(=O)c1[nH]/c(=N/C(=O)c2[nH]nc(c2)c2ccccc2OC)/sc1C |
| 45183940 | COc1cc(CNCc2ccccc2F)ccc1OCC(CN1CCCC1)O |
| 45179373 | COc1cc(OC)ccc1CNC(=O)CCC1CCCN(C1)Cc1c[nH]cn1 |
| 72885799 | COc1cc(OC)ccc1CNC(=O)CCC1CCCN(C1)C(=O)C(N)(C)C |
| 45223257 | COc1cc(ccc1OCC(CN(C(C)C)C)O)CN1CCC(CC1)O |
| 50827384 | CCc1ccc(cc1)c1noc2c1ncn(c2=O)CCC(=O)NCc1ccc(cc1OC)OC |
| 71694387 | COCc1onc(c1)CC1(COC1)NCc1ccc(cc1O)OC |
| 75452351 | OC(Cn1cnc2c(c1=O)ccnc2)COc1ccc(cc1C)C |
| 45200947 | COc1cc(CNCc2ccccc2F)ccc1OCC(CN1CCC(CC1)O)O |
| 53195855 | COc1cc(OC)ccc1CNC(=O)CN(c1sc2c(n1)n(nc2C)c1cccc(c1)C)C |
| 72904150 | COc1cc(ccc1OCC(CN1CCCC1)O)CN(C1CCOCC1)C |
| 84585732 | CCN/C(=N/C)/NCC(Oc1cccc(c1)OC)C |
| 51369692 | O=C(Cn1c(=O)cc(c2c1cccc2)c1onc(n1)c1ccccn1)NCc1ccccc1Cl |
| 7161243 | COc1ccc(cc1)NS(=O)(=O)c1cnc([nH]c1=O)O |
| 53162202 | COc1ccc(c(c1)OC)CNC(=O)Cc1nnc(o1)c1ccc2c(c1)cccn2 |
| 122632830 | O=c1[nH]c2c([nH]1)ccnc(n2)N1CCN(CC1)C(=O)c1cccc(c1)Cc1n[nH]c(=O)c2c1cccc2 |
| 122632806 | O=C(c1cccc(c1)Cc1n[nH]c(=O)c2c1cccc2)N1CCN(CC1)c1ccc2c(n1)nc([nH]2)C(F)(F)F |
| 124159248 | O=C(NC1CC(C1)(F)F)COc1cccc(c1)c1nc(Nc2ccc(cc2)c2c[nH]nc2)c2c(n1)coc2 |
| 117664608 | C1CC(CNC1)OC2=NC(=CN=C2)C3=CNC4=C3C=C(C=C4)C5=CN=C6C(=C5)C=CN6 |
| 91383988 | C1CN(CCC1(C(=O)N)NC2=CC=CC=C2)C(=O)C3=C(C=CC=C3)C4=CC=C(C=C5C=C6C=CNC=C6N5)C4=O |
| 71233838 | CN1CCN(CC1)C(=O)C2=CC3=C(N2)C=CC=C3NC4=NC=CC(=N4)C5=NC=CC(=C5)OC6CCNC6=O |
| 70801150 | C1CC2C(NC3=C(C2OC1CNS(=O)(=O)CCCN4CCC(C4)O)C=C(=C3)C(F)(F)F)C5CC=CC=C5 |
| 124159163 | O=C(NC1CCC1)COc1cccc(c1)c1nc(Nc2ccc(cc2)c2c[nH]nc2)c2c(n1)cncc2 |
| 123414035 | COc1ccc(cc1)C2=NC3=C(N2)CCCC4=C1c=CC#CC5=CC6=C(C(=C5)F)N=C(N6)C7C#CCCN7 |
| 86969663 | NC(=O)c1ccc(cc1)N1CC[NH](CC1)Cc1nc(=O)c2c(n1)n([nH]c2)c1ccccc1 |
| 70798546 | O=C1C[NH2]CCN1c1cnc2c(n1)cc(cc2)c1cccc2c(c1)nc(o2)N |
| 87645825 | CC(C)C1=CC(=C2NNC(=O)N2CC3=CC=C(C=C3)CN4CCC(C4)O)C(=O)C=C1O |
| 117664706 | C1CC(CNC1)OC2=NC(=CN=C2)C3=CNC4=C3C=C(C=C4)C5=CC=C(C=C5)NC(=O)C6CC6 |
| 78043513 | CN(C)C(=O)C1=CC2=C(N1)C=CC(=C2)NC3=NC=CC(=N3)C4=NC=CC(=C4)OC5CCNC5=O |
| 89764001 | N#Cc1ccnc(c1)Nc1cc(cc(n1)c1cncc(c1)OC1CC[NH](CC1)CC(=O)N)C1CC1 |
| 90160604 | CCOC(=O)C1(CCC1)C2CCC(CC2)OC3=NC4=NC(=C(C=C4N3)Cl)C5=CC=C(C=C5)C6=CCN(CC6)C(=O)CO |
| 99115528 | CC(C(=O)NC1=CC(=CC=C1)F)N2CCN(CC2)C(=O)NC3=CC=C(C=C3)C4=NNC(=N4)C5CC5 |
| 55459608 | COc1cc(ccc1OCC(=O)N)C(=O)OCC(=O)N1c2ccccc2NC(=O)C21CCCC2 |
| 69808272 | CC(C)(CC1=CC=CC(=C1)CC(=O)N2CCCC2C(=O)N)NCC(C3=CC=C(C=C3)O)O |
| 90430808 | C1CC2CC1C(N2)C(=O)NC(CC3=C(C=C(C=C3)N4C=C(N=N4)CCN)F)C#N |
| 9822981 | CC(C1=NC=CC(=N1)N2CCC(CC2)C3CCN(CC3)C4=CC=C(C(=C4)C(C)O)O |
| 70907322 | C1C(C1NCC(=O)N)C2=CC(=C(C=C2)OCC3=CC=CC=C3)C4=CC(=CC=C4)C(=O)N |
| 124159301 | CC[NH]1CCc2c(Cl)c(Nc1ccc(cc1)c1cn[nH]c1)nc(n2)c1cccc(c1)OCC(=O)NC1CCC1 |
| 2941977 | Cc1ccc2c(c1)c(c1ccccc1)c(n2CC(CN1C(=O)CNC1=O)O)c1ccccc1 |
| 118729948 | N#Cc1c(ncnc1N)NC(c1nc2ccc(cc2c1c1ccccn1)Cl)F)C |
| 56755716 | Cc1ccc2c(n1)ccc(c2)C1(O)CCN(CC1)Cc1c[nH]nc1C(=O)O |
| 5930665 | N#C/C(=C\1/SC(C(=O)N1c1ccccc1)Cc1ccc(c(c1)C)C)/C(=O)N |
| 59634638 | N#Cc1c(ncnc1N)NC(c1nc2ccc(cc2c1c1ccccc1)O)F)C |
| 118729950 | N#Cc1c(ncnc1N)NC(c1nc2ccc(cc2c1c1cccccn1)N1CCOCC1)F)C |
| 16012201 | CC1=CC=CC=C1CN2C3=CC=CC=C3C4=C2C(=O)N(N=C4)CC(=O)NCC5=CC=CC=C5OC |
| 3133124 | CC1=CC=C(C=C1)S(=O)(=O)N(CC(CN2C(=O)C(NC2=O)(C)C)O)C3=CC=CC=C3 |
| 4350310 | COC1=CC(=C(C=C1)C2C(=C(OC3=NNC(=C23)C4=CC=C(C=C4)Cl)Cl)N)C#N)O |
| 17411683 | CC1(C(=O)N(C(=O)N1)CC(=O)NCC(C2=CC=C(C=C2)OC)C3=CNC4=CC=CC=C43)C |
| 15987563 | CC1=CC(=CC=C1)NC2=NC(=NC(=C2S(=O)c3=CC=CC=C3)N)C |
| 49872831 | CC(C1=NC2=C(C=C(C=C2)F)C(=C1C3=CC=CC=C3)OC)NC4=NC=NC(=C4C#N)N |
| 53023028 | CC1=CC2=CC(=C3NOC(=N3)CCC(=O)NC4=CC=C(C=C4)F)C(=O)N=C2C=C1 |
| 20892206 | COC1=CC=CC=C1CNC(=O)CN2C(=O)C3=C(C=N2)C4=CC=CC=C4N3CC5=CC=CC=C5F |
| 57487127 | CN1C=NC(=N1)S(=O)(=O)NCCOC2=CC(CCC(C3=CC=C(C=C4)Cl)Cl)N)C=C2 |
| 4625911 | CC1=CC=C(C(S1)C)C2=C3C(C(=C(OC3=NN2)N)C#N)C4=CC=NC5=CC=CC=C54 |
| 6060815 | CC1=CC(=CC=C1)CC2C(=O)N(C(=C(C#N)C(=O)N)S2)C3=CC=C(C=C3)Cl |
| 49871864 | CC(C1=C(C=C2C=C(C=CC2=N1)F)C3=CC=CC=N3)NC4=NC=NC(=C4C#N)N |
| 49872924 | CC(C1=NC2=C(C=C(C=C2)C2)F)C1C3=CC=CC=C3)NCCO)NC4=NC=NC(=C4C#N)N |
| 118767337 | Cc1nc2ccccc2c(c1)c1cccc(c1)C(=O)N(C1COCC1O)C |
| 118729947 | N#Cc1c(ncnc1N)NC(c1nc2ccc(cc2c1c1ccccc1)NCCN(C)C)F)C |
| 662825 | Cc1ccc(cc1S(=O)(=O)NCCN1CCOCC1)c1n[nH]c(=O)c2c1cccc2 |
| 5779743 | N#C/C(=C\1/SC(C(=O)N1c1ccc(cc1)Br)Cc1ccccc1C)/C(=O)N |
| 17028423 | Cc1ccc2c(c1)c(C)c(n2CC(CN1C(=O)CNC1=O)O)C |

TABLE 2-continued

LIST OF WITHAFERIN A ANALOGS AND DERIVATIVES BASED ON SIMILARITY

| | |
|---|---|
| 44827367 | Cc1ccc(cc1)S(=O)(=O)N1CCN(CC1)CCNC(=O)C(Oc1ccc(cc1)Cl)(C)C |
| 119680299 | OC1CNC(C1)C(=O)NCC(c1c[nH]c2c1cccc2)c1cccccc1 |
| 24507888 | N#Cc1c(N)[nH]nc1CCCN(c1nnc(c2c1cccc2)C)C |
| 2945746 | N#CC1=C(N)Oc2c(C1c1cccccc1Cl)c(n[nH]2)c1cc(sc1C)C |
| 46349707 | COc1cc(OC)ccc1CNC(=O)CN1C(=O)CCn2c1cc(n2)c1cn(c2c1cccc2)C |
| 49870793 | N#Cc1c(ncnc1N)NC(c1nc2ccccn2c(=O)c1c1cc(F)cc(c1)F)C |
| 33072330 | CC(C1=NC(=O)C2=CC=CC=C2N1)OC(=O)C3=CC(=CC=C3)CN4C(=O)CNC4=O |
| 71748271 | C1COC(CN1S(=O)(=O)C2=C(NC3=C2C=C(C=C3)Cl)C(=O)N)COC4=CC=CC=C4C5=CN=CC=C5 |
| 22041656 | CC1=NN(C(=O)N1CC(=O)NC2CNC2)C3=CC(=C(C=C3)Cl)C(=O)NC(C4CCCCCC4)O |
| 123198033 | CN(CCO)C1CCN(C1)C(=O)C2=C(C=CC(=C2)CC3=NNC(=O)C4=CC=CC=C43)F |
| 46979601 | CC1=CC(=C(C=C1C2=CSC(=N2)NC(=O)C3CCCN(C3)CC(=O)N)C)OC |
| 70652336 | C1CC(CN(C1)C(C2=CC=CC=C2F)C(=O)N)NC(=O)C3=CC4=C(C=C3)NN=C4C5=CC=NC=C5 |
| 60172075 | CCC(=O)C1=CC=C(C(=C1)F)C2=C(C=CC(=N2)C(=O)NC3=C(C=CN=C3)C4CC(C(C(C4)N)O)C)F)F |
| 93055418 | CCC1C(=O)NC2=C(O1)C=C(C(=C2)C)S(=O)(=O)N3CCCC(C3)C(=O)NC4=NC=CC(=C4)C |
| 24566921 | O=C(Nc1ccc(cc1)SCc1cccnc1)CCc1nc(=O)c2c(n1)n[nH]c2)c1ccccc1 |
| 98842572 | CC1=NC(=CC=C1)NC(=O)C2CCCN(C2)S(=O)(=O)C3=C(C=C4C(=C3)OCC(=O)N4)Cl |
| 56228696 | CC(CNC(=O)c1ccc(c(c1)C)NC(=O)c1ccc(o1)S(=O)(=O)NC(C)(C)C)C |
| 52609602 | CC1CN(CCO1)C(CNC(=O)C2=CC(=CC=C2)OCC(=O)N)C3=C(C=CC=C3Cl)F |
| 56848892 | CN(C1CCN(C1)C2=NC=NC3=C2C=CN3)C4=NC=C(C=C4)S(=O)(=O)N5CCNCC5 |
| 91591490 | C1C(CC1O)C2=NC=C3N2C=C(N=C3N)C4=C(C5=C(C=C4)C=CC(=N5)C6=CC=CC=N6)F |
| 25132374 | C[NH]1CCN(CC1)c1ccc2c(c1)n(cc2)S(=O)(=O)c1ccc2c(c1)OCC(=O)N2 |
| 55815828 | C1CC(CN(C1)S(=O)(=O)C2=C(C=C3C(=C2)OCC(=O)N3)Cl)C(=O)NC4=NC=C(C=C4)Cl |
| 50764747 | CCC1C(=O)NC2=C(O1)C=C(C(=C2)C)S(=O)(=O)N3CCCC(C3)C(=O)NC4=C(C=CC=N4)C |
| 55930504 | C1CC(CN(C1)C(=O)C2=CC3=C(C=C2)NC(=O)CO3)C(=O)NC4=NC=C(C=C4)Cl |
| 56480103 | CC1CC1C(=O)NC2=CC=CC(=C2)C(=O)N(C)C(C)C3=CC(=CC=C3)S(=O)(=O)N |
| 110155360 | CNC1=NC=NC(=C1)N2CCCC(C2)(CN(C)C(=O)C3=CC=C(C=C3)CN4CCCC4)O |
| 46962362 | CC1=NC=CC(=N1)C2=CC(=CC=C2)C3=NOC(=N3)CN4CCCC(C4)O |
| 110223478 | CC1=NC=CC(=N1)C2=CC(=CC=C2)C3=NOC(=N3)CN4CCCCC4CO |
| 68805087 | CC1C(CC(N1C)C(=O)N)NC(=O)C2=C(C=CN=C2)NC3=NC(=NC=C3OC)C4=C(C=CC(=C4)Cl)F |
| 121902150 | CC1=C2C(=O)NN(C2=NC(=C1CC(=O)N3CCCC(C3)CCC(=O)O)C)C |
| 99734486 | CCC1C(=O)NC2=C(O1)C=C(C(=C2)C)S(=O)(=O)N3CCCC(C3)C(=O)NC4=CC=CC(=N4)C |
| 56461293 | CC1=C(C=C(C=C1)C(=O)N(C)C(C)C2=CC(=CC=C2)S(=O)(=O)N)S(=O)(=O)N3CCCCC3 |
| 72883558 | CC1=C(C(=NC(=N1)N)C)CC(=O)N2CCCC(C2)C3=CC(=O)N=C(N3)C |
| 98745718 | CCC1C(=O)NC2=C(O1)C=C(C(=C2)C)S(=O)(=O)N3CCCC(C3)C(=O)NCC4CCCN4CC |
| 58844439 | CC(C1C2CC(=C(N2C1=O)C(=O)O)C3=CC=C(C=C3)CC(=O)NC4=NOC=C4)O |
| 90252533 | CC1CN(CC(C1O)N)C2=C(C=NC=C2)NC3=NC=C4N3N=C(C=C(C5=C(C=CC(=C5F)C(=O)NC(C)C)F |
| 90147510 | CC1CNCCN1C2=CC(=NC(=N2)OC3=CC=C4C(=C3F)C=C(N4C)F)NC5=NNC(=C5)C |
| 118290322 | CC1=C(C=CC(=C1)C2=CN(C(=N2)C3CCN(CC3)C4=C(C(=NC=N4)Cl)C(C)C5CNC5)F |
| 89847932 | C1CNCCC1N2C=C(C=N2)C3=NN4C(NN=C4C(C5=CC6=C(C=C5)N=CC=C6)(F)F)N=C3 |
| 118239786 | CC1CNCC2=C1C(=NC(=N2)C3=C(N=C4N3C=C(C=C4C)NCC)NCC5=CC=CC=C5 |
| 10225131 | C1=CC=C(C=C1)C(C(=O)NC2=CC=CC(=C2)C(=N)N)NC3=CC=C(C=C3)C4=NC=CNC4=O |
| 4295433 | C1C(OC(OC1C2=CC=C(C=C2)CO)C3=CC=C(C=C3)NC(=O)C4=CN=CC=C4)CN5C=NC6=CC=CC=C65 |
| 118924150 | CN(C)CCNC1=CC(=CC(=C1)C2=CC=CC3=NC(=C4C5=CC(=NC=C5NN4)C6=CC(=CN=C6)OCC7=CC=CC=C7)N=C32)F |
| 11648848 | CC1=C2C=C(C=CC2=NN1)C3=NC=C(N=N3)N(CC4=CC=CC=C4)CC5=CC=CC=C5)N6CCNCC6 |
| 29134585 | COC1=C(C=CC(=C1)C2C3=C(C(=O)N2CCC4=CNC5=CC=CC=C54)NN=C3C6=CC=C(C=C6)F)O |
| 122685373 | CC1CNCC2=C1C(=NC(=N2)N3C4=CC=CC(=C4N3)C(=O)N)NCC5=CC=CC=C5 |
| 57037399 | CCC(C(=O)N)NC(=O)C(CCN1CCC(C(C1)C)C2=CC(=CC=C2)O)NC=C3 |
| 67070056 | CS(=O)(=O)NC1=CC=C(C=C1)C=CC2=CC(=CC=C2)C3=CC=CNC3=O)C4(CC4)CO |
| 68210132 | CC1=CC=C(C(=O)N1)CNC(=O)C2=C3C(=CN(C3=CC=C2)C4=CC(=NC=C4)N5CCNCC5)C(C)(C)C)C |
| 68516837 | CC1=C2C(=CC=NC2=NN1)OC3=NC=C(C=N3)N(C4=CC=C(C=C4)F)C(=O)C5(CC5)C(=O)N |
| 44488135 | CC1CN(C(=O)C2=C(C=CC(=C2)NC(=O)N)NC3=CC=C(C=C3)OC1CN(C)C4=CC=NC=C4)C(C)CO |
| 68688918 | Fc1ccc(cc1)N(C(=O)C1(CC1)C(=O)N)c1ccc(c(c1)F)Oc1ccnc(c1)NC(=O)N1CCC1 |
| 265237 | CC1=C(C(=O)OC(C1)C(C)C2CCC3C2(CCC4C3CC5C6(C4(C(=O)C=CC6O)C)O5)C)CO |
| 118701146 | CC1=C(C(=O)OC(C1)C(C)C2CCC3C2(CCC4C3CC5C6(C4(C(=O)C=CC6O)C)O5)C)CO |
| 102357982 | CC1=C(C(=O)OC(C1)C(C)C2CCC3C2(CCC4C3CC5C6(C4(C(=O)C=CC6O)C)O5)C)CO |
| 90670450 | CC1=C(C(=O)OC(C1)C(C)C2CCC3C2(CCC4C3CC5C6(C4(C(=O)C=CC6O)C)O5)C)CO |
| 73707417 | CC1=C(C(=O)OC(C1)C(C)C2CCC3C2(CCC4C3CC5C6(C4(C(=O)C=CC6O)C)O5)C)CO |
| 71772576 | CC1=C(C(=O)OC(C1)C(C)C2CCC3C2(CCC4C3CC5C6(C4(C(=O)C=CC6O)C)O5)C)CO |
| 58443792 | CC1=C(C(=O)OC(C1)C(C)C2CCC3C2(CCC4C3CC5C6(C4(C(=O)C=CC6O)C)O5)C)CO |
| 57519534 | CC1=C(C(=O)OC(C1)C(C)C2CCC3C2(CCC4C3CC5C6(C4(C(=O)C=CC6O)C)O5)C)CO |
| 50990201 | CC1=C(C(=O)OC(C1)C(C)C2CCC3C2(CCC4C3CC5C6(C4(C(=O)C=CC6O)C)O5)C)CO |
| 49864510 | CC1=C(C(=O)OC(C1)C(C)C2CCC3C2(CCC4C3CC5C6(C4(C(=O)C=CC6O)C)O5)C)CO |
| 46200067 | CC1=C(C(=O)OC(C1)C(C)C2CCC3C2(CCC4C3CC5C6(C4(C(=O)C=CC6O)C)O5)C)CO |
| 45489105 | CC1=C(C(=O)OC(C1)C(C)C2CCC3C2(CCC4C3CC5C6(C4(C(=O)C=CC6O)C)O5)C)CO |
| 45110486 | CC1=C(C(=O)OC(C1)C(C)C2CCC3C2(CCC4C3CC5C6(C4(C(=O)C=CC6O)C)O5)C)CO |
| 44411346 | CC1=C(C(=O)OC(C1)C(C)C2CCC3C2(CCC4C3CC5C6(C4(C(=O)C=CC6O)C)O5)C)CO |
| 16760705 | CC1=C(C(=O)OC(C1)C(C)C2CCC3C2(CCC4C3CC5C6(C4(C(=O)C=CC6O)C)O5)C)CO |
| 16745397 | CC1=C(C(=O)OC(C1)C(C)C2CCC3C2(CCC4C3CC5C6(C4(C(=O)C=CC6O)C)O5)C)CO |
| 9825988 | CC1=C(C(=O)OC(C1)C(C)C2CCC3C2(CCC4C3CC5C6(C4(C(=O)C=CC6O)C)O5)C)CO |
| 5315320 | CC1=C(C(=O)OC(C1)C(C)C2CCC3C2(CCC4C3CC5C6(C4(C(=O)C=CC6O)C)O5)C)CO |
| 5287384 | CC1=C(C(=O)OC(C1)C(C)C2CCC3C2(CCC4C3CC5C6(C4(C(=O)C=CC6O)C)O5)C)CO |
| 580064 | CC1=C(C(=O)OC(C1)C(C)C2CCC3C2(CCC4C3CC5C6(C4(C(=O)C=CC6O)C)O5)C)CO |
| 118701104 | CC1=C(C(=O)OC(C1)C(C)(C2CCC3C2(CCC4C3CC5C6(C4(C(=O)C=CC6O)C)O5)C)C |
| 118103569 | CC1=C(C(=O)OC(C1)C(C)C2CCC3C2(CCC4C3CC5C6(C4(C(=O)C=CC6O)C)O5)C)CO |
| 102435651 | CC1=C(C(=O)OC(C1)C(C)C2CCC3C2(CCC4C3CC5C6(C4(C(=O)C=CC6O)C)O5)C)C |
| 102357984 | CC1=C(C(=O)OC(C1)C(C)C2CCC3C2(CCC4C3CC5C6(C4(C(=O)C=CC6O)C)O5)C)COC(=O)C |
| 102357983 | CC1=C(C(=O)OC(C1)C(C)C2CCC3C2(CCC4C3CC5C6(C4(C(=O)C=CC6O)C)O5)C)COC(=O)C |

TABLE 2-continued

LIST OF WITHAFERIN A ANALOGS AND DERIVATIVES BASED ON SIMILARITY

| | |
|---|---|
| 99576035 | CC1=C(C(=O)OC(C1)C(C)C2CCC3C2(CCC4C3CC5C6(C4(C(=O)C=CC6O)C)O5)C)C |
| 99576034 | CC1=C(C(=O)OC(C1)C(C)C2CCC3C2(CCC4C3CC5C6(C4(C(=O)C=CC6O)C)O5)C)C |
| 99576033 | CC1=C(C(=O)OC(C1)C(C)C2CCC3C2(CCC4C3CC5C6(C4(C(=O)C=CC6O)C)O5)C)C |
| 99576032 | CC1=C(C(=O)OC(C1)C(C)C2CCC3C2(CCC4C3CC5C6(C4(C(=O)C=CC6O)C)O5)C)C |
| 90670454 | CC1=C(C(=O)OC(C1)C(C)C2CCC3C2(CCC4C3CC5C6(C4(C(=O)C=CC6O)C)O5)C)COC(=O)C |
| 88949019 | CC1=C(C(=O)OC(C1)C(C)C2CCC3C2(CCC4C3CC5C6(C4C(=O)C=CC6O)O5)C)C |
| 88949008 | CC1=C(C(=O)OC(C1)C(C)C2CCC3C2(CCC4C3CC5C6(C4C(=O)C=CC6O)O5)C)CO |
| 88949005 | CC1=C(C(=O)OC(C1)C(C)C2CCC3C2(CCC4C3CC5C6(C4C(=O)C=CC6O)O5)C)CO |
| 88948987 | CC1=C(C(=O)OC(C1)C(C)C2CCC3C2(CCC4C3CC5C6(C4C(=O)C=CC6O)O5)C)C |
| 76787555 | CCC1=C(CC(OC1=O)C(C)C2CCC3C2(CCC4C3CC5C6(C4(C(=O)C=CC6O)C)O5)C)C |
| 75093323 | CC1=C(C(=O)OC(C1)C(C)C2CCC3C2(CCC4C3CC5C6(C4(C(=O)C=CC6O)C)O5)C)COC(=O)C |
| 74039188 | CC1=C(C(=O)OC(C1)C(C)(C2CCC3C2(CCC4C3CC5C6(C4(C(=O)C=CC6O)C)O5)C)CO |
| 66575620 | CC1=C(C(=O)OC(C1)C(C)C2CCC3C2(CCC4C3CC5C6(C4(C(=O)C=CC6O)C)O5)C)C |
| 58443799 | CC1=C(C(=O)OC(C1)C(C)C2CCC3C2(CCC4C3CC5C6(C4(C(=O)C=CC6O)C)O5)C)COC(=O)C |
| 58443790 | CC1=C(C(=O)OC(C1)C(C)C2CCC3C2(CCC4C3CC5C6(C4(C(=O)C=CC6O)C)O5)C)COC(=O)C |
| 58443786 | CCC1=C(CC(OC1=O)C(C)C2CCC3C2(CCC4C3CC5C6(C4(C(=O)C=CC6O)C)O5)C)C |
| 57328756 | CC1=C(C(=O)OC(C1)C(C)C2CCC3C2(CCC4C3CC5C6(C4(C(=O)C=CC6O)C)O5)C)COC(=O)C |
| 53477765 | CC1=C(C(=O)OC(C1)C(C)(C2CCC3C2(CCC4C3CC5C6(C4(C(=O)C=CC6O)C)O5)C)OC |
| 49864537 | CC1=C(C(=O)OC(C1)C(C)C2CCC3C2(CCC4C3CC5C6(C4(C(=O)C=CC6O)C)O5)C)OC |
| 45111761 | CC1=C(C(=O)OC(C1)C(C)C2CCC3C2(CCC4C3CC5C6(C4(C(=O)C=CC6O)C)O5)C)COC(=O)C |
| 23266163 | CC1=C(C(=O)OC(C1)C(C)C2CCC3C2(CCC4C3CC5C6(C4(C(=O)C=CC6O)C)O5)C)OCO |
| 23266155 | CC1=C(C(=O)OC(C1)C(C)C2CCC3C2(CCC4C3CC5C6(C4(C(=O)C=CC6O)C)O5)C)C |
| 10163222 | CC1=C(C(=O)OC(C1)C(C)C2CCC3C2(CCC4C3CC5C6(C4(C(=O)C=CC6O)C)O5)C)OCO |
| 10161347 | CC1=C(C(=O)OC(C1)C(C)C2CCC3C2(CCC4C3CC5C6(C4(C(=O)C=CC6O)C)O5)C)C |
| 9825989 | CC1=C(C(=O)OC(C1)C(C)(C2CCC3C2(CCC4C3CC5C6(C4(C(=O)C=CC6O)C)O5)C)OC |
| 5315323 | CC1=C(C(=O)OC(C1)C(C)C2CCC3C2(CCC4C3CC5C6(C4(C(=O)C=CC6O)C)O5)C)C |
| 5287385 | CC1=C(C(=O)OC(C1)C(C)C2CCC3C2(CCC4C3CC5C6(C4(C(=O)C=CC6O)C)O5)C)OC |
| 301758 | CC1=C(C(=O)OC(C1)C(C)C2CCC3C2(CCC4C3CC5C6(C4(C(=O)C=CC6O)C)O5)C)C |
| 301754 | CC1=C(C(=O)OC(C1)C(C)(C2CCC3C2(CCC4C3CC5C6(C4(C(=O)C=CC6O)C)O5)C)OC |
| 161671 | CC1=C(C(=O)OC(C1)C(C)(C2CCC3C2(CCC4C3CC5C6(C4(C(=O)C=CC6O)C)O5)C)OC |
| 91799372 | CC1=C(C(=O)OC(C1)C(C)C2CCC3C2(CCC4C3CC5C6(C4(C(=O)C=CC6OC)C)O5)C)CO |
| 91088392 | CC1=C(C(=O)OC(C1)C(C)C2CCC3C2(CCC4C3CC5C6(C4(C(=O)C=CC6O)C(C)C)O5)C)COC(=O)C |
| 90670455 | CC1=C(C(=O)OC(C1)C(C)C2CCC3C2(CCC4C3CC5C6(C4(C(=O)C=CC6OC(=O)C)C)O5)C)CO |
| 90670440 | CC1=C(C(=O)OC(C1)C(C)C2CCC3C2(CCC4C3CC5C6(C4(C(=O)C=CC6OC(=O)C)C)O5)C)CO |
| 88948980 | CC1=C(C(=O)OC(C1)C(C)C2CCC3C2(CCC4C3CC5C6(C4C(=O)C=CC6OC(=O)C)O5)C)CO |
| 88858700 | CC1=C(C(=O)OC(C1)C(C)C2CCC3C2(CCC4C3CC5C6(C4(C(=O)C=CC6O)CO)O5)C)CO |
| 88858699 | CC1=C(C(=O)OC(C1)C(C)C2CCC3C2(CCC4C3CC5C6(C4(C(=O)C=CC6O)CO)O5)C)C |
| 88858695 | CCC1=C(CC(OC1=O)C(C)C2CCC3C2(CCC4C3CC5C6(C4(C(=O)C=CC6O)CO)O5)C)C |
| 76385927 | CC1=C(C(=O)OC(C1)C(C)C2CCC3C2(CCC4C3CC5C6(C4(C(=O)C=CC6O)COC(=O)C)O5)C)C |
| 76385901 | CC1=C(C(=O)OC(C1)C(C)C2CCC3C2(CCC4C3CC5C6(C4(C(=O)C=CC6O)CO)O5)C)C |
| 76385900 | CC1=C(C(=O)OC(C1)C(C)C2CCC3C2(CCC4C3CC5C6(C4(C(=O)C=CC6O)CO)O5)C)CO |
| 75093324 | CC1=C(C(=O)OC(C1)C(C)C2CCC3C2(CCC4C3CC5C6(C4(C(=O)C=CC6OC(=O)C)C)O5)C)CO |
| 60148726 | CC1=C(C(=O)OC(C1)C(C)C2CCC3C2(CCC4C3CC5C6(C4(C(=O)C=CC6O)CO)O5)C)CO |
| 60148725 | CC1=C(C(=O)OC(C1)C(C)C2CCC3C2(CCC4C3CC5C6(C4(C(=O)C=CC6O)CO)O5)C)C |
| 58443800 | CC1=C(C(=O)OC(C1)C(C)C2CCC3C2(CCC4C3CC5C6(C4(C(=O)C=CC6OC(=O)C)C)O5)C)CO |
| 56649400 | CC1=C(C(=O)OC(C1)C(C)C2CCC3C2(CCC4C3CC5C6(C4(C(=O)C=CC6O)COC(=O)C)O5)C)C |
| 56649344 | CC1=C(C(=O)OC(C1)C(C)C2CCC3C2(CCC4C3CC5C6(C4(C(=O)C=CC6O)CO)O5)C)C |
| 56649343 | CC1=C(C(=O)OC(C1)C(C)C2CCC3C2(CCC4C3CC5C6(C4(C(=O)C=CC6O)CO)O5)C)CO |
| 45111762 | CC1=C(C(=O)OC(C1)C(C)C2CCC3C2(CCC4C3CC5C6(C4(C(=O)C=CC6OC(=O)C)C)O5)C)CO |
| 102263665 | CC1=C(C(=O)OC(C1)C(C)(C2(CCC3C2(CCC4C3CC5C6(C4(C(=O)C=CC6O)C)O5)C)O)C |
| 85435491 | CC1=C(C(=O)OC(C1)C(C)C2(CCC3C2(CCC4C3CC5C6(C4(C(=O)C=CC6O)C)O5)C)O)CO |
| 77145374 | CC1=C(C(=O)OC(C1)C(=C2C(CC3C2(CCC4C3CC5C6(C4(C(=O)C=CC6O)C)O5)C)O)C |
| 76313669 | CC1=C(C(=O)OC(C1)C(C)C2CCC3C2(CCC4C3CC5C6(C4(C(=O)C=CC6O)CO)O5)COC(=O)C |
| 76309946 | CC1=C(C(=O)OC(C1)C(C)C2CCC3C2(CCC4C3CC5C6(C4(C(=O)C=CC6O)COC(=O)C)O5)CO |
| 75202433 | CC1=C(C(=O)OC(C1)C(C)C2(CCC3C2(CCC4C3CC5C6(C4(C(=O)C=CC6O)C)O5)C)O)C |
| 75202432 | CC1=C(C(=O)OC(C1)C(C)C2(CCC3C2(CCC4C3CC5C6(C4(C(=O)C=CC6O)C)O5)C)O)CO |
| 74039186 | CC1=C(C(=O)OC(C1)C(C)(C2(CCC3C2(CCC4C3CC5C6(C4(C(=O)C=CC6O)C)O5)C)O)C |
| 73306656 | CC1=C(C(=O)OC(C1)C(C)C2(CCC3C2(CCC4C3CC5C6(C4(C(=O)C=CC6O)C)O5)C)O)C |
| 66572429 | CC1=C(C(=O)OC(C1)C(=C2C(CC3C2(CCC4C3CC5C6(C4(C(=O)C=CC6O)C)O5)C)O)CO |
| 23266161 | CC1=C(C(=O)OC(C1)C(C)(C2(CCC3C2(CCC4C3CC5C6(C4(C(=O)C=CC6O)C)O5)C)O)C |
| 21679019 | CC1=C(C(=O)OC(C1)C(C)C2CCC3C2(CCC4C3CC5C6(C4(C(=O)C=CC6OC(=O)C)C)O5)C)OC |
| 16680447 | CC1=C(C(=O)OC(C1)C(C)C2(CCC3C2(CCC4C3CC5C6(C4(C(=O)C=CC6O)C)O5)C)O)C |
| 13743204 | CC1=C(C(=O)OC(C1)C(C)C2CCC3C2(CCC4C3CC5C6(C4(C(=O)C=CC6OC(=O)C)C)O5)C)OC |
| 12147447 | CC1=C(C(=O)OC(C1)C(C)C2CCC3C2(CCC4C3CC5C6(C4(C(=O)C=CC6O)C)O5)C)OCO |
| 10277877 | CC1=C(C(=O)OC(C1)C(C)C2(CCC3C2(CCC4C3CC5C6(C4(C(=O)C=CC6O)C)O5)C)O)C |
| 101911601 | CC1=C(C(=O)OC(C1)C(C)C2C(=O)CC3C2(CCC4C3CC5C6(C4(C(=O)C=CC6)C)O5)C)CO |
| 101664554 | CC1=C(C(=O)OC(C1)C(C)C2C(CC3C2(CCC4C3CC5C6(C4(C(=O)C=CC6O)C)O5)C)OC(=O)C |
| 89809195 | CC(C1CCC2C1(CCC3C2CC4C5(C3(C(=O)C=CC5O)C)O4)C)C(CC=C(CO)C(=O)O)C)O |
| 89255535 | CC1=C(C(=O)OC(C1)C(C)(C2CCC3C2(CCC4C3CC5C6(C4(C(=O)C=CC6)C)O5)C)C |
| 89245303 | CC1=C(C(=O)OC(C1)C(C)(C2CCC3C2(CCC4C3CC5C6(C4(C(=O)C=CC6)C)O5)C)OC |
| 88858701 | CC1=C(C(=O)OC(C1)C(C)C2CCC3C2(CCC4C3CC5C6(C4(C(=O)C=CC6OC(=O)C)CO)O5)C)C |
| 88858696 | CCC1=C(CC(OC1=O)C(C)C2CCC3C2(CCC4C3CC5C6(C4(C(=O)C=CC6OC(=O)C)CO)O5)C)C |
| 78172794 | CC1=C(C(=O)OC(C1)C(C)C2(CCC3C2(CCC4C3CC5C6(C4(C(=O)C=CC6O)C)O5)C)C=O |
| 76320888 | CC1=C(C(=O)OC(C1)C(C)C2CCC3C2(CCC4C3CC5C6(C4(C(=O)C=CC6OC)C)CO)O5)C)CO |
| 73820037 | CC1=C(C(=O)OC(C1)C(C)C2C(CC3C2(CCC4C3CC5C6(C4(C(=O)C=CC6O)C)O5)C)O)C |
| 73211831 | CC1=C(C(=O)OC(C1)C(C)C2CCC3C2(CCC4C3CC5C6(C4(C(=O)C=CC6O)COC(=O)C)O5)C)COC(=O)C |
| 73106251 | CC1=C(C(=O)OC(C1)C(C)C2CCC3C2(CCC4C3CC5C6(C4(C(=O)C=CC6O)C)O5)CO)C |
| 57369720 | CC1=C(COC1=O)CC(C(C)C2CCC3C2(CCC4C3CC5C6(C4(C(=O)C=CC6O)C)O5)C)O |

TABLE 2-continued

LIST OF WITHAFERIN A ANALOGS AND DERIVATIVES BASED ON SIMILARITY

| | |
|---|---|
| 54606507 | CC1=C(C(=O)OC(C1)C(C)C2CCC3C2(CCC4C3CC5C6(C4(C(=O)C=CC6O)C)O5)COC(=O)C)C |
| 44566999 | CC1=C(C(=O)OC(C1)C(C)C2C(CC3C2(CCC4C3CC5C6(C4(C(=O)C=CC6O)C)O5)C)O)C |
| 21670294 | CC1=C(C(=O)OC(C1)C(C)C2CCC3C2(CCC4C3CC5C6(C4(C(=O)C=CC6O)C)O5)CO)C |
| 21670293 | CC1=C(C(=O)OC(C1)C(C)C2C(CC3C2(CCC4C3CC5C6(C4(C(=O)C=CC6O)C)O5)C)O)C |
| 12304656 | CC1=C(C(=O)OC(C1)C(C)C2CCC3C2(CCC4C3CC5C6(C4(C(=O)C=CC6)C)O5)C)CO |
| 11798584 | CC1=C(C(=O)OC(C1)C(C)C2CCC3C2(CCC4C3CC5C6(C4(C(=O)C=CC6O)C)O5)CO)C |
| 10814230 | CC1=C(C(=O)OC(C1)C(C)C2C(CC3C2(CCC4C3CC5C6(C4(C(=O)C=CC6O)C)O5)C)O)C |
| 10321754 | CC1=C(C(=O)OC(C1)C(C)C2CCC3C2(CCC4C3CC5C6(C4(C(=O)C=CC6)C)O5)C)CO |
| 421514 | CC1=C(C(=O)OC(C1)C(C)C2CCC3C2(CCC4C3CC5C6(C4(C(=O)C=CC6O)C)O5)COC(=O)C)C |
| 268945 | CC1=C(C(=O)OC(C1)C(C)C2CCC3C2(CCC4C3CC5C6(C4(C(=O)C=CC6)C)O5)CO |
| 176114 | CC1=C(C(=O)OC(C1)C(C)C2CCC3C2(CCC4C3CC5C6(C4(C(=O)C=CC6O)C)O5)C)C=O |
| 21199 | CC1=C(COC1=O)CC(C(C)C2CCC3C2(CCC4C3CC5C6(C4(C(=O)C=CC6O)C)O5)C)O |
| 101712447 | CC1=C(C(=O)OC(C1)C(C)C2CCC3C2(CCC4C3CC5C6(C4(C(=O)C=CC6)CO)O5)C)CO |
| 101379930 | CC1=C(C(=O)OC(C1)C(C)C2=CCC3C2(CCC4C3CC5C6(C4(C(=O)C=CC6O)C)O5)C)C |
| 91522203 | CC1=C(C(=O)OC(C1)C(C)C2CCC3C2(CCC45C3CC6C7(C4(C5=C)C(=O)C=CC7O)O6)C)CO |
| 91379801 | CC1C23C14C(=O)C=CC(C45C(O5)CC2C6CCC(C6(CC3)C)C(C)C7CC(=C(C(=O)O7)CO)C)O |
| 90785396 | CC1C23C14C(=O)C=CC(C45C(O5)CC2C6CCC(C6(CC3)C)C(C)C7CC(=C(C(=O)O7)COC(=O)C)C)O |
| 90733653 | CCC1=C(CC(OC1=O)C(C)C2CCC3C2(CCC45C3CC6C7(C4(C5C)C(=O)C=CC7O)O6)C)C |
| 89809194 | CC(C1CCC2C1(CCC3C2CC4C5(C3(C(=O)C=CC5O)C)O4)C)C(=C(C)CO)C(=O)O |
| 89409052 | CC1=C(C(=O)OC(C1)C(C)(C2(CCC3C2(CCC4C3CC5C6(C4(C(=O)C=CC6O)C)O5)C)O)O)C |
| 89092202 | CC1=C(C(=O)OC(C1)C(C)C2CCC3C2(CCC45C3CC6C7(C4(C5)C(=O)C=CC7O)O6)C)CO |
| 85218520 | CC1=C(C(=O)OC(C1)C(C)C2CCC3C2(CCC4C3CC5C6(C4(C(=O)C=CC6)C)O5)C)CO |
| 77913313 | CC1=C(C(=O)OC(C1)C(C)C2CC=C3C2(CCC4C3CC5C6(C4(C(=O)C=CC6O)C)O5)C |
| 77913312 | CC1=C(C(=O)OC(C1)C(C)C2=CCC3C2(CCC4C3CC5C6(C4(C(=O)C=CC6O)C)O5)C)CO |
| 76459879 | CC1=C(C(=O)OC(C1)C(C)C2CCC3C2(CC(C4C3CC5C6(C4(C(=O)C=CC6O)C)O5)O)C)CO |
| 73823412 | CC1=C(C(=O)OC(C1)C(C)(C2CCC3C2(CCC4C3CC5C6(C4(C(=O)C=CC6OC(=O)C)C)O5)C)O)COC(=O)C |
| 73800274 | CC1=C(C(=O)OC(C1)C(C)(C2CCC3C2(CCC4C3CC5C6(C4(C(=O)C=CC6O)C)O5)CO)O)C |
| 73797121 | CC1=C(C(=O)OC(C1)C(C)C2=CCC3C2(CCC4C3CC5C6(C4(C(=O)C=CC6O)C)O5)C)C |
| 71477945 | CC1=C(C(=O)OC(C1)C(C)C2CC=C3C2(CCC4C3CC5C6(C4(C(=O)C=CC6O)C)O5)C)C |
| 71477799 | CC1=C(C(=O)OC(C1)C(C)C2=CCC3C2(CCC4C3CC5C6(C4(C(=O)C=CC6O)C)O5)C)CO |
| 70690365 | CC1=C(C(=O)OC(C1)C(C)C2CC=C3C2(CCC4C3CC5C6(C4(C(=O)C=CC6O)C)O5)C |
| 70690364 | CC1=C(C(=O)OC(C1)C(C)C2=CCC3C2(CCC4C3CC5C6(C4(C(=O)C=CC6O)C)O5)C)CO |
| 56926114 | CC1=C(C(=O)OC(C1)C(C)C2CCC3C2(CC(C4C3CC5C6(C4(C(=O)C=CC6O)C)O5)O)C)CO |
| 21679025 | CC1=C(C(=O)OC(C1)C(C)(C2CCC3C2(CCC4C3CC5C6(C4(C(=O)C=CC6OC(=O)C)C)O5)C)O)COC(=O)C |
| 21606687 | CC1=C(C(=O)OC(C1)C(C)(C2CCC3C2(CCC4C3CC5C6(C4(C(=O)C=CC6O)C)O5)CO)O)C |
| 21574482 | CC1=C(C(=O)OC(C1)C(C)C2=CCC3C2(CCC4C3CC5C6(C4(C(=O)C=CC6O)C)O5)C)C |
| 10767272 | CC1=C(C(=O)OC(C1)C(C)(C2CCC3C2(CCC4C3CC5C6(C4(C(=O)C=CC6O)C)O5)CO)O)C |
| 10648050 | CC1=C(C(=O)OC(C1)C(C)C2CCC3C2(CCC4C3CC5C6(C4(C(=O)C=CC6)C)O5)C)CO |
| 10458125 | CC1=C(C(=O)OC(C1)C(C)(C2CCC3C2(CCC4C3CC5C6(C4(C(=O)C=CC6O)C)O5)CO)O)C |
| 102435647 | CC1=C(C(=O)OC(C1)C(C)C2CCC3C2(CCC4C3CCC5(C4(C(=O)C=CC5O)C)O)C)CO |
| 91365744 | CC1C23C14C(=O)C=CC(C45C(O5)CC2C6CCC(C6(CC3)C)C(C)C7CC(=C(C(=O)O7)CO)C)OC(=O)C |
| 90670452 | CC1=C(C(=O)OC(C1)C(C)C2CC(C3C2(CCC4C3CC5C6(C4(C(=O)C=CC6O)C)O5)C)O)CO |
| 90670451 | CC1=C(C(=O)OC(C1)C(C)C2CCC3C2(C(C4C3CC5C6(C4(C(=O)C=CC6O)C)O5)O)C)CO |
| 90670442 | CC1=C(C(=O)OC(C1)C(C)C2CCC3C2(CCC4C3CC5C6(C4(C(=O)C=CC6O)C)O5)COS(=O)(=O)O |
| 88858698 | CC1=C(C(=O)OC(C1)C(C)C2CCC3C2(CCC4C3CC5C6(C4(C(=O)C=CC6OC(=O)C)C)O5)COC(=O)C |
| 85332099 | CC1=C(C(=O)OC(C1)C(C)C2CC(C3C2(CCC4C3CC5C6(C4(C(=O)C=CC6O)C)O5)C)O)CO |
| 85326709 | CC1=C(C(=O)OC(C1)C(C)C2CCC3C2(C(C4C3CC5C6(C4(C(=O)C=CC6O)C)O5)O)C)CO |
| 76385925 | CC1=C(C(=O)OC(C1)C(C)C2CCC3C2(CCC4C3CC5C6(C4(C(=O)C=CC6OC(=O)C)C)O5)COC(=O)C |
| 76385914 | CC1=C(C(=O)OC(C1)C(C)C2CCC3C2(CC(C4C3CC5C6(C4(C(=O)C=CC6O)CO)O5)O)C)CO |
| 75202434 | CC1=C(C(=O)OC(C1)C(C)C2CCC3C2(CCC4C3CCC5(C4(C(=O)C=CC5O)C)O)C)CO |
| 75093296 | CC1=C(C(=O)OC(C1)C(C)C2CCC3C2(CCC4C3CC5C6(C4(C(=O)C=CC6O)C)O5)COS(=O)(=O)O |
| 73945208 | CC1=C(C(=O)OC(C1)C(C)C2CCC3C2(CCC4C3CC5C6(C4(C(=O)C=CC6O)C)O5)C)CO |
| 73823413 | CC1=C(C(=O)OC(C1)C(C)(C2(CCC3C2(CCC4C3CC5C6(C4(C(=O)C=CC6OC(=O)C)C)O5)C)O)O)C |
| 73197334 | CC1=C(C(=O)OC(C1)C(C)(C2CCC3C2(CCC4C3CC5C6(C4(C(=O)C=CC6O)C)O5)COC(=O)C)O)C |
| 60148727 | CC1=C(C(=O)OC(C1)C(C)C2CCC3C2(CCC4C3CC5C6(C4(C(=O)C=CC6OC(=O)C)CO)O5)COC(=O)C |
| 58443789 | CC1=C(C(=O)OC(C1)C(C)C2CCC3C2(CCC4C3CC5C6(C4(C(=O)C=CC6O)C)O5)COS(=O)(=O)O |
| 56649398 | CC1=C(C(=O)OC(C1)C(C)C2CCC3C2(CCC4C3CC5C6(C4(C(=O)C=CC6OC(=O)C)C)O5)COC(=O)C |
| 56649372 | CC1=C(C(=O)OC(C1)C(C)C2CCC3C2(CC(C4C3CC5C6(C4(C(=O)C=CC6O)CO)O5)O)C)CO |
| 45111619 | CC1=C(C(=O)OC(C1)C(C)C2CCC3C2(CCC4C3CC5C6(C4(C(=O)C=CC6O)C)O5)COS(=O)(=O)O |
| 21679026 | CC1=C(C(=O)OC(C1)C(C)(C2(CCC3C2(CCC4C3CC5C6(C4(C(=O)C=CC6OC(=O)C)C)O5)C)O)O)C |
| 15519705 | CC1=C(C(=O)OC(C1)C(C)(C2CCC3C2(CCC4C3CC5C6(C4(C(=O)C=CC6O)C)O5)COC(=O)C)O)C |
| 10459594 | CC1=C(C(=O)OC(C1)C(C)(C2CCC3C2(CCC4C3CC5C6(C4(C(=O)C=CC6O)C)O5)COC(=O)C)O)C |
| 10163221 | CC1=C(C(=O)OC(C1)C(C)C2CC(C3C2(CCC4C3CC5C6(C4(C(=O)C=CC6O)C)O5)C)O)CO |
| 10141001 | CC1=C(C(=O)OC(C1)C(C)C2CCC3C2(C(C4C3CC5C6(C4(C(=O)C=CC6O)C)O5)O)C)CO |
| 102504535 | C4CC(OC(=O)C1C)C(C)C2CCC3C2(CCC4C3CC5C6(C4(C(=O)C=CC6O)C)O5)C |
| 102504532 | CC1CC(OC(=O)C1C)C(C)(C2CCC3C2(CCC4C3CC5C6(C4(C(=O)C=CC6O)C)O5)C)O |
| 102435648 | CC1=C(C(=O)OC(C1)C(C)C2CCC3C2(CCC4C3CCC5(C4(C(=O)C=CC5O)C)O)C)C |
| 102317091 | CC1=C(C(=O)OC(C1)C(CO)C2CCC3C2(CCC4C3CC(C5(C4(C(=O)C=CC5)C)O)O)C)CO |
| 101911600 | CC1=C(C(=O)OC(C1)C(C)C2C(CC3C2(CCC4C3CC5C6(C4(C(=O)C=CC6)C)O5)C)O)CO |
| 101911595 | CC1=C(C(=O)OC(C1)C(C)C2C(=O)CC3C2(CCC4C3CC(C5(C4(C(=O)C=CC5)C)O)O)C)CO |
| 101710595 | CC1=C(C(=O)OC(C1)C(C)(C2CCC3C2(CCC4C3C5C(O5)C6(C4(C(=O)C=CC6)C)O)C)O)CO |
| 101630647 | CC1=C(C(=O)OC(C1)C(C)C2CCC3C2(CC(C4C3C5C(O5)C6(C4(C(=O)C=CC6)C)O)O)C)CO |
| 101419548 | CC1=C(C(=O)OC(C1)C(C)C2CCC3C2(CC(C4C3C5C(O5)C6(C4(C(=O)C=CC6)C)O)O)C)CO |
| 101281364 | CC1=C(C(=O)OC(C1O)C(C)C2CCC3C2(CCC4C3C5C(O5)C6(C4(C(=O)C=CC6)C)O)C |
| 101231931 | CC1CC(OC(=O)C1C)C(C)C2CCC3C2(CCC4C3CC5C6(C4(C(=O)C=CC6O)C)O5)C |
| 101168804 | CC1=C(C(=O)OC(C1)C(C)C2CCC3C2(CCC4C3CC(C5(C4(C(=O)C=CC5O)C)O)O)C)C |
| 91453196 | CCCC1C(=O)OC(CC1(C)C)C(C)C2CCC3C2(CCC4C3CC5C6(C4(C(=O)C=CC6O)C)O5)C |
| 91438857 | CC1=C(C(OC(C1)C(C)C2CCC3C2(CCC4C3CC5C6(C4(C(=O)C=CC6O)C)O5)C)O)CO |

TABLE 2-continued

LIST OF WITHAFERIN A ANALOGS AND DERIVATIVES BASED ON SIMILARITY

| | |
|---|---|
| 90670441 | CC1=C(C(=O)OC(C1)C(C)C2CCC3C2(CCC4C3CC5C6(C4(C(=O)C=CC6OC(=O)C)O5)C)C |
| 89333022 | CC1CC(OC(=O)C1C)C(C)C2CCC3C2(CCC4C3CC5C6(C4(C(=O)C=CC6O)C)O5)C |
| 89091907 | CC1=C(C(=O)OC(C1)C(C)C2CCC3C2(CCC4C3CC5C6(C4(C(=O)C=CC6O)C)O5)C)CCC(C)(C)[Si](C)(C)O |
| 88949020 | CC1=C(C(=O)OC(C1)C(C)C2CCC3C2(CCC4C3CC5C6(C4(C(=O)C=CC6O)O)O5)C)C |
| 88949018 | CC1=C(C(=O)OC(C1)C(C)C2CCC3C2(CCC4C3CC5C6(C4(C(=O)C=CC6O)O)O5)C)CO |
| 88949011 | CC1=C(C(=O)OC(C1)C(C)C2CCC3C2(CCC4C3CC5C6(C4C(=O)C=CC6OC(=O)C)O5)C)C |
| 77911018 | CC1=C(C(=O)OC(C1)C(C)C2CCC3C2(CCC4C3CC(C5(C4(C(=O)C=CC5O)C)O)O)C)CO |
| 77145375 | CC1=C(C(=O)OC(C1)C(C)C2CCC3C2(CCC4C3CC5C6(C4(C(=O)C=CC6O)C)O5)C)COC(C)(C)OC=O |
| 76787558 | CCC1=C(CC(OC1=O)C(C)C2CCC3C2(CCC4C3CC5C6(C4(C(=O)C=CC6OC(=O)C)C)O5)C)C |
| 76787557 | CC1=C(C(=O)OC(C1)C(C)C2CCC3C2(CCC4C3CC5C6(C4(C(=O)C=CC6O)C)O5)C)CO[Si](C)(C)C(C)(C)C |
| 75239042 | CC1=C(C(=O)OC(C1)C(C)(C2CCC3C2(C(CC4C3CC5C6(C4(C(=O)C=CC6O)C)O5)O)C)O)C |
| 74039190 | CC1CC(OC(=O)C1C)C(C)(C2CCC3C2(CCC4C3CC5C6(C4(C(=O)C=CC6O)C)O5)C)O |
| 74039189 | CC1CC(OC(=O)C1C)C(C)(C2CCC3C2(CCC4C3CC5C6(C4(C(=O)C=CC6O)C)O5)C |
| 74039182 | CC1=C(C(=O)OC(C1O)C(C)C2CCC3C2(CCC4C3C5C(O5)C6(C4(C(=O)C=CC6)C)O)C)C |
| 73820038 | CC1=C(C(=O)OC(C1)C(C)C2C(CC3C2(CCC4C3CC5C6(C4(C(=O)C=CC6O)C)O5)C=O)O)C |
| 73800706 | CC1=C(C(=O)OC(C1)C(C)C2CCC3C2(C(CC4C3C5C(O5)C6(C4(C(=O)C=CC6)C)O)O)C)CO |
| 73310064 | CC1=C(C(=O)OC(C1)C(C)C2CCC3C2(CCC4C3CC5C6(C4(C(=O)C=CC6O)C)O5)COC(=O)O)C |
| 73306621 | CC1=C(C(=O)OC(C1)C(C)(C23C(O2)CC4C3(CCC5C4CC6C7(C5(C(=O)C=CC7O)C)O6)C)O)C |
| 73306620 | CC1=C(C(=O)OC(C1)C(C)C23C(O2)CC4C3(CCC5C4CC6C7(C5(C(=O)C=CC7O)C)O6)C)C |
| 73306373 | CC1=C(C(=O)OC(C1)C(C)C2(C(CC3=C2CCC4C3CC5C6(C4(C(=O)C=CC6O)C)O5)C)C |
| 72663555 | CC1=C(C(=O)OC(C1)C(C)C2C(C(C3C2(CCC4C3CC5C6(C4(C(=O)C=CC6O)COC(=O)C)O5)C)O)CO |
| 72663554 | CC1=C(C(=O)OC(C1)C(C)C2CC(C3C2(CCC4C3CC5C6(C4(C(=O)C=CC6O)CO)O5)C)O)CO |
| 72544656 | CC1=C(C(=O)OC(C1)C(C)C2CCC3C2(CCC4C3CC5C6(C4(C(=O)C=CC6O)I)O)O5)C)CO |
| 71477797 | CC1=C(C(=O)OC(C1)C(C)C2CCC3C2(CCC4C3CC5C6(C4(C(=O)C=CC6O)C)O5)C)CO[Si](C)(C)C(C)(C)C |
| 70684083 | CC1=C(C(=O)OC(C1)C(C)C2CCC3C2(CCC4C3CC(C5(C4(C(=O)C=CC5O)C)O)O)C)CO |
| 66572430 | CC1=C(C(=O)OC(C1)C(C)C2CCC3C2(CCC4C3CC5C6(C4(C(=O)C=CC6O)C)O5)C)COC(C)(C)OC=O |
| 66572355 | CC1=C(C(=O)OC(C1)C(C)C2CCC3C2(CCC4C3CC5C6(C4(C(=O)C=CC6O)C)O5)C)CO[Si](C)(C)C(C)(C)C |
| 60148720 | CC1=C(C(=O)OC(C1)C(C)C2CC(C3C2(CCC4C3CC5C6(C4(C(=O)C=CC6O)COC(=O)C)O5)C)O)CO |
| 60148719 | CC1=C(C(=O)OC(C1)C(C)C2CC(C3C2(CCC4C3CC5C6(C4(C(=O)C=CC6O)CO)O5)C)O)CO |
| 58443793 | CCC1=C(CC(OC1=O)C(C)C2CCC3C2(CCC4C3CC5C6(C4(C(=O)C=CC6OC(=O)C)C)O5)C)C |
| 58443791 | CC1=C(C(=O)OC(C1)C(C)C2CCC3C2(CCC4C3CC5C6(C4(C(=O)C=CC6O)C)O5)C)CO[Si](C)(C)C(C)(C)C |
| 56841147 | CC1=C(C(=O)OC(C1)C(CO)C2CCC3C2(CCC4C3CC(C5(C4(C(=O)C=CC5O)C)O)O)C)CO |
| 56677887 | CC1=C(C(=O)OC(C1)C(C)(C2CCC3C2(C(CC4C3CC5C6(C4(C(=O)C=CC6O)O5)O)O)C)C |
| 53398767 | CC1=C(C(=O)OC(C1)C(C)C2CCC3C3C5C(O5)C6(C4(C(=O)C=CC6)C)O)C)CO |
| 49799448 | CC1=C(C(=O)OC(C1)C(C)(C2CCC3C2(C(CC4C3CC5C6(C4(C(=O)C=CC6O)O5)O)O)C |
| 46872824 | CC1=C(C(=O)OC(C1)C(C)(C2CCC3C2(C(CC4C3CC5C6(C4(C(=O)C=CC6O)O5)O)C)CO |
| 44631508 | CC1=C(C(=O)OC(C1O)C(C)C2CCC3C2(CCC4C3C5C(O5)C6(C4(C(=O)C=CC6)C)O)C)C |
| 44576309 | CC1=C(C(=O)OC(C1)C(C)C2CCC3C2(CCC4C3C5C(O5)C6(C4(C(=O)C=CC6)C)O)C)CO |
| 44423094 | CC1=C(C(OC(C1)C(C)(C2CCC3C2(CCC4C3CC5C6(C4(C(=O)C=CC6O)C)O5)C)O)O)C |
| 23266167 | CC1CC(OC(=O)C1C)C(C)(C2CCC3C2(CCC4C3CC5C6(C4(C(=O)C=CC6O)C)C)O |
| 23266166 | CC1CC(OC(=O)C1C)C(C)C2CCC3C2(CCC4C3CC5C6(C4(C(=O)C=CC6O)C)O5)C |
| 23266156 | CC1=C(C(=O)OC(C1O)C(C)C2CCC3C2(CCC4C3C5C(O5)C6(C4(C(=O)C=CC6)C)O)C)C |
| 22210256 | CC1=C(C(=O)OC(C1)C(CO)C2CCC3C2(CCC4C3CC(C5(C4(C(=O)C=CC5O)C)O)O)C)CO |
| 21670295 | CC1=C(C(=O)OC(C1)C(C)C2C(CC3C2(CCC4C3CC5C6(C4(C(=O)C=CC6O)C)O5)C=O)O)C |
| 21607602 | CC1=C(C(=O)OC(C1)C(C)C2CCC3C2(C(CC4C3C5C(O5)C6(C4(C(=O)C=CC6)C)O)O)C)CO |
| 16720560 | CC1=C(C(=O)OC(C1)C(C)C2CCC3C2(CCC4C3CC5C6(C4(C(=O)C=CC6O)C)O5)COC(=O)O)C |
| 16680370 | CC1=C(C(=O)OC(C1)C(C)(C23C(O2)CC4C3(CCC5C4CC6C7(C5(C(=O)C=CC7O)C)O6)C)O)C |
| 16680369 | CC1=C(C(=O)OC(C1)C(C)C23C(O2)CC4C3(CCC5C4CC6C7(C5(C(=O)C=CC7O)C)O6)C)C |
| 16679812 | CC1=C(C(=O)OC(C1)C(C)C2(C(CC3=C2CCC4C3CC5C6(C4(C(=O)C=CC6O)C)O5)C)C |
| 15858981 | CC1=C(C(=O)OC(C1)C(C)C2CCC3C2(CCC4C3C5C(O5)C6(C4(C(=O)C=CC6)C)O)C)CO |
| 11305931 | CC1=C(C(=O)OC(C1)C(C)C2CCC3C2(CCC4C3C5C(O5)C6(C4(C(=O)C=CC6)C)O)C)CO |
| 11134251 | CC1CC(OC(=O)C1C)C(C)C2CCC3C2(CCC4C3CC5C6(C4(C(=O)C=CC6O)C)O5)C |
| 10814731 | CC1=C(C(=O)OC(C1)C(C)C2C(CC3C2(CCC4C3CC5C6(C4(C(=O)C=CC6O)O5)C=O)O)C |
| 10413210 | CC1=C(C(=O)OC(C1)C(C)C2CCC3C2(CCC4C3CC(C5(C4(C(=O)C=CC5O)C)O)O)C)CO |
| 10344751 | CC1=C(C(=O)OC(C1)C(C)C2CCC3C2(CCC4C3CC(C5(C4(C(=O)C=CC5)C)O)O)C)CO |
| 10051187 | CC1=C(C(=O)OC(C1)C(CO)C2CCC3C2(CCC4C3CC(C5(C4(C(=O)C=CC5)C)O)O)C)CO |
| 10005030 | CC1CC(OC(=O)C1C)C(C)(C2CCC3C2(CCC4C3CC5C6(C4(C(=O)C=CC6O)C)O5)C)O |
| 3808690 | CC1=C(C(=O)OC(C1)C(C)C2CCC3C2(CCC4C3CC(C5(C4(C(=O)C=CC5)C)O)O)C)CO |
| 496218 | CC1=C(C(=O)OC(C1)C(CO)C2CCC3C2(CCC4C3CC(C5(C4(C(=O)C=CC5)C)O)O)C)CO |
| 387980 | CC1=C(C(=O)OC(C1)C(CO)C2CCC3C2(CCC4C3CC(C5(C4(C(=O)C=CC5)C)O)O)C)CO |
| 268947 | CC1=C(C(=O)OC(C1)C(C)C2CCC3C2(CCC4C3CC(C5(C4(C(=O)C=CC5)C)O)O)C)CO |
| 102435652 | CC1=C(C(=O)OC(C1)C(C)C2(CCC3C2(CCC4C3CCC5(C4(C(=O)C=CC5O)C)O)O)C |
| 102435650 | CC1=C(C(=O)OC(C1)C(C)C2(CCC3C2(CCC4C3CCC5(C4(C(=O)C=CC5O)C)O)O)CO |
| 102262595 | CC1=C(C(=O)OC(C1)C(C)C2(C(CC3C2(CCC4C3CC5C6(C4(C(=O)C=CC6O)C)O5)C)OC(=O)C)C |
| 102065719 | CC1=C(C(=O)OC(C1)C(C)C2(C(CC3C2(CCC4C3CC5C6(C4(C(=O)C=CC6O)C)O5)O)O)C |
| 101664458 | CC1=C(C(=O)OC(C1)C(C)C2C(CC3C2(CCC4C3CC5C6(C4(C(=O)C=CC6O)O5)COC(=O)C)OC(=O)C)C |
| 101630646 | CC1=C(C(=O)OC(C1)C(CO)C2CCC3C2(CCC4C3CC(C5(C4(C(=O)C=CC5)C)O)O)C)C |
| 101420306 | CC1=C(C(=O)OC(C1)C(C)C2C(CC3C2(CCC4C3CC5C6(C4(C(=O)C=CC6O)C)O5)COC(=O)C)OC(=O)C |
| 101403753 | CC1C(=CC(OC1=O)C(C)(C2CCC3C2CC4C3CC5C6(C4(C(=O)C=CC6)C)OC(=O)C)O)C |
| 101316930 | CC1=C(C(=O)OC(C1)C(C)C2CCC3C2(C(CC4C3C5C(O5)C6(C4(C(=O)C=CC6)C)O)O)C)CO |
| 101131180 | CC1=C(C(=O)OC(C1)C(CO)C2CCC3C2(CCC4C3CC(C5(C4(C(=O)C=CC5)C)O)O)C)COC |
| 99606234 | CC(C1CCC2(C1(CCC3C2CC4C5(C3(C(=O)C=CC5O)C)O4)C)O)C6CC=C(C(=O)O6)CO |
| 90987835 | CCCOC1C=CC(=O)C2(C13CO(O3)CC4C2CCC5(C4CCC5C(C(=O)O6)COC(=O)C)C)C |
| 90984131 | CCCC1=C(C(=O)OC(C1)C(C)C2CCCC3CC4C5(O4)C(C=C(=O)C5(C3CCC2)C)CO |
| 85123263 | CC1CC(OC(=O)C1C)C(C)(C2CCC3C2(CCC4C3CC5C6(C4(C(=O)C=CC6O)C)O5)C)O |
| 77987113 | CC1=C(C(=O)OC(C1)C(C)C2CCC3C2(CCC4C3C(C5C6(C4(C(=O)C=CC6O)C)O5)O)C)C |
| 75072256 | CC1=C(C(=O)OC(C1)C(C)C2(CCC3C2(CCC4C3CC5C6(C4(C(=O)C=CC6)CO)O5)C)O)C |
| 75072251 | CC1=C(C(=O)OC(C1)C(C)C2CCC3C2(C(CC4C3C5C(O5)C6(C4(C(=O)C=CC6)O)O)C)C |

TABLE 2-continued

LIST OF WITHAFERIN A ANALOGS AND DERIVATIVES BASED ON SIMILARITY

| | |
|---|---|
| 74039187 | CC1=C(C(=O)OC(C1)C(C)(C2CCC3(C2(CCC4C3CC5C6(C4(C(=O)C=CC6O)C)O5)C)O)O)C |
| 74039185 | CC1=C(C(=O)OC(C1)C(C)(C2CCC3C2(CCC4C3CC5C6(C4(C(=O)C=CC6O)C)O5)O)C)C |
| 73123620 | CC1=C(C(=O)OC(C1)C(C)(C2CCC3C2(CCC4C3CC5C6(C4(C(=O)C=CC6)C)O5)COC(=O)C)O)C |
| 73021842 | CC1=C(C(=O)OC(C1)C(C2CCC3C2(CCC4C3C5C(O5)C6(C4(C(=O)C=CC6)C)O)C)O)C |
| 71481106 | CC1=C(C(=O)OC(C1)C(C)C2CCC3C2(CCC4C3C(C5C6(C4(C(=O)C=CC6O)C)O5)O)C)C |
| 58443787 | CC1=C(C(=O)OC(C1)C(C)C2CCC3C2(CCC4C3CC5C6(C4(C(=O)C=CC6=O)C)O5)C)CO |
| 53398686 | CC(C1CCC2(C1(CCC3C2CC4C5(C3(C(=O)C=CC5O)C)O4)C)O)C6CC=C(C(=O)O6)CO |
| 45111621 | CC1=C(C(=O)OC(C1)C(C)C2CCC3C2(CCC4C3CC5C6(C4(C(=O)C=CC6=O)C)O5)C)CO |
| 44566997 | CC1=C(C(=O)OC(C1)C(C)C2(CCC3C2(CCC4C3CC5C6(C4(C(=O)C=CC6)CO)O5)C)O)C |
| 44566979 | CC1=C(C(=O)OC(C1)C(C)C2CCC3C2(CCC4C3C5C(O5)C6(C4(C(=O)C=CC6)O)O)C)C |
| 44423097 | CC1=C(C(OC(C1)C(C)(C2(CCC3C2(CCC4C3CC5C6(C4(C(=O)C=CC6O)C)O5)C)O)O)O)C |
| 44423090 | CC1=C(C(OC(C1)C(C)C2(CCC3C2(CCC4C3CC5C6(C4(C(=O)C=CC6O)C)O5)C)O)O)C |
| 23266162 | CC1=C(C(=O)OC(C1)C(C)(C2CCC3(C2(CCC4C3CC5C6(C4(C(=O)C=CC6O)C)O5)C)O)O)C |
| 23266160 | CC1=C(C(=O)OC(C1)C(C)(C2CCC3C2(CCC4C3C(C5C6(C4(C(=O)C=CC6O)C)O5)O)C)O)C |
| 23266158 | CC1=C(C(=O)OC(C1)C(C)C2CCC3(C2(CCC4C3CC5C6(C4(C(=O)C=CC6O)C)O5)C)C |
| 14836386 | CC1=C(C(=O)OC(C1)C(C)C2CCC3C2(CCC4C3CC5C6(C4(C(=O)C=CC6=O)C)O5)C)CO |
| 12070588 | CC1CC(OC(=O)C1C(C)(C2(CCC3C2(CCC4C3CC5C6(C4(C(=O)C=CC6O)C)O5)C)O)O |
| 11844626 | CC1=C(C(=O)OC(C1)C(C)(C2CCC3C2(CCC4C3CC5C6(C4(C(=O)C=CC6)C)O5)COC(=O)C)O)C |
| 11590622 | CC1=C(C(=O)OC(C1)C(C2CCC3C2(CCC4C3C5C(O5)C6(C4(C(=O)C=CC6)C)O)C)O)C |
| 11038269 | CC1CC(OC(=O)C1C(C)(C2(CCC3C2(CCC4C3CC5C6(C4(C(=O)C=CC6O)C)O5)C)O)O |
| 10368236 | CC1CC(OC(=O)C1C(C)(C2(CCC3C2(CCC4C3CC5C6(C4(C(=O)C=CC6O)C)O5)C)O)O |
| 10277878 | CC1=C(C(=O)OC(C1)C(C)C2CCC3(C2(CCC4C3CC5C6(C4(C(=O)C=CC6O)C)O5)CO)C)C |
| 10228028 | CC1=C(C(=O)OC(C1)C(C)(C2CCC3C2(CCC4C3CC5C6(C4(C(=O)C=CC6=O)C)O5)C)O)C |
| 10095500 | CC1=C(C(=O)OC(C1)C(C)C2(CCC3C2(CCC4C3CC5C6(C4(C(=O)C=CC6)C)O5)C)O)C |
| 321579 | CC1=C(C(=O)OC(C1)C(C)C2CCC3(C2(CCC4C3CC5C6(C4(C(=O)C=CC6O)C)O5)C)O)CO |
| 301755 | CC1=C(C(=O)OC(C1)C(C)C2CCC3(C2(CCC4C3CC5C6(C4(C(=O)C=CC6O)C)O5)C)O)C |
| 165541 | CC1=C(C(=O)OC(C1)C(C)C2CCC3C2(CCC4C3CC5C6(C4(C(=O)C=CC6=O)C)O5)C)CO |
| 102579381 | CC1CC(OC(=O)C1CO)C(C)C2CCC3C2(CCC4C3CC5C6(C4(C(=O)C=CC6O)C)O5)C |
| 102357986 | CC1=C(C(=O)OC(C1)C(C)C2CCC3C2(CCC4C3CC5C6(C4(C(=O)C=CC6OC(=O)C)C)O5)C)COC(=O)C |
| 102357981 | CC1=C(C(=O)OC(C1)C(C)C2CCC3C2(CCC4C3CC5C6(C4(C(=O)C=CC6OC(=O)C)C)O5)C)COC(=O)C |
| 102330662 | CC1CC(OC(=O)C1C(C)(C2C(CC3C2(CCC4C3CC5C6(C4(C(=O)C=CC6O)C)O5)C)O)O |
| 102065718 | CC1=C(C(=O)OC(C1)C(C)C2(C(CC3C2(CCC4C3CC5C6(C4(C(=O)C=CC6)C)O5)OC(=O)C)O)C |
| 101911592 | CC1=C(C(=O)OC(C1)C(C)C2C(=O)CC3C2(CCC4C3CC(C5(C4(C(=O)C=CC5)C)O)O)C)C |
| 101005224 | CC1=C(C(=O)OC(C1)C(C)C2CCC3C2(CCC4C3C(C5C6(C4(C(=O)C=CC6O)C)O5)OC(=O)C)C)C |
| 100990383 | CC1=C(C(=O)OC(C1)C(C)C2CC(C3(C2(CCC4C3CC5C6(C4(C(=O)C=CC6O)C)O5)C)O)O)C |
| 99567692 | CC1=C(C(=O)OC(C1)C(C)(C2CCC3C2(CCC4C3C5C(O5)C6(C4(C(=O)C=CC6)C)O)C)O)C |
| 99567691 | CC1=C(C(=O)OC(C1)C(C)(C2CCC3C2(CCC4C3C5C(O5)C6(C4(C(=O)C=CC6)C)O)C)O)C |
| 99567690 | CC1=C(C(=O)OC(C1)C(C)(C2CCC3C2(CCC4C3C5C(O5)C6(C4(C(=O)C=CC6)C)O)C)O)C |
| 99567689 | CC1=C(C(=O)OC(C1)C(C)(C2CCC3C2(CCC4C3C5C(O5)C6(C4(C(=O)C=CC6)C)O)C)O)C |
| 90705667 | CC1CC(=O)C2(C3CCC4(C(C3CC5C2(C1O)O5)CCC4C(=C(C(=O)O6)C)O)C |
| 90670456 | CC1=C(C(=O)OC(C1)C(C)C2CCC3C2(CCC4C3CC5C6(C4(C(=O)C=CC6OC(=O)C)C)O5)C)COC(=O)C |
| 90670449 | CC1=C(C(=O)OC(C1)C(C)C2CCC3C2(CCC4C3CC(C5(C4(C(=O)C=CC5)C)O)OC(=O)C)C)COC(=O)C |
| 90670448 | CC1=C(C(=O)OC(C1)C(C)C2CCC3C2(CCC4C3CC(C5(C4(C(=O)C=CC5OC(=O)C)C)O)OC(=O)C)C)COC(=O)C |
| 90670446 | CC1=C(C(=O)OC(C1)C(C)C2CCC3C2(CCC4C3C5C(O5)C6(C4(C(=O)C=CC6)C)O)C)COC(=O)C |
| 90473517 | CC1=C(C(=O)OC(C1)C(C)C2CCC3C2(CCC4C3CC5C6(C4(C(=O)C=CC6)C)O5)C)COC(=O)C |
| 89092194 | CCCC1(C(CCC1C(C)C2CC(=C(C(=O)O2)COC(=O)C)C)C3CC4C5(O4)C(C=CC(=O)C56C3C6)O)C |
| 89092040 | CC1=C(C(=O)OC(C1)C(C)C2CCC3C2(CCCC4C5C3CCC6C7(C45C(=O)C=CC7O)O6)C)CO |
| 89092028 | CC1=C(C(=O)OC(C1)C(C)C2CCC3C2(CCCC4C5C3CCC6C7(C45C(=O)C=CC7O)O6)C)CO |
| 89064896 | CC1=C(C(=O)OC(C1)C(C)C2CCC3C2(CCC4C3CC5C(C4(C)C(=O)C)(O5)C(C(C)O)O)C)CO |
| 88948989 | CC1=C(C(=O)OC(C1)C(C)C2CCC3C2(CCC4C3CC5C6(C4C(=O)CCC6O)O5)C)CO |
| 88858697 | CCC1=C(CC(OC1=O)C(C)C2CCC3C2(CCC4C3CC5C6(C4(C(=O)C=CC6OC(=O)C)COC(=O)C)O5)C |
| 85857395 | CC(C)CCCC(C)C1CCC2C1(CCC3C2CC4C5(C3(C(=O)C=CC5OC(=O)C)O4)C |
| 85836925 | CC(C)CCCC(C)C1CCC2C1(CCC3C2CC4C5(C3(C(=O)C=CC5O)C)O4)C |
| 78384890 | CC1=C(C(=O)OC(C1)C(C)C2CC(C3(C2(CCC4C3CC5C6(C4(C(=O)C=CC6O)C)O5)C)O)O)C |
| 76385933 | CC1=C(C(=O)OC(C1)C(C)C2CCC3C2(CCC4C3CC5C6(C4(C(=O)C=CC6OC(=O)C)COC(=O)C)O5)C |
| 76385926 | CC1=C(C(=O)OC(C1)C(C)C2CCC3C2(CCC4C3CC5C6(C4(C(=O)C=CC6OC(=O)C)COC(=O)C)O5)C)COC(=O)C |
| 76328113 | CCC(=O)OCC1=C(CC(OC1=O)C(C)C2CCC3C2(CCC4C3CC5C6(C4(C(=O)C=CC6OC(=O)CC)COC(=O)CC)O5)C |
| 75072261 | CC1CC(OC(=O)C1C(C)(C2C(CC3C2(CCC4C3CC5C6(C4(C(=O)C=CC6O)C)O5)C)O)O |
| 75072250 | CC1=C(C(=O)OC(C1)C(=C2C(CC3C2(CCC4C3C5C(O5)C6(C4(C(=O)C=CC6)C)O)C)C)C |
| 73981783 | CC1=C(C(=O)OC(C1)C(C)(C2CCC3C2(CCC4C3C(C5C6(C4(C(=O)C=CC6O)C)O5)OC(=O)C)C)O)C |
| 73797122 | CC1=C(C(=O)OC(C1)C(C)C2CCC3C2(CCC4C3C5C(O5)C6(C4(C(=O)C=CC6)C)O)C)CO |
| 73306655 | CC1=C(C(=O)OC(C1)C(C)C2(CCC3C2(CCC4C3CC(C5(C4(C(=O)C=CC5)C)O)O)C)O)C |
| 73306622 | CC1=C(C(=O)OC(C1O)C(C)C23C(O2)CC4C3(CCC5C4CC6C7(C5(C(=O)C=CC7O)C)O6)C)C |
| 72835716 | CC1CC(OC(=O)C1CO)C(C)C2CCC3C2(CCC4C3CC5C6(C4(C(=O)C=CC6O)C)O5)C |
| 72544875 | CC1=C(C(=O)OC(C1)C(C)C2CCC3C2(CCC4C3CC5C6(C47COC(=O)CCC(=O)OC6C=CC7=O)O5)C)COC(=O)C |
| 72544874 | CC1=C(C(=O)OC(C1)C(C)C2CCC3C2(CCC4C3CC5C6(C4(C(=O)C=CC6OC(=O)CCC=C)COC(=O)CCC=C)O5)C)COC(=O)C |
| 58443796 | CC1=C(C(=O)OC(C1)C(C)C2CCC3C2(CCC4C3CC5C6(C4(C(=O)C=CC6OC(=O)C)C)O5)C)COC(=O)C |
| 57523801 | CC1=C(C(=O)OC(C1)C(C)C2CCC3C2(CCC4C3CC5C6(C4(C(=O)C=CC6OC(=O)C)COC(=O)C)O5)C)COC(=O)C |
| 56649416 | CC1=C(C(=O)OC(C1)C(C)C2CCC3C2(CCC4C3CC5C6(C4(C(=O)C=CC6OC(=O)C)COC(=O)C)O5)C)C |
| 56649399 | CC1=C(C(=O)OC(C1)C(C)C2CCC3C2(CCC4C3CC5C6(C4(C(=O)C=CC6OC(=O)C)COC(=O)C)O5)C)COC(=O)C |
| 45111623 | CC1=C(C(=O)OC(C1)C(C)C2CCC3C2(CCC4C3CC5C6(C4(C(=O)C=CC6OC(=O)C)C)O5)C)COC(=O)C |
| 44567005 | CC1CC(OC(=O)C1C(C)(C2C(CC3C2(CCC4C3CC5C6(C4(C(=O)C=CC6O)C)O5)C)O)O |
| 44566978 | CC1=C(C(=O)OC(C1)C(=C2C(CC3C2(CCC4C3C5C(O5)C6(C4(C(=O)C=CC6)C)O)C)C)C |
| 44566977 | CC1=C(C(=O)OC(C1)C(=C2C(CC3C2(CCC4C3C5C(O5)C6(C4(C(=O)C=CC6)C)O)C)C)C |
| 22524628 | CC1=C(C(=O)OC(C1)C(C)(C2CCC3C2(CCC4C3C(C5C6(C4(C(=O)C=CC6O)C)O5)OC(=O)C)C)O)C |
| 21574483 | CC1=C(C(=O)OC(C1)C(C)C2CCC3C2(CCC4C3C5C(O5)C6(C4(C(=O)C=CC6)C)O)C)CO |
| 16680446 | CC1=C(C(=O)OC(C1)C(C)C2(CCC3C2(CCC4C3CC(C5(C4(C(=O)C=CC5O)C)O)O)C)O)C |
| 16680371 | CC1=C(C(=O)OC(C1O)C(C)C23C(O2)CC4C3(CCC5C4CC6C7(C5(C(=O)C=CC7O)C)O6)C)C |

TABLE 2-continued

LIST OF WITHAFERIN A ANALOGS AND DERIVATIVES BASED ON SIMILARITY

| | |
|---|---|
| 16215490 | CCOC12CC=CC(=O)C1(C3CCC4(C(C3CC2O)(CCC4(C(C)(C5CC(=C(C(=O)O5)C)C)O)O)C)C)C |
| 15411208 | CC1=C(C(=O)OC(C1)C(C)C2CCC3C2(CCC4C3CC5C6(C4(C(=O)CCC6O)C)O5)C)CO |
| 14236712 | CC1=C(C(=O)OC(C1)C(C)C2CCC3C2(CCC4C3CC5C(O5)C6(C4(C(=O)C=CC6)C)O)C)C |
| 14236711 | CC1=C(C(=O)OC(C1)C(C)C2CCC3C2(CCC4C3CC5C(O5)C6(C4(C(=O)C=CC6)C)O)C)C |
| 14236710 | CC1=C(C(=O)OC(C1)C(C)(C2CCC3C2(CCC4C3CC5C(O5)C6(C4(C(=O)C=CC6)C)O)C)O)C |
| 11408847 | CC1CC(OC(=O)C1CO)C(C)C2CCC3C2(CCC4C3CC5C6(C4(C(=O)C=CC6O)C)O5)C |
| 11294368 | CC1=C(C(=O)OC(C1)C(C)(C2CCC3C2(CCC4C3CC5C(O5)C6(C4(C(=O)C=CC6)C)O)C)O)C |
| 11070744 | CC1=C(C(=O)OC(C1)C(C)C2CCC3C2(CCC4C3CC5C6(C4(C(=O)CCC6O)C)O5)C)CO |
| 10814142 | CC1=C(C(=O)OC(C1)C(=C2C(CC3C2(CCC4C3CC5C(O5)C6(C4(C(=O)C=CC6)C)O)C)C)C)C |
| 10576254 | CC1=C(C(=O)OC(C1)C(=C2C(CC3C2(CCC4C3CC5C(O5)C6(C4(C(=O)C=CC6)C)O)C)C)C)C |
| 10480656 | CC1CC(OC(=O)C1C)C(C)(C2C(CC3C2(CCC4C3CC5C6(C4(C(=O)C=CC6O)C)O5)C)O)O |
| 10457436 | CC1=C(C(=O)OC(C1)C(C)(C2CCC3C2(CCC4C3C(C5C6(C4(C(=O)C=CC6)C)O)C)C)C)C |
| 10434957 | CC1=C(C(=O)OC(C1)C(C)C2CCC3C2(CCC4C3CC5C6(C4(C(=O)CCC6O)C)O5)C)CO |
| 10096775 | CC1=C(C(=O)OC(C1)C2(C3CCC4C3(CCC5C4CC6C7(C5(C(=O)C=CC7O)C)O6)C(=O)O2)C)C |
| 5458717 | CC1=C(C(=O)OC(C1)C(C)C2CCC3C2(CCC4C3CC5C6(C4(C(=O)C=CC6OC(=O)C)O5)C)COC(=O)C |
| 5317154 | CC1=C(C(=O)OC(C1)C(C)C2CC(C3(C2(CCC4C3CC5C6(C4(C(=O)C=CC6O)C)O5)C)O)C)C |
| 5315458 | CC1=C(C(=O)OC(C1)C(C)(C2CCC3C2(CCC4C3C(C5C6(C4(C(=O)C=CC6)C)O5)OC(=O)C)C)O)C |
| 580587 | CC1=C(C(=O)OC(C1)C(C)C2CCC3C2(CCC4C3CC5C6(C4(C(=O)C=CC6OC(=O)C)C)O5)C)C=O |
| 433361 | CC1=C(C(=O)OC(C1)C(C)C2CCC3C2(CCC4C3CC5C6(C4(C(=O)C=CC6OC(=O)C)C)O5)C)COC(=O)C |
| 418033 | CC1=C(C(=O)OC(C1)C(C)C2CCC3C2(CCC4C3CC5C6(C4(C(=O)CCC6O)C)O5)C)CO |
| 310015 | CC1=C(C(=O)OC(C1)C(C)(C2(CCC3C2(CCC4C3CC(C5(C4(C(=O)C=CC5)C)O)C)C)O)O)C |
| 193708 | CC1=C(C(=O)OC(C1)C(C)(C2CCC3C2(CCC4C3C(C5C(O5)C6(C4(C(=O)C=CC6)C)O)C)C)C)C |
| 73056 | CC1=C(C(=O)OC(C1)C(C)C2CCC3C2(CCC4C3CC5C6(C4(C(=O)C=CC6OC(=O)C)C)O5)C)COC(=O)C |
| 102064899 | CC1=C(CC(OC1=O)C(C)(C2(CCC3(C2(CCC4C3CC5C6(C4(C(=O)C=CC6)C)O5)C)O)O)C)CO |
| 101958392 | CC1=C(C(=O)OC(C1)C(C)(C2CCC3C2(CCC4C3CC5C(O5)C6(C4(C(=O)C=CC6)C)O)C)O)C |
| 101844470 | CC1=C(C(=O)OC(C1)C(=C2CCC3C2(CCC4C3CC5C(O5)C6(C4(C(=O)C=CC6)C)O)COC(=O)C)C)C |
| 101844370 | CC1=CCC(OC1=O)C(C)C2(CCC3C2(C(CC4C3CC5C(O5)C6(C4(C(=O)C=CC6)C)O)O)C)O |
| 101804281 | CC1=C(C(=O)OC(C1)C(C)(C2(CCC3(C2(CCC4C3CC5C6(C4(C(=O)C=CC6O)C)O5)C)O)O)C)C |
| 101801014 | CC1C(=O)OC(CC1(C)O)C(C)(C2C(CC3C2(CCC4C3CC5C6(C4(C(=O)C=CC6O)C)O5)C)OC(=O)C)O |
| 101664459 | CC1=C(C(=O)OC(C1)C(C)C2C(CC3C2(C(CC4C3CC5C6(C4(C(=O)C=CC6O)C)O5)OC(=O)C)C)OC(=O)C)C |
| 101468625 | CC1=C(C(=O)OC(C1)C(C)(C2=CCC3(C2(CCC4C3CC5C6(C4(C(=O)C=CC6O)C)O5)C)O)O)C |
| 101420307 | CC1=C(C(=O)OC(C1)C(C)C2C(CC3C2(C(CC4C3CC5C6(C4(C(=O)C=CC6O)C)O5)OC(=O)C)C)OC(=O)C)C |
| 101317813 | CC1=C(C(=O)OC(C1)C(C)C2CC(C3(C2(CCC4C3CC5C6(C4(C(=O)C=CC6)C)O5)C)O)OC(=O)C)C |
| 101038760 | CC1=C(C(=O)OC(C1)C(C)C2(CC=C3C2(CCC4C3CC(C5(C4(C(=O)C=CC5)C)OC)C)C)O)O)C |
| 99576255 | CC1=C(C(=O)OC(C1)C(C)(C2(CCC3(C2(CCC4C3CC5C6(C4(C(=O)C=CC6)C)O5)C)O)O)O)C |
| 99576254 | CC1=C(C(=O)OC(C1)C(C)(C2(CCC3(C2(CCC4C3CC5C6(C4(C(=O)C=CC6)C)O5)C)O)O)O)C |
| 99576253 | CC1=C(C(=O)OC(C1)C(C)(C2(CCC3(C2(CCC4C3CC5C6(C4(C(=O)C=CC6)C)O5)C)O)O)O)C |
| 99576252 | CC1=C(C(=O)OC(C1)C(C)(C2(CCC3(C2(CCC4C3CC5C6(C4(C(=O)C=CC6)C)O5)C)O)O)O)C |
| 89092195 | CC1=C(C(=O)OC(C1)C(C)C2CCC3C2(CCCC4C5C3CC6C7(C45C(=O)C=CC7OC(=O)C)O6)C)CO |
| 89092046 | CCCC1(C(CCC1C(C)C2CC(=C(=O)O2)COS(=O)(=O)C)C3CC4C5(C6(C4C(=O)C5(C3)CC)O)C |
| 88949016 | CC1=C(C(=O)OC(C1)C(C)C2CCC3C2(CCC4C3CC5C6(C4C(=O)CCC6O)O5)C)C |
| 88949015 | CCOOCC12C3CCC4(C(C3CC5C1(O5)C(C=CC2=O)OC(=O)C)CCC4C(C)C6CC(=C(C(=O)O6)C)C)C |
| 88858709 | CC1=C(C(=O)OC(C1)C(C)C2CCC3C2(CCC4C3CC5C6(C4(C(=O)CCC6OCO)O5)C)CO |
| 88507988 | CC1CC2C3CCC4=CC(=O)C=C4(C35C(O5)C2C1=C(C(CC(=O)O)O)O)C |
| 88507909 | CC1CC2C3CCC4=CC(=O)CCC4(C35C(O5)CC2(C1=C(C(CC(=O)O)O)O)C |
| 85842937 | CC(C)CCCC(C)C1CCC2C1(CCC3C2CCCC4(C3(C(=O)C=CC4OC(=O)C)C)O)C |
| 85252359 | CC1=C(C(=O)OC(C1)C(=C2C(=O)CC3C2(CCC4C3C5C(O5)C6(C4(C(=O)C=CC6)C)C)C)C)C |
| 85172857 | CC1=C(C(=O)OC(C1)C(C)C2CCC3C2(C=O)CC4C3CC5C6(C4(C(=O)C=CC6)C)O5)C)C |
| 76787560 | CCC1=C(CC(OC1=O)C(C)C2CCC3C2(CCC4C3CC5C6(C4(C(=O)C=CC6OS(=O)=O)C)O)O5)C)C |
| 76023361 | CC1C(=O)OC(CC1(C)O)C(C)(C2C(CC3C2(CCC4C3CC5C6(C4(C(=O)C=CC6O)C)O5)C)O)O |
| 74323736 | CC1=C(C(=O)OC(C1)C(C)C2(CCC3C2(C(CC4C3CC5C(O5)C6(C4(C(=O)C=CC6)C)O)O)C)C)C |
| 74034727 | CC1=C(C(=O)OC(C1)C(C)C2CCC3C2(C5=CC=CC(=O)C45C)O)C |
| 73823419 | CC1=C(C(=O)OC(C1)C(C)(C2(CC=C3C2(CCC4C3CC(C5(C4(C(=O)C=CC5)C)O)O)C)O)O)C |
| 73800765 | CC1=C(CC(OC1=O)C(C)(C2CCC3(C2(CCC4C3CC5C6(C4(C(=O)C=CC6)C)O5)C)O)O)O)CO |
| 58443798 | CCC1=C(CC(OC1=O)C(C)C2CCC3C2(CCC4C3CC5C6(C4(C(=O)C=CC6OS(=O)=O)C)O5)C)C |
| 53360900 | CC1C(=O)OC(CC1(C)O)C(C)(C2C(CC3C2(CCC4C3CC5C6(C4(C(=O)C=CC6O)C)O)C)O)O |
| 49827071 | CC1=C(C(=O)OC(C1)C(COC(=O)C)C2CCC3C2(CCC4C3CC5C6(C4(C(=O)C=CC6)C)O5)C)COC(=O)C |
| 24814038 | CC1=C(C(=O)OC(C1)C(C)C2(CCC3C2(C(CC4C3CC5C(O5)C6(C4(C(=O)C=CC6)C)O)O)C)C)C |
| 23265654 | CC1=C(C(=O)OC(C1)C(C)(C2(CCC3(C2(CCC4C3CC5C6(C4(C(=O)C=CC6O)C)O5)C)O)O)O)C |
| 23253886 | CC1=C(C(=O)OC(C1)C(C)(C2CCC3C2(CCC4C3CC(C5=CC=CC(=O)C45C)O)O)C |
| 21679037 | CC1=C(C(=O)OC(C1)C(C)(C2(CC=C3C2(CCC4C3CC(C5(C4(C(=O)C=CC5)C)O)O)C)O)O)C |
| 21607725 | CC1=C(CC(OC1=O)C(C)(C2(CCC3(C2(CCC4C3CC5C6(C4(C(=O)C=CC6)C)O5)C)O)O)O)CO |
| 21595082 | CC1=C(C(=O)OC(C1)C(C)C2CC(C3(C2(CCC4C3CC5C6(C4(C(=O)C=CC6)C)O5)C)O)OC(=O)C)C |
| 10742847 | CC1=C(C(=O)OC(C1)C(=C2C(=O)CC3C2(CCC4C3CC5C(O5)C6(C4(C(=O)C=CC6)C)C)C)C)C |
| 10528283 | CC1=C(C(=O)OC(C1)C(C)C2CCC3C2(C(=O)CC4C3CC5C6(C4(C(=O)C=CC6)C)O5)C)C |
| 10141855 | CC1=C(C(=O)OC(C1)C(C)(C2(CC=C3C2(CCC4C3CC(C5(C4(C(=O)C=CC5O)C)O)O)C)O)O)C |
| 3836120 | CC1=C(C(=O)OC(C1)C(C)(C2(CCC3C2(CCC4C3CC5C6(C4(C(=O)C=CC6O)C)O5)C)O)O)C |
| 592382 | CC1=C(C(=O)OC(C1)C(C)(C2(CCC3C2(CCC4C3C(C5C6(C4(C(=O)C=CC6)C)O5)O)C)O)O)C |
| 496243 | CC1=C(C(=O)OC(C1)C(COC(=O)C)C2CCC3C2(CCC4C3CC5C6(C4(C(=O)C=CC6)C)O5)C)COC(=O)C |
| 435365 | CC1=C(C(=O)OC(C1)C(C)C2CC(C3(C2(CCC4C3CC5C6(C4(C(=O)C=CC6)C)O5)C)O)OC(=O)C)C |
| 435219 | CC1=C(C(=O)OC(C1)C(C)(C2(CC=C3C2(CCC4C3CC(C5(C4(C(=O)C=CC5O)C)O)O)C)O)O)C |
| 388300 | CC1=C(C(=O)OC(C1)C(COC(=O)C)C2CCC3C2(CCC4C3CC5C6(C4(C(=O)C=CC6)C)O5)C)COC(=O)C |
| 263436 | CC1=C(C(=O)OC(C1)C(C)C2CCC3C2(CCC4C3CC5C6(C4(C(=O)CCC6O)C)O5)C)C |
| 73621 | CC1=C(C(=O)OC(C1)C(C)(C2(CCC3(C2(CCC4C3CC5C6(C4(C(=O)C=CC6)C)O5)C)O)O)O)C |
| 102471217 | CC1=C(C(=O)OC(C1)C(C)(C2(CC(C3(C2(CCC4C3CC5C6(C4(C(=O)C=CC6)C)O5)C)O)O)O)O)C |
| 102066413 | CC1=C(C(=O)OC(C1)C(C)C2CCC3C2(CCC4C3(C5C(O5)C6(C4(C(=O)C=CC6)C)O)C)C)C |
| 101942518 | CC1=C(C(=O)OC(C1)C(C)C2(CCC3C2(CCC4C3CC5C(O5)C6(C4(C(=O)C=CC6)C)O)C)C)C |
| 101713202 | CC1=C(C(=O)OC(C1)C(C)C2(C(CC3C2(CCC4C3CC5C(O5)C6(C4(C(=O)C=CC6)C)O)C)O)C)C |

TABLE 2-continued

LIST OF WITHAFERIN A ANALOGS AND DERIVATIVES BASED ON SIMILARITY

| | |
|---|---|
| 101403752 | CC1C(=CC(OC1=O)C(C)(C2CCC3(C2(CCC4C3CC(C5(C4(C(=O)C=CC5)C)O)O)CO)C)O)C |
| 101130899 | CC12CCC3C(C1CCC2C(C)(C4CC(C(C(=O)O4)(C)O)(C)O)O)CC5C6(C3(C(=O)C=CC6O)C)O5 |
| 101005225 | CC1=C(C(=O)OC(C1)C)(C2CC(C3C2(CCC4C3CC5C6(C4(C(=O)C=CC6O)C)O5)OC(=O)C)C)OC(=O)C)O)C |
| 99576247 | CC1=C(C(=O)OC(C1)C)(C)(C2(CCC3(C2(CCC4C3CC5C6(C4(C(=O)C=CC6)C)O5)C)O)O)O)C |
| 99576246 | CC1=C(C(=O)OC(C1)C)(C)(C2(CCC3(C2(CCC4C3CC5C6(C4(C(=O)C=CC6)C)O5)C)O)O)O)C |
| 99576245 | CC1=C(C(=O)OC(C1)C)(C)(C2(CCC3(C2(CCC4C3CC5C6(C4(C(=O)C=CC6)C)O5)C)O)O)O)C |
| 99576244 | CC1=C(C(=O)OC(C1)C)(C)(C2(CCC3(C2(CCC4C3CC5C6(C4(C(=O)C=CC6)C)O5)C)O)O)O)C |
| 99575095 | CC1=C(C(=O)OC(C1)C)(C)C2C(CC3C2(CCC4C3C5C(O5)C6(C4(C(=O)C=CC6)C)O)C)O)C |
| 99575094 | CC1=C(C(=O)OC(C1)C)(C)C2C(CC3C2(CCC4C3C5C(O5)C6(C4(C(=O)C=CC6)C)O)C)O)C |
| 99575093 | CC1=C(C(=O)OC(C1)C)(C)C2C(CC3C2(CCC4C3C5C(O5)C6(C4(C(=O)C=CC6)C)O)C)O5 |
| 99575092 | CC1=C(C(=O)OC(C1)C)(C)C2C(CC3C2(CCC4C3C5C(O5)C6(C4(C(=O)C=CC6)C)O)C)O)C |
| 99571105 | CC1=C(C(=O)OC(C1)C)(C)C2CCC3C2(CCC4C3CC(C5=CC=CC(=O)C45C)O)C)CO |
| 99571104 | CC1=C(C(=O)OC(C1)C)(C)C2CCC3C2(CCC4C3CC(C5=CC=CC(=O)C45C)O)C)CO |
| 99571103 | CC1=C(C(=O)OC(C1)C)(C)C2CCC3C2(CCC4C3CC(C5=CC=CC(=O)C45C)O)C)CO |
| 99571102 | CC1=C(C(=O)OC(C1)C)(C)C2CCC3C2(CCC4C3CC(C5=CC=CC(=O)C45C)O)C)CO |
| 99567961 | CC1=C(C(=O)OC(C1)C)(C)C2C(CC3C2(CCC4C3C5C(O5)C6(C4(C(=O)C=CC6)C)O)C)O)C |
| 99567960 | CC1=C(C(=O)OC(C1)C)(C)C2C(CC3C2(CCC4C3C5C(O5)C6(C4(C(=O)C=CC6)C)O)C)O)C |
| 99567959 | CC1=C(C(=O)OC(C1)C)(C)C2C(CC3C2(CCC4C3C5C(O5)C6(C4(C(=O)C=CC6)C)O)C)O)C |
| 99567958 | CC1=C(C(=O)OC(C1)C)(C)C2C(CC3C2(CCC4C3C5C(O5)C6(C4(C(=O)C=CC6)C)O)C)O)C |
| 91809632 | CC1=C(C(=O)OC(C1)C)(C)C2CCC3C2(C(=O)CC4C3C5C(O5)C6(C4(C(=O)C=CC6)C)O)C)C |
| 91535074 | CCC1=C(CC(OC1=O)C(C)(C2CCC3C2(CCC45C3COC6(C4C5C)C(=O)C=CC6O)C)C)C |
| 90670443 | CC1=C(C(=O)OC(C1)C)(C)C2CCC3C2(CCC4C3CC5C6(C4(C(=O)C=CC6OS(=O)(=O)O)C)O5)C)COS(=O)(=O)O |
| 89255534 | CC1CC(OC(=O)C1)C(C)(C2CCC3C2(CCC4C3CC5C6(C4(C(=O)C=CC6)C)O5)C)O |
| 89245302 | CC1CC(OC(=O)C1)C(C)(C2CCC3C2(CCC4C3CC5C6(C4(C(=O)C=CC6)C)O5)C)O |
| 88858705 | CC1=C(C(=O)OC(C1)C)(C)C2CCC3C2(CCC4C3CC5C6(C4(C(=O)CCC6O)CO)O5)C)C |
| 85244687 | CC1=C(C(=O)OC(C1)C=C2(CC3C2(CCC4C3C5C(O5)C6(C4(C(=O)C=CC6)C)O)C)OC(=O)C)C)C |
| 85191725 | CC1=C(C2(C(=O)C=C3CCC4C3(C2(CC5C6C(C(=O)C=CC7)C)O6)O)C)CO)OC1=O)C |
| 85182572 | CC1=C(C(=O)OC(C1)C)(C)C2(C(CC3C2(CCC4C3C5C(O5)C6(C4(C(=O)C=CC6)C)O)C)O)C |
| 78200674 | CC1=C(C(=O)OC(C1)C)(C)(C2C(CC3C2(CCC4C3C(C5C6(C4(C(=O)C=CC6O)C)O5)OC(=O)C)C)OC(=O)C)O)C |
| 78019496 | CC1CC2C3CCC(C3(CCC2C4(C1(C(C=CC4=O)O)C)C)C)C(C)C5CC(=C(C(=O)O5)CO)C |
| 77846436 | CC1=C(C(=O)OC(C1)C)(C)C2CCC3C2(CCC4C3C5C(O5)C6(C4(C(=O)C=CC6)C)O)O)C |
| 75093297 | CC1=C(C(=O)OC(C1)C)(C)C2CCC3C2(CCC4C3CC5C6(C4(C(=O)C=CC6OS(=O)(=O)O)C)O5)C)COS(=O)(=O)O |
| 75072260 | CC1=C(C(=O)OC(C1)C)(C)C2CCC3C2(CCC4C3C(C5C6(C4(C(=O)C=CC6OC(=O)C)C)O5)OC(=O)C)C)O)C |
| 74110113 | CC1=C(C(=O)OC(C1)C)(C)C2CC(C3C2(C(CC4C3C5C(O5)C6(C4(C(=O)C=CC6)C)O)O)C)O)C |
| 74039536 | CC1=C(C(=O)OC(C1)C)(C)(C2(CCC3=C4CCC5(C(C=CC(=O)C5(C4CCC32C)C)O)O)O)O)C |
| 74034725 | CC1=C(C(=O)OC(C1)C)(C)C2CCC3C2(CCC4C3CC(C5=CC=CC(=O)C45C)O)COC(=O)C |
| 73823416 | CC1=C(C(=O)OC(C1)C)(C)(C2(CCC3(C2(CCC4C3CC5C6(C4(C(=O)C=CC6OC(=O)C)C)O5)C)O)O)O)C |
| 73823410 | CC1=C(C(=O)OC(C1)C)(C)(C2CCC3(C2(CCC4C3CC5C6(C4(C(=O)C=CC6OC(=O)C)C)O5)C)O)O)C |
| 73802223 | CC(C)C(C)CCC(C)C1CCC2C1(CC(C3C2CC(C45C3(C(=O)C=CC4O5)C)O)O)C |
| 73802222 | CC(C)C(C)C=CC(C)C1CCC2C1(CC(C3C2CC(C45C3(C(=O)C=CC4O5)C)O)O)C |
| 73800707 | CC1=C(C(=O)OC(C1)C)(C)C2CCC3C2(C(CC4C3C5C(O5)C6(C4(C(=O)C=CC6)C)O)OC(=O)C)C)COC(=O)C |
| 73800270 | CC1=C(C(=O)OC(C1)C)C2(C3CCC4C3(CCC5C4CC6C7(C5(C(=O)C=CC7O)C)O6)C(O2)O)C)C |
| 73353768 | CC1=C(C(=O)OC(C1)C)(C)(C2CCC3C2(CCC4C3(C5C(O5)C6(C4(C(=O)C=CC6)C)O)O)O)O)C |
| 73324216 | CC1=C(C(=O)OC(C1)C)(C)(C2(CC(C3(C2(CCC4C3CC5C6(C4(C(=O)C=CC6)C)O5)C)O)O)O)O)C |
| 73211836 | CC1=C(C(=O)OC(C1)C)(C)C2CCC3C2(CCC4C3CC5C6(C4(C(=O)C=CC6)COC(=O)C)O5)C)COC(=O)C |
| 73123619 | CC1=C(C(=O)OC(C1)C)(C)(C2(CCC3C2(CCC4C3CC(C5(C4(C(=O)C=CC5)C)O)O)CO)C)O)C |
| 73100450 | CC1=C(C(=O)OC(C1)C)(C)C2(CCC3C2(CCC4C3CC5C6(C4(C(=O)CCC6O)C)O5)C)O)CO |
| 73077149 | CC1C(=O)OC(CC1(C)O)C(C)(C2CCC3C2(CCC4C3CC5C6(C4(C(=O)C=CC6O)C)O5)C)O)O |
| 72544433 | CC1=C(C(=O)OC(C1)C)(C)C2CCC3C2(CCC4C3CC5C6(C4(C(=O)C=CC6OC(=O)N(C)C)CO)O5)C)CO |
| 71167047 | CC1CC2C3CCC(C3(CCC2C4(C1(C(C=CC4=O)O)C)C)C)C(C)C5CC(=C(C(=O)O5)CO)C |
| 52931499 | CC1=C(C(=O)OC(C1)C)(C)C2CC(C3C2(C(CC4C3C5C(O5)C6(C4(C(=O)C=CC6)C)O)O)C)O)C |
| 50909326 | CC1=C(C(=O)OC(C1)C)(C)C2CCC3C2(C(=O)CC4C3C5C(O5)C6(C4(C(=O)C=CC6)C)O)C)C |
| 45359706 | CC1=C(C(=O)OC(C1)C)(C)C2C(CC3C2(CCC4C3C5C(O5)C6(C4(C(=O)C=CC6)C)O)C)O)C |
| 45111620 | CC1=C(C(=O)OC(C1)C)(C)C2CCC3C2(CCC4C3CC5C6(C4(C(=O)C=CC6OS(=O)(=O)O)C)O5)C)COS(=O)(=O)O |
| 44567004 | CC1=C(C(=O)OC(C1)C)(C)(C2CCC3C2(CCC4C3C(C5C6(C4(C(=O)C=CC6OC(=O)C)C)O5)OC(=O)C)C)O)C |
| 44566968 | CC1=C(C(=O)OC(C1)C2(C3CCC4C3(CCC5C4CC6C7(C5(C(=O)C=CC7O)C)O6)C(O2)O)C)C |
| 42610658 | CC1=C(C(=O)OC(C1)C)(C)C2=CC(C3(C2(CCC4C3CC5C6(C4(C(=O)C=CC6)C)O5)C)O)OC(=O)C)C |
| 23727871 | CC1=C(C(=O)OC(C1)C)(C)C2CC(C3C2(C(CC4C3C5C(O5)C6(C4(C(=O)C=CC6)C)O)O)C)O)C |
| 23267120 | CC1=C(C(=O)OC(C1)C)(C)(C2(CCC3=C4CCC5(C(C=CC(=O)C5(C4CCC32C)C)O)O)O)O)C |
| 23265672 | CC1=C(C(=O)OC(C1)C)(C)(C2(CCC3C2(CCC4C3CC5C6(C4(C(=O)C=CC6OC(=O)C)C)O5)C)O)O)C |
| 23253884 | CC1=C(C(=O)OC(C1)C)(C)C2CCC3C2(CCC4C3CC(C5=CC=CC(=O)C45C)O)COC(=O)C |
| 21679035 | CC1=C(C(=O)OC(C1)C)(C)(C2(CCC3C2(CCC4C3C5C(O5)C6(C4(C(=O)C=CC6)C)O)C)O)O)C |
| 21679033 | CC1=C(C(=O)OC(C1)C)(C)(C2(CCC3C2(CCC4C3CC5C6(C4(C(=O)C=CC6OC(=O)C)C)O5)C)O)O)C |
| 21679027 | CC1=C(C(=O)OC(C1)C)(C)(C2(CCC3C2(CCC4C3C5C(O5)C6(C4(C(=O)C=CC6)C)O)C)O)O)C |
| 21679024 | CC1=C(C(=O)OC(C1)C)(C)(C2(CCC3C2(CCC4C3CC5C6(C4(C(=O)C=CC6)C)O5)C)O)O)C |
| 21679018 | CC1=C(C(=O)OC(C1)C)(C)(C2CCC3(C2(CCC4C3CC5C6(C4(C(=O)C=CC6OC(=O)C)C)O5)C)O)O)C |
| 21607603 | CC1=C(C(=O)OC(C1)C)(C)C2CCC3C2(C(CC4C3C5C(O5)C6(C4(C(=O)C=CC6)C)O)OC(=O)C)C)COC(=O)C |
| 21606679 | CC1=C(C(=O)OC(C1)C)C2(C3CCC4C3(CCC5C4CC6C7(C5(C(=O)C=CC7O)C)O6)C(O2)O)C)C |
| 21606678 | CC1=C(C(=O)OC(C1)C)C2(C3CCC4C3(CCC5C4CC6C7(C5(C(=O)C=CC7O)C)O6)C(O2)O)C)C |
| 21575410 | CC(C)C(C)CCC(C)C1CCC2C1(CC(C3C2CC(C45C3(C(=O)C=CC4O5)C)O)O)C |
| 21575409 | CC(C)C(C)C=CC(C)C1CCC2C1(CC(C3C2CC(C45C3(C(=O)C=CC4O5)C)O)O)C |
| 16757497 | CC1=C(C(=O)OC(C1)C)(C)(C2(CC(C3(C2(CCC4C3CC5C6(C4(C(=O)C=CC6)C)O5)C)O)O)O)O)C |
| 14779030 | CC1=C(C(=O)OC(C1)C)(C)C2=CC(C3(C2(CCC4C3CC5C6(C4(C(=O)C=CC6)C)O5)C)O)OC(=O)C)C |
| 14605180 | CC1=C(C(=O)OC(C1)C)(C)(C2(CCC3C2(CCC4C3C5C(O5)C6(C4(C(=O)C=CC6)C)O)C)O)O)C |
| 12444955 | CC1=C(C(=O)OC(C1)C)(C)C2CCC3C2(C(=O)CC4C3C5C(O5)C6(C4(C(=O)C=CC6)C)O)C)C |
| 12444953 | CC1=C(C(=O)OC(C1)C)(C)C2CCC3C2(C(=O)CC4C3C5C(O5)C6(C4(C(=O)C=CC6)C)O)C)C |
| 12304664 | CC1=C(C(=O)OC(C1)C)(C)(C2(CCC3C2(C(CC4C3CC(C5(C4(C(=O)C=CC5)C)O)O)O)C)O)CO |
| 12070589 | CC1C(=O)OC(CC1(C)O)C(C)(C2(CCC3C2(CCC4C3CC5C6(C4(C(=O)C=CC6O)C)O5)C)O)O |

TABLE 2-continued

LIST OF WITHAFERIN A ANALOGS AND DERIVATIVES BASED ON SIMILARITY

| | |
|---|---|
| 11844625 | CC1=C(C(=O)OC(C1)C(C)(C2CCC3C2(CCC4C3CC(C5(C4(C(=O)C=CC5)C)O)O)CO)O)C |
| 11785089 | CC1=C(C(=O)OC(C1)C(C)C2(CCC3C2(CCC4C3CC5C6(C4(C(=O)CCC6O)C)O5)C)O)CO |
| 11730849 | CC1C(=O)OC(CC1(C)O)C(C)(C2(CCC3C2(CCC4C3CC5C6(C4(C(=O)C=CC6O)C)O5)C)O)O |
| 11408805 | CC1=C(C(=O)OC(C1)C(C)C2(CCC3C2(CCC4C3C5C(O5)C6(C4(C(=O)C=CC6)C)O)C)O)C |
| 10791040 | CC1=C(C(=O)OC(C1)C2(C3CCC4C3(CCC5C4CC6C7(C5(C(=O)C=CC7O)C)O6)C(O2)O)C)C |
| 10720495 | CC1=C(C(=O)OC(C1)C(=C2C(CC3C2(CCC5C(O5)C6(C4(C(=O)C=CC6)C)O)C)OC(=O)C)C |
| 10576702 | CC1=C(C2(C(=O)C(=C3CCC4C3(C2(CC5C4CC6C7(C5(C(=O)C=CC7)C)O6)O)C)CO)OC1=O)C |
| 10552958 | CC1=C(C(=O)OC(C1)C(C)C2(C(CC3C2(CCC4C3C5C(O5)C6(C4(C(=O)C=CC6)C)C)O)O)C |
| 10413803 | CC1C(=O)OC(CC1(C)O)C(C)(C2(CCC3C2(CCC4C3CC5C6(C4(C(=O)C=CC6O)C)O5)C)O)O |
| 10413139 | CC1=C(C(=O)OC(C1)C(C)(C2(CCC3C2(CCC4C3CC5C6(C4(C(=O)C=CC6)C)O5)C)O)O)C |
| 10301870 | CC1=C(C(=O)OC(C1)C(C)C2=CC(C3(C2(CCC4C3CC5C6(C4(C(=O)C=CC6O)C)O5)C)O)OC(=O)C |
| 9806892 | CC1=C(C(=O)OC(C1)C(C)C2=CC(C3(C2(CCC4C3CC5C6(C4(C(=O)C=CC6O)C)O5)C)O)OC(=O)C |
| 5315322 | CC1=C(C(=O)OC(C1)C(C)C2CCC3C2(C(=O)CC4C3C5C(O5)C6(C4(C(=O)C=CC6)C)O)C |
| 3935211 | CC1=C(C(=O)OC(C1)C(C)C2CCC3C2(CCC4C3CC(C5=CC=CC(=O)C45C)O)C)CO |
| 3372729 | CC1=C(C(=O)OC(C1)C(C)(C2(CCC3C2(CCC4C3CC5C6(C4(C(=O)C=CC6)C)O5)C)O)O)C |
| 3084736 | CC1=C(C(=O)OC(C1)C(C)C2CCC3C2(C(=O)CC4C3C5C(O5)C6(C4(C(=O)C=CC6)C)O)C |
| 3034071 | CC1=C(C(=O)OC(C1)C(C)(C2(CCC3C2(CCC4C3CC5C6(C4(C(=O)C=CC6)C)O5)C)O)O)C |
| 636567 | CC1=C(C(=O)OC(C1)C(C)(C2C(CC3C2(CCC4C3C(C5C6(C4(C(=O)C=CC6O)C)O5)OC(=O)C)C)OC(=O)C)O)C |
| 301757 | CC1=C(C(=O)OC(C1)C(C)C2(CCC3C2(CCC4C3C5C(O5)C6(C4(C(=O)C=CC6)C)O)C)O)C |
| 301751 | CC1=C(C(=O)OC(C1)C(C)(C2(CCC3C2(CCC4C3CC5C6(C4(C(=O)C=CC6)C)O5)C)O)O)C |
| 268946 | CC1=C(C(=O)OC(C1)C(C)C2CCC3C2(CCC4C3CC(C5=CC=CC(=O)C45C)O)C)CO |
| 147647 | CC1=C(C(=O)OC(C1)C(C)C2=CC(C3(C2(CCC4C3CC5C6(C4(C(=O)C=CC6O)C)O5)C)O)OC(=O)C)C |
| 265237 | CC1=C(C(=O)OC(C1)C(C)C2CCC3C2(CCC4C3CC5C6(C4(C(=O)C=CC6O)C)O5)C)CO |
| 9825988 | CC1=C(C(=O)OC(C1)C(C)C2CCC3C2(CCC4C3CC5C6(C4(C(=O)C=CC6O)C)O5)C)CO |
| 15411208 | CC1=C(C(=O)OC(C1)C(C)C2CCC3C2(CCC4C3CC5C6(C4(C(=O)CCC6O)C)O5)C)CO |
| 11070744 | CC1=C(C(=O)OC(C1)C(C)C2CCC3C2(CCC4C3CC5C6(C4(C(=O)CCC6O)C)O5)C)CO |
| 50907377 | CC1=C(C(=O)OC(C1)C(C)C2CC3C4(C2(CCC5C4CC6C7(C5(C(=O)C=CC7O)C)O6)C)O3)CO |
| 10141001 | CC1=C(C(=O)OC(C1)C(C)C2CCC3C2(C(CC4C3CC5C6(C4(C(=O)C=CC6O)C)O5)O)C)CO |
| 10161347 | CC1=C(C(=O)OC(C1)C(C)C2CCC3C2(CCC4C3CC5C6(C4(C(=O)C=CC6O)C)O5)C)C |
| 165541 | CC1=C(C(=O)OC(C1)C(C)C2CCC3C2(CCC4C3CC5C6(C4(C(=O)C=CC6=O)C)O5)C)CO |
| 50990201 | CC1=C(C(=O)OC(C1)C(C)C2CCC3C2(CCC4C3CC5C6(C4(C(=O)C=CC6O)C)O5)C)CO |
| 11785089 | CC1=C(C(=O)OC(C1)C(C)C2(CCC3C2(CCC4C3CC5C6(C4(C(=O)CCC6O)C)O5)C)O)CO |
| 23266163 | CC1=C(C(=O)OC(C1)C(C)(C2CCC3C2(CCC4C3CC5C6(C4(C(=O)C=CC6O)C)O5)C)O)CO |
| 11408847 | CC1CC(OC(=O)C1CO)C(C)C2CCC3C2(CCC4C3CC5C6(C4(C(=O)C=CC6O)C)O5)C |
| 5315320 | CC1=C(C(=O)OC(C1)C(C)C2CCC3C2(CCC4C3CC5C6(C4(C(=O)C=CC6O)C)O5)C)CO |
| 176114 | CC1=C(C(=O)OC(C1)C(C)C2CCC3C2(CCC4C3CC5C6(C4(C(=O)C=CC6O)C)O5)C)C=O |
| 56926114 | CC1=C(C(=O)OC(C1)C(C)C2CCC3C2(CC(C4C3CC5C6(C4(C(=O)C=CC6O)C)O5)O)C)CO |
| 88948989 | CC1=C(C(=O)OC(C1)C(C)C2CCC3C2(CCC4C3CC5C6(C4C(=O)CCC6O)O5)C)CO |
| 71772576 | CC1=C(C(=O)OC(C1)C(C)C2CCC3C2(CCC4C3CC5C6(C4(C(=O)C=CC6O)C)O5)C)CO |
| 11798584 | CC1=C(C(=O)OC(C1)C(C)C2CCC3C2(CCC4C3CC5C6(C4(C(=O)C=CC6O)C)O5)C)C |
| 11145377 | CC1=C(C(=O)OC(C1)C(C)C2CCC3C2(CCC4C3CC5C6(C4(C(=O)CC(C6O)O)C)O5)C)CO |
| 5458778 | CC1=C(C(=O)OC(C1)C(C)C2CCC3C2(CCC4C3CC5C6(C4(C(=O)C=C(C6O)N7CC7)C)O5)C)CO |
| 5287384 | CC1=C(C(=O)OC(C1)C(C)C2CCC3C2(CCC4C3CC5C6(C4(C(=O)C=CC6O)C)O5)C)CO |
| 90670439 | CC1=C(C(=O)OC(C1)C(C)C2CCC3C2(CCC4C3CC=C5C4(C(=O)C=CC5O)C)O)CO |
| 45489105 | CC1=C(C(=O)OC(C1)C(C)C2CCC3C2(CCC4C3CC=C5C6(C4(C(=O)C=CC6O)C)O5)C)CO |
| 46939432 | CC1=C(C(=O)OC(C1)C(=C2C(CC3C2(CCC4C3CC=C5C4(C(=O)C=CC5O)C)O)C)C)CO |
| 23266155 | CC1=C(C(=O)OC(C1)C(C)C2CCC3C2(CCC4C3CC5C6(C4(C(=O)C=CC6O)C)O5)C)C |
| 16760705 | CC1=C(C(=O)OC(C1)C(C)C2CCC3C2(CCC4C3CC5C6(C4(C(=O)C=CC6O)C)O5)C)CO |
| 16745397 | CC1=C(C(=O)OC(C1)C(C)C2CCC3C2(CCC4C3CC5C6(C4(C(=O)C=CC6O)C)O5)C)CO |
| 10648050 | CC1=C(C(=O)OC(C1)C(C)C2CCC3C2(CCC4C3CC5C6(C4(C(=O)C=CC6CO)O5)C)CO |
| 88858700 | CC1=C(C(=O)OC(C1)C(C)C2CCC3C2(CCC4C3CC5C6(C4(C(=O)C=CC6CO)O5)C)CO |
| 70690365 | CC1=C(C(=O)OC(C1)C(C)C2CC=C3C2(CCC4C3CC5C6(C4(C(=O)C=CC6O)C)O5)C)C |
| 23266158 | CC1=C(C(=O)OC(C1)C(C)C2CCC3(C2(CCC4C3CC5C6(C4(C(=O)C=CC6O)C)O5)C)O)C |
| 66572429 | CC1=C(C(=O)OC(C1)C(=C2C(CC3C2(CCC4C3CC5C6(C4(C(=O)C=CC6O)C)O5)C)O)C)CO |
| 90670452 | CC1=C(C(=O)OC(C1)C(C)C2CC(C3C2(CCC4C3CC5C6(C4(C(=O)C=CC6O)C)O5)C)O)CO |
| 53477765 | CC1=C(C(=O)OC(C1)C(C)(C2CCC3C2(CCC4C3CC5C6(C4(C(=O)C=CC6O)C)O5)C)O)C |
| 11134251 | CC1CC(OC(=O)C1C)C(C)C2CCC3C2(CCC4C3CC5C6(C4(C(=O)C=CC6O)C)O5)C |
| 10814731 | CC1=C(C(=O)OC(C1)C(C)C2C(CC3C2(CCC4C3CC5C6(C4(C(=O)C=CC6O)C)O5)C=O)O)C |
| 10028564 | CC1=C(C(=O)OC(C1)C(C)C2CCC3C2(CCC4C3CC(C5(C4(C(=O)C=CC5)C)Cl)O)C)CO |
| 56649372 | CC1=C(C(=O)OC(C1)C(C)C2CCC3C2(CC(C4C3CC5C6(C4(C(=O)C=CC6O)CO)O5)O)C)CO |
| 21670295 | CC1=C(C(=O)OC(C1)C(C)C2C(CC3C2(CCC4C3CC5C6(C4(C(=O)C=CC6O)C)O5)C=O)O)C |
| 10814230 | CC1=C(C(=O)OC(C1)C(C)C2C(CC3C2(CCC4C3CC5C6(C4(C(=O)C=CC6O)C)O5)C)O)C |
| 5287385 | CC1=C(C(=O)OC(C1)C(C)(C2CCC3C2(CCC4C3CC5C6(C4(C(=O)C=CC6O)C)O5)C)O)C |
| 161671 | CC1=C(C(=O)OC(C1)C(C)(C2CCC3C2(CCC4C3CC5C6(C4(C(=O)C=CC6O)C)O5)C)O)C |
| 91799372 | CC1=C(C(=O)OC(C1)C(C)C2CCC3C2(CCC4C3CC5C6(C4(C(=O)C=CC6O)C)O5)C)CO |
| 90670450 | CC1=C(C(=O)OC(C1)C(C)C2CCC3C2(CCC4C3CC5C6(C4(C(=O)C=CC6O)C)O5)C)CO |
| 23266167 | CC1CC(OC(=O)C1C)C(C)(C2CCC3C2(CCC4C3CC5C6(C4(C(=O)C=CC6O)C)O5)C)O |
| 56649343 | CC1=C(C(=O)OC(C1)C(C)C2CCC3C2(CCC4C3CC5C6(C4(C(=O)C=CC6CO)O5)C)CO |
| 44566999 | CC1=C(C(=O)OC(C1)C(C)C2C(CC3C2(CCC4C3CC5C6(C4(C(=O)C=CC6O)C)O5)C)O)C |
| 10277878 | CC1=C(C(=O)OC(C1)C(C)C2CCC3(C2(CCC4C3CC5C6(C4(C(=O)C=CC6O)C)O5)CO)O)C |
| 88949016 | CC1=C(C(=O)OC(C1)C(C)C2CCC3C2(CCC4C3CC5C6(C4C(=O)CCC6O)O5)C)C |
| 57403080 | CC1=C(C(=O)OC(C1)C(C)C2CCC3C2(CCC4C3CC5C6(C4(C(=O)C(C6O)O)C)O5)C)CO |
| 49864510 | CC1=C(C(=O)OC(C1)C(C)C2CCC3C2(CCC4C3CC5C6(C4(C(=O)C=CC6O)C)O5)C)CO |
| 23266166 | CC1CC(OC(=O)C1C)C(C)C2CCC3C2(CCC4C3CC5C6(C4(C(=O)C=CC6O)C)O5)C |
| 90670451 | CC1=C(C(=O)OC(C1)C(C)C2CCC3C2(C(CC4C3CC5C6(C4(C(=O)C=CC6O)C)O5)O)C)CO |
| 88858703 | CCCC(=O)C2(C3C(CC4C2(C1O)O4)C5CCC(C5(CC3O)C)C(C)C6CC(=C(C(=O)O6)C)C |
| 12304656 | CC1=C(C(=O)OC(C1)C(C)C2CCC3C2(CCC4C3CC5C6(C4(C(=O)C=CC6)C)O5)C)CO |
| 12147447 | CC1=C(C(=O)OC(C1)C(C)C2(CCC3C2(CCC4C3CC5C6(C4(C(=O)C=CC6O)C)O5)C)O)CO |

TABLE 2-continued

LIST OF WITHAFERIN A ANALOGS AND DERIVATIVES BASED ON SIMILARITY

| ID | SMILES |
|---|---|
| 57519534 | CC1=C(C(=O)OC(C1)C(C)C2CCC3C2(CCC4C3CC5C6(C4(C(=O)C=CC6O)C)O5)C)CO |
| 21670293 | CC1=C(C(=O)OC(C1)C(C)C2C(CC3C2(CCC4C3CC5C6(C4(C(=O)C=CC6O)C)O5)C)O)C |
| 10005030 | CC1CC(OC(=O)C1C)C(C)(C2CCC3C2(CCC4C3CC5C6(C4(C(=O)C=CC6O)C)O5)C)O |
| 88949008 | CC1=C(C(=O)OC(C1)C(C)C2CCC3C2(CCC4C3CC5C6(C4C(=O)C=CC6O)O5)C)CO |
| 50925597 | CC1=C(C(=O)OC(C1)C(C)C2CCC3C4(C2(CCC5C4CC6C7(C5(C(=O)C=CC7O)C)O6)C)O3)CO |
| 46939433 | CC1=C(C(=O)OC(C1)C(=C2C(CC3C2(CCC4C3CC=C5C4(C(=O)C=CC5)C)C)O)C)O |
| 46872824 | CC1=C(C(=O)OC(C1)C(C)(C2CCC3C2(C(CC4C3CC5C6(C4(C(=O)C=CC6O)C)O5)O)C)O)C |
| 10095500 | CC1=C(C(=O)OC(C1)C(C)C2(CCC3C2(CCC4C3CC5C6(C4(C(=O)C=CC6)C)O5)C)O)C |
| 88949017 | CC1=C(C(=O)OC(C1)C(C)C2CCC3C2(CCC4C3CC5C6(C4C(=O)CC(C6O)O)O5)C)CO |
| 46198373 | CC(C1CCC2C1(CCC3C2CC4C5(C3(C(=O)C=CC5O)C)O4)C)C6CC7(C(O7)(C(O6)O)C)C |
| 21606687 | CC1=C(C(=O)OC(C1)C(C)(C2CCC3C2(CCC4C3CC5C6(C4(C(=O)C=CC6O)C)O5)CO)O)C |
| 16680447 | CC1=C(C(=O)OC(C1)C(C)C2(CCC3C2(CCC4C3CC5C6(C4(C(=O)C=CC6O)C)O5)C)O)C |
| 10321754 | CC1=C(C(=O)OC(C1)C(C)C2CCC3C2(CCC4C3CC5C6(C4(C(=O)C=CC6)C)O5)C)CO |
| 10163221 | CC1=C(C(=O)OC(C1)C(C)C2CC(C3C2(CCC4C3CC5C6(C4(C(=O)C=CC6O)C)O5)C)O)CO |
| 88949019 | CC1=C(C(=O)OC(C1)C(C)C2CCC3C2(CCC4C3CC5C6(C4C(=O)C=CC6O)O5)C)C |
| 88948987 | CC1=C(C(=O)OC(C1)C(C)C2CCC3C2(CCC4C3CC5C6(C4C(=O)C=CC6O)O5)C)C |
| 60148726 | CC1=C(C(=O)OC(C1)C(C)C2CCC3C2(CCC4C3CC5C6(C4(C(=O)C=CC6O)CO)O5)C)CO |
| 23266162 | CC1=C(C(=O)OC(C1)C(C)(C2CCC3(C2(CCC4C3CC5C6(C4(C(=O)C=CC6O)C)O5)C)O)O)C |
| 15519705 | CC1=C(C(=O)OC(C1)C(C)(C2CCC3C2(CCC4C3CC5C6(C4(C(=O)C=CC6O)C)O5)COC(=O)C)O)C |
| 10767272 | CC1=C(C(=O)OC(C1)C(C)(C2CCC3C2(CCC4C3CC5C6(C4(C(=O)C=CC6O)C)O5)C)O)C |
| 10228028 | CC1=C(C(=O)OC(C1)C(C)(C2CCC3C(C2(CCC4C3CC5C6(C4(C(=O)C=CC6O)C)O5)C)O)O)C |
| 88858709 | CC1=C(C(=O)OC(C1)C(C)C2CCC3C2(CCC4C3CC5C6(C4(C(=O)CCC6O)CO)O5)C)CO |
| 70686221 | CC1=C(C(=O)OC(C1)C(C)C2CCC3C2(CCC4C3CC(C5(C4(C(=O)CC5)C)C=O)O)C)CO |
| 56649344 | CC1=C(C(=O)OC(C1)C(C)C2CCC3C2(CCC4C3CC5C6(C4(C(=O)C=CC6O)CO)O5)C)C |
| 49864537 | CC1=C(C(=O)OC(C1)C(C)(C2CCC3C2(CCC4C3CC5C6(C4(C(=O)C=CC6O)C)O5)C)O)C |
| 10458125 | CC1=C(C(=O)OC(C1)C(C)(C2CCC3C2(CCC4C3CC5C6(C4(C(=O)C=CC6O)C)O5)CO)O)C |
| 66572354 | CC1=C(C(=O)OC(C1)C(C)C2CCC3C2(CCC4C3CC(C5(C4(C(=O)C=CC5)C)C=O)O)C)CO |
| 56926115 | CC1=C(C(=O)OC(C1)C(C)C2CCC3C2(CCC4C3CC5C6(C4(C(=O)CC(C6O)OC)CO)O5)C)CO |
| 46939434 | CC1=C(C(=O)OC(C1)C(=C2C(CC3C2(CCC4C3CC=C5C4(C(=O)C=CC5=O)C)C)O)C)CO |
| 23266161 | CC1=C(C(=O)OC(C1)C(C)(C2(CCC3C2(CCC4C3CC5C6(C4(C(=O)C=CC6O)C)O5)C)O)O)C |
| 21670294 | CC1=C(C(=O)OC(C1)C(C)C2CCC3C2(CCC4C3CC5C6(C4(C(=O)CC(C6O)O)C)O5)CO)C |
| 16680715 | CC1=C(C(=O)OC(C1)C(C)(C2CCC3C2(CCC4C3CC5C6(C4(C(=O)CC(C6O)OC)C)O5)C)O)C |
| 12070588 | CC1CC(OC(=O)C1C)C(C)(C2(CCC3C2(CCC4C3CC5C6(C4(C(=O)C=CC6O)C)O5)C)O)O |
| 11038269 | CC1CC(OC(=O)C1C)C(C)(C2(CCC3C2(CCC4C3CC5C6(C4(C(=O)C=CC6O)C)O5)C)O)O |
| 54606507 | CC1=C(C(=O)OC(C1)C(C)C2CCC3C2(CCC4C3CC5C6(C4(C(=O)C=CC6O)C)O5)COC(=O)C)C |
| 44567005 | CC1CC(OC(=O)C1C)C(C)(C2(CCC3C2(CCC4C3CC5C6(C4(C(=O)C=CC6O)C)O5)C)O)O |
| 10767792 | CC1=C(C(=O)OC(C1)C(C)C2CCC3C2(CCC4C3CC5C6(C4(C(=O)CC(C6O)OC)C)O5)C)CO |
| 476483 | CC1CC(OC(=O)C1C)C(C)C2CCC3C2(CCC4C3CCC5C4(CCCC5O)C)C |
| 268946 | CC1=C(C(=O)OC(C1)C(C)C2CCC3C2(CCC4C3CC(C5=CC=CC(=O)C45C)O)C)CO |
| 23266164 | CC1=C(C(=O)OC(C1)C(C)C2CCC3C2(CCC4C3CC(C5C4(C(=O)C=CC5)Cl)O)C)CO |
| 12304664 | CC1=C(C(=O)OC(C1)C(C)C2CCC3C2(C(CC4C3CC(C5(C4(C(=O)C=CC5)C)O)O)O)C)CO |
| 10528446 | CC1=C(C(=O)OC(C1)C(C)C2CCC3C2(CCC4C3CC5C6(C4(C(=O)CCC6)CO)O5)C)CO |
| 5458717 | CC1=C(C(=O)OC(C1)C(C)C2CCC3C2(CCC4C3CC5C6(C4(C(=O)C=CC6OC(=O)C)C)O5)C)COC(=O)C |
| 88948978 | CC1CC(OC(=O)C1C)C(C)C2CCC3C2(CCC4C3CC5C6(C4C(=O)CCC6O)O5)C |
| 16720560 | CC1=C(C(=O)OC(C1)C(C)C2CCC3C2(CCC4C3CC5C6(C4(C(=O)C=CC6O)C)O5)COC(=O)C)C |
| 88949005 | CC1=C(C(=O)OC(C1)C(C)C2CCC3C2(CCC4C3CC5C6(C4C(=O)C=CC6O)O5)C)CO |
| 72945677 | CC1=C(C(=O)OC(C1)C(C)C2CCC3C2(CCC4C3CC5C6(C47COC(C6O)CC7=O)O5)C)CO |
| 88858695 | CCC1=C(CC(OC1=O)C(C)C2CCC3C2(CCC4C3CC5C6(C4(C(=O)C=CC6O)C)O5)C)C |
| 21679032 | CC1=C(C(=O)OC(C1)C(C)(C2CCC3(C2(CCC4C3CC=C5C4(C(=O)C=CC5)C)C)O)O)CO |
| 14605183 | CC12CCC3C(C1CCC2C(C)(C4CC5(C(O5)(C(=O)O4)C)C)O)CC6C7(C3(C(=O)C=CC7O)C)O6 |
| 11512113 | CC1=C(CC(OC1=O)C(C)C2CCC3C2(CCC4C3CC5C6(C4(C(=O)CC(C6O)OC)C(=O)O)O5)C)CO |
| 71481106 | CC1=C(C(=O)OC(C1)C(C)C2CCC3C2(CCC4C3CC(C5C6(C4(C(=O)C=CC6O)C)O5)C)C |
| 70690364 | CC1=C(C(=O)OC(C1)C(C)C2=CCC3C2(CCC4C3CC5C6(C4(C(=O)C=CC6O)C)O5)C)CO |
| 56649416 | CC1=C(C(=O)OC(C1)C(C)C2CCC3C2(CCC4C3CC5C6(C4(C(=O)C=CC6OC(=O)C)COC(=O)C)O5)C |
| 12070589 | CC1C(=O)OC(CC1(C)O)C(C)(C2(CCC3C2(CCC4C3CC5C6(C4(C(=O)C=CC6O)C)O5)C)O)O |
| 10720368 | CC1=C(C(=O)OC(C1)C(C)C2CCC3C2(CCC4C3CC(C5C4(C(=O)CCC5O)CO)O)O)CO |
| 5315323 | CC1=C(C(=O)OC(C1)C(C)C2CCC3C2(CCC4C3CC5C6(C4(C(=O)C=CC6O)C)O5)C)C |
| 88858705 | CC1=C(C(=O)OC(C1)C(C)C2CCC3C2(CCC4C3CC5C6(C4(C(=O)CCC6O)CO)O5)C)C |
| 53495499 | CC1=C(C(=O)OC(C1)C(C)C2CCC3C2(CCC4C3CC5C6(C4(C(=O)CC(C6O)N=[N+]=[N-])C)O5)C)CO |
| 15747012 | CC1=C(C(=O)OC(C1)C(C)C2CCC3C2(CCC4C3CC(C56C4(CCC5C6)C)OC)C)C |
| 56926117 | CC1=C(C(=O)OC(C1)C(C)C2CCC3C2(CCC4C3CC=C5C4(C(=O)C=CC5)CO |
| 46198372 | CC(C1CC2(C(O2)(C(O1)O)C)C)C3C(CC4C3(CCC5C4CC6C7(C5(C(=O)C=CC7O)C)O6)C)OC(=O)C |
| 21679019 | CC1=C(C(=O)OC(C1)C(C)(C2CCC3C2(CCC4C3CC5C6(C4(C(=O)C=CC6OC(=O)C)C)O5)C)O)C |
| 16680631 | CCCCOC1CC(=O)C2(C3CCC4(C(C3CC5C2(C1O)O5)CC6C4O6)C)C7CC(=C(C(=O)O7)C)C)C |
| 88949020 | CC1=C(C(=O)OC(C1)C(C)C2CCC3C2(CCC4C3CC5C6(C4(C(=O)C=CC6O)O)O5)C |
| 53495632 | CC1=C(C(=O)OC(C1)C(C)C2CCC3C2(CCC4C3CC5C6(C4(C(=O)CC(C6O)SCC7=CC=CO7)C)O5)C)CO |
| 44631487 | CC1=C(C(=O)OC(C1)C(C)C2CCC3C2(CCC4C3CC(C5(C4(C(=O)C=CC5)C)Cl)O)C)CO |
| 15251339 | CC1CCC(OC1=O)C(C)C2CCC3C2(CCC4C3CC(C56C4(CCC5C6)C)OC)C |
| 11038270 | CC1=C(C(=O)OC(C1)C(C)C2CCC3C2(CCC4C3CC5C6(C4(C(=O)CC(C6O)O)C)O5)C)CO |
| 88949018 | CC1=C(C(=O)OC(C1)C(C)C2CCC3C2(CCC4C3CC5C6(C4(C(=O)C=CC6O)O)O5)C)CO |
| 10984509 | CC1=C(C(=O)OC(C1)C(C)C2CCC3C2(CCC4C3CC5C6(C4(C(=O)CCC6OC7C(=O)C7(C)C)C)O5)C)CO |
| 21574482 | CC1=C(C(=O)OC(C1)C(C)C2=CCC3C2(CCC4C3CC5C6(C4(C(=O)C=CC6O)C)O5)C |
| 15519706 | CC1=C(C(=O)OC(C1)C(C)(C2CCC3C2(CCC4C3CC=C5C4(C(=O)C=CC5O)C)COC(=O)C)O)C |
| 15251338 | CC(C1CCC2C1(CCC3C2CC(C45C3(CCC4C5)OC)C)C6CCCC(=O)O6 |
| 462178 | CC1=C(C(=O)OC(C1)C(C)C2CCC3C2(CCC4C3CC5C6(C4(C(=O)C=C(C6O)N7CC7)C)O5)C)CO |
| 89333022 | CC1CC(OC(=O)C1C)C(C)C2CCC3C2(CCC4C3CC5C6(C4(C(=O)C=CC6O)C)O5)C |
| 50899672 | CC(C1CCC2C1(CCC3C2CCC4=C3C=CC(=C4)O)C)C5CC=C(C(=O)O5)CO |
| 23266165 | CC1=C(C(=O)OC(C1)C(C)C2CCC3C2(CCC4C3CC(C5(C4(C(=O)C=CC5)C)O)Cl)C)CO |

TABLE 2-continued

LIST OF WITHAFERIN A ANALOGS AND DERIVATIVES BASED ON SIMILARITY

| | | |
|---|---|---|
| 16680369 | CC1=C(C(=O)OC(C1)C(C)C23C(O2)CC4C3(CCC5C4CC6C7(C5(C(=O)C=CC7O)C)O6)C)C | |
| 21628725 | CC1=C(C(=O)OC(C1)C(C)(C2CCC3C2(CCC4C3CC5C6(C4(C(=O)C=CC6NCC7=CC=CC=C7)C)O5)C)O)C | |

| Pubchem CID | InChi | IUPAC Name |
|---|---|---|
| 56928031 | InChI=1S/C27H23N3O3/c31-25-21-13-7-8-14-22(21)26(32)24(23(25)28-27(33)19-9-3-1-4-10-19)30-17-15-29(16-18-30)20-11-5-2-6-12-20/h1-14H,15-18H2,(H,28,33) | N-[1,4-dioxo-3-(4-phenylpiperazin-1-yl)naphthalen-2-yl]benzamide |
| 50904531 | InChI=1S/C25H22N4O2/c30-24(28-16-15-19-9-7-8-10-20(19)17-28)29-18-23(26-27-29)25(31,21-11-3-1-4-12-21)22-13-5-2-6-14-22/h1-14,18,31H,15-17H2 | 3,4-dihydro-1H-isoquinolin-2-yl-[4-[hydroxy(diphenyl)methyl]triazol-1-yl]methanone |
| 16293465 | InChI=1S/C25H22N4O5S/c26-35(33,34)19-10-8-16(9-11-19)12-13-27-24(31)17-4-3-5-18(14-17)28-25(32)21-15-23(30)29-22-7-2-1-6-20(21)22/h1-11,14-15H,12-13H2,(H,27,31)(H,28,32)(H,29,30)(H2,26,33,34) | 2-oxo-N-[3-[2-(4-sulfamoylphenyl)ethylcarbamoyl]phenyl]-1H-quinoline-4-carboxamide |
| 135584558 | InChI=1S/C24H23ClN6O2/c1-15-7-2-3-8-16(15)14-31-22-20(28-29-31)23(32)27-21(26-22)17-9-6-12-30(13-17)24(33)18-10-4-5-11-19(18)25/h2-5,7-8,10-11,17H,6,9,12-14H2,1H3,(H,26,27,32) | 5-[1-(2-chlorobenzoyl)piperidin-3-yl]-3-[(2-methylphenyl)methyl]-3H-[1,2,3]triazolo[4,5-d]pyrimidin-7-ol |
| 119045958 | InChI=1S/C15H19N3O2/c19-12(7-11-3-1-2-4-11)9-18-10-17-14-8-16-6-5-13(14)15(18)20/h5-6,8,10-12,19H,1-4,7,9H2 | 3-(3-cyclopentyl-2-hydroxypropyl)-3H,4H-pyrido[3,4-d]pyrimidin-4-one |
| 45918956 | InChI=1S/C13H15N3O5S/c1-8(2)21-10-5-3-9(4-6-10)16-22(19,20)11-7-14-13(18)15-12(11)17/h3-8,16H,1-2H3,(H2,14,15,17,18) | 2-hydroxy-6-oxo-N-[4-(propan-2-yloxy)phenyl]-1,6-dihydropyrimidine-5-sulfonamide |
| 47610414 | InChI=1S/C17H26N2O4/c1-18-17(21)11-23-15-8-3-12(9-16(15)22-2)10-19-13-4-6-14(20)7-5-13/h3,8-9,13-14,19-20H,4-7,10-11H2,1-2H3,(H,18,21) | 2-[4-[[(4-hydroxycyclohexyl)amino]methyl]-2-methoxyphenoxy]-N-methylacetamide |
| 40957584 | InChI=1S/C24H32N2O6S/c1-16(2)11-12-26-19-9-7-17(13-20(19)32-15-24(3,4)23(26)27)25-33(28,29)22-10-8-18(30-5)14-21(22)31-6/h7-10,13-14,16,25H,11-12,15H2,1-6H3 | N-[3,3-dimethyl-5-(3-methylbutyl)-4-oxo-2H-1,5-benzoxazepin-8-yl]-2,4-dimethoxybenzenesulfonamide |
| 45597893 | InChI=1S/C22H34N2O3S/c1-26-20-7-6-18(21(14-20)27-2)15-23-22(25)8-5-17-4-3-11-24(16-17)19-9-12-28-13-10-19/h6-7,14,17,19H,3-5,8-13,15-16H2,1-2H3,(H,23,25) | N-[(2,4-dimethoxyphenyl)methyl]-3-[1-(thian-4-yl)piperidin-3-yl]propanamide |

TABLE 2-continued

LIST OF WITHAFERIN A ANALOGS AND DERIVATIVES BASED ON SIMILARITY

| | | |
|---|---|---|
| 39336661 | InChI=1S/C14H11FN4O2/c1-21-12-6-8(15)2-3-9(12)11-4-5-17-14-10(13(16)20)7-18-19(11)14/h2-7H,1H3,(H2,16,20) | 7-(4-fluoro-2-methoxyphenyl)pyrazolo[1,5-a]pyrimidine-3-carboxamide |
| 7161251 | InChI=1S/C16H13N3O5S/c20-15-14(10-17-16(21)18-15)25(22,23)19-11-6-8-13(9-7-11)24-12-4-2-1-3-5-12/h1-10,19H,(H2,17,18,20,21) | 2-hydroxy-6-oxo-N-(4-phenoxyphenyl)-1,6-dihydropyrimidine-5-sulfonamide |
| 45194095 | InChI=1S/C24H34N2O4/c1-18-4-3-5-19(12-18)14-25-15-20-6-7-23(24(13-20)29-2)30-17-22(28)16-26-10-8-21(27)9-11-26/h3-7,12-13,21-22,25,27-28H,8-11,14-17H2,1-2H3 | 1-[2-hydroxy-3-[2-methoxy-4-[[(3-methylphenyl)methylamino]methyl]phenoxy]propyl]piperidin-4-ol |
| 53024242 | InChI=1S/C20H23N3O5/c1-12-13(2)28-19-18(12)20(25)23(11-22-19)8-7-17(24)21-10-14-5-6-15(26-3)9-16(14)27-4/h5-6,9,11H,7-8,10H2,1-4H3,(H,21,24) | N-[(2,4-dimethoxyphenyl)methyl]-3-(5,6-dimethyl-4-oxofuro[2,3-d]pyrimidin-3-yl)propanamide |
| 71702747 | InChI=1S/C17H16N4O4S/c1-9-14(16(23)25-3)18-17(26-9)19-15(22)12-8-11(20-21-12)10-6-4-5-7-13(10)24-2/h4-8H,1-3H3,(H,20,21)(H,18,19,22) | methyl (2Z)-2-{[3-(2-methoxyphenyl)-1H-pyrazole-5-carbonyl]imino}-5-methyl-2,3-dihydro-1,3-thiazole-4-carboxylate |
| 45183940 | InChI=1S/C22H29FN2O3/c1-27-22-12-17(13-24-14-18-6-2-3-7-20(18)23)8-9-21(22)28-16-19(26)15-25-10-4-5-11-25/h2-3,6-9,12,19,24,26H,4-5,10-11,13-16H2,1H3 | 1-[4-[[(2-fluorophenyl)methylamino]methyl]-2-methoxyphenoxy]-3-pyrrolidin-1-ylpropan-2-ol |
| 45179373 | InChI=1S/C21H30N4O3/c1-27-19-7-6-17(20(10-19)28-2)11-23-21(26)8-5-16-4-3-9-25(13-16)14-18-12-22-15-24-18/h6-7,10,12,15-16H,3-5,8-9,11,13-14H2,1-2H3,(H,22,24)(H,23,26) | N-[(2,4-dimethoxyphenyl)methyl]-3-{1-[(1H-imidazol-4-yl)methyl]piperidin-3-yl}propanamide |
| 72885799 | InChI=1S/C21H33N3O4/c1-21(2,22)20(26)24-11-5-6-15(14-24)7-10-19(25)23-13-16-8-9-17(27-3)12-18(16)28-4/h8-9,12,15H,5-7,10-11,13-14,22H2,1-4H3,(H,23,25) | 3-[1-(2-amino-2-methylpropanoyl)piperidin-3-yl]-N-[(2,4-dimethoxyphenyl)methyl]propanamide |
| 45223257 | InChI=1S/C20H34N2O4/c1-15(2)21(3)13-18(24)14-26-19-6-5-16(11-20(19)25-4)12-22-9-7-17(23)8-10-22/h5-6,11,15,17-18,23-24H,7-10,12-14H2,1-4H3 | 1-[[4-[2-hydroxy-3-[methyl(propan-2-yl)amino]propoxy]-3-methoxyphenyl]methyl]piperidin-4-ol |
| 50827384 | InChI=1S/C25H26N4O5/c1-4-16-5-7-17(8-6-16)22-23-24(34-28-22)25(31)29(15-27-23)12-11-21(30)26-14-18-9-10-19(32-2)13-20(18)33-3/h5-10,13,15H,4,11-12,14H2,1-3H3,(H,26,30) | N-[(2,4-dimethoxyphenyl)methyl]-3-[3-(4-ethylphenyl)-7-oxo-[1,2]oxazolo[4,5-d]pyrimidin-6-yl]propanamide |

TABLE 2-continued

LIST OF WITHAFERIN A ANALOGS AND DERIVATIVES BASED ON SIMILARITY

| | | |
|---|---|---|
| 71694387 | InChI=1S/C17H22N2O5/c1-21-9-15-5-13(19-24-15)7-17(10-23-11-17)18-8-12-3-4-14(22-2)6-16(12)20/h3-6,18,20H,7-11H2,1-2H3 | 5-methoxy-2-[[[3-[[5-(methoxymethyl)-1,2-oxazol-3-yl]methyl]oxetan-3-yl]amino]methyl]phenol |
| 75452351 | InChI=1S/C18H19N3O3/c1-12-3-4-17(13(2)7-12)24-10-14(22)9-21-11-20-16-8-19-6-5-15(16)18(21)23/h3-8,11,14,22H,9-10H2,1-2H3 | 3-[3-(2,4-dimethylphenoxy)-2-hydroxypropyl]pyrido[3,4-d]pyrimidin-4-one |
| 45200947 | InChI=1S/C23H31FN2O4/c1-29-23-12-17(13-25-14-18-4-2-3-5-21(18)24)6-7-22(23)30-16-20(28)15-26-10-8-19(27)9-11-26/h2-7,12,19-20,25,27-28H,8-11,13-16H2,1H3 | 1-[3-[4-[[(2-fluorophenyl)methylamino]methyl]-2-methoxyphenoxy]-2-hydroxypropyl]piperidin-4-ol |
| 53195855 | InChI=1S/C24H27N5O3S/c1-15-7-6-8-18(11-15)29-23-22(16(2)27-29)33-24(26-23)28(3)14-21(30)25-13-17-9-10-19(31-4)12-20(17)32-5/h6-12H,13-14H2,1-5H3,(H,25,30) | N-[(2,4-dimethoxyphenyl)methyl]-2-[methyl-[3-methyl-1-(3-methylphenyl)pyrazolo[3,4-d][1,3]thiazol-5-yl]amino]acetamide |
| 72904150 | InChI=1S/C21H34N2O4/c1-22(18-7-11-26-12-8-18)14-17-5-6-20(21(13-17)25-2)27-16-19(24)15-23-9-3-4-10-23/h5-6,13,18-19,24H,3-4,7-12,14-16H2,1-2H3 | 1-[2-methoxy-4-[[methyl(oxan-4-yl)amino]methyl]phenoxy]-3-pyrrolidin-1-ylpropan-2-ol |
| 84585732 | InChI=1S/C14H23N3O2.HI/c1-5-16-14(15-3)17-10-11(2)19-13-8-6-7-12(9-13)18-4;/h6-9,11H,5,10H2,1-4H3,(H2,15,16,17);1H | (Z)—N-ethyl-N'-[2-(3-methoxyphenoxy)propyl]-N''-methylguanidine hydroiodide |
| 51369692 | InChI=1S/C25H18ClN5O3/c26-19-9-3-1-7-16(19)14-28-22(32)15-31-21-11-4-2-8-17(21)18(13-23(31)33)25-29-24(30-34-25)20-10-5-6-12-27-20/h1-13H,14-15H2,(H,28,32) | N-[(2-chlorophenyl)methyl]-2-[2-oxo-4-(3-pyridin-2-yl-1,2,4-oxadiazol-5-yl)quinolin-1-yl]acetamide |
| 7161243 | InChI=1S/C11H11N3O5S/c1-19-8-4-2-7(3-5-8)14-20(17,18)9-6-12-11(16)13-10(9)15/h2-6,14H,1H3,(H2,12,13,15,16) | 2-hydroxy-N-(4-methoxyphenyl)-6-oxo-1,6-dihydropyrimidine-5-sulfonamide |
| 53162202 | InChI=1S/C22H20N4O4/c1-28-17-7-5-16(19(11-17)29-2)13-24-20(27)12-21-25-26-22(30-21)15-6-8-18-14(10-15)4-3-9-23-18/h3-11H,12-13H2,1-2H3,(H,24,27) | N-[(2,4-dimethoxyphenyl)methyl]-2-(5-quinolin-6-yl-1,3,4-oxadiazol-2-yl)acetamide |
| 122632830 | InChI=1S/C26H23N7O3/c34-24-19-7-2-1-6-18(19)21(30-31-24)15-16-4-3-5-17(14-16)25(35)33-12-10-32(11-13-33)22-9-8-20-23(28-22)29-26(36)27-20/h1-9,14H,10-13,15H2,(H,31,34)(H2,27,28,29,36) | 4-[[3-[4-(2-oxo-1,3-dihydroimidazo[4,5-b]pyridin-5-yl)piperazine-1-carbonyl]phenyl]methyl]-2H-phthalazin-1-one |
| 122632806 | InChI=1S/C27H22F3N7O2/c28-27(29,30)26-31-20-8-9-22(32-23(20)33-26)36-10-12-37(13-11- | 4-[[3-[4-[2-(trifluoromethyl)-1H-imidazo[4,5-b]pyridin-5- |

TABLE 2-continued

LIST OF WITHAFERIN A ANALOGS AND DERIVATIVES BASED ON SIMILARITY

| | | |
|---|---|---|
| | 36)25(39)17-5-3-4-16(14-17)15-21-18-6-1-2-7-19(18)24(38)35-34-21/h1-9,14H,10-13,15H2,(H,35,38)(H,31,32,33) | yl]piperazine-1-carbonyl]phenyl]methyl]-2H-phthalazin-1-one |
| 124159248 | InChI=1S/C27H24F2N6O3/c28-27(29)9-20(10-27)32-24(36)15-38-21-3-1-2-17(8-21)25-34-23-14-37-13-22(23)26(35-25)33-19-6-4-16(5-7-19)18-11-30-31-12-18/h1-8,11-12,20H,9-10,13-15H2,(H,30,31)(H,32,36)(H,33,34,35) | N-(3,3-difluorocyclobutyl)-2-[3-[4-[4-(1H-pyrazol-4-yl)anilino]-5,7-dihydrofuro[3,4-d]pyrimidin-2-yl]phenoxy]acetamide |
| 117664608 | InChI=1S/C24H22N6O/c1-2-18(11-25-6-1)31-23-14-26-13-22(30-23)20-12-28-21-4-3-15(9-19(20)21)17-8-16-5-7-27-24(16)29-10-17/h3-5,7-10,12-14,18,25,28H,1-2,6,11H2,(H,27,29) | 5-[3-(6-piperidin-3-yloxypyrazin-2-yl)-1H-indol-5-yl]-1H-pyrrolo[2,3-b]pyridine |
| 91383988 | InChI=1S/C33H31N5O3/c34-32(41)33(37-25-5-2-1-3-6-25)14-17-38(18-15-33)30(39)19-22-9-11-23(12-10-22)26-7-4-8-27(31(26)40)28-20-24-13-16-35-21-29(24)36-28/h1-13,16,20-21,35-37H,14-15,17-19H2,(H2,34,41) | 4-anilino-1-[2-[4-[5-(1,6-dihydropyrrolo[2,3-c]pyridin-2-ylidene)-6-oxocyclohexa-1,3-dien-1-yl]phenyl]acetyl]piperidine-4-carboxamide |
| 71233838 | InChI=1S/C27H28N8O3/c1-34-10-12-35(13-11-34)26(37)23-15-17-14-18(2-3-20(17)32-23)31-27-30-8-5-21(33-27)22-16-19(4-7-28-22)38-24-6-9-29-25(24)36/h2-5,7-8,14-16,24,32H,6,9-13H2,1H3,(H,29,36)(H,30,31,33)/t24-/m0/s1 | (3S)-3-[2-[2-[[2-(4-methylpiperazine-1-carbonyl)-1H-indol-5-yl]amino]pyrimidin-4-yl]pyridin-4-yl]oxypyrrolidin-2-one |
| 70801150 | InChI=1S/C27H36F3N3O4S/c28-27(29,30)19-7-10-24-23(15-19)26-22(25(32-24)18-5-2-1-3-6-18)9-8-21(37-26)16-31-38(35,36)14-4-12-33-13-11-20(34)17-33/h1-3,5,7,10,15,18,20-22,25-26,31-32,34H,4,6,8-9,11-14,16-17H2/t18?,20-,21-,22+,25+,26+/m1/s1 | N-[[(2R,4aS,5S,10bS)-5-cyclohexa-2,4-dien-1-yl-9-(trifluoromethyl)-3,4,4a,5,6,10b-hexahydro-2H-pyrano[3,2-c]quinolin-2-yl]methyl]-3-[(3R)-3-hydroxypyrrolidin-1-yl]propane-1-sulfonamide |
| 124159163 | InChI=1S/C28H25N7O2/c36-26(32-21-4-2-5-21)17-37-23-6-1-3-19(13-23)27-34-25-16-29-12-11-24(25)28(35-27)33-22-9-7-18(8-10-22)20-14-30-31-15-20/h1,3,6-16,21H,2,4-5,17H2,(H,30,31)(H,32,36)(H,33,34,35) | N-cyclobutyl-2-[3-[4-[4-(1H-pyrazol-4-yl)anilino]pyrido[3,4-d]pyrimidin-2-yl]phenoxy]acetamide |
| 123414035 | InChI=1S/C30H27FN6/c31-22-16-19(17-26-28(22)37-30(35-26)25-6-2-4-14-33-25)8-7-18-9-11-21-20(15-18)10-12-23-27(21)36-29(34-23)24-5-1-3-13-32-24/h9,11,15-17,24-25,32-33H,1,3-5,10,12-14H2,(H,34,36)(H,35,37) | 7-[2-[(4,5-didehydro-1,2,3,6-tetrahydropyridin-6-yl)-7-fluoro-3H-benzimidazol-5-yl]ethynyl]-2-piperidin-2-yl-4,5-dihydro-3H-benzo[e]benzimidazole |

TABLE 2-continued

LIST OF WITHAFERIN A ANALOGS AND DERIVATIVES BASED ON SIMILARITY

| | | |
|---|---|---|
| 86969663 | InChI=1S/C23H23N7O2/c24-21(31)16-6-8-17(9-7-16)29-12-10-28(11-13-29)15-20-26-22-19(23(32)27-20)14-25-30(22)18-4-2-1-3-5-18/h1-9,14,25H,10-13,15H2,(H2,24,31) | 4-[4-[(4-oxo-1-phenyl-2H-pyrazolo[3,4-d]pyrimidin-6-yl)methyl]piperazin-1-yl]benzamide |
| 70798546 | InChI=1S/C19H16N6O2/c20-19-24-15-8-12(2-4-16(15)27-19)11-1-3-13-14(7-11)23-17(9-22-13)25-6-5-21-10-18(25)26/h1-4,7-9,21H,5-6,10H2,(H2,20,24) | 1-[7-(2-amino-1,3-benzoxazol-5-yl)quinoxalin-2-yl]piperazin-2-one |
| 87645825 | InChI=1S/C23H28N4O4/c1-14(2)18-9-19(21(30)10-20(18)29)22-24-25-23(31)27(22)12-16-5-3-15(4-6-16)11-26-8-7-17(28)13-26/h3-6,9-10,14,17,24,28-29H,7-8,11-13H2,1-2H3,(H,25,31)/b22-19-/t17-/m0/s1 | (5E)-5-(4-hydroxy-6-oxo-3-propan-2-ylcyclohexa-2,4-dien-1-ylidene)-4-[[4-[[(3S)-3-hydroxypyrrolidin-1-yl]methyl]phenyl]methyl]-1,2,4-triazolidin-3-one |
| 117664706 | InChI=1S/C27H27N5O2/c33-27(18-3-4-18)31-20-8-5-17(6-9-20)19-7-10-24-22(12-19)23(14-30-24)25-15-29-16-26(32-25)34-21-2-1-11-28-13-21/h5-10,12,14-16,18,21,28,30H,1-4,11,13H2,(H,31,33) | N-[4-[3-(6-piperidin-3-yloxypyrazin-2-yl)-1H-indol-5-yl]phenyl]cyclopropanecarboxamide |
| 78043513 | InChI=1S/C24H23N7O3/c1-31(2)23(33)20-12-14-11-15(3-4-17(14)29-20)28-24-27-9-6-18(30-24)19-13-16(5-8-25-19)34-21-7-10-26-22(21)32/h3-6,8-9,11-13,21,29H,7,10H2,1-2H3,(H,26,32)(H,27,28,30) | N,N-dimethyl-5-[[4-[4-(2-oxopyrrolidin-3-yl)oxypyridin-2-yl]pyrimidin-2-yl]amino]-1H-indole-2-carboxamide |
| 89764001 | InChI=1S/C26H27N7O2/c27-13-17-3-6-30-25(9-17)32-26-12-19(18-1-2-18)11-23(31-26)20-10-22(15-29-14-20)35-21-4-7-33(8-5-21)16-24(28)34/h3,6,9-12,14-15,18,21H,1-2,4-5,7-8,16H2,(H2,28,34)(H,30,31,32) | 2-[4-[5-[6-[(4-cyanopyridin-2-yl)amino]-4-cyclopropylpyridin-2-yl]pyridin-3-yl]oxypiperidin-1-yl]acetamide |
| 90160604 | InChI=1S/C32H37ClN4O5/c1-2-41-30(40)32(14-3-15-32)23-8-10-24(11-9-23)42-31-34-26-18-25(33)28(35-29(26)36-31)22-6-4-20(5-7-22)21-12-16-37(17-13-21)27(39)19-38/h4-7,12,18,23-24,38H,2-3,8-11,13-17,19H2,1H3,(H,34,35,36) | ethyl 1-[4-[[6-chloro-5-[4-[1-(2-hydroxyacetyl)-3,6-dihydro-2H-pyridin-4-yl]phenyl]-1H-imidazo[4,5-b]pyridin-2-yl]oxy]cyclohexyl]cyclobutane-1-carboxylate |
| 99115528 | InChI=1S/C25H28FN7O2/c1-16(24(34)27-21-4-2-3-19(26)15-21)32-11-13-33(14-12-32)25(35)28-20-9-7-18(8-10-20)23-29-22(30-31-23)17-5-6-17/h2-4,7-10,15-17H,5-6,11-14H2,1H3,(H,27,34)(H,28,35)(H,29,30,31)/t16-/m0/s1 | N-[4-(5-cyclopropyl-1H-1,2,4-triazol-3-yl)phenyl]-4-[(2S)-1-(3-fluoroanilino)-1-oxopropan-2-yl]piperazine-1-carboxamide |

TABLE 2-continued

LIST OF WITHAFERIN A ANALOGS AND DERIVATIVES BASED ON SIMILARITY

| | | |
|---|---|---|
| 55459608 | InChI=1S/C24H25N3O7/c1-32-19-12-15(8-9-18(19)33-13-20(25)28)22(30)34-14-21(29)27-17-7-3-2-6-16(17)26-23(31)24(27)10-4-5-11-24/h2-3,6-9,12H,4-5,10-11,13-14H2,1H3,(H2,25,28)(H,26,31) | [2-oxo-2-(3-oxospiro[4H-quinoxaline-2,1'-cyclopentane]-1-yl)ethyl] 4-(2-amino-2-oxoethoxy)-3-methoxybenzoate |
| 69808272 | InChI=1S/C25H33N3O4/c1-25(2,27-16-22(30)19-8-10-20(29)11-9-19)15-18-6-3-5-17(13-18)14-23(31)28-12-4-7-21(28)24(26)32/h3,5-6,8-11,13,21-22,27,29-30H,4,7,12,14-16H2,1-2H3,(H2,26,32)/t21-,22?/m0/s1 | (2S)-1-[2-[3-[2-[[2-hydroxy-2-(4-hydroxyphenyl)ethyl]amino]-2-methylpropyl]phenyl]acetyl]pyrrolidine-2-carboxamide |
| 90430808 | InChI=1S/C20H24FN7O/c21-18-9-17(28-11-15(5-6-22)26-27-28)4-2-12(18)7-16(10-23)25-20(29)19-13-1-3-14(8-13)24-19/h2,4,9,11,13-14,16,19,24H,1,3,5-8,22H2,(H,25,29)/t13-,14+,16-,19-/m0/s1 | (1S,2S,4R)—N-[(1S)-2-[4-[4-(2-aminoethyl)triazol-1-yl]-2-fluorophenyl]-1-cyanoethyl]-3-azabicyclo[2.2.1]heptane-2-carboxamide |
| 9822981 | InChI=1S/C22H32N6O2/c1-15(29)21-23-9-3-19(25-21)27-11-5-17(6-12-27)18-7-13-28(14-8-18)20-4-10-24-22(26-20)16(2)30/h3,4,9-10,15-18,29-30H,5-8,11-14H2,1-2H3/t15-,16-/m1/s1 | (1R)-1-[4-[4-[1-[2-[(1R)-1-hydroxyethyl]pyrimidin-4-yl]piperidin-4-yl]piperidin-1-yl]pyrimidin-2-yl]ethanol |
| 70907322 | InChI=1S/C25H25N3O3/c26-24(29)14-28-22-13-20(22)18-9-10-23(31-15-16-5-2-1-3-6-16)21(12-18)17-7-4-8-19(11-17)25(27)30/h1-12,20,22,28H,13-15H2,(H2,26,29)(H2,27,30)/t20?,22-/m0/s1 | 3-[5-[(2S)-2-[(2-amino-2-oxoethyl)amino]cyclopropyl]-2-phenylmethoxyphenyl]benzamide |
| 124159301 | InChI=1S/C30H33M7O2/c1-2-37-14-13-27-26(18-37)30(34-24-11-9-20(10-12-24)22-16-31-32-17-22)36-29(35-27)21-5-3-8-25(15-21)39-19-28(38)33-23-6-4-7-23/h3,5,8-12,15-17,23H,2,4,6-7,13-14,18-19H2,1H3,(H,31,32)(H,33,38)(H,34,35,36) | N-cyclobutyl-2-[3-[6-ethyl-4-[(1H-pyrazol-4-yl)anilino]-7,8-dihydro-5H-pyrido[4,3-d]pyrimidin-2-yl]phenoxy]acetamide |
| 2941977 | InChI=1S/C27H25N3O3/c1-18-12-13-23-22(14-18)25(19-8-4-2-5-9-19)26(20-10-6-3-7-11-20)29(23)16-21(31)17-30-24(32)15-28-27(30)33/h2-14,21,31H,15-17H2,1H3,(H,28,33) | 3-[2-hydroxy-3-(5-methyl-2,3-diphenylindol-1-yl)propyl]imidazolidine-2,4-dione |
| 118729948 | InChI=1S/C21H15ClFN7/c1-11(29-21-14(9-24)20(25)27-10-28-21)19-17(16-4-2-3-7-26-16)18(22)13-8-12(23)5-6-15(13)30-19/h2-8,10-11H,1H3,(H3,25,27,28,29) | 4-amino-6-[1-(4-chloro-6-fluoro-3-pyridin-2-ylquinolin-2-yl)ethylamino]pyrimidine-5-carbonitrile |

TABLE 2-continued

LIST OF WITHAFERIN A ANALOGS AND DERIVATIVES BASED ON SIMILARITY

| | | |
|---|---|---|
| 56755716 | InChI=1S/C20H22N4O3/c1-13-2-3-14-10-16(4-5-17(14)22-13)20(27)6-8-24(9-7-20)12-15-11-21-23-18(15)19(25)26/h2-5,10-11,27H,6-9,12H2,1H3,(H,21,23)(H,25,26) | 4-[[4-hydroxy-4-(2-methylquinolin-6-yl)piperidin-1-yl]methyl]-1H-pyrazole-5-carboxylic acid |
| 5930665 | InChI=1S/C21H19N3O2S/c1-13-8-9-15(10-14(13)2)11-18-20(26)24(16-6-4-3-5-7-16)21(27-18)17(12-22)19(23)25/h3-10,18H,11H2,1-2H3,(H2,23,25)/b21-17- | (2Z)-2-cyano-2-[5-[(3,4-dimethylphenyl)methyl]-4-oxo-3-phenyl-1,3-thiazolidin-2-ylidene]acetamide |
| 59634638 | InChI=1S/C22H17FN6O/c1-12(28-22-16(10-24)21(25)26-11-27-22)19-18(13-5-3-2-4-6-13)20(30)15-9-14(23)7-8-17(15)29-19/h2-9,11-12H,1H3,(H,29,30)(H3,25,26,27,28) | 4-amino-6-[1-(6-fluoro-4-oxo-3-phenyl-1H-quinolin-2-yl)ethylamino]pyrimidine-5-carbonitrile |
| 118729950 | InChI=1S/C25H23FN8O/c1-15(32-25-18(13-27)24(28)30-14-31-25)22-21(20-4-2-3-7-29-20)23(34-8-10-35-11-9-34)17-12-16(26)5-6-19(17)33-22/h2-7,12,14-15H,8-11H2,1H3,(H3,28,30,31,32)/t15-/m0/s1 | 4-amino-6-[[(1S)-1-(6-fluoro-4-morpholin-4-yl-3-pyridin-2-ylquinolin-2-yl)ethyl]amino]pyrimidine-5-carbonitrile |
| 16012201 | InChI=1S/C28H26N4O3/c1-19-9-3-4-11-21(19)17-31-24-13-7-6-12-22(24)23-16-30-32(28(34)27(23)31)18-26(33)29-15-20-10-5-8-14-25(20)35-2/h3-14,16H,15,17-18H2,1-2H3,(H,29,33) | N-[(2-methoxyphenyl)methyl]-2-[5-[(2-methylphenyl)methyl]-4-oxopyridazino[4,5-b]indol-3-yl]acetamide |
| 3133124 | InChI=1S/C21H25N3O5S/c1-15-9-11-18(12-10-15)30(28,29)24(16-7-5-4-6-8-16)14-17(25)13-23-19(26)21(2,3)22-20(23)27/h4-12,17,25H,13-14H2,1-3H3,(H,22,27) | N-[3-(4,4-dimethyl-2,5-dioxoimidazolidin-1-yl)-2-hydroxypropyl]-4-methyl-N-phenylbenzenesulfonamide |
| 4350310 | InChI=1S/C20H14Cl2N4O3/c1-28-15-7-9(3-5-14(15)27)16-11(8-23)19(24)29-20-17(16)18(25-26-20)10-2-4-12(21)13(22)6-10/h2-7,16,27H,24H2,1H3,(H,25,26) | 6-amino-3-(3,4-dichlorophenyl)-4-(4-hydroxy-3-methoxyphenyl)-2,4-dihydropyrano[2,3-c]pyrazole-5-carbonitrile |
| 17411683 | InChI=1S/C24H26N4O4/c1-24(2)22(30)28(23(31)27-24)14-21(29)26-12-18(15-8-10-16(32-3)11-9-15)19-13-25-20-7-5-4-6-17(19)20/h4-11,13,18,25H,12,14H2,1-3H3,(H,26,29)(H,27,31) | 2-(4,4-dimethyl-2,5-dioxoimidazolidin-1-yl)-N-[2-(1H-indol-3-yl)-2-(4-methoxyphenyl)ethyl]acetamide |
| 15987563 | InChI=1S/C18H18N4O2S/c1-12-7-6-8-14(11-12)22-18-16(17(19)20-13(2)21-18)25(23,24)15-9-4-3-5-10-15/h3-11H,1-2H3,(H3,19,20,21,22) | 5-(benzenesulfonyl)-2-methyl-4-N-(3-methylphenyl)pyrimidine-4,6-diamine |
| 49872831 | InChI=1S/C23H19FN6O/c1-13(29-23-17(11-25)22(26)27-12-28-23)20-19(14-6-4-3-5-7-14)21(31-2)16-10- | 4-amino-6-[[(1S)-1-(6-fluoro-4-methoxy-3-phenylquinolin-2-yl)ethyl]amino]pyrimidine-5-carbonitrile |

TABLE 2-continued

LIST OF WITHAFERIN A ANALOGS AND DERIVATIVES BASED ON SIMILARITY

| | | |
|---|---|---|
| | 15(24)8-9-18(16)30-20/h3-10,12-13H,1-2H3,(H3,26,27,28,29)/t13-/m0/s1 | |
| 53023028 | InChI=1S/C21H17FN4O3/c1-12-2-7-17-13(10-12)11-16(21(28)24-17)20-25-19(29-26-20)9-8-18(27)23-15-5-3-14(22)4-6-15/h2-7,10-11,26H,8-9H2,1H3,(H,23,27)/b20-16- | N-(4-fluorophenyl)-3-[(3Z)-3-(6-methyl-2-oxoquinolin-3-ylidene)-1,2,4-oxadiazol-5-yl]propanamide |
| 20892206 | InChI=1S/C27H23FN4O3/c1-35-24-13-7-3-8-18(24)14-29-25(33)17-32-27(34)26-21(15-30-32)20-10-4-6-12-23(20)31(26)16-19-9-2-5-11-22(19)28/h2-13,15H,14,16-17H2,1H3,(H,29,33) | 2-[5-[(2-fluorophenyl)methyl]-4-oxopyridazino[4,5-b]indol-3-yl]-N-[(2-methoxyphenyl)methyl]acetamide |
| 57487127 | InChI=1S/C22H25Cl2N5O3S/c1-29-13-26-22(28-29)33(30,31)27-8-9-32-16-5-3-15-4-7-21(25)18(17(15)12-16)10-14-2-6-19(23)20(24)11-14/h2-3,5-6,11-13,18,21,27H,4,7-10,25H2,1H3 | N-[2-[[7-amino-8-[(3,4-dichlorophenyl)methyl]-5,6,7,8-tetrahydronaphthalen-2-yl]oxy]ethyl]-1-methyl-1,2,4-triazole-3-sulfonamide |
| 4625911 | InChI=1S/C21H17N5OS/c1-10-7-13(11(2)28-10)19-18-17(14(8-22)20(23)27-21(18)26-25-19)15-9-24-16-6-4-3-5-12(15)16/h3-7,9,17,24H,23H2,1-2H3,(H,25,26) | 6-amino-3-(2,5-dimethylthiophen-3-yl)-4-(1H-indol-3-yl)-2,4-dihydropyrano[2,3-c]pyrazole-5-carbonitrile |
| 6060815 | InChI=1S/C20H16ClN3O2S/c1-12-3-2-4-13(9-12)10-17-19(26)24(15-7-5-14(21)6-8-15)20(27-17)16(11-22)18(23)25/h2-9,17H,10H2,1H3,(H2,23,25)/b20-16- | (2Z)-2-[3-(4-chlorophenyl)-5-[(3-methylphenyl)methyl]-4-oxo-1,3-thiazolidin-2-ylidene]-2-cyanoacetamide |
| 49871864 | InChI=1S/C21H16FN7/c1-12(28-21)16-16(10-23)20(24)26-11-27-21)19-15(18-4-2-3-7-25-18)9-13-8-14(22)5-6-17(13)29-19/h2-9,11-12H,1H3,(H3,24,26,27,28) | 4-amino-6-[1-(6-fluoro-3-pyridin-2-ylquinolin-2-yl)ethylamino]pyrimidine-5-carbonitrile |
| 49872924 | InChI=1S/C24H22FN7O/c1-14(31-24-18(12-26)23(27)29-13-30-24)21-20(15-5-3-2-4-6-15)22(28-9-10-33)17-11-16(25)7-8-19(17)32-21/h2-8,11,13-14,33H,9-10H2,1H3,(H,28,32)(H3,27,29,30,31) | 4-amino-6-[1-[6-fluoro-4-(2-hydroxyethylamino)-3-phenylquinolin-2-yl]ethylamino]pyrimidine-5-carbonitrile |
| 118767337 | InChI=1S/C22H22N2O3/c1-14-10-18(17-8-3-4-9-19(17)23-14)15-6-5-7-16(11-15)22(26)24(2)20-12-27-13-21(20)25/h3-11,20-21,25H,12-13H2,1-2H3/t20-,21-/m0/s1 | N-[(3S,4R)-4-hydroxyoxolan-3-yl]-N-methyl-3-(2-methylquinolin-4-yl)benzamide |
| 118729947 | InChI=1S/C26H27FN8/c1-16(33-26-20(14-28)25(29)31-15-32-26)23-22(17-7-5-4-6-8-17)24(30-11-12-35(2)3)19-13-18(27)9-10-21(19)34-23/h4- | 4-amino-6-[[(1S)-1-4-[2-[(dimethylamino)ethylamino]-6-fluoro-3-phenylquinolin-2-yl]ethyl]amino]pyrimidine-5-carbonitrile |

TABLE 2-continued

LIST OF WITHAFERIN A ANALOGS AND DERIVATIVES BASED ON SIMILARITY

| | | |
|---|---|---|
| | 10,13,15-16H,11-12H2,1-3H3,(H,30,34)(H3,29,31,32,33)/t16-/m0/s1 | |
| 662825 | InChI=1S/C21H24N4O4S/c1-15-6-7-16(20-17-4-2-3-5-18(17)21(26)24-23-20)14-19(15)30(27,28)22-8-9-25-10-12-29-13-11-25/h2-7,14,22H,8-13H2,1H3,(H,24,26) | 2-methyl-N-(2-morpholin-4-ylethyl)-5-(4-oxo-3H-phthalazin-1-yl)benzenesulfonamide |
| 5779743 | InChI=1S/C20H16BrN3O2S/c1-12-3-2-4-13(9-12)10-17-19(26)24(15-7-5-14(21)6-8-15)20(27-17)16(11-22)18(23)25/h2-9,17H,10H2,1H3,(H2,23,25)/b20-16- | (2Z)-2-[3-(4-bromophenyl)-5-[(3-methylphenyl)methyl]-4-oxo-1,3-thiazolidin-2-ylidene]-2-cyanoacetamide |
| 17028423 | InChI=1S/C17H21N3O3/c1-10-4-5-15-14(6-10)11(2)12(3)19(15)8-13(21)9-20-16(22)7-18-17(20)23/h4-6,13,21H,7-9H2,1-3H3,(H,18,23) | 3-[2-hydroxy-3-(2,3,5-trimethylindol-1-yl)propyl]imidazolidine-2,4-dione |
| 44827367 | InChI=1S/C23H30ClN3O4S/c1-18-4-10-21(11-5-18)32(29,30)27-16-14-26(15-17-27)13-12-25-22(28)23(2,3)31-20-8-6-19(24)7-9-20/h4-11H,12-17H2,1-3H3,(H,25,28) | 2-(4-chlorophenoxy)-2-methyl-N-[2-[4-(4-methylphenyl)sulfonylpiperazin-1-yl]ethyl]propanamide |
| 119680299 | InChI=1S/C21H23N3O2•ClH/c25-15-10-20(22-11-15)21(26)24-12-17(14-6-2-1-3-7-14)18-13-23-19-9-5-4-8-16(18)19;/h1-9,13,15,17,20,22-23,25H,10-12H2,(H,24,26);1H | 4-hydroxy-N-[2-(1H-indol-3-yl)-2-phenylethyl]pyrrolidine-2-carboxamide hydrochloride |
| 24507888 | InChI=1S/C17H19N7/c1-11-12-6-3-4-7-13(12)17(23-20-11)24(2)9-5-8-15-14(10-18)16(19)22-21-15/h3-4,6-7H,5,8-9H2,1-2H3,(H3,19,21,22) | 5-amino-3-{3-[methyl(4-methylphthalazin-1-yl)amino]propyl}-1H-pyrazole-4-carbonitrile |
| 2945746 | InChI=1S/C19H15ClN4OS/c1-9-7-12(10(2)26-9)17-16-15(11-5-3-4-6-14(11)20)13(8-21)18(22)25-19(16)24-23-17/h3-7,15H,22H2,1-2H3,(H,23,24) | 6-amino-4-(2-chlorophenyl)-3-(2,5-dimethylthiophen-3-yl)-1H,4H-pyrano[2,3-c]pyrazole-5-carbonitrile |
| 46349707 | InChI=1S/C26H27N5O4/c1-29-15-20(19-6-4-5-7-22(19)29)21-13-25-30(26(33)10-11-31(25)28-21)16-24(32)27-14-17-8-9-18(34-2)12-23(17)35-3/h4-9,12-13,15H,10-11,14,16H2,1-3H3,(H,27,32) | N-[(2,4-dimethoxyphenyl)methyl]-2-[2-(1-methylindol-3-yl)-5-oxo-6,7-dihydropyrazolo[1,5-a]pyrimidin-4-yl]acetamide |
| 49870793 | InChI=1S/C21H15F2N7O/c1-11(28-20-15(9-24)19(25)26-10-27-20)18-17(12-6-13(22)8-14(23)7-12)21(31)30-5-3-2-4-16(30)29-18/h2-8,10-11H,1H3,(H3,25,26,27,28) | 4-amino-6-[1-[3-(3,5-difluorophenyl)-4-oxopyrido[1,2-a]pyrimidin-2-yl]ethylamino]pyrimidine-5-carbonitrile |
| 33072330 | InChI=1S/C21H18N4O5/c1-12(18-23-16-8-3-2-7-15(16)19(27)24-18)30-20(28)14-6-4-5-13(9-14)11-25-17(26)10-22-21(25)29/h2-9,12H,10- | [(1R)-1-(4-oxo-1H-quinazolin-2-yl)ethyl] 3-[(2,5-dioxoimidazolidin-1-yl)methyl]benzoate |

TABLE 2-continued

LIST OF WITHAFERIN A ANALOGS AND DERIVATIVES BASED ON SIMILARITY

| | | |
|---|---|---|
| | 11H2,1H3,(H,22,29)(H,23, 24,27)/t12-/m1/s1 | |
| 71748271 | InChI=1S/C25H23ClN4O5S/ c26-17-7-8-21-20(12-17)24(23(29-21)25(27)31)36(32,33)30-10-11-34-18(14-30)15-35-22-6-2-1-5-19(22)16-4-3-9-28-13-16/h1-9,12-13,18,29H,10-11,14-15H2,(H2,27,31)/t18-/m0/s1 | 5-chloro-3-[(2S)-2-[(2-pyridin-3-ylphenoxy)methyl]morpholin-4-yl]sulfonyl-1H-indole-2-carboxamide |
| 22041656 | InChI=1S/C23H31ClN6O4/ c1-14-28-30(23(34)29(14)13-20(31)26-16-11-25-12-16)17-8-9-19(24)18(10-17)22(33)27-21(32)15-6-4-2-3-5-7-15/h8-10,15-16,21,25,32H,2-7,11-13H2,1H3,(H,26,31)(H,27, 33) | 5-[4-[2-(azetidin-3-ylamino)-2-oxoethyl]-3-methyl-5-oxo-1,2,4-triazol-1-yl]-2-chloro-N-[cycloheptyl(hydroxy)methyl]benzamide |
| 123198033 | InChI=1S/C23H25FN4O3/ c1-27(10-11-29)16-8-9-28(14-16)23(31)19-12-15(6-7-20(19)24)13-21-17-4-2-3-5-18(17)22(30)26-25-21/h2-7,12,16,29H,8-11,13-14H2,1H3,(H,26,30) | 4-[[4-fluoro-3-[3-[2-hydroxyethyl(methyl)amino]pyrrolidine-1-carbonyl]phenyl]methyl]-2H-phthalazin-1-one |
| 46979601 | InChI=1S/C20H26N4O3S/ c1-12-8-17(27-3)13(2)7-15(12)16-11-28-20(22-16)23-19(26)14-5-4-6-24(9-14)10-18(21)25/h7-8,11,14H,4-6,9-10H2,1-3H3,(H2,21,25)(H,22,23, 26) | 1-(2-amino-2-oxoethyl)-N-[4-(4-methoxy-2,5-dimethylphenyl)-1,3-thiazol-2-yl]piperidine-3-carboxamide |
| 70652336 | InChI=1S/C26H25FN6O2/ c27-21-6-2-1-5-19(21)24(25(28)34)33-13-3-4-18(15-33)30-26(35)17-7-8-22-20(14-17)23(32-31-22)16-9-11-29-12-10-16/h1-2,5-12,14,18,24H,3-4,13,15H2,(H2,28,34)(H, 30,35)(H,31,32)/t18-, 24?/m1/s1 | N-[(3R)-1-[2-amino-1-(2-fluorophenyl)-2-oxoethyl]piperidin-3-yl]-3-pyridin-4-yl-1H-indazole-5-carboxamide |
| 60172075 | InChI=1S/C27H27F3N4O3/ c1-3-23(35)15-9-18(29)24(19(30)10-15)25-17(28)4-5-21(33-25)27(37)34-22-12-32-7-6-16(22)14-8-13(2)26(36)20(31)11-14/h4-7,9-10,12-14,20,26,36H,3,8,11,31H2, 1-2H3,(H,34,37)/t13-, 14+,20+,26+/m0/s1 | N-[4-[(1R,3R,4R,5S)-3-amino-4-hydroxy-5-methylcyclohexyl]pyridin-3-yl]-6-(2,6-difluoro-4-propanoylphenyl)-5-fluoropyridine-2-carboxamide |
| 93055418 | InChI=1S/C23H28N4O5S/ c1-4-18-23(29)25-17-11-15(3)20(12-19(17)32-18)33(30,31)27-9-5-6-16(13-27)22(28)26-21-10-14(2)7-8-24-21/h7-8,10-12,16,18H,4-6,9,13H2,1-3H3,(H,25,29)(H,24,26,28)/ t16-,18+/m0/s1 | (3S)-1-[[(2R)-2-ethyl-6-methyl-3-oxo-4H-1,4-benzoxazin-7-yl]sulfonyl]-N-(4-methylpyridin-2-yl)piperidine-3-carboxamide |
| 24566921 | InChI=1S/C26H22N6O2S/ c33-24(29-19-8-10-21(11-9-19)35-17-18-5-4-14-27-15-18)13-12-23-30-25-22(26(34)31-23)16-28-32(25)20-6-2-1-3-7-20/h1-11,14- | 3-(4-oxo-1-phenyl-2H-pyrazolo[3,4-d]pyrimidin-6-yl)-N-[4-(pyridin-3-ylmethylsulfanyl)phenyl]propanamide |

TABLE 2-continued

LIST OF WITHAFERIN A ANALOGS AND DERIVATIVES BASED ON SIMILARITY

| | | |
|---|---|---|
| | 16,28H,12-13,17H2,(H,29,33) | |
| 98842572 | InChI=1S/C20H21ClN4O5S/c1-12-4-2-6-18(22-12)24-20(27)13-5-3-7-25(10-13)31(28,29)17-9-16-15(8-14(17)21)23-19(26)11-30-16/h2,4,6,8-9,13H,3,5,7,10-11H2,1H3,(H,23,26)(H,22,24,27)/t13-/m1/s1 | (3R)-1-[(6-chloro-3-oxo-4H-1,4-benzoxazin-7-yl)sulfonyl]-N-(6-methylpyridin-2-yl)piperidine-3-carboxamide |
| 56228696 | InChI=1S/C21H29N3O5S/c1-13(2)12-22-19(25)15-7-8-16(14(3)11-15)23-20(26)17-9-10-18(29-17)30(27,28)24-21(4,5)6/h7-11,13,24H,12H2,1-6H3,(H,22,25)(H,23,26) | 5-(tert-butylsulfamoyl)-N-[2-methyl-4-(2-methylpropylcarbamoyl)phenyl]furan-2-carboxamide |
| 52609602 | InChI=1S/C22H25ClFN3O4/c1-14-12-27(8-9-30-14)19(21-17(23)6-3-7-18(21)24)11-26-22(29)15-4-2-5-16(10-15)31-13-20(25)28/h2-7,10,14,19H,8-9,11-13H2,1H3,(H2,25,28)(H,26,29)/t14-,19+/m1/s1 | 3-(2-amino-2-oxoethoxy)-N-[(2R)-2-(2-chloro-6-fluorophenyl)-2-[(2R)-2-methylmorpholin-4-yl]ethyl]benzamide |
| 56848892 | InChI=1S/C20H26N8O2S/c1-26(15-5-9-27(13-15)20-17-4-6-22-19(17)24-14-25-20)18-3-2-16(12-23-18)31(29,30)28-10-7-21-8-11-28/h2-4,6,12,14-15,21H,5,7-11,13H2,1H3,(H,22,24,25)/t15-/m1/s1 | N-methyl-5-piperazin-1-ylsulfonyl-N-[(3R)-1-(7H-pyrrolo[2,3-d]pyrimidin-4-yl)pyrrolidin-3-yl]pyridin-2-amine |
| 91591490 | InChI=1S/C24H19FN6O/c25-21-16(6-4-13-5-7-18(29-22(13)21)17-3-1-2-8-27-17)19-12-31-20(23(26)30-19)11-28-24(31)14-9-15(32)10-14/h1-8,11-12,14-15,32H,9-10H2,(H2,26,30) | 3-[8-amino-6-(8-fluoro-2-pyridin-2-ylquinolin-7-yl)imidazo[1,5-a]pyrazin-3-yl]cyclobutan-1-ol |
| 25132374 | InChI=1S/C21H22N4O4S/c1-23-8-10-24(11-9-23)16-3-2-15-6-7-25(19(15)12-16)30(27,28)17-4-5-18-20(13-17)29-14-21(26)22-18/h2-7,12-13H,8-11,14H2,1H3,(H,22,26) | 7-[6-(4-methylpiperazin-1-yl)indol-1-yl]sulfonyl-4H-1,4-benzoxazin-3-one |
| 55815828 | InChI=1S/C19H18Cl2N4O5S/c20-12-3-4-17(22-8-12)24-19(27)11-2-1-5-25(9-11)31(28,29)16-7-15-14(6-13(16)21)23-18(26)10-30-15/h3-4,6-8,11H,1-2,5,9-10H2,(H,23,26)(H,22,24,27) | 1-[(6-chloro-3-oxo-4H-1,4-benzoxazin-7-yl)sulfonyl]-N-(5-chloropyridin-2-yl)piperidine-3-carboxamide |
| 50764747 | InChI=1S/C23H28N4O5S/c1-4-18-23(29)25-17-11-15(3)20(12-19(17)32-18)33(30,31)27-10-6-8-16(13-27)22(28)26-21-14(2)7-5-9-24-21/h5,7,9,11-12,16,18H,4,6,8,10,13H2,1-3H3,(H,25,29)(H,24,26,28) | 1-[(2-ethyl-6-methyl-3-oxo-4H-1,4-benzoxazin-7-yl)sulfonyl]-N-(3-methylpyridin-2-yl)piperidine-3-carboxamide |
| 55930504 | InChI=1S/C20H19ClN4O4/c21-14-4-6-17(22-9-14)24-19(27)13-2-1-7- | N-(5-chloropyridin-2-yl)-1-(3-oxo-4H-1,4-benzoxazine-7- |

TABLE 2-continued

LIST OF WITHAFERIN A ANALOGS AND DERIVATIVES BASED ON SIMILARITY

| | | |
|---|---|---|
| | 25(10-13)20(28)12-3-5-15-16(8-12)29-11-18(26)23-15/h3-6,8-9,13H,1-2,7,10-11H2,(H,23,26)(H,22,24,27) | carbonyl)piperidine-3-carboxamide |
| 56480103 | InChI=1S/C21H25N3O4S/c1-13-10-19(13)20(25)23-17-8-4-7-16(11-17)21(26)24(3)14(2)15-6-5-9-18(12-15)29(22,27)28/h4-9,11-14,19H,10H2,1-3H3,(H,23,25)(H2,22,27,28) | N-methyl-3-[(2-methylcyclopropanecarbonyl)amino]-N-[1-(3-sulfamoylphenyl)ethyl]benzamide |
| 110155360 | InChI=1S/C24H34N6O2/c1-25-21-14-22(27-18-26-21)30-13-5-10-24(32,17-30)16-28(2)23(31)20-8-6-19(7-9-20)15-29-11-3-4-12-29/h6-9,14,18,32H,3-5,10-13,15-17H2,1-2H3,(H,25,26,27) | N-[[3-hydroxy-1-[6-(methylamino)pyrimidin-4-yl]piperidin-3-yl]methyl]-N-methyl-4-(pyrrolidin-1-ylmethyl)benzamide |
| 46962362 | InChI=1S/C19H21N5O2/c1-13-20-8-7-17(21-13)14-4-2-5-15(10-14)19-22-18(26-23-19)12-24-9-3-6-16(25)11-24/h2,4-5,7-8,10,16,25H,3,6,9,11-12H2,1H3 | 1-[[3-[3-(2-methylpyrimidin-4-yl)phenyl]-1,2,4-oxadiazol-5-yl]methyl]piperidin-3-ol |
| 110223478 | InChI=1S/C20H23N5O2/c1-14-21-9-8-18(22-14)15-5-4-6-16(11-15)20-23-19(27-24-20)12-25-10-3-2-7-17(25)13-26/h4-6,8-9,11,17,26H,2-3,7,10,12-13H2,1H3 | [1-[[3-[3-(2-methylpyrimidin-4-yl)phenyl]-1,2,4-oxadiazol-5-yl]methyl]piperidin-2-yl]methanol |
| 68805087 | InChI=1S/C24H25ClFN7O3/c1-12-18(9-19(21(27)34)33(12)2)31-24(35)15-10-28-7-6-17(15)30-23-20(36-3)11-29-22(32-23)14-8-13(25)4-5-16(14)26/h4-8,10-12,18-19H,9H2,1-3H3,(H2,27,34)(H,31,35)(H,28,29,30,32) | N-(5-carbamoyl-1,2-dimethylpyrrolidin-3-yl)-4-[[2-(5-chloro-2-fluorophenyl)-5-methoxypyrimidin-4-yl]amino]pyridine-3-carboxamide |
| 121902150 | InChI=1S/C19H26N4O4/c1-11-14(12(2)20-18-17(11)19(27)21-22(18)3)9-15(24)23-8-4-5-13(10-23)6-7-16(25)26/h13H,4-10H2,1-3H3,(H,21,27)(H,25,26) | 3-[1-[2-(1,4,6-trimethyl-3-oxo-2H-pyrazolo[3,4-b]pyridin-5-yl)acetyl]piperidin-3-yl]propanoic acid |
| 99734486 | InChI=1S/C23H28N4O5S/c1-4-18-23(29)25-17-11-14(2)20(12-19(17)32-18)33(30,31)27-10-6-8-16(13-27)22(28)26-21-9-5-7-15(3)24-21/h5,7,9,11-12,16,18H,4,6,8,10,13H2,1-3H3,(H,25,29)(H,24,26,28/t16-,18+/m1/s1 | (3R)-1-[[(2S)-2-ethyl-6-methyl-3-oxo-4H-1,4-benzoxazin-7-yl]sulfonyl]-N-(6-methylpyridin-2-yl)piperidine-3-carboxamide |
| 56461293 | InChI=1S/C22H29N3O5S2/c1-16-10-11-19(15-21(16)32(29,30)25-12-5-4-6-13-25)22(26)24(3)17(2)18-8-7-9-20(14-18)31(23,27)28/h7-11,14-15,17H,4-6,12- | N,4-dimethyl-3-piperidin-1-ylsulfonyl-N-[1-(3-sulfamoylphenyl)ethyl]benzamide |

TABLE 2-continued

LIST OF WITHAFERIN A ANALOGS AND DERIVATIVES BASED ON SIMILARITY

| | | |
|---|---|---|
| | 13H2,1-3H3,(H2,23,27,28) | |
| 72883558 | InChI=1S/C18H24N6O2/c1-10-14(11(2)21-18(19)20-10)7-17(26)24-6-4-5-13(9-24)15-8-16(25)23-12(3)22-15/h8,13H,4-7,9H2,1-3H3,(H2,19,20,21)(H,22,23,25) | 6-[1-[2-(2-amino-4,6-dimethylpyrimidin-5-yl)acetyl]piperidin-3-yl]-2-methyl-1H-pyrimidin-4-one |
| 98745718 | InChI=1S/C24H36N4O5S/c1-4-20-24(30)26-19-12-16(3)22(13-21(19)33-20)34(31,32)28-11-6-8-17(15-28)23(29)25-14-18-9-7-10-27(18)5-2/h12-13,17-18,20H,4-11,14-15H2,1-3H3,(H,25,29)(H,26,30)/t17-,18+,20+/m1/s1 | (3R)-1-[[(2S)-2-ethyl-6-methyl-3-oxo-4H-1,4-benzoxazin-7-yl]sulfonyl]-N-[[(2S)-1-ethylpyrrolidin-2-yl]methyl]piperidine-3-carboxamide |
| 58844439 | InChI=1S/C20H19N3O6/c1-10(24)17-14-9-13(18(20(27)28)23(14)19(17)26)12-4-2-11(3-5-12)8-16(25)21-15-6-7-29-22-15/h2-7,10,14,17,24H,8-9H2,1H3,(H,27,28)(H,21,22,25)/t10-,14-,17-/m1/s1 | (5R,6S)-6-[(1R)-1-hydroxyethyl]-3-[4-[2-(1,2-oxazol-3-ylamino)-2-oxoethyl]phenyl]-7-oxo-1-azabicyclo[3.2.0]hept-2-ene-2-carboxylic acid |
| 90252533 | InChI=1S/C27H30F2M8O2/c1-14(2)33-26(39)17-5-6-18(28)23(24(17)29)20-7-4-16-10-32-27(37(16)35-20)34-21-11-31-9-8-22(21)36-12-15(3)25(38)19(30)13-36/h4-11,14-13,30H2,1-3H3,(H,32,34)(H,33,39)/t15-,19+,25+/m0/s1 | 3-[7-[[4-[(3R,4R,5S)-3-amino-4-hydroxy-5-methylpiperidin-1-yl]pyridin-3-yl]amino]imidazo[1,5-b]pyridazin-2-yl]-2,4-difluoro-N-propan-2-ylbenzamide |
| 90147510 | InChI=1S/C22H24F2M8O/c1-11-6-14-20(24)16(8-15(23)21(14)26)11)33-22-28-17(27-18-7-12(2)30-31-18)9-19(29-22)32-5-4-25-10-13(32)3/h6-9,13,25-26H,4-5,10H2,1-3H3,(H2,27,28,29,30,31) | 2-[(4,7-difluoro-2-methyl-1H-indol-5-yl)oxy]-6-(2-methylpiperazin-1-yl)-N-(5-methyl-1H-pyrazol-3-yl)pyrimidin-4-amine |
| 118290322 | InChI=1S/C24H29ClFN7/c1-14-9-17(3-4-19(14)26)20-12-33(15(2)18-10-28-11-18)23(31-20)16-5-7-32(8-6-16)24-21(25)22(27)29-13-30-24/h3-4,9,12-13,15-16,18,28H,5-8,10-11H2,1-2H3,(H2,27,29,30) | 6-[4-[1-[1-(azetidin-3-yl)ethyl]-4-(4-fluoro-3-methylphenyl)imidazol-2-yl]piperidin-1-yl]-5-chloropyrimidin-4-amine |
| 89847932 | InChI=1S/C22H21F2N9/c23-22(24,16-3-4-18-14(10-16)2-1-7-26-18)20-29-30-21-27-12-19(31-33(20)21)15-11-28-32(13-15)17-5-8-25-9-6-17/h1-4,7,10-13,17,21,25,30H,5-6,8-9H2 | 6-[difluoro-[6-(1-piperidin-4-ylpyrazol-4-yl)-1,8a-dihydro-[1,2,4]triazolo[4,3-b][1,2,4]triazin-3-yl]methyl]quinoline |
| 118239786 | InChI=1S/C24H25N7O/c1-14-11-26-13-18-19(14)22(27-12-16-7-4-3-5-8-16)30-23(29-18)20-15(2)28-24-17(21(25)32)9-6-10-31(20)24/h3- | 3-[4-(benzylamino)-5-methyl-5,6,7,8-tetrahydropyrido[3,4-d]pyrimidin-2-yl]-2-methylimidazo[1,2-a]pyridine-8-carboxamide |

TABLE 2-continued

LIST OF WITHAFERIN A ANALOGS AND DERIVATIVES BASED ON SIMILARITY

| | | |
|---|---|---|
| | 10,14,26H,11-13H2,1-2H3,(H2,25,32)(H,27,29,30) | |
| 10225131 | InChI=1S/C25H22N6O2/c26-23(27)18-7-4-8-20(15-18)31-25(33)22(16-5-2-1-3-6-16)30-19-11-9-17(10-12-19)21-24(32)29-14-13-28-21/h1-15,22,30H,(H3,26,27)(H,29,32)(H,31,33) | N-(3-carbamimidoylphenyl)-2-[4-(2-oxo-1H-pyrazin-3-yl)anilino]-2-phenylacetamide |
| 4295433 | InChI=1S/C31H28N4O4/c36-19-21-7-9-22(10-8-21)29-16-26(18-35-20-33-27-5-1-2-6-28(27)35)38-31(39-29)23-11-13-25(14-12-23)34-30(37)24-4-3-15-32-17-24/h1-15,17,20,26,29,31,36H,16,18-19H2,(H,34,37) | N-[4-[4-(benzimidazol-1-ylmethyl)-6-[4-(hydroxymethyl)phenyl]-1,3-dioxan-2-yl]phenyl]pyridine-3-carboxamide |
| 118924150 | InChI=1S/C35H31FN8O/c1-44(2)12-11-38-26-14-23(13-25(36)16-26)28-9-6-10-30-33(28)41-35(40-30)34-29-17-31(39-20-32(29)42-43-34)24-15-27(19-37-18-24)45-21-22-7-4-3-5-8-22/h3-10,13-20,38,42-43H,11-12,21H2,1-2H3/b35-34+ | N-[3-fluoro-5-[(2E)-2-[5-(5-phenylmethoxypyridin-3-yl)-1,2-dihydropyrazolo[3,4-c]pyridin-3-ylidene]benzimidazol-4-yl]phenyl]-N',N'-dimethylethane-1,2-diamine |
| 11648848 | InChI=1S/C29H30N8/c1-21-25-18-24(12-13-26(25)33-32-21)27-31-28(36-16-14-30-15-17-36)29(35-34-27)37(19-22-8-4-2-5-9-22)20-23-10-6-3-7-11-23/h2-13,18,30H,14-17,19-20H2,1H3,(H,32,33) | N,N-dibenzyl-3-(3-methyl-2H-indazol-5-yl)-5-piperazin-1-yl-1,2,4-triazin-6-amine |
| 29134585 | InChI=1S/C28H23FN4O3/c1-36-23-14-17(8-11-22(23)34)27-24-25(16-6-9-19(29)10-7-16)31-32-26(24)28(35)33(27)13-12-18-15-30-21-5-3-2-4-20(18)21/h2-11,14-15,27,30,34H,12-13H2,1H3,(H,31,32)/t27-/m0/s1 | (4S)-3-(4-fluorophenyl)-4-(4-hydroxy-3-methoxyphenyl)-5-[2-(1H-indol-3-yl)ethyl]-1,4-dihydropyrrolo[3,4-c]pyrazol-6-one |
| 122685373 | InChI=1S/C23H23N7O/c1-14-10-25-13-18-20(14)22(26-11-15-6-3-2-4-7-15)29-23(28-18)30-19-9-5-8-16(21(24)31)17(19)12-27-30/h2-9,12,14,25H,10-11,13H2,1H3,(H2,24,31)(H,26,28,29) | 1-[4-(benzylamino)-5-methyl-5,6,7,8-tetrahydropyrido[3,4-d]pyrimidin-2-yl]indazole-4-carboxamide |
| 57037399 | InChI=1S/C27H37N3O3/c1-4-24(25(28)32)29-26(33)23(20-9-6-5-7-10-20)13-15-30-16-14-27(3,19(2)18-30)21-11-8-12-22(31)17-21/h5-12,17,19,23-24,31H,4,13-16,18H2,1-3H3,(H2,28,32)(H,29,33) | N-(1-amino-1-oxobutan-2-yl)-4-[4-(3-hydroxyphenyl)-3,4-dimethylpiperidin-1-yl]-2-phenylbutanamide |
| 67070056 | InChI=1S/C24H24N2O4S/c1-31(29,30)26-21-8-6-17(7-9-21)4-5-18-13-19(22-3-2-12-25-23(22)28)15-20(14-18)24(16-27)10-11-24/h2-9,12-15,26-27H,10- | N-[4-[(E)-2-[3-[1-(hydroxymethyl)cyclopropyl]-5-(2-oxo-1H-pyridin-3-yl)phenyl]ethenyl]phenyl]methanesulfonamide |

TABLE 2-continued

LIST OF WITHAFERIN A ANALOGS AND DERIVATIVES BASED ON SIMILARITY

| | | |
|---|---|---|
| | 11,16H2,1H3,(H,25,28)/b5-4+ | |
| 68210132 | InChI=1S/C30H36N6O2/c1-18(2)36-17-20(4)28-24(29)37)33-16-25-19(3)12-21(5)34-30(25)38)13-23(14-26(28)36)22-6-7-32-27(15-22)35-10-8-31-9-11-35/h6-7,12-15,17-18,31H,8-11,16H2,1-5H3,(H,33,37)(H,34,38) | N-[(4,6-dimethyl-2-oxo-1H-pyridin-3-yl)methyl]-3-methyl-6-(2-piperazin-1-ylpyridin-4-yl)-1-propan-2-ylindole-4-carboxamide |
| 68516837 | InChI=1S/C22H18FN7O3/c1-12-17-16(6-9-25-18(17)29-28-12)33-21-26-10-15(11-27-21)30(14-4-2-13(23)3-5-14)20(32)22(7-8-22)19(24)31/h2-6,9-11H,7-8H2,1H3,(H2,24,31)(H,25,28,29) | 1-N'-(4-fluorophenyl)-1-N'-[2-[(3-methyl-2H-pyrazolo[3,4-b]pyridin-4-yl)oxy]pyrimidin-5-yl]cyclopropane-1,1-dicarboxamide |
| 44488135 | InChI=1S/C30H37N5O4/c1-21-17-35(22(2)20-36)29(37)16-24-15-26(33-30(38)32-25-7-5-4-6-8-25)9-10-27(24)39-28(21)19-34(3)18-23-11-13-31-14-12-23/h4-15,21-22,28,36H,16-20H2,1-3H3,(H2,32,33,38)/t21-,22-,28+/m1/s1 | 1-[(2R,3R)-5-[(2R)-1-hydroxypropan-2-yl]-3-methyl-2-[[methyl(pyridin-4-ylmethyl)amino]methyl]-6-oxo-2,3,4,7-tetrahydro-1,5-benzoxazonin-9-yl]-3-phenylurea |
| 68688918 | InChI=1S/C26H23F2N5O4/c27-16-2-4-17(5-3-16)33(24(35)26(9-10-26)23(29)34)18-6-7-21(20(28)14-18)37-19-8-11-30-22(15-19)31-25(36)32-12-1-13-32/h2-8,11,14-15H,1,9-10,12-13H2,(H2,29,34)(H,30,31,36) | 1-N'-[4-[2-(azetidine-1-carbonylamino)pyridin-4-yl]oxy-3-fluoropbenyl]-1-N'-(4-fluorophenyl)cyclopropane-1,1-dicarboxamide |
| 265237 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-,21+,23-,24+,26+,27-,28+/m0/s1 | NA |
| 118701146 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16?,18+,19-,20-,21?,23-,24+,26+,27-,28+/m0/s1 | NA |
| 102357982 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-, | NA |

TABLE 2-continued

LIST OF WITHAFERIN A ANALOGS AND DERIVATIVES BASED ON SIMILARITY

| | | |
|---|---|---|
| | 21?,23+,24+,26+,27-,28+/m0/s1 | |
| 90670450 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-,21+,23+,24+,26+,27-,28+/m0/s1 | NA |
| 73707417 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15?,16-,18-,19-,20?,21+,23+,24-,26+,27-,28+/m1/s1 | NA |
| 71772576 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18?,19-,20-,21+,23-,24+,26?,27-,28+/m0/s1 | NA |
| 58443792 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16?,18?,19?,20?,21?,23+,24+,26+,27-,28+/m0/s1 | NA |
| 57519534 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20+,21+,23-,24+,26+,27-,28+/m0/s1 | NA |
| 50990201 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-,21?,23-,24+,26+,27-,28+/m0/s1 | NA |
| 49864510 | InChI=1S/C28H38O6/c1-14-11-21(33-25(32)17(14)13- | NA |

TABLE 2-continued

LIST OF WITHAFERIN A ANALOGS AND DERIVATIVES BASED ON SIMILARITY

| | | |
|---|---|---|
| | 29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-,21-,23-,24+,26+,27-,28+/m0/s1 | |
| 46200067 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16?,18?,19?,20?,21?,23-,24+,26+,27-,28?/m0/s1 | NA |
| 45489105 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20?,21+,23-,24+,26+,27-,28+/m0/s1 | NA |
| 45110486 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16?,18?,19?,20?,21?,23+,24+,26+,27-,28?/m0/s1 | NA |
| 44411346 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16?,18?,19?,20?,21?,23-,24+,26+,27-,28+/m0/s1 | NA |
| 16760705 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19?,20?,21+,23-,24+,26+,27-,28+/m0/s1 | NA |
| 16745397 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1- | NA |

TABLE 2-continued

LIST OF WITHAFERIN A ANALOGS AND DERIVATIVES BASED ON SIMILARITY

| | | |
|---|---|---|
| | 4H3/t15-,16?,18?,19-,20?,21?,23-,24+,26+,27-,28+/m0/s1 | |
| 9825988 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15?,16-,18+,19-,20-,21?,23-,24+,26+,27-,28+/m0/s1 | NA |
| 5315320 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18?,19?,20?,21?,23?,24+,26+,27-,28+/m0/s1 | NA |
| 5287384 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18?,19?,20-,21+,23-,24+,26+,27-,28+/m0/s1 | NA |
| 580064 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3| NA |
| 118701104 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16?,17-,18-,19-,21-,22?,23+,25-,26-,27+,28+/m0/s1 | NA |
| 118103569 | InChI=1S/C29H40O6/c1-15-12-22(34-26(33)19(15)14-30)16(2)11-17-5-6-20-18-13-25-29(35-25)24(32)8-7-23(31)28(29,4)21(18)9-10-27(17,20)3/h7-8,16-18,20-22,24-25,30,32H,5-6,9-14H2,1-4H3/t16-,17?,18-,20-,21-,22+,24-,25+,27+,28-,29+/m0/s1 | NA |
| 102435651 | InChI=1S/C28H38O5/c1-14-12-21(32-25(31)15(14)2)16(3)18-6-7-19-17-13-24-28(33-24)23(30)9-8- | NA |

TABLE 2-continued

LIST OF WITHAFERIN A ANALOGS AND DERIVATIVES BASED ON SIMILARITY

| | | |
|---|---|---|
| | 22(29)27(28,5)20(17)10-11-26(18,19)4/h8-9,16-21,23-24,30H,6-7,10-13H2,1-5H3/t16-,17-,18+,19-,20-,21?,23-,24+,26+,27-,28+/m0/s1 | |
| 102357984 | InChI=1S/C30H40O7/c1-15-12-23(36-27(34)19(15)14-35-17(3)31)16(2)20-6-7-21-18-13-26-30(37-26)25(33)9-8-24(32)29(30,5)22(18)10-11-28(20,21)4/h8-9,16,18,20-23,25-26,33H,6-7,10-14H2,1-5H3/t16-,18-,20+,21-,22-,23?,25+,26+,28+,29-,30+/m0/s1 | NA |
| 102357983 | InChI=1S/C30H40O7/c1-15-12-23(36-27(34)19(15)14-35-17(3)31)16(2)20-6-7-21-18-13-26-30(37-26)25(33)9-8-24(32)29(30,5)22(18)10-11-28(20,21)4/h8-9,16,18,20-23,25-26,33H,6-7,10-14H2,1-5H3/t16-,18-,20+,21-,22-,23?,25-,26+,28+,29-,30+/m0/s1 | NA |
| 99576035 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16-,17+,18-,19+,20+,21-,23+,24-,26-,27+,28+/m1/s1 | NA |
| 99576034 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16-,17+,18-,19+,20+,21+,23+,24-,26-,27+,28+/m1/s1 | NA |
| 99576033 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16-,17-,18+,19-,20-,21+,23-,24+,26+,27-,28+/m0/s1 | NA |
| 99576032 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16-,17-,18+,19-,20-,21-,23-,24+,26+,27-,28-/m0/s1 | NA |

TABLE 2-continued

LIST OF WITHAFERIN A ANALOGS AND DERIVATIVES BASED ON SIMILARITY

| | | |
|---|---|---|
| 90670454 | InChI=1S/C30H40O7/c1-15-12-23(36-27(34)19(15)14-35-17(3)31)16(2)20-6-7-21-18-13-26-30(37-26)25(33)9-8-24(32)29(30,5)22(18)10-11-28(20,21)4/h8-9,16,18,20-23,25-26,33H,6-7,10-14H2,1-5H3/t16-,18-,20+,21-,22-,23+,25+,26+,28+,29-,30+/m0/s1 | NA |
| 88949019 | InChI=1S/C27H36O5/c1-13-11-21(31-25(30)14(13)2)15(3)18-5-6-19-17-12-23-27(32-23)22(29)8-7-20(28)24(27)16(17)9-10-26(18,19)4/h7-8,15-19,21-24,29H,5-6,9-12H2,1-4H3/t15-,16?,17+,18+,19-,21-,22-,23+,24?,26+,27+/m0/s1 | NA |
| 88949008 | InChI=1S/C27H36O6/c1-13-10-21(32-25(31)17(13)12-28)14(2)18-4-5-19-16-11-23-27(33-23)22(30)7-6-20(29)24(27)15(16)8-9-26(18,19)3/h6-7,14-16,18-19,21-24,28,30H,4-5,8-12H2,1-3H3/t14-,15-,16+,18+,19-,21+,22-,23+,24?,26+,27+/m0/s1 | NA |
| 88949005 | InChI=1S/C27H36O6/c1-13-10-21(32-25(31)17(13)12-28)14(2)18-4-5-19-16-11-23-27(33-23)22(30)7-6-20(29)24(27)15(16)8-9-26(18,19)3/h6-7,14-16,18-19,21-24,28,30H,4-5,8-12H2,1-3H3/t14-,15-,16+,18?,19-,21+,22-,23+,24?,26+,27+/m0/s1 | NA |
| 88948987 | InChI=1S/C27H36O5/c1-13-11-21(31-25(30)14(13)2)15(3)18-5-6-19-17-12-23-27(32-23)22(29)8-7-20(28)24(27)16(17)9-10-26(18,19)4/h7-8,15-19,21-24,29H,5-6,9-12H2,1-4H3/t15-,16-,17+,18?,19-,21+,22-,23+,24?,26+,27+/m0/s1 | NA |
| 76787555 | InChI=1S/C29H40O5/c1-6-17-15(2)13-22(33-26(17)32)16(3)19-7-8-20-18-14-25-29(34-25)24(31)10-9-23(30)28(29,5)21(18)11-12-27(19,20)4/h9-10,16,18-22,24-25,31H,6-8,11-14H2,1-5H3 | NA |
| 75093323 | InChI=1S/C30H40O7/c1-15-12-23(36-27(34)19(15)14-35-17(3)31)16(2)20-6-7-21-18-13-26-30(37-26)25(33)9-8-24(32)29(30,5)22(18)10-11-28(20,21)4/h8-9,16,18,20-23,25- | NA |

TABLE 2-continued

LIST OF WITHAFERIN A ANALOGS AND DERIVATIVES BASED ON SIMILARITY

| | | |
|---|---|---|
| | 26,33H,6-7,10-14H2,1-5H3 | |
| 74039188 | InChI=1S/C28H38O7/c1-14-11-22(34-24(32)16(14)13-29)27(4,33)19-6-5-17-15-12-23-28(35-23)21(31)8-7-20(30)26(28,3)18(15)9-10-25(17,19)2/h7-8,15,17-19,21-23,29,31,33H,5-6,9-13H2,1-4H3 | NA |
| 66575620 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16-,17?,18+,19?,20?,21+,23-,24+,26+,27-,28+/m0/s1 | NA |
| 58443799 | InChI=1S/C30H40O7/c1-15-12-23(36-27(34)19(15)14-35-17(3)31)16(2)20-6-7-21-18-13-26-30(37-26)25(33)9-8-24(32)29(30,5)22(18)10-11-28(20,21)4/h8-9,16,18,20-23,25-26,33H,6-7,10-14H2,1-5H3/t16-,18?,20?,21?,22?,23?,25+,26+,28+,29-,30+/m0/s1 | NA |
| 58443790 | InChI=1S/C30H40O7/c1-15-12-23(36-27(34)19(15)14-35-17(3)31)16(2)20-6-7-21-18-13-26-30(37-26)25(33)9-8-24(32)29(30,5)22(18)10-11-28(20,21)4/h8-9,16,18,20-23,25-26,33H,6-7,10-14H2,1-5H3/t16-,18?,20?,21?,22?,23?,25-,26+,28+,29-,30+/m0/s1 | NA |
| 58443786 | InChI=1S/C29H40O5/c1-6-17-15(2)13-22(33-26(17)32)16(3)19-7-8-20-18-14-25-29(34-25)24(31)10-9-23(30)28(29,5)21(18)11-12-27(19,20)4/h9-10,16,18-22,24-25,31H,6-8,11-14H2,1-5H3/t16-,18?,19?,20?,21?,22?,24+,25+,27+,28-,29+/m0/s1 | NA |
| 57328756 | InChI=1S/C30H40O7/c1-15-12-23(36-27(34)19(15)14-35-17(3)31)16(2)20-6-7-21-18-13-26-30(37-26)25(33)9-8-24(32)29(30,5)22(18)10-11-28(20,21)4/h8-9,16,18,20-23,25-26,33H,6-7,10-14H2,1-5H3/t16-,18-,20+,21-,22-,23+,25-,26+,28+,29-,30+/m0/s1 | NA |
| 53477765 | InChI=1S/C28H38O6/c1-14-12-22(33- | NA |

TABLE 2-continued

LIST OF WITHAFERIN A ANALOGS AND DERIVATIVES BASED ON SIMILARITY

| | | |
|---|---|---|
| | 24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16-,17-,18-,19-,21-,22+,23+,25-,26-,27+,28?/m0/s1 | |
| 49864537 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16-,17-,18-,19-,21-,22-,23+,25-,26-,27+,28+/m0/s1 | NA |
| 45111761 | InChI=1S/C30H40O7/c1-15-12-23(36-27(34)19(15)14-35-17(3)31)16(2)20-6-7-21-18-13-26-30(37-26)25(33)9-8-24(32)29(30,5)22(18)10-11-28(20,21)4/h8-9,16,18,20-23,25-26,33H,6-7,10-14H2,1-5H3/t16-,18?,20?,21?,22?,23?,25+,26+,28+,29-,30?/m0/s1 | NA |
| 23266163 | InChI=1S/C28H38O7/c1-14-11-22(34-24(32)16(14)13-29)27(4,33)19-6-5-17-15-12-23-28(35-23)21(31)8-7-20(30)26(28,3)18(15)9-10-25(17,19)2/h7-8,15,17-19,21-23,29,31,33H,5-6,9-13H2,1-4H3/t15-,17-,18-,19-,21-,22+,23+,25-,26-,27+,28+/m0/s1 | NA |
| 23266155 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16-,17-,18+,19-,20-,21+,23-,24+,26+,27-,28+/m0/s1 | NA |
| 10163222 | InChI=1S/C28H38O7/c1-14-11-22(34-24(32)16(14)13-29)27(4,33)19-6-5-17-15-12-23-28(35-23)21(31)8-7-20(30)26(28,3)18(15)9-10-25(17,19)2/h7-8,15,17-19,21-23,29,31,33H,5-6,9-13H2,1-4H3/t15?,17?,18?,19?,21-,22?,23+,25-,26-,27+,28?/m0/s1 | NA |
| 10161347 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16?,17-, | NA |

TABLE 2-continued

LIST OF WITHAFERIN A ANALOGS AND DERIVATIVES BASED ON SIMILARITY

| ID | InChI | |
|---|---|---|
| | 18+,19-,20-,21?,23-,24+,26+,27-,28+/m0/s1 | |
| 9825989 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16?,17?,18?,19?,21-,22?,23+,25-,26-,27+,28?/m0/s1 | NA |
| 5315323 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16-,17-,18?,19?,20?,21?,23?,24+,26+,27-,28+/m0/s1 | NA |
| 5287385 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16-,17?,18-,19?,21-,22+,23+,25-,26-,27+,28+/m0/s1 | NA |
| 301758 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3 | NA |
| 301754 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3 | NA |
| 161671 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16-,17-,18-,19-,21-,22+,23+,25-,26-,27+,28+/m0/s1 | NA |
| 91799372 | InChI=1S/C29H40O6/c1-15-12-22(34-26(32)18(15)14-30)16(2)19-6-7-20-17-13-25-29(35-25)24(33-5)9-8-23(31)28(29,4)21(17)10-11-27(19,20)3/h8-9,16-17,19-22,24-25,30H,6-7,10-14H2,1-5H3/t16-,17-,19+,20-,21-,22+,24-,25+,27+,28-,29+/m0/s1 | NA |

TABLE 2-continued

LIST OF WITHAFERIN A ANALOGS AND DERIVATIVES BASED ON SIMILARITY

| | | |
|---|---|---|
| 91088392 | InChI=1S/C32H44O7/c1-16(2)31-24-11-12-30(6)22(18(4)25-13-17(3)21(29(36)38-25)15-37-19(5)33)7-8-23(30)20(24)14-28-32(31,39-28)27(35)10-9-26(31)34/h9-10,16,18,20,22-25,27-28,35H,7-8,11-15H2,1-6H3 | NA |
| 90670455 | InChI=1S/C30H40O7/c1-15-12-23(36-27(34)19(15)14-31)16(2)20-6-7-21-18-13-26-30(37-26)25(35-17(3)32)9-8-24(33)29(30,5)22(18)10-11-28(20,21)4/h8-9,16,18,20-23,25-26,31H,6-7,10-14H2,1-5H3/t16-,18-,20+,21-,22-,23+,25+,26+,28+,29-,30+/m0/s1 | NA |
| 90670440 | InChI=1S/C30H40O7/c1-15-12-23(36-27(34)19(15)14-31)16(2)20-6-7-21-18-13-26-30(37-26)25(35-17(3)32)9-8-24(33)29(30,5)22(18)10-11-28(20,21)4/h8-9,16,18,20-23,25-26,31H,6-7,10-14H2,1-5H3/t16-,18-,20+,21-,22-,23+,25+,26+,28+,29-,30+/m0/s1 | NA |
| 88948980 | InChI=1S/C29H38O7/c1-14-11-23(35-27(33)19(14)13-30)15(2)20-5-6-21-18-12-25-29(36-25)24(34-16(3)31)8-7-22(32)26(29)17(18)9-10-28(20,21)4/h7-8,15,17-18,20-21,23-26,30H,5-6,9-13H2,1-4H3/t15-,17?,18+,20+,21-,23+,24-,25+,26?,28+,29+/m0/s1 | NA |
| 88858700 | InChI=1S/C28H38O7/c1-14-10-21(34-25(33)17(14)12-29)15(2)18-4-5-19-16-11-24-28(35-24)23(32)7-6-22(31)27(28,13-30)20(16)8-9-26(18,19)3/h6-7,15-16,18-21,23-24,29-30,32H,4-5,8-13H2,1-3H3/t15-,16-,18?,19-,20-,21+,23-,24+,26+,27-,28+/m0/s1 | NA |
| 88858699 | InChI=1S/C28H38O6/c1-14-11-21(33-25(32)15(14)2)16(3)18-5-6-19-17-12-24-28(34-24)23(31)8-7-22(30)27(28,13-29)20(17)9-10-26(18,19)4/h7-8,16-21,23-24,29,31H,5-6,9-13H2,1-4H3/t16-,17-,18?,19-,20-,21+,23-,24+,26+,27-,28+/m0/s1 | NA |
| 88858695 | InChI=1S/C29H40O6/c1-5-17-15(2)12-22(34-26(17)33)16(3)19-6-7-20-18-13-25-29(35- | NA |

TABLE 2-continued

LIST OF WITHAFERIN A ANALOGS AND DERIVATIVES BASED ON SIMILARITY

| | | |
|---|---|---|
| | 25)24(32)9-8-23(31)28(29,14-30)21(18)10-11-27(19,20)4/h8-9,16,18-22,24-25,30,32H,5-7,10-14H2,1-4H3/t16-,18-,19?,20-,21-,22+,24-,25+,27+,28-,29+/m0/s1 | |
| 76385927 | InChI=1S/C30H40O7/c1-15-12-23(36-27(34)16(15)2)17(3)20-6-7-21-19-13-26-30(37-26)25(33)9-8-24(32)29(30,14-35-18(4)31)22(19)10-11-28(20,21)5/h8-9,17,19-23,25-26,33H,6-7,10-14H2,1-5H3 | NA |
| 76385901 | InChI=1S/C28H38O6/c1-14-11-21(33-25(32)15(14)2)16(3)18-5-6-19-17-12-24-28(34-24)23(31)8-7-22(30)27(28,13-29)20(17)9-10-26(18,19)4/h7-8,16-21,23-24,29,31H,5-6,9-13H2,1-4H3 | NA |
| 76385900 | InChI=1S/C28H38O7/c1-14-10-21(34-25(33)17(14)12-29)15(2)18-4-5-19-16-11-24-28(35-24)23(32)7-6-22(31)27(28,13-30)20(16)8-9-26(18,19)3/h6-7,15-16,18-21,23-24,29-30,32H,4-5,8-13H2,1-3H3 | NA |
| 75093324 | InChI=1S/C30H40O7/c1-15-12-23(36-27(34)19(15)14-31)16(2)20-6-7-21-18-13-26-30(37-26)25(35-17(3)32)9-8-24(33)29(30,5)22(18)10-11-28(20,21)4/h8-9,16,18,20-23,25-26,31H,6-7,10-14H2,1-5H3 | NA |
| 60148726 | InChI=1S/C28H38O7/c1-14-10-21(34-25(33)17(14)12-29)15(2)18-4-5-19-16-11-24-28(35-24)23(32)7-6-22(31)27(28,13-30)20(16)8-9-26(18,19)3/h6-7,15-16,18-21,23-24,29-30,32H,4-5,8-13H2,1-3H3/t15?,16-,18+,19-,20-,21?,23-,24+,26+,27-,28+/m0/s1 | NA |
| 60148725 | InChI=1S/C28H38O6/c1-14-11-21(33-25(32)15(14)2)16(3)18-5-6-19-17-12-24-28(34-24)23(31)8-7-22(30)27(28,13-29)20(17)9-10-26(18,19)4/h7-8,16-21,23-24,29,31H,5-6,9-13H2,1-4H3/t16?,17-,18+,19-,20-,21?,23-,24+,26+,27-,28+/m0/s1 | NA |
| 58443800 | InChI=1S/C30H40O7/c1-15-12-23(36-27(34)19(15)14- | NA |

TABLE 2-continued

LIST OF WITHAFERIN A ANALOGS AND DERIVATIVES BASED ON SIMILARITY

| | | |
|---|---|---|
| | 31)16(2)20-6-7-21-18-13-26-30(37-26)25(35-17(3)32)9-8-24(33)29(30,5)22(18)10-11-28(20,21)4/h8-9,16,18,20-23,25-26,31H,6-7,10-14H2,1-5H3/t16-,18?,20?,21?,22?,23?,25+,26+,28+,29-,30+/m0/s1 | |
| 56649400 | InChI=1S/C30H40O7/c1-15-12-23(36-27(34)16(15)2)17(3)20-6-7-21-19-13-26-30(37-26)25(33)9-8-24(32)29(30,14-35-18(4)31)22(19)10-11-28(20,21)5/h8-9,17,19-23,25-26,33H,6-7,10-14H2,1-5H3/t17-,19-,20+,21-,22-,23+,25-,26+,28+,29-,30+/m0/s1 | NA |
| 56649344 | InChI=1S/C28H38O6/c1-14-11-21(33-25(32)15(14)2)16(3)18-5-6-19-17-12-24-28(34-24)23(31)8-7-22(30)27(28,13-29)20(17)9-10-26(18,19)4/h7-8,16-21,23-24,29,31H,5-6,9-13H2,1-4H3/t16-,17-,18+,19-,20-,21+,23-,24+,26+,27-,28+/m0/s1 | NA |
| 56649343 | InChI=1S/C28H38O7/c1-14-10-21(34-25(33)17(14)12-29)15(2)18-4-5-19-16-11-24-28(35-24)23(32)7-6-22(31)27(28,13-30)20(16)8-9-26(18,19)3/h6-7,15-16,18-21,23-24,29-30,32H,4-5,8-13H2,1-3H3/t15-,16-,18+,19-,20-,21+,23-,24+,26+,27-,28+/m0/s1 | NA |
| 45111762 | InChI=1S/C30H40O7/c1-15-12-23(36-27(34)19(15)14-31)16(2)20-6-7-21-18-13-26-30(37-26)25(35-17(3)32)9-8-24(33)29(30,5)22(18)10-11-28(20,21)4/h8-9,16,18,20-23,25-26,31H,6-7,10-14H2,1-5H3/t16-,18?,20?,21?,22?,23?,25+,26+,28+,29-,30?/m0/s1 | NA |
| 102263665 | InChI=1S/C28H38O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,16-18,20-22,30,32-33H,8-13H2,1-5H3/t16-,17-,18-,20-,21+,22+,24-,25-,26+,27+,28+/m0/s1 | NA |
| 85435491 | InChI=1S/C28H38O7/c1-14-11-20(34-24(32)17(14)13-29)15(2)27(33)10-8-18-16-12-23-28(35-23)22(31)6-5- | NA |

TABLE 2-continued

LIST OF WITHAFERIN A ANALOGS AND DERIVATIVES BASED ON SIMILARITY

| | | |
|---|---|---|
| | 21(30)26(28,4)19(16)7-9-25(18,27)3/h5-6,15-16,18-20,22-23,29,31,33H,7-13H2,1-4H3 | |
| 77145374 | InChI=1S/C28H36O7/c1-13-9-20(34-25(33)16(13)12-29)14(2)24-19(30)11-18-15-10-23-28(35-23)22(32)6-5-21(31)27(28,4)17(15)7-8-26(18,24)3/h5-6,15,17-20,22-23,29-30,32H,7-12H2,1-4H3 | NA |
| 76313669 | InChI=1S/C30H40O8/c1-15-11-23(37-27(35)19(15)13-36-17(3)32)16(2)20-5-6-21-18-12-26-30(38-26)25(34)8-7-24(33)29(30,14-31)22(18)9-10-28(20,21)4/h7-8,16,18,20-23,25-26,31,34H,5-6,9-14H2,1-4H3/t16-,18-,20+,21-,22-,23+,25-,26+,28+,29-,30+/m0/s1 | NA |
| 76309946 | InChI=1S/C30H40O8/c1-15-11-23(37-27(35)19(15)13-31)16(2)20-5-6-21-18-12-26-30(38-26)25(34)8-7-24(33)29(30,14-36-17(3)32)22(18)9-10-28(20,21)4/h7-8,16,18,20-23,25-26,31,34H,5-6,9-14H2,1-4H3/t16-,18-,20+,21-,22-,23+,25-,26+,28+,29-,30+/m0/s1 | NA |
| 75202433 | InChI=1S/C28H38O6/c1-14-12-20(33-24(31)15(14)2)16(3)27(32)11-9-18-17-13-23-28(34-23)22(30)7-6-21(29)26(28,5)19(17)8-10-25(18,27)4/h6-7,16-20,22-23,30,32H,8-13H2,1-5H3/t16-,17?,18?,19?,20-,22+,23-,25+,26+,27+,28-/m1/s1 | NA |
| 75202432 | InChI=1S/C28H38O7/c1-14-11-20(34-24(32)17(14)13-29)15(2)27(33)10-8-18-16-12-23-28(35-23)22(31)6-5-21(30)26(28,4)19(16)7-9-25(18,27)3/h5-6,15-16,18-20,22-23,29,31,33H,7-13H2,1-4H3/t15-,16?,18?,19?,20-,22+,23-,25+,26+,27+,28-/m1/s1 | NA |
| 74039186 | InChI=1S/C28H38O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,16-18,20-22,30,32-33H,8-13H2,1-5H3 | NA |
| 73306656 | InChI=1S/C28H38O6/c1-14-12-20(33-24(31)15(14)2)16(3)27(32) | NA |

TABLE 2-continued

LIST OF WITHAFERIN A ANALOGS AND DERIVATIVES BASED ON SIMILARITY

| | | |
|---|---|---|
| | 11-9-18-17-13-23-28(34-23)22(30)7-6-21(29)26(28,5)19(17)8-10-25(18,27)4/h6-7,16-20,22-23,30,32H,8-13H2,1-5H3 | |
| 66572429 | InChI=1S/C28H36O7/c1-13-9-20(34-25(33)16(13)12-29)14(2)24-19(30)11-18-15-10-23-28(35-23)22(32)6-5-21(31)27(28,4)17(15)7-8-26(18,24)3/h5-6,15,17-20,22-23,29-30,32H,7-12H2,1-4H3/b24-14+/t15-,17+,18+,19+,20-,22+,23-,26+,27+,28-/m1/s1 | NA |
| 23266161 | InChI=1S/C28H38O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,16-18,20-22,30,32-33H,8-13H2,1-5H3/t16-,17-,18-,20-,21+,22+,24-,25-,26-,27+,28+/m0/s1 | NA |
| 21679019 | InChI=1S/C30H40O7/c1-15-13-24(36-26(33)16(15)2)29(6,34)21-8-7-19-18-14-25-30(37-25)23(35-17(3)31)10-9-22(32)28(30,5)20(18)11-12-27(19,21)4/h9-10,18-21,23-25,34H,7-8,11-14H2,1-6H3/t18-,19-,20-,21-,23-,24+,25+,27-,28-,29+,30+/m0/s1 | NA |
| 16680447 | InChI=1S/C28H38O6/c1-14-12-20(33-24(31)15(14)2)16(3)27(32)11-9-18-17-13-23-28(34-23)22(30)7-6-21(29)26(28,5)19(17)8-10-25(18,27)4/h6-7,16-20,22-23,30,32H,8-13H2,1-5H3/t16-,17+,18+,19+,20-,22+,23-,25+,26+,27+,28-/m1/s1 | NA |
| 13743204 | InChI=1S/C30H40O7/c1-15-13-24(36-26(33)16(15)2)29(6,34)21-8-7-19-18-14-25-30(37-25)23(35-17(3)31)10-9-22(32)28(30,5)20(18)11-12-27(19,21)4/h9-10,18-21,23-25,34H,7-8,11-14H2,1-6H3 | NA |
| 12147447 | InChI=1S/C28H38O7/c1-14-11-20(34-24(32)17(14)13-29)15(2)27(33)10-8-18-16-12-23-28(35-23)22(31)6-5-21(30)26(28,4)19(16)7-9-25(18,27)3/h5-6,15-16,18-20,22-23,29,31,33H,7-13H2,1-4H3/t15-,16+,18+,19+,20-,22+,23-,25+,26+,27+,28-/m1/s1 | NA |
| 10277877 | InChI=1S/C28H38O7/c1-14-12-21(34- | NA |

TABLE 2-continued

LIST OF WITHAFERIN A ANALOGS AND DERIVATIVES BASED ON SIMILARITY

| | | |
|---|---|---|
| | 23(31)15(14)2)26(5,32)27(33)11-9-17-16-13-22-28(35-22)20(30)7-6-19(29)25(28,4)18(16)8-10-24(17,27)3/h6-7,16-18,20-22,30,32-33H,8-13H2,1-5H3/t16?,17?,18?,20-,21?,22+,24-,25-,26-,27-,28?/m0/s1 | |
| 101911601 | InChI=1S/C28H36O6/c1-14-10-21(33-25(32)17(14)13-29)15(2)24-20(30)12-19-16-11-23-28(34-23)8-5-6-22(31)27(28,4)18(16)7-9-26(19,24)3/h5-6,15-16,18-19,21,23-24,29H,7-13H2,1-4H3/t15-,16-,18+,19+,21-,23-,24+,26+,27+,28-/m1/s1 | NA |
| 101664554 | InChI=1S/C30H40O7/c1-14-11-21(36-27(34)15(14)2)16(3)26-22(35-17(4)31)13-20-18-12-25-30(37-25)24(33)8-7-23(32)29(30,6)19(18)9-10-28(20,26)5/h7-8,16,18-22,24-26,33H,9-13H2,1-6H3/t16-,18-,19+,20+,21-,22-,24+,25-,26+,28+,29+,30-/m1/s1 | NA |
| 89809195 | InChI=1S/C28H40O7/c1-14(17(13-29)25(33)34)11-21(30)15(2)18-5-6-19-16-12-24-28(35-24)23(32)8-7-22(31)27(28,4)20(16)9-10-26(18,19)3/h7-8,15-16,18-21,23-24,29-30,32H,5-6,9-13H2,1-4H3,(H,33,34)/b17-14+/t15-,16-,18+,19-,20-,21?,23?,24?,26+,27-,28?/m0/s1 | NA |
| 89255535 | InChI=1S/C28H38O5/c1-15-13-22(32-24(30)16(15)2)27(5,31)20-9-8-18-17-14-23-28(33-23)11-6-7-21(29)26(28,4)19(17)10-12-25(18,20)3/h6-7,17-20,22-23,31H,8-14H2,1-5H3/t17?,18?,19?,20?,22?,23-,25+,26+,27-,28-/m1/s1 | NA |
| 89245303 | InChI=1S/C28H38O5/c1-15-13-22(32-24(30)16(15)2)27(5,31)20-9-8-18-17-14-23-28(33-23)11-6-7-21(29)26(28,4)19(17)10-12-25(18,20)3/h6-7,17-20,22-23,31H,8-14H2,1-5H3/t17?,18?,19?,20-,22?,23+,25-,26-,27+,28+/m0/s1 | NA |
| 88858701 | InChI=1S/C30H40O7/c1-15-12-23(36-27(34)16(15)2)17(3)20-6-7-21-19-13-26-30(37-26)25(35-18(4)32)9-8-24(33)29(30,14-31)22(19)10-11-28(20,21)5/h8-9,17,19-23,25-26,31H,6-7,10- | NA |

TABLE 2-continued

LIST OF WITHAFERIN A ANALOGS AND DERIVATIVES BASED ON SIMILARITY

| | | |
|---|---|---|
| | 14H2,1-5H3/t17-,19-,<br>20+,21-,22-,23+,25-,<br>26+,28+,29-,30+/m0/s1 | |
| 88858696 | InChI=1S/C31H42O7/c1-<br>6-19-16(2)13-24(37-<br>28(19)35)17(3)21-7-8-<br>22-20-14-27-31(38-<br>27)26(36-18(4)33)10-9-<br>25(34)30(31,15-<br>32)23(20)11-12-<br>29(21,22)5/h9-10,17,20-<br>24,26-27,32H,6-8,11-<br>15H2,1-5H3/t17-,20-,<br>21?,22-,23-,24+,26-,<br>27+,29+,30-,31+/m0/s1 | NA |
| 78172794 | InChI=1S/C28H36O6/c1-<br>14-11-21(33-<br>25(32)17(14)13-<br>29)15(2)18-5-6-19-16-<br>12-24-28(34-24)23(31)8-<br>7-22(30)27(28,4)20(16)9-<br>10-26(18,19)3/h7-<br>8,13,15-16,18-21,23-<br>24,31H,5-6,9-12H2,1-<br>4H3 | NA |
| 76320888 | InChI=1S/C30H40O8/c1-<br>15-11-23(37-<br>27(35)19(15)13-<br>31)16(2)20-5-6-21-18-<br>12-26-30(38-26)25(36-<br>17(3)33)8-7-<br>24(34)29(30,14-<br>32)22(18)9-10-<br>28(20,21)4/h7-<br>8,16,18,20-23,25-26,31-<br>32H,5-6,9-14H2,1-<br>4H3/t16-,18-,20+,21-,22-,<br>23+,25-,26+,28+,29-,<br>30+/m0/s1 | NA |
| 73820037 | InChI=1S/C28H38O6/c1-<br>13-10-20(33-<br>25(32)14(13)2)15(3)24-<br>19(29)12-18-16-11-23-<br>28(34-23)22(31)7-6-<br>21(30)27(28,5)17(16)8-9-<br>26(18,24)4/h6-7,15-<br>20,22-24,29,31H,8-<br>12H2,1-5H3 | NA |
| 73211831 | InChI=1S/C32H42O9/c1-<br>16-12-25(40-<br>29(37)21(16)14-38-<br>18(3)33)17(2)22-6-7-23-<br>20-13-28-32(41-<br>28)27(36)9-8-<br>26(35)31(32,15-39-<br>19(4)34)24(20)10-11-<br>30(22,23)5/h8-<br>9,17,20,22-25,27-<br>28,36H,6-7,10-15H2,1-<br>5H3/t17-,20-,22+,23-,24-,<br>25+,27-,28+,30+,31-,<br>32+/m0/s1 | NA |
| 73106251 | InChI=1S/C28H38O6/c1-<br>14-11-21(33-<br>25(32)15(14)2)16(3)18-<br>5-6-20-17-12-24-28(34-<br>24)23(31)8-7-<br>22(30)26(28,4)19(17)9-<br>10-27(18,20)13-29/h7-<br>8,16-21,23-24,29,31H,5-<br>6,9-13H2,1-4H3 | NA |
| 57369720 | InChI=1S/C28H38O6/c1-<br>14-16(13-33-<br>25(14)32)11-<br>21(29)15(2)18-5-6-19-<br>17-12-24-28(34-<br>24)23(31)8-7-<br>22(30)27(28,4)20(17)9- | NA |

TABLE 2-continued

LIST OF WITHAFERIN A ANALOGS AND DERIVATIVES BASED ON SIMILARITY

| | | |
|---|---|---|
| | 10-26(18,19)3/h7-8,15,17-21,23-24,29,31H,5-6,9-13H2,1-4H3 | |
| 54606507 | InChI=1S/C30H40O7/c1-15-12-23(36-27(34)16(15)2)17(3)20-6-7-22-19-13-26-30(37-26)25(33)9-8-24(32)28(30,5)21(19)10-11-29(20,22)14-35-18(4)31/h8-9,17,19-23,25-26,33H,6-7,10-14H2,1-5H3/t17-,19+,20+,21-,22-,23+,25-,26+,28-,29-,30+/m0/s1 | NA |
| 44566999 | InChI=1S/C28H38O6/c1-13-10-20(33-25(32)14(13)2)15(3)24-19(29)12-18-16-11-23-28(34-23)22(31)7-6-21(30)27(28,5)17(16)8-9-26(18,24)4/h6-7,15-20,22-24,29,31H,8-12H2,1-5H3/t15-,16-,17+,18+,19+,20-,22+,23-,24+,26+,27+,28-/m1/s1 | NA |
| 21670294 | InChI=1S/C28H38O6/c1-14-11-21(33-25(32)15(14)2)16(3)18-5-6-20-17-12-24-28(34-24)23(31)8-7-22(30)26(28,4)19(17)9-10-27(18,20)13-29/h7-8,16-21,23-24,29,31H,5-6,9-13H2,1-4H3/t16-,17+,18+,19-,20-,21+,23-,24+,26-,27-,28+/m0/s1 | NA |
| 21670293 | InChI=1S/C28H38O6/c1-13-10-20(33-25(32)14(13)2)15(3)24-19(29)12-18-16-11-23-28(34-23)22(31)7-6-21(30)27(28,5)17(16)8-9-26(18,24)4/h6-7,15-20,22-24,29,31H,8-12H2,1-5H3/t15-,16-,17+,18+,19-,20-,22+,23-,24+,26+,27+,28-/m1/s1 | NA |
| 12304656 | InChI=1S/C28H38O5/c1-15-12-22(32-25(31)18(15)14-29)16(2)19-7-8-20-17-13-24-28(33-24)10-5-6-23(30)27(28,4)21(17)9-11-26(19,20)3/h5-6,16-17,19-22,24,29H,7-14H2,1-4H3/t16-,17-,19+,20-,21-,22+,24+,26+,27-,28+/m0/s1 | NA |
| 11798584 | InChI=1S/C28H38O6/c1-14-11-21(33-25(32)15(14)2)16(3)18-5-6-20-17-12-24-28(34-24)23(31)8-7-22(30)26(28,4)19(17)9-10-27(18,20)13-29/h7-8,16-21,23-24,29,31H,5-6,9-13H2,1-4H3/t16-,17+,18+,19-,20-,21?,23-,24+,26-,27-,28+/m0/s1 | NA |
| 10814230 | InChI=1S/C28H38O6/c1-13-10-20(33-25(32)14(13)2)15(3)24-19(29)12-18-16-11-23-28(34-23)22(31)7-6-21(30)27(28,5)17(16)8-9- | NA |

TABLE 2-continued

LIST OF WITHAFERIN A ANALOGS AND DERIVATIVES BASED ON SIMILARITY

| | | |
|---|---|---|
| | 26(18,24)4/h6-7,15-20,22-24,29,31H,8-12H2,1-5H3/t15-,16-,17+,18+,19-,20?,22+,23-,24+,26+,27+,28-/m1/s1 | |
| 10321754 | InChI=1S/C28H38O5/c1-15-12-22(32-25(31)18(15)14-29)16(2)19-7-8-20-17-13-24-28(33-24)10-5-6-23(30)27(28,4)21(17)9-11-26(19,20)3/h5-6,16-17,19-22,24,29H,7-14H2,1-4H3/t16?,17-,19+,20-,21-,22?,24+,26+,27-,28+/m0/s1 | NA |
| 421514 | InChI=1S/C30H40O7/c1-15-12-23(36-27(34)16(15)2)17(3)20-6-7-22-19-13-26-30(37-26)25(33)9-8-24(32)28(30,5)21(19)10-11-29(20,22)14-35-18(4)31/h8-9,17,19-23,25-26,33H,6-7,10-14H2,1-5H3 | NA |
| 268945 | InChI=1S/C28H38O5/c1-15-12-22(32-25(31)18(15)14-29)16(2)19-7-8-20-17-13-24-28(33-24)10-5-6-23(30)27(28,4)21(17)9-11-26(19,20)3/h5-6,16-17,19-22,24,29H,7-14H2,1-4H3 | NA |
| 176114 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h7-8,13,15-16,18-21,23-24,31H,5-6,9-12H2,1-4H3/t15-,16-,18+,19-,20-,21+,23-,24+,26+,27-,28+/m0/s1 | NA |
| 21199 | InChI=1S/C28H38O6/c1-14-16(13-33-25(14)32)11-21(29)15(2)18-5-6-19-17-12-24-28(34-24)23(31)8-7-22(30)27(28,4)20(17)9-10-26(18,19)3/h7-8,15,17-21,23-24,29,31H,5-6,9-13H2,1-4H3/t15-,17?,18?,19?,20?,21-,23+,24-,26?,27?,28-/m1/s1 | NA |
| 101712447 | InChI=1S/C28H38O6/c1-15-11-22(33-25(32)18(15)13-29)16(2)19-6-7-20-17-12-24-28(34-24)9-4-5-23(31)27(28,14-30)21(17)8-10-26(19,20)3/h4-5,16-17,19-22,24,29-30H,6-14H2,1-3H3/t16-,17-,19+,20-,21-,22+,24+,26+,27-,28+/m0/s1 | NA |
| 101379930 | InChI=1S/C28H36O5/c1-14-12-21(32-25(31)15(14)2)16(3)18- | NA |

TABLE 2-continued

LIST OF WITHAFERIN A ANALOGS AND DERIVATIVES BASED ON SIMILARITY

| | | |
|---|---|---|
| | 6-7-19-17-13-24-28(33-24)23(30)9-8-22(29)27(28,5)20(17)10-11-26(18,19)4/h6,8-9,16-17,19-21,23-24,30H,7,10-13H2,1-5H3/t16-,17-,19-,20-,21?,23-,24+,26+,27-,28+/m0/s1 | |
| 91522203 | InChI=1S/C29H36O6/c1-14-11-21(34-25(33)17(14)13-30)15(2)18-5-6-19-20-12-24-29(35-24)23(32)8-7-22(31)28(29)16(3)27(20,28)10-9-26(18,19)4/h7-8,15,18-21,23-24,30,32H,3,5-6,9-13H2,1-2,4H3 | NA |
| 91379801 | InChI=1S/C29H38O6/c1-14-11-21(34-25(33)17(14)13-30)15(2)18-5-6-19-20-12-24-29(35-24)23(32)8-7-22(31)28(29)16(3)27(20,28)10-9-26(18,19)4/h7-8,15-16,18-21,23-24,30,32H,5-6,9-13H2,1-4H3 | NA |
| 90785396 | InChI=1S/C31H40O7/c1-15-12-23(37-27(35)19(15)14-36-18(4)32)16(2)20-6-7-21-22-13-26-31(38-26)25(34)9-8-24(33)30(31)17(3)29(22,30)11-10-28(20,21)5/h8-9,16-17,20-23,25-26,34H,6-7,10-14H2,1-5H3 | NA |
| 90733653 | InChI=1S/C30H40O5/c1-6-18-15(2)13-22(34-26(18)33)16(3)19-7-8-20-21-14-25-30(35-25)24(32)10-9-23(31)29(30)17(4)28(21,29)12-11-27(19,20)5/h9-10,16-17,19-22,24-25,32H,6-8,11-14H2,1-5H3 | NA |
| 89809194 | InChI=1S/C28H40O7/c1-14(13-29)16(25(33)34)11-21(30)15(2)18-5-6-19-17-12-24-28(35-24)23(32)8-7-22(31)27(28,4)20(17)9-10-26(18,19)3/h7-8,15,17-21,23-24,29-30,32H,5-6,9-13H2,1-4H3,(H,33,34)/t15-,17-,18+,19-,20-,21?,23?,24?,26+,27-,28?/m0/s1 | NA |
| 89409052 | InChI=1S/C28H38O6/c1-15-13-21(33-23(30)16(15)2)26(5,31)28(32)12-9-18-17-14-22-27(34-22)10-6-7-20(29)25(27,4)19(17)8-11-24(18,28)3/h6-7,17-19,21-22,31-32H,8-14H2,1-5H3/t17?,18?,19?,21?,22-,24+,25+,26+,27-,28+/m1/s1 | NA |

TABLE 2-continued

LIST OF WITHAFERIN A ANALOGS AND DERIVATIVES BASED ON SIMILARITY

| | | |
|---|---|---|
| 89092202 | InChI=1S/C28H36O6/c1-14-10-20(33-24(32)16(14)12-29)15(2)17-4-5-18-19-11-23-28(34-23)22(31)7-6-21(30)27(28)13-26(19,27)9-8-25(17,18)3/h6-7,15,17-20,22-23,29,31H,4-5,8-13H2,1-3H3/t15-,17?,18?,19?,20?,22+,23+,25+,26?,27+,28+/m0/s1 | NA |
| 85218520 | InChI=1S/C28H38O6/c1-5-11-22(33-25(32)18(15)13-29)16(2)19-6-7-20-17-12-24-28(34-24)9-4-5-23(31)27(28,14-30)21(17)8-10-26(19,20)3/h4-5,16-17,19-22,24,29-30H,6-14H2,1-3H3 | NA |
| 77913313 | InChI=1S/C28H36O5/c1-14-12-21(32-25(31)15(14)2)16(3)18-6-7-19-17-13-24-28(33-24)23(30)9-8-22(29)27(28,5)20(17)10-11-26(18,19)4/h7-9,16-18,20-21,23-24,30H,6,10-13H2,1-5H3 | NA |
| 77913312 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h5,7-8,15-16,19-21,23-24,29,31H,6,9-13H2,1-4H3 | NA |
| 76459879 | InChI=1S/C28H38O7/c1-13-9-20(34-25(33)16(13)12-29)14(2)17-5-6-18-15-10-23-28(35-23)22(32)8-7-21(31)27(28,4)24(15)19(30)11-26(17,18)3/h7-8,14-15,17-20,22-24,29-30,32H,5-6,9-12H2,1-4H3 | NA |
| 73823412 | InChI=1S/C32H42O9/c1-16-13-26(40-28(36)20(16)15-38-17(2)33)31(6,37)23-8-7-21-19-14-27-32(41-27)25(39-18(3)34)10-9-24(35)30(32,5)22(19)11-12-29(21,23)4/h9-10,19,21-23,25-27,37H,7-8,11-15H2,1-6H3 | NA |
| 73800274 | InChI=1S/C28H38O7/c1-14-11-22(34-24(32)15(14)2)26(4,33)19-6-5-18-16-12-23-28(35-23)21(31)8-7-20(30)25(28,3)17(16)9-10-27(18,19)13-29/h7-8,16-19,21-23,29,31,33H,5-6,9-13H2,1-4H3 | NA |
| 73797121 | InChI=1S/C28H36O5/c1-14-12-21(32-25(31)15(14)2)16(3)18-6-7-19-17-13-24-28(33-24)23(30)9-8- | NA |

TABLE 2-continued

LIST OF WITHAFERIN A ANALOGS AND DERIVATIVES BASED ON SIMILARITY

| | | |
|---|---|---|
| | 22(29)27(28,5)20(17)10-11-26(18,19)4/h6,8-9,16-17,19-21,23-24,30H,7,10-13H2,1-5H3 | |
| 71477945 | InChI=1S/C28H36O5/c1-14-12-21(32-25(31)15(14)2)16(3)18-6-7-19-17-13-24-28(33-24)23(30)9-8-22(29)27(28,5)20(17)10-11-26(18,19)4/h7-9,16-18,20-21,23-24,30H,6,10-13H2,1-5H3/t16-,17?,18?,20?,21+,23-,24+,26+,27-,28+/m0/s1 | NA |
| 71477799 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h5,7-8,15-16,19-21,23-24,29,31H,6,9-13H2,1-4H3/t15-,16?,19?,20?,21+,23-,24+,26+,27-,28+/m0/s1 | NA |
| 70690365 | InChI=1S/C28H36O5/c1-14-12-21(32-25(31)15(14)2)16(3)18-6-7-19-17-13-24-28(33-24)23(30)9-8-22(29)27(28,5)20(17)10-11-26(18,19)4/h7-9,16-18,20-21,23-24,30H,6,10-13H2,1-5H3/t16-,17-,18+,20-,21+,23-,24+,26+,27-,28+/m0/s1 | NA |
| 70690364 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h5,7-8,15-16,19-21,23-24,29,31H,6,9-13H2,1-4H3/t15-,16-,19-,20-,21+,23-,24+,26+,27-,28+/m0/s1 | NA |
| 56926114 | InChI=1S/C28H38O7/c1-13-9-20(34-25(33)16(13)12-29)14(2)17-5-6-18-15-10-23-28(35-23)22(32)8-7-21(31)27(28,4)24(15)19(30)11-26(17,18)3/h7-8,14-15,17-20,22-24,29-30,32H,5-6,9-12H2,1-4H3/t14-,15-,17+,18-,19-,20+,22-,23+,24+,26+,27+,28+/m0/s1 | NA |
| 21679025 | InChI=1S/C32H42O9/c1-16-13-26(40-28(36)20(16)15-38-17(2)33)31(6,37)23-8-7-21-19-14-27-32(41-27)25(39-18(3)34)10-9-24(35)30(32,5)22(19)11-12-29(21,23)4/h9-10,19,21-23,25-27,37H,7-8,11-15H2,1-6H3/t19-,21-,22-,23-,25-, | NA |

TABLE 2-continued

LIST OF WITHAFERIN A ANALOGS AND DERIVATIVES BASED ON SIMILARITY

| | | |
|---|---|---|
| | 26+,27+,29-,30-,31+,32+/m0/s1 | |
| 21606687 | InChI=1S/C28H38O7/c1-14-11-22(34-24(32)15(14)2)26(4,33)19-6-5-18-16-12-23-28(35-23)21(31)8-7-20(30)25(28,3)17(16)9-10-27(18,19)13-29/h7-8,16-19,21-23,29,31,33H,5-6,9-13H2,1-4H3/t16-,17+,18+,19-,21+,22-,23-,25+,26-,27-,28-/m1/s1 | NA |
| 21574482 | InChI=1S/C28H36O5/c1-14-12-21(32-25(31)15(14)2)16(3)18-6-7-19-17-13-24-28(33-24)23(30)9-8-22(29)27(28,5)20(17)10-11-26(18,19)4/h6,8-9,16-17,19-21,23-24,30H,7,10-13H2,1-5H3/t16-,17-,19-,20-,21+,23-,24+,26+,27-,28+/m0/s1 | NA |
| 10767272 | InChI=1S/C28H38O7/c1-14-11-22(34-24(32)15(14)2)26(4,33)19-6-5-18-16-12-23-28(35-23)21(31)8-7-20(30)25(28,3)17(16)9-10-27(18,19)13-29/h7-8,16-19,21-23,29,31,33H,5-6,9-13H2,1-4H3/t16-,17+,18+,19-,21+,22?,23-,25+,26-,27-,28-/m1/s1 | NA |
| 10648050 | InChI=1S/C28H38O6/c1-15-11-22(33-25(32)18(15)13-29)16(2)19-6-7-20-17-12-24-28(34-24)9-4-5-23(31)27(28,14-30)21(17)8-10-26(19,20)3/h4-5,16-17,19-22,24,29-30H,6-14H2,1-3H3/t16-,17-,19+,20-,21-,22?,24+,26+,27-,28+/m0/s1 | NA |
| 10458125 | InChI=1S/C28H38O7/c1-14-11-22(34-24(32)15(14)2)26(4,33)19-6-5-18-16-12-23-28(35-23)21(31)8-7-20(30)25(28,3)17(16)9-10-27(18,19)13-29/h7-8,16-19,21-23,29,31,33H,5-6,9-13H2,1-4H3/t16?,17?,18?,19-,21+,22?,23-,25+,26-,27-,28?/m1/s1 | NA |
| 102435647 | InChI=1S/C28H40O6/c1-15-13-22(34-25(32)18(15)14-29)16(2)19-5-6-20-17-9-12-28(33)24(31)8-7-23(30)27(28,4)21(17)10-11-26(19,20)3/h7-8,16-17,19-22,24,29,31,33H,5-6,9-14H2,1-4H3/t16-,17-,19+,20-,21-,22?,24-,26+,27-,28-/m0/s1 | 2-[(1S)-1-[(4S,5R,8S,9S,10R,13S,14S,17R)-4,5-dihydroxy-10,13-dimethyl-1-oxo-6,7,8,9,11,12,14,15,16,17-decahydro-4H-cyclopenta[a]phenanthren-17-yl]ethyl]-5-(hydroxymethyl)-4-methyl-2,3-dihydropyran-6-one |
| 91365744 | InChI=1S/C31H40O7/c1-15-12-23(37- | NA |

TABLE 2-continued

LIST OF WITHAFERIN A ANALOGS AND DERIVATIVES BASED ON SIMILARITY

| | | |
|---|---|---|
| | 27(35)19(15)14-32)16(2)20-6-7-21-22-13-26-31(38-26)25(36-18(4)33)9-8-24(34)30(31)17(3)29(22,30)11-10-28(20,21)5/h8-9,16-17,20-23,25-26,32H,6-7,10-14H2,1-5H3 | |
| 90670452 | InChI=1S/C28H38O7/c1-13-9-20(34-25(33)16(13)12-29)14(2)18-11-19(30)24-15-10-23-28(35-23)22(32)6-5-21(31)27(28,4)17(15)7-8-26(18,24)3/h5-6,14-15,17-20,22-24,29-30,32H,7-12H2,1-4H3/t14-,15+,17-,18+,19+,20+,22-,23+,24+,26+,27-,28+/m0/s1 | NA |
| 90670451 | InChI=1S/C28H38O7/c1-13-9-20(34-25(33)16(13)12-29)14(2)17-5-6-18-15-10-24-28(35-24)22(31)8-7-21(30)27(28,4)19(15)11-23(32)26(17,18)3/h7-8,14-15,17-20,22-24,29,31-32H,5-6,9-12H2,1-4H3/t14-,15-,17+,18-,19-,20+,22-,23+,24+,26+,27-,28+/m0/s1 | NA |
| 90670442 | InChI=1S/C28H38O9S/c1-14-11-21(36-25(31)17(14)13-35-38(32,33)34)15(2)18-5-6-19-16-12-24-28(37-24)23(30)8-7-22(29)27(28,4)20(16)9-10-26(18,19)3/h7-8,15-16,18-21,23-24,30H,5-6,9-13H2,1-4H3,(H,32,33,34)/t15-,16-,18+,19-,20-,21+,23-,24+,26+,27-,28+/m0/s1 | NA |
| 88858698 | InChI=1S/C32H42O9/c1-16-12-25(40-29(37)21(16)14-38-18(3)34)17(2)22-6-7-23-20-13-28-32(41-28)27(39-19(4)35)9-8-26(36)31(32,15-33)24(20)10-11-30(22,23)5/h8-9,17,20,22-25,27-28,33H,6-7,10-15H2,1-5H3/t17-,20-,22?,23-,24-,25+,27-,28+,30+,31-,32+/m0/s1 | NA |
| 85332099 | InChI=1S/C28H38O7/c1-13-9-20(34-25(33)16(13)12-29)14(2)18-11-19(30)24-15-10-23-28(35-23)22(32)6-5-21(31)27(28,4)17(15)7-8-26(18,24)3/h5-6,14-15,17-20,22-24,29-30,32H,7-12H2,1-4H3 | NA |
| 85326709 | InChI=1S/C28H38O7/c1-13-9-20(34-25(33)16(13)12-29)14(2)17-5-6-18-15- | NA |

TABLE 2-continued

LIST OF WITHAFERIN A ANALOGS AND DERIVATIVES BASED ON SIMILARITY

| | | |
|---|---|---|
| | 10-24-28(35-24)22(31)8-7-21(30)27(28,4)19(15)11-23(32)26(17,18)3/h7-8,14-15,17-20,22-24,29,31-32H,5-6,9-12H2,1-4H3 | |
| 76385925 | InChI=1S/C32H42O9/c1-16-12-25(40-29(37)21(16)14-38-18(3)34)17(2)22-6-7-23-20-13-28-32(41-28)27(39-19(4)35)9-8-26(36)31(32,15-33)24(20)10-11-30(22,23)5/h8-9,17,20,22-25,27-28,33H,6-7,10-15H2,1-5H3 | NA |
| 76385914 | InChI=1S/C28H38O8/c1-13-8-20(35-25(34)16(13)11-29)14(2)17-4-5-18-15-9-23-28(36-23)22(33)7-6-21(32)27(28,12-30)24(15)19(31)10-26(17,18)3/h6-7,14-15,17-20,22-24,29-31,33H,4-5,8-12H2,1-3H3 | NA |
| 75202434 | InChI=1S/C28H40O6/c1-15-13-22(34-25(32)18(15)14-29)16(2)19-5-6-20-17-9-12-28(33)24(31)8-7-23(30)27(28,4)21(17)10-11-26(19,20)3/h7-8,16-17,19-22,24,29,31,33H,5-6,9-14H2,1-4H3/t16-,17?,19+,20?,21?,22+,24-,26+,27-,28-/m0/s1 | (2R)-2-[(1S)-1-[(4S,5R,10R,13S,17R)-4,5-dihydroxy-10,13-dimethyl-1-oxo-6,7,8,9,11,12,14,15,16,17-decahydro-4H-cyclopenta[a]phenanthren-17-yl]ethyl]-5-(hydroxymethyl)-4-methyl-2,3-dihydropyran-6-one |
| 75093296 | InChI=1S/C28H38O9S/c1-14-11-21(36-25(31)17(14)13-35-38(32,33)34)15(2)18-5-6-19-16-12-24-28(37-24)23(30)8-7-22(29)27(28,4)20(16)9-10-26(18,19)3/h7-8,15-16,18-21,23-24,30H,5-6,9-13H2,1-4H3,(H,32,33,34) | NA |
| 73945208 | InChI=1S/C29H40O5/c1-15-11-17(12-23(31)19(15)14-30)16(2)20-5-6-21-18-13-26-29(34-26)25(33)8-7-24(32)28(29,4)22(18)9-10-27(20,21)3/h7-8,16-18,20-22,25-26,30,33H,5-6,9-14H2,1-4H3/t16-,17+,18?,20?,21?,22?,25?,26?,27?,28?,29?/m1/s1 | NA |
| 73823413 | InChI=1S/C30H40O8/c1-15-13-23(37-25(33)16(15)2)28(6,34)29(35)12-10-19-18-14-24-30(38-24)22(36-17(3)31)8-7-21(32)27(30,5)20(18)9-11-26(19,29)4/h7-8,18-20,22-24,34-35H,9-14H2,1-6H3 | NA |
| 73197334 | InChI=1S/C30H40O8/c1-15-12-24(37-26(34)16(15)2)28(5,35)21- | NA |

TABLE 2-continued

LIST OF WITHAFERIN A ANALOGS AND DERIVATIVES BASED ON SIMILARITY

| | | |
|---|---|---|
| | 7-6-20-18-13-25-30(38-25)23(33)9-8-22(32)27(30,4)19(18)10-11-29(20,21)14-36-17(3)31/h8-9,18-21,23-25,33,35H,6-7,10-14H2,1-5H3 | |
| 60148727 | InChI=1S/C32H42O9/c1-16-12-25(40-29(37)21(16)14-38-18(3)34)17(2)22-6-7-23-20-13-28-32(41-28)27(39-19(4)35)9-8-26(36)31(32,15-33)24(20)10-11-30(22,23)5/h8-9,17,20,22-25,27-28,33H,6-7,10-15H2,1-5H3/t17?,20-,22+,23-,24-,25?,27-,28+,30+,31-,32+/m0/s1 | NA |
| 58443789 | InChI=1S/C28H38O9S/c1-14-11-21(36-25(31)17(14)13-35-38(32,33)34)15(2)18-5-6-19-16-12-24-28(37-24)23(30)8-7-22(29)27(28,4)20(16)9-10-26(18,19)3/h7-8,15-16,18-21,23-24,30H,5-6,9-13H2,1-4H3,(H,32,33,34)/t15-,16?,18?,19?,20?,21?,23-,24+,26+,27-,28+/m0/s1 | NA |
| 56649398 | InChI=1S/C32H42O9/c1-16-12-25(40-29(37)21(16)14-38-18(3)34)17(2)22-6-7-23-20-13-28-32(41-28)27(39-19(4)35)9-8-26(36)31(32,15-33)24(20)10-11-30(22,23)5/h8-9,17,20,22-25,27-28,33H,6-7,10-15H2,1-5H3/t17-,20-,22+,23-,24-,25+,27-,28+,30+,31-,32+/m0/s1 | NA |
| 56649372 | InChI=1S/C28H38O8/c1-13-8-20(35-25(34)16(13)11-29)14(2)17-4-5-18-15-9-23-28(36-23)22(33)7-6-21(32)27(28,12-30)24(15)19(31)10-26(17,18)3/h6-7,14-15,17-20,22-24,29-31,33H,4-5,8-12H2,1-3H3/t14-,15-,17+,18-,19-,20+,22-,23+,24+,26+,27+,28+/m0/s1 | NA |
| 45111619 | InChI=1S/C28H38O9S/c1-14-11-21(36-25(31)17(14)13-35-38(32,33)34)15(2)18-5-6-19-16-12-24-28(37-24)23(30)8-7-22(29)27(28,4)20(16)9-10-26(18,19)3/h7-8,15-16,18-21,23-24,30H,5-6,9-13H2,1-4H3,(H,32,33,34)/t15-,16?,18?,19?,20?,21?,23-,24+,26+,27-,28?/m0/s1 | NA |
| 21679026 | InChI=1S/C30H40O8/c1-15-13-23(37-25(33)16(15)2)28(6,34)29 | NA |

TABLE 2-continued

LIST OF WITHAFERIN A ANALOGS AND DERIVATIVES BASED ON SIMILARITY

| | | |
|---|---|---|
| | (35)12-10-19-18-14-24-30(38-24)22(36-17(3)31)8-7-21(32)27(30,5)20(18)9-11-26(19,29)4/h7-8,18-20,22-24,34-35H,9-14H2,1-6H3/t18-,19-,20-,22-,23+,24+,26-,27-,28-,29+,30+/m0/s1 | |
| 15519705 | InChI=1S/C30H40O8/c1-15-12-24(37-26(34)16(15)2)28(5,35)21-7-6-20-18-13-25-30(38-25)23(33)9-8-22(32)27(30,4)19(18)10-11-29(20,21)14-36-17(3)31/h8-9,18-21,23-25,33,35H,6-7,10-14H2,1-5H3/t18-,19+,20+,21-,23+,24-,25-,27+,28-,29-,30-/m1/s1 | NA |
| 10459594 | InChI=1S/C30H40O8/c1-15-12-24(37-26(34)16(15)2)28(5,35)21-7-6-20-18-13-25-30(38-25)23(33)9-8-22(32)27(30,4)19(18)10-11-29(20,21)14-36-17(3)31/h8-9,18-21,23-25,33,35H,6-7,10-14H2,1-5H3/t18?,19?,20?,21?,23-,24+,25+,27-,28+,29+,30+/m0/s1 | NA |
| 10163221 | InChI=1S/C28H38O7/c1-13-9-20(34-25(33)16(13)12-29)14(2)18-11-19(30)24-15-10-23-28(35-23)22(32)6-5-21(31)27(28,4)17(15)7-8-26(18,24)3/h5-6,14-15,17-20,22-24,29-30,32H,7-12H2,1-4H3/t14?,15-,17+,18-,19+,20?,22+,23-,24-,26-,27+,28-/m1/s1 | NA |
| 10141001 | InChI=1S/C28H38O7/c1-13-9-20(34-25(33)16(13)12-29)14(2)17-5-6-18-15-10-24-28(35-24)22(31)8-7-21(30)27(28,4)19(15)11-23(32)26(17,18)3/h7-8,14-15,17-20,22-24,29,31-32H,5-6,9-12H2,1-4H3/t14?,15-,17+,18-,19-,20?,22-,23-,24+,26+,27-,28+/m0/s1 | NA |
| 102504535 | InChI=1S/C28H40O5/c1-14-12-21(32-25(31)15(14)2)16(3)18-6-7-19-17-13-24-28(33-24)23(30)9-8-22(29)27(28,5)20(17)10-11-26(18,19)4/h8-9,14-21,23-24,30H,6-7,10-13H2,1-5H3/t14-,15+,16-,17-,18+,19-,20-,21?,23-,24+,26+,27-,28+/m0/s1 | NA |
| 102504532 | InChI=1S/C28H40O6/c1-14-12-22(33-24(31)15(14)2)27(5,32)19-7-6-17-16-13-23-28(34-23)21(30)9-8-20(29)26(28,4)18(16)10-11-25(17,19)3/h8-9,14- | NA |

TABLE 2-continued

LIST OF WITHAFERIN A ANALOGS AND DERIVATIVES BASED ON SIMILARITY

| | | |
|---|---|---|
| | 19,21-23,30,32H,6-7,10-13H2,1-5H3/t14-,15+,16-,17-,18-,19-,21-,22?,23+,25-,26-,27+,28+/m0/s1 | |
| 102435648 | InChI=1S/C28H40O5/c1-15-14-22(33-25(31)16(15)2)17(3)19-6-7-20-18-10-13-28(32)24(30)9-8-23(29)27(28,5)21(18)11-12-26(19,20)4/h8-9,17-22,24,30,32H,6-7,10-14H2,1-5H3/t17-,18-,19+,20-,21-,22?,24-,26+,27-,28-/m0/s1 | 2-[(1S)-1-[(4S,5R,8S,9S,10R,13S,14S,17R)-4,5-dihydroxy-10,13-dimethyl-1-oxo-6,7,8,9,11,12,14,15,16,17-decahydro-4H-cyclopenta[a]phenanthren-17-yl]ethyl]-4,5-dimethyl-2,3-dihydropyran-6-one |
| 102317091 | InChI=1S/C28H40O7/c1-15-11-22(35-25(33)17(15)13-29)18(14-30)20-7-6-19-16-12-24(32)28(34)9-4-5-23(31)27(28,3)21(16)8-10-26(19,20)2/h4-5,16,18-22,24,29-30,32,34H,6-14H2,1-3H3/t16-,18-,19-,20+,21-,22+,24+,26-,27-,28-/m0/s1 | (2R)-2-[(1R)-1-[(5R,6R,8S,9S,10R,13S,14S,17R)-5,6-dihydroxy-10,13-dimethyl-1-oxo-6,7,8,9,11,12,14,15,16,17-decahydro-4H-cyclopenta[a]phenanthren-17-yl]-2-hydroxyethyl]-5-(hydroxymethyl)-4-methyl-2,3-dihydropyran-6-one |
| 101911600 | InChI=1S/C28H38O6/c1-14-10-21(33-25(32)17(14)13-29)15(2)24-20(30)12-19-16-11-23-28(34-23)8-5-6-22(31)27(28,4)18(16)7-9-26(19,24)3/h5-6,15-16,18-21,23-24,29-30H,7-13H2,1-4H3/t15-,16-,18+,19+,20-,21-,23-,24+,26+,27+,28-/m1/s1 | NA |
| 101911595 | InChI=1S/C28H38O7/c1-14-10-21(35-25(33)17(14)13-29)15(2)24-20(30)12-19-16-11-23(32)28(34)8-5-6-22(31)27(28,4)18(16)7-9-26(19,24)3/h5-6,15-16,18-19,21,23-24,29,32,34H,7-13H2,1-4H3/t15-,16-,18+,19+,21-,23-,24+,26+,27+,28+/m1/s1 | (5R,6R,8S,9S,10R,13S,14S,17R)-5,6-dihydroxy-17-[(1S)-1-[(2R)-5-(hydroxymethyl)-4-methyl-6-oxo-2,3-dihydropyran-2-yl]ethyl]-10,13-dimethyl-4,6,7,8,9,11,12,14,15,17-decahydrocyclopenta[a]phenanthrene-1,16-dione |
| 101710595 | InChI=1S/C28H38O7/c1-14-12-20(34-24(31)15(14)13-29)27(4,32)18-8-7-16-21-17(9-11-25(16,18)2)26(3)19(30)6-5-10-28(26,33)23-22(21)35-23/h5-6,16-18,20-23,29,32-33H,7-13H2,1-4H3/t16-,17-,18-,20?,21-,22-,23-,25-,26-,27+,28-/m0/s1 | NA |
| 101630647 | InChI=1S/C28H38O7/c1-13-10-19(34-25(32)15(13)12-29)14(2)16-7-8-17-22-18(11-21(31)26(16,17)3)27(4)20(30)6-5-9-28(27,33)24-23(22)35-24/h5-6,14,16-19,21-24,29,31,33H,7-12H2,1-4H3/t14-,16+,17-,18-,19+,21+,22-,23-,24-,26+,27-,28-/m0/s1 | NA |

TABLE 2-continued

LIST OF WITHAFERIN A ANALOGS AND DERIVATIVES BASED ON SIMILARITY

| | | |
|---|---|---|
| 101419548 | InChI=1S/C28H38O7/c1-13-10-19(34-25(32)15(13)12-29)14(2)16-7-8-17-22-18(11-21(31)26(16,17)3)27(4)20(30)6-5-9-28(27,33)24-23(22)35-24/h5-6,14,16-19,21-24,29,31,33H,7-12H2,1-4H3/t14-,16+,17-,18-,19+,21?,22-,23-,24-,26+,27-,28-/m0/s1 | NA |
| 101281364 | InChI=1S/C28H38O6/c1-13-14(2)25(31)34-22(21(13)30)15(3)16-8-9-17-20-18(10-12-26(16,17)4)27(5)19(29)7-6-11-28(27,32)24-23(20)33-24/h6-7,15-18,20-24,30,32H,8-12H2,1-5H3/t15-,16+,17-,18-,20-,21-,22-,23-,24-,26+,27-,28-/m0/s1 | NA |
| 101231931 | InChI=1S/C28H40O5/c1-14-12-21(32-25(31)15(14)2)16(3)18-6-7-19-17-13-24-28(33-24)23(30)9-8-22(29)27(28,5)20(17)10-11-26(18,19)4/h8-9,14-21,23-24,30H,6-7,10-13H2,1-5H3/t14-,15?,16-,17-,18+,19-,20-,21+,23-,24+,26+,27-,28+/m0/s1 | NA |
| 101168804 | InChI=1S/C28H40O6/c1-14-12-21(34-25(32)15(14)2)16(3)18-6-7-19-17-13-24(31)28(33)23(30)9-8-22(29)27(28,5)20(17)10-11-26(18,19)4/h8-9,16-21,23-24,30-31,33H,6-7,10-13H2,1-5H3/t16-,17-,18+,19-,20-,21+,23-,24-,26+,27-,28+/m0/s1 | (2R)-4,5-dimethyl-2-[(1S)-1-[(4S,5S,6S,8S,9S,10R,13S,14S,17R)-4,5,6-trihydroxy-10,13-dimethyl-1-oxo-6,7,8,9,11,12,14,15,16,17-decahydro-4H-cyclopenta[a]phenanthren-17-yl]ethyl]-2,3-dihydropyran-6-one |
| 91453196 | InChI=1S/C31H46O5/c1-7-8-22-27(34)35-23(16-28(22,3)4)17(2)19-9-10-20-18-15-26-31(36-26)25(33)12-11-24(32)30(31,6)21(18)13-14-29(19,20)5/h11-12,17-23,25-26,33H,7-10,13-16H2,1-6H3 | NA |
| 91438857 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h7,15-16,18-21,23-25,29,31-32H,5-6,9-13H2,1-4H3 | NA |
| 90670441 | InChI=1S/C30H40O6/c1-15-13-23(35-27(33)16(15)2)17(3)20-7-8-21-19-14-26-30(36-26)25(34-18(4)31)10-9-24(32)29(30,6)22(19)11-12-28(20,21)5/h9-10,17,19-23,25-26H,7-8,11-14H2,1-6H3/t17-,19-,20+,21-,22-,23+,25-,26+,28-,29-,30+/m0/s1 | NA |
| 89333022 | InChI=1S/C28H40O5/c1-14-12-21(32-25(31)15(14)2)16(3)18- | NA |

TABLE 2-continued

LIST OF WITHAFERIN A ANALOGS AND DERIVATIVES BASED ON SIMILARITY

| | | |
|---|---|---|
| | 6-7-19-17-13-24-28(33-24)23(30)9-8-22(29)27(28,5)20(17)10-11-26(18,19)4/h8-9,14-21,23-24,30H,6-7,10-13H2,1-5H3/t14-,15+,16+,17?,18?,19?,20?,21?,23+,24-,26-,27+,28-/m1/s1 | |
| 89091907 | InChI=1S/C34H52O6Si/c1-19-17-26(39-30(37)21(19)13-15-31(3,4)41(7,8)38)20(2)23-9-10-24-22-18-29-34(40-29)28(36)12-11-27(35)33(34,6)25(22)14-16-32(23,24)5/h11-12,20,22-26,28-29,36,38H,9-10,13-18H2,1-8H3/t20-,22?,23?,24?,25?,26?,28+,29+,32+,33-,34+/m0/s1 | NA |
| 88949020 | InChI=1S/C27H36O6/c1-13-11-20(32-24(30)14(13)2)15(3)17-5-6-18-16-12-23-27(33-23)22(29)8-7-21(28)26(27,31)19(16)9-10-25(17,18)4/h7-8,15-20,22-23,29,31H,5-6,9-12H2,1-4H3/t15-,16-,17?,18-,19-,20+,22-,23+,25+,26?,27+/m0/s1 | NA |
| 88949018 | InChI=1S/C27H36O7/c1-13-10-20(33-24(31)16(13)12-28)14(2)17-4-5-18-15-11-23-27(34-23)22(30)7-6-21(29)26(27,32)19(15)8-9-25(17,18)3/h6-7,14-15,17-20,22-23,28,30,32H,4-5,8-12H2,1-3H3/t14-,15-,17?,18-,19?,20+,22-,23+,25+,26?,27+/m0/s1 | NA |
| 88949011 | InChI=1S/C29H38O6/c1-14-12-23(34-27(32)15(14)2)16(3)20-6-7-21-19-13-25-29(35-25)24(33-17(4)30)9-8-22(31)26(29)18(19)10-11-28(20,21)5/h8-9,16,18-21,23-26H,6-7,10-13H2,1-5H3/t16-,18?,19+,20+,21-,23+,24-,25+,26+,28+,29+/m0/s1 | NA |
| 77911018 | InChI=1S/C28H40O7/c1-14-11-21(35-25(33)17(14)13-29)15(2)18-5-6-19-16-12-24(32)28(34)23(31)8-7-22(30)27(28,4)20(16)9-10-26(18,19)3/h7-8,15-16,18-21,23-24,29,31-32,34H,5-6,9-13H2,1-4H3 | 5-(hydroxymethyl)-4-methyl-2-[1-(4,5,6-trihydroxy-10,13-dimethyl-1-oxo-6,7,8,9,11,12,14,15,16,17-decahydro-4H-cyclopenta[a]phenanthren-17-yl)ethyl]-2,3-dihydropyran-6-one |
| 77145375 | InChI=1S/C32H44O8/c1-17-13-24(39-28(36)20(17)15-37-29(3,4)38-16-33)18(2)21-7-8-22-19-14-27-32(40-27)26(35)10-9-25(34)31(32,6)23(19)11-12-30(21,22)5/h9-10,16,18-19,21-24,26- | NA |

TABLE 2-continued

LIST OF WITHAFERIN A ANALOGS AND DERIVATIVES BASED ON SIMILARITY

| | | |
|---|---|---|
| | 27,35H,7-8,11-15H2,1-6H3 | |
| 76787558 | InChI=1S/C31H42O6/c1-7-19-16(2)14-24(36-28(19)34)17(3)21-8-9-22-20-15-27-31(37-27)26(35-18(4)32)11-10-25(33)30(31,6)23(20)12-13-29(21,22)5/h10-11,17,20-24,26-27H,7-9,12-15H2,1-6H3 | NA |
| 76787557 | InChI=1S/C34H52O6Si/c1-19-16-26(39-30(37)22(19)18-38-41(8,9)31(3,4)5)20(2)23-10-11-24-21-17-29-34(40-29)28(36)13-12-27(35)33(34,7)25(21)14-15-32(23,24)6/h12-13,20-21,23-26,28-29,36H,10-11,14-18H2,1-9H3 | NA |
| 75239042 | InChI=1S/C28H38O7/c1-13-10-22(34-24(32)14(13)2)27(5,33)18-7-6-16-15-11-23-28(35-23)20(30)9-8-19(29)26(28,4)17(15)12-21(31)25(16,18)3/h8-9,15-18,20-23,30-31,33H,6-7,10-12H2,1-5H3 | NA |
| 74039190 | InChI=1S/C28H40O6/c1-14-12-22(33-24(31)15(14)2)27(5,32)19-7-6-17-16-13-23-28(34-23)21(30)9-8-20(29)26(28,4)18(16)10-11-25(17,19)3/h8-9,14-19,21-23,30,32H,6-7,10-13H2,1-5H3 | NA |
| 74039189 | InChI=1S/C28H40O5/c1-14-12-21(32-25(31)15(14)2)16(3)18-6-7-19-17-13-24-28(33-24)23(30)9-8-22(29)27(28,5)20(17)10-11-26(18,19)4/h8-9,14-21,23-24,30H,6-7,10-13H2,1-5H3 | NA |
| 74039182 | InChI=1S/C28H38O6/c1-13-14(2)25(31)34-22(21(13)30)15(3)16-8-9-17-20-18(10-12-26(16,17)4)27(5)19(29)7-6-11-28(27,32)24-23(20)33-24/h6-7,15-18,20-24,30,32H,8-12H2,1-5H3 | NA |
| 73820038 | InChI=1S/C28H36O7/c1-13-9-20(34-25(33)14(13)2)15(3)24-19(30)11-18-16-10-23-28(35-23)22(32)6-5-21(31)26(28,4)17(16)7-8-27(18,24)12-29/h5-6,12,15-20,22-24,30,32H,7-11H2,1-4H3 | NA |
| 73800706 | InChI=1S/C28H38O7/c1-13-10-19(34-25(32)15(13)12-29)14(2)16-7-8-17-22-18(11-21(31)26(16,17)3)27(4)20(30)6-5-9-28(27,33)24-23(22)35-24/h5-6,14,16-19,21-24,29,31,33H,7-12H2,1-4H3 | NA |

TABLE 2-continued

LIST OF WITHAFERIN A ANALOGS AND DERIVATIVES BASED ON SIMILARITY

| | | |
|---|---|---|
| 73310064 | InChI=1S/C29H38O8/c1-14-11-21(36-25(32)15(14)2)16(3)18-5-6-20-17-12-24-29(37-24)23(31)8-7-22(30)27(29,4)19(17)9-10-28(18,20)13-35-26(33)34/h7-8,16-21,23-24,31H,5-6,9-13H2,1-4H3,(H,33,34) | NA |
| 73306621 | InChI=1S/C28H36O7/c1-13-10-20(33-23(31)14(13)2)26(5,32)28-22(35-28)12-17-15-11-21-27(34-21)19(30)7-6-18(29)25(27,4)16(15)8-9-24(17,28)3/h6-7,15-17,19-22,30,32H,8-12H2,1-5H3 | NA |
| 73306620 | InChI=1S/C28H36O6/c1-13-10-19(32-24(31)14(13)2)15(3)27-23(33-27)12-18-16-11-22-28(34-22)21(30)7-6-20(29)26(28,5)17(16)8-9-25(18,27)4/h6-7,15-19,21-23,30H,8-12H2,1-5H3 | NA |
| 73306373 | InChI=1S/C28H36O6/c1-13-10-20(33-25(32)14(13)2)15(3)26(4)18-6-7-19-17(16(18)11-23(26)31)12-24-28(34-24)22(30)9-8-21(29)27(19,28)5/h8-9,15,17,19-20,22-24,30-31H,6-7,10-12H2,1-5H3 | NA |
| 72663555 | InChI=1S/C30H40O9/c1-14-9-22(38-27(36)18(14)12-31)15(2)20-11-21(33)26-17-10-25-30(39-25)24(35)6-5-23(34)29(30,13-37)16(3)32)19(17)7-8-28(20,26)4/h5-6,15,17,19-22,24-26,31,33,35H,7-13H2,1-4H3 | NA |
| 72663554 | InChI=1S/C28H38O8/c1-13-8-20(35-25(34)16(13)11-29)14(2)18-10-19(31)24-15-9-23-28(36-23)22(33)5-4-21(32)27(28,12-30)17(15)6-7-26(18,24)3/h4-5,14-15,17-20,22-24,29-31,33H,6-12H2,1-3H3 | NA |
| 72544656 | InChI=1S/C28H37IO7/c1-13-8-21(35-25(34)16(13)11-30)14(2)17-4-5-18-15-9-23-28(36-23)22(32)10-20(29)24(33)27(28,12-31)19(15)6-7-26(17,18)3/h10,14-15,17-19,21-23,30-32H,4-9,11-12H2,1-3H3/t14-,15-,17+,18-,19-,21+,22-,23+,26+,27-,28+/m0/s1 | NA |
| 71477797 | InChI=1S/C34H52O6Si/c1-19-16-26(39-30(37)22(19)18-38-41(8,9)31(3,4)5)20(2)23-10-11-24-21-17-29- | NA |

TABLE 2-continued

LIST OF WITHAFERIN A ANALOGS AND DERIVATIVES BASED ON SIMILARITY

| | | |
|---|---|---|
| | 34(40-29)28(36)13-12-27(35)33(34,7)25(21)14-15-32(23,24)6/h12-13,20-21,23-26,28-29,36H,10-11,14-18H2,1-9H3/t20-,21?,23+,24?,25?,26+,28-,29+,32+,33-,34+/m0/s1 | |
| 70684083 | InChI=1S/C28H40O7/c1-14-11-21(35-25(33)17(14)13-29)15(2)18-5-6-19-16-12-24(32)28(34)23(31)8-7-22(30)27(28,4)20(16)9-10-26(18,19)3/h7-8,15-16,18-21,23-24,29,31-32,34H,5-6,9-13H2,1-4H3/t15-,16-,18+,19-,20-,21+,23-,24-,26+,27-,28+/m0/s1 | (2R)-5-(hydroxymethyl)-4-methyl-2-[(1S)-1-[(4S,5S,6S,8S,9S,10R,13S,14S,17R)-4,5,6-trihydroxy-10,13-dimethyl-1-oxo-6,7,8,9,11,12,14,15,16,17-decahydro-4H-cyclopenta[a]phenanthren-17-yl]ethyl]-2,3-dihydropyran-6-one |
| 66572430 | InChI=1S/C32H44O8/c1-17-13-24(39-28(36)20(17)15-37-29(3,4)38-16-33)18(2)21-7-8-22-19-14-27-32(40-27)26(35)10-9-25(34)31(32,6)23(19)11-12-30(21,22)5/h9-10,16,18-19,21-24,26-27,35H,7-8,11-15H2,1-6H3/t18-,19-,21+,22-,23-,24+,26-,27+,30+,31-,32+/m0/s1 | NA |
| 66572355 | InChI=1S/C34H52O6Si/c1-19-16-26(39-30(37)22(19)18-38-41(8,9)31(3,4)5)20(2)23-10-11-24-21-17-29-34(40-29)28(36)13-12-27(35)33(34,7)25(21)14-15-32(23,24)6/h12-13,20-21,23-26,28-29,36H,10-11,14-18H2,1-9H3/t20-,21-,23+,24-,25-,26+,28-,29+,32+,33-,34+/m0/s1 | NA |
| 60148720 | InChI=1S/C30H40O9/c1-14-9-22(38-27(36)18(14)12-31)15(2)20-11-21(33)26-17-10-25-30(39-25)24(35)6-5-23(34)29(30,13-37-16(3)32)19(17)7-8-28(20,26)4/h5-6,15,17,19-22,24-26,31,33,35H,7-13H2,1-4H3/t15?,17-,19+,20-,21+,22?,24+,25-,26-,28-,29+,30-/m1/s1 | NA |
| 60148719 | InChI=1S/C28H38O8/c1-13-8-20(35-25(34)16(13)11-29)14(2)18-10-19(31)24-15-9-23-28(36-23)22(33)5-4-21(32)27(28,12-30)17(15)6-7-26(18,24)3/h4-5,14-15,17-20,22-24,29-31,33H,6-12H2,1-3H3/t14?,15-,17+,18-,19+,20?,22+,23-,24-,26-,27+,28-/m1/s1 | NA |
| 58443793 | InChI=1S/C31H42O6/c1-7-19-16(2)14-24(36-28(19)34)17(3)21-8-9-22-20-15-27-31(37- | NA |

TABLE 2-continued

LIST OF WITHAFERIN A ANALOGS AND DERIVATIVES BASED ON SIMILARITY

| | | |
|---|---|---|
| | 27)26(35-18(4)32)11-10-25(33)30(31,6)23(20)12-13-29(21,22)5/h10-11,17,20-24,26-27H,7-9,12-15H2,1-6H3/t17-,20?,21?,22?,23?,24?,26+,27+,29+,30-,31+/m0/s1 | |
| 58443791 | InChI=1S/C34H52O6Si/c1-19-16-26(39-30(37)22(19)18-38-41(8,9)31(3,4)5)20(2)23-10-11-24-21-17-29-34(40-29)28(36)13-12-27(35)33(34,7)25(21)14-15-32(23,24)6/h12-13,20-21,23-26,28-29,36H,10-11,14-18H2,1-9H3/t20-,21?,23?,24?,25?,26?,28+,29+,32+,33-,34+/m0/s1 | NA |
| 56841147 | InChI=1S/C28H40O7/c1-15-11-22(35-25(33)17(15)13-29)18(14-30)20-7-6-19-16-12-24(32)28(34)9-4-5-23(31)27(28,3)21(16)8-10-26(19,20)2/h4-5,16,18-22,24,29-30,32,34H,6-14H2,1-3H3/t16-,18-,19?,20+,21-,22+,24+,26-,27-,28-/m0/s1 | (2R)-2-[(1R)-1-[(5R,6R,8S,9S,10R,13S,17R)-5,6-dihydroxy-10,13-dimethyl-1-oxo-6,7,8,9,11,12,14,15,16,17-decahydro-4H-cyclopenta[a]phenanthren-17-yl]-2-hydroxyethyl]-5-methyl-2,3-dihydropyran-6-one |
| 56677887 | InChI=1S/C27H36O7/c1-12-9-21(33-24(31)13(12)2)26(4,32)18-7-5-16-14-11-22-27(34-22)19(29)8-6-17(28)23(27)15(14)10-20(30)25(16,18)3/h6,8,14-16,18-23,29-30,32H,5,7,9-11H2,1-4H3 | NA |
| 53398767 | InChI=1S/C28H38O6/c1-14-12-20(33-25(31)16(14)13-29)15(2)17-7-8-18-22-19(9-11-26(17,18)3)27(4)21(30)6-5-10-28(27,32)24-23(22)34-24/h5-6,15,17-20,22-24,29,32H,7-13H2,1-4H3 | NA |
| 49799448 | InChI=1S/C27H36O7/c1-12-9-21(33-24(31)13(12)2)26(4,32)18-7-5-16-14-11-22-27(34-22)19(29)8-6-17(28)23(27)15(14)10-20(30)25(16,18)3/h6,8,14-16,18-23,29-30,32H,5,7,9-11H2,1-4H3/t14-,15+,16+,18+,19+,20-,21-,22-,23+,25+,26+,27-/m1/s1 | NA |
| 46872824 | InChI=1S/C28H38O7/c1-13-10-22(34-24(32)14(13)2)27(5,33)18-7-6-16-15-11-23-28(35-23)20(30)9-8-19(29)26(28,4)17(15)12-21(31)25(16,18)3/h8-9,15-18,20-23,30-31,33H,6-7,10-12H2,1-5H3/t15-,16-,17-,18-,20-,21+,22+,23+,25-,26-,27+,28+/m0/s1 | NA |

TABLE 2-continued

LIST OF WITHAFERIN A ANALOGS AND DERIVATIVES BASED ON SIMILARITY

| | | |
|---|---|---|
| 44631508 | InChI=1S/C28H38O6/c1-13-14(2)25(31)34-22(21(13)30)15(3)16-8-9-17-20-18(10-12-26(16,17)4)27(5)19(29)7-6-11-28(27,32)24-23(20)33-24/h6-7,15-18,20-24,30,32H,8-12H2,1-5H3/t15-,16+,17?,18?,20?,21?,22?,23-,24-,26+,27-,28-/m0/s1 | NA |
| 44576309 | InChI=1S/C28H38O6/c1-14-12-20(33-25(31)16(14)13-29)15(2)17-7-8-18-22-19(9-11-26(17,18)3)27(4)21(30)6-5-10-28(27,32)24-23(22)34-24/h5-6,15,17-20,22-24,29,32H,7-13H2,1-4H3/t15-,17+,18-,19-,20+,22-,23-,24-,26+,27-,28-/m0/s1 | NA |
| 44423094 | InChI=1S/C28H40O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-24,30-32H,6-7,10-13H2,1-5H3/t16-,17-,18-,19?,21-,22+,23+,24?,25-,26-,27+,28+/m0/s1 | NA |
| 23266167 | InChI=1S/C28H40O6/c1-14-12-22(33-24(31)15(14)2)27(5,32)19-7-6-17-16-13-23-28(34-23)21(30)9-8-20(29)26(28,4)18(16)10-11-25(17,19)3/h8-9,14-19,21-23,30,32H,6-7,10-13H2,1-5H3/t14-,15+,16-,17-,18-,19-,21-,22+,23+,25-,26-,27+,28+/m0/s1 | NA |
| 23266166 | InChI=1S/C28H40O5/c1-14-12-21(32-25(31)15(14)2)16(3)18-6-7-19-17-13-24-28(33-24)23(30)9-8-22(29)27(28,5)20(17)10-11-26(18,19)4/h8-9,14-21,23-24,30H,6-7,10-13H2,1-5H3/t14-,15+,16-,17-,18+,19-,20-,21+,23-,24+,26+,27-,28+/m0/s1 | NA |
| 23266156 | InChI=1S/C28H38O6/c1-13-14(2)25(31)34-22(21(13)30)15(3)16-8-9-17-20-18(10-12-26(16,17)4)27(5)19(29)7-6-11-28(27,32)24-23(20)33-24/h6-7,15-18,20-24,30,32H,8-12H2,1-5H3/t15-,16+,17-,18-,20-,21?,22-,23-,24-,26+,27-,28-/m0/s1 | NA |
| 22210256 | InChI=1S/C28H40O7/c1-15-11-22(35-25(33)17(15)13-29)18(14-30)20-7-6-19-16-12-24(32)28(34)9-4-5-23(31)27(28,3)21(16)8-10-26(19,20)2/h4-5,16,18-22,24,29-30,32,34H,6-14H2,1- | 2-[1-[(8S,9S,10R,13S,14S,17R)-5,6-dihydroxy-10,13-dimethyl-1-oxo-6,7,8,9,11,12,14,15,16,17-decahydro-4H-Cyclopenta[a]phenanthren-17-yl]-2- |

TABLE 2-continued

LIST OF WITHAFERIN A ANALOGS AND DERIVATIVES BASED ON SIMILARITY

| | | |
|---|---|---|
| | 3H3/t16-,18?,19-,20+,21-,22?,24?,26-,27-,28?/m0/s1 | hydroxyethyl]-5-(hydroxymethyl)-4-methyl-2,3-dihydropyran-6-one |
| 21670295 | InChI=1S/C28H36O7/c1-13-9-20(34-25(33)14(13)2)15(3)24-19(30)11-18-16-10-23-28(35-23)22(32)6-5-21(31)26(28,4)17(16)7-8-27(18,24)12-29/h5-6,12,15-20,22-24,30,32H,7-11H2,1-4H3/t15-,16-,17+,18+,19-,20-,22+,23-,24+,26+,27-,28-/m1/s1 | NA |
| 21607602 | InChI=1S/C28H38O7/c1-13-10-19(34-25(32)15(13)12-29)14(2)16-7-8-17-22-18(11-21(31)26(16,17)3)27(4)20(30)6-5-9-28(27,33)24-23(22)35-24/h5-6,14,16-19,21-24,29,31,33H,7-12H2,1-4H3/t14-,16+,17-,18-,19+,21-,22-,23-,24-,26+,27-,28-/m0/s1 | NA |
| 16720560 | InChI=1S/C29H38O8/c1-14-11-21(36-25(32)15(14)2)16(3)18-5-6-20-17-12-24-29(37-24)23(31)8-7-22(30)27(29,4)19(17)9-10-28(18,20)13-35-26(33)34/h7-8,16-21,23-24,31H,5-6,9-13H2,1-4H3,(H,33,34)/t16-,17+,18+,19-,20-,21+,23-,24+,27-,28-,29+/m0/s1 | NA |
| 16680370 | InChI=1S/C28H36O7/c1-13-10-20(33-23(31)14(13)2)26(5,32)28-22(35-28)12-17-15-11-21-27(34-21)19(30)7-6-18(29)25(27,4)16(15)8-9-24(17,28)3/h6-7,15-17,19-22,30,32H,8-12H2,1-5H3/t15-,16+,17+,19+,20-,21-,22-,24+,25+,26+,27-,28-/m1/s1 | NA |
| 16680369 | InChI=1S/C28H36O6/c1-13-10-19(32-24(31)14(13)2)15(3)27-23(33-27)12-18-16-11-22-28(34-22)21(30)7-6-20(29)26(28,5)17(16)8-9-25(18,27)4/h6-7,15-19,21-23,30H,8-12H2,1-5H3/t15-,16-,17+,18+,19-,21+,22-,23-,25+,26+,27-,28-/m1/s1 | NA |
| 16679812 | InChI=1S/C28H36O6/c1-13-10-20(33-25(32)14(13)2)15(3)26(4)18-6-7-19-17(16(18)11-23(26)31)12-24-28(34-24)22(30)9-8-21(29)27(19,28)5/h8-9,15,17,19-20,22-24,30-31H,6-7,10-12H2,1-5H3/t15-,17+,19+,20-,22+,23-,24-,26-,27+,28-/m1/s1 | NA |
| 15858981 | InChI=1S/C28H38O6/c1-14-12-20(33-25(31)16(14)13- | NA |

TABLE 2-continued

LIST OF WITHAFERIN A ANALOGS AND DERIVATIVES BASED ON SIMILARITY

| | | |
|---|---|---|
| | 29)15(2)17-7-8-18-22-19(9-11-26(17,18)3)27(4)21(30)6-5-10-28(27,32)24-23(22)34-24/h5-6,15,17-20,22-24,29,32H,7-13H2,1-4H3/t15-,17+,18-,19-,20?,22-,23-,24-,26+,27-,28-/m0/s1 | |
| 11305931 | InChI=1S/C28H38O6/c1-14-12-20(33-25(31)16(14)13-29)15(2)17-7-8-18-22-19(9-11-26(17,18)3)27(4)21(30)6-5-10-28(27,32)24-23(22)34-24/h5-6,15,17-20,22-24,29,32H,7-13H2,1-4H3/t15-,17?,18?,19?,20?,22?,23-,24-,26+,27-,28-/m0/s1 | NA |
| 11134251 | InChI=1S/C28H40O5/c1-14-12-21(32-25(31)15(14)2)16(3)18-6-7-19-17-13-24-28(33-24)23(30)9-8-22(29)27(28,5)20(17)10-11-26(18,19)4/h8-9,14-21,23-24,30H,6-7,10-13H2,1-5H3/t14-,15+,16+,17+,18?,19+,20+,21?,23+,24-,26-,27+,28-/m1/s1 | NA |
| 10814731 | InChI=1S/C28H36O7/c1-13-9-20(34-25(33)14(13)2)15(3)24-19(30)11-18-16-10-23-28(35-23)22(32)6-5-21(31)26(28,4)17(16)7-8-27(18,24)12-29/h5-6,12,15-20,22-24,30,32H,7-11H2,1-4H3/t15-,16-,17+,18+,19-,20?,22+,23-,24+,26+,27-,28-/m1/s1 | NA |
| 10413210 | InChI=1S/C28H40O7/c1-14-11-21(35-25(33)17(14)13-29)15(2)18-5-6-19-16-12-24(32)28(34)23(31)8-7-22(30)27(28,4)20(16)9-10-26(18,19)3/h7-8,15-16,18-21,23-24,29,31-32,34H,5-6,9-13H2,1-4H3/t15?,16-,18+,19-,20-,21+,23-,24-,26+,27-,28+/m0/s1 | (2R)-5-(hydroxymethyl)-4-methyl-2-[1-[(4S,5S,6S,8S,9S,10R,13S,14S,17R)-4,5,6-trihydroxy-10,13-dimethyl-1-oxo-6,7,8,9,11,12,14,15,16,17-decahydro-4H-Cyclopenta[a]phenanthren-17-yl]ethyl]-2,3-dihydropyran-6-one |
| 10344751 | InChI=1S/C28H40O6/c1-15-12-22(34-25(32)18(15)14-29)16(2)19-7-8-20-17-13-24(31)28(33)10-5-6-23(30)27(28,4)21(17)9-11-26(19,20)3/h5-6,16-17,19-22,24,29,31,33H,7-14H2,1-4H3/t16?,17?,19-,20?,21?,22?,24-,26-,27+,28+/m1/s1 | 2-[1-[(5R,6R,10R,13S,17R)-5,6-dihydroxy-10,13-dimethyl-1-oxo-6,7,8,9,11,12,14,15,16,17-decahydro-4H-cyclopenta[a]phenanthren-17-yl]ethyl]-5-(hydroxymethyl)-4-methyl-2,3-dihydropyran-6-one |
| 10051187 | InChI=1S/C28H40O7/c1-15-11-22(35-25(33)17(15)13-29)18(14-30)20-7-6-19-16-12-24(32)28(34)9-4-5-23(31)27(28,3)21(16)8-10-26(19,20)2/h4- | (2R)-2-[(1R)-1-[(5R,6R,10R,13S)-5,6-dihydroxy-10,13-dimethyl-1-oxo-6,7,8,9,11,12,14,15,16,17-decahydro-4H-cyclopenta[a]phenanthren- |

TABLE 2-continued

LIST OF WITHAFERIN A ANALOGS AND DERIVATIVES BASED ON SIMILARITY

| | | |
|---|---|---|
| | 5,16,18-22,24,29-30,32,34H,6-14H2,1-3H3/t16?,18-,19?,20?,21?,22+,24+,26-,27-,28-/m0/s1 | 17-yl]-2-hydroxyethyl]-5-(hydroxymethyl)-4-methyl-2,3-dihydropyran-6-one |
| 10005030 | InChI=1S/C28H40O6/c1-14-12-22(33-24(31)15(14)2)27(5,32)19-7-6-17-16-13-23-28(34-23)21(30)9-8-20(29)26(28,4)18(16)10-11-25(17,19)3/h8-9,14-19,21-23,30,32H,6-7,10-13H2,1-5H3/t14-,15+,16?,17?,18?,19?,21-,22?,23+,25-,26-,27+,28+/m0/s1 | NA |
| 3808690 | InChI=1S/C28H40O6/c1-15-12-22(34-25(32)18(15)14-29)16(2)19-7-8-20-17-13-24(31)28(33)10-5-6-23(30)27(28,4)21(17)9-11-26(19,20)3/h5-6,16-17,19-22,24,29,31,33H,7-14H2,1-4H3 | 2-[1-(5,6-dihydroxy-10,13-dimethyl-1-oxo-6,7,8,9,11,12,14,15,16,17-decahydro-4H-cyclopenta[a]phenanthren-17-yl)ethyl]-5-(hydroxymethyl)-4-methyl-2,3-dihydropyran-6-one |
| 496218 | InChI=1S/C28H40O7/c1-15-11-22(35-25(33)17(15)13-29)18(14-30)20-7-6-19-16-12-24(32)28(34)9-4-5-23(31)27(28,3)21(16)8-10-26(19,20)2/h4-5,16,18-22,24,29-30,32,34H,6-14H2,1-3H3 | 2-[1-(5,6-dihydroxy-10,13-dimethyl-1-oxo-6,7,8,9,11,12,14,15,16,17-decahydro-4H-cyclopenta[a]phenanthren-17-yl)-2-hydroxyethyl]-5-(hydroxymethyl)-4-methyl-2,3-dihydropyran-6-one |
| 387980 | InChI=1S/C28H40O7/c1-15-11-22(35-25(33)17(15)13-29)18(14-30)20-7-6-19-16-12-24(32)28(34)9-4-5-23(31)27(28,3)21(16)8-10-26(19,20)2/h4-5,16,18-22,24,29-30,32,34H,6-14H2,1-3H3/t16?,18-,19?,20+,21?,22+,24+,26-,27-,28-/m0/s1 | (2R)-2-[(1R)-1-[(5R,6R,10R,13S,17R)-5,6-dihydroxy-10,13-dimethyl-1-oxo-6,7,8,9,11,12,14,15,16,17-decahydro-4H-cyclopenta[a]phenanthren-17-yl]-2-hydroxyethyl]-5-(hydroxymethyl)-4-methyl-2,3-dihydropyran-6-one |
| 268947 | InChI=1S/C28H40O6/c1-15-12-22(34-25(32)18(15)14-29)16(2)19-7-8-20-17-13-24(31)28(33)10-5-6-23(30)27(28,4)21(17)9-11-26(19,20)3/h5-6,16-17,19-22,24,29,31,33H,7-14H2,1-4H3/t16-,17-,19+,20-,21-,22+,24+,26+,27-,28-/m0/s1 | (2R)-2-[(1S)-1-[(5R,6R,8S,9S,10R,13S,14S,17R)-5,6-dihydroxy-10,13-dimethyl-1-oxo-6,7,8,9,11,12,14,15,16,17-decahydro-4H-cyclopenta[a]phenanthren-17-yl]ethyl]-5-(hydroxymethyl)-4-methyl-2,3-dihydropyran-6-one |
| 102435652 | InChI=1S/C28H40O6/c1-15-14-21(34-24(31)16(15)2)17(3)27(32)13-10-19-18-8-12-28(33)23(30)7-6-22(29)26(28,5)20(18)9-11-25(19,27)4/h6-7,17-21,23,30,32-33H,8-14H2,1-5H3/t17-,18+,19+,20+,21?,23+,25+,26+,27+,28+/m1/s1 | 4,5-dimethyl-2-[(1R)-1-[(4S,5R,8S,9S,10R,13S,14S,17S)-4,5,17-trihydroxy-10,13-dimethyl-1-oxo-4,6,7,8,9,11,12,14,15,16-decahydrocyclopenta[a]phenanthren-17-yl]ethyl]-2,3-dihydropyran-6-one |
| 102435650 | InChI=1S/C28H40O7/c1-15-13-21(35- | 5-(hydroxymethyl)-4-methyl-2-[(1R)-1- |

TABLE 2-continued

LIST OF WITHAFERIN A ANALOGS AND DERIVATIVES BASED ON SIMILARITY

| | | |
|---|---|---|
| | 24(32)18(15)14-29)16(2)27(33)12-9-19-17-7-11-28(34)23(31)6-5-22(30)26(28,4)20(17)8-10-25(19,27)3/h5-6,16-17,19-21,23,29,31,33-34H,7-14H2,1-4H3/t16-,17+,19+,20+,21?,23+,25+,26+,27+,28+/m1/s1 | [(4S,5R,8S,9S,10R,13S,14S,17S)-4,5,17-trihydroxy-10,13-dimethyl-1-oxo-4,6,7,8,9,11,12,14,15,16-decahydrocyclopenta[a]phenanthren-17-yl]ethyl]-2,3-dihydropyran-6-one |
| 102262595 | InChI=1S/C30H40O8/c1-14-11-21(37-26(34)15(14)2)16(3)29(35)24(36-17(4)31)13-20-18-12-25-30(38-25)23(33)8-7-22(32)28(30,6)19(18)9-10-27(20,29)5/h7-8,16,18-21,23-25,33,35H,9-13H2,1-6H3/t16-,18-,19+,20+,21-,23+,24-,25-,27+,28+,29-,30-/m1/s1 | NA |
| 102065719 | InChI=1S/C28H38O6/c1-14-11-20(33-24(31)15(14)2)16(3)28(32)22(30)13-19-17-12-23-27(34-23)9-6-7-21(29)26(27,5)18(17)8-10-25(19,28)4/h6-7,16-20,22-23,30,32H,8-13H2,1-5H3/t16-,17-,18+,19+,20-,22-,23-,25+,26+,27-,28-/m1/s1 | NA |
| 101664458 | InChI=1S/C32H42O9/c1-15-11-23(40-29(37)16(15)2)17(3)28-24(39-19(5)34)13-22-20-12-27-32(41-27)26(36)8-7-25(35)30(32,6)21(20)9-10-31(22,28)14-38-18(4)33/h7-8,17,20-24,26-28,36H,9-14H2,1-6H3/t17-,20-,21+,22+,23-,24-,26+,27-,28+,30+,31-,32-/m1/s1 | NA |
| 101630646 | InChI=1S/C28H40O6/c1-15-12-22(34-25(32)16(15)2)18(14-29)20-8-7-19-17-13-24(31)28(33)10-5-6-23(30)27(28,4)21(17)9-11-26(19,20)3/h5-6,17-22,24,29,31,33H,7-14H2,1-4H3/t17-,18-,19-,20+,21-,22+,24+,26-,27-,28-/m0/s1 | (2R)-2-[(1R)-1-[(5R,6R,8S,9S,10R,13S,14S,17R)-5,6-dihydroxy-10,13-dimethyl-1-oxo-6,7,8,9,11,12,14,15,16,17-decahydro-4H-cyclopenta[a]phenanthren-17-yl]-2-hydroxyethyl]-4,5-dimethyl-2,3-dihydropyran-6-one |
| 101420306 | InChI=1S/C32H42O9/c1-15-11-23(40-29(37)16(15)2)17(3)28-24(39-19(5)34)13-22-20-12-27-32(41-27)26(36)8-7-25(35)30(32,6)21(20)9-10-31(22,28)14-38-18(4)33/h7-8,17,20-24,26-28,36H,9-14H2,1-6H3/t17-,20-,21+,22+,23?,24?,26?,27?,28+,30+,31-,32?/m1/s1 | NA |
| 101403753 | InChI=1S/C31H42O7/c1-17-14-24(37-26(34)18(17)2)29(6,35)22-10-12-27(4)21-15-25-31(38-25)11-7-8-23(33)28(31,5)20(21)9-13-30(22,27)16-36-19(3)32/h7-8,14,18,20- | NA |

TABLE 2-continued

LIST OF WITHAFERIN A ANALOGS AND DERIVATIVES BASED ON SIMILARITY

| | | |
|---|---|---|
| | 22,24-25,35H,9-13,15-16H2,1-6H3/t18?,20-,21+,22+,24+,25+,27-,28-,29+,30-,31+/m0/s1 | |
| 101316930 | InChI=1S/C28H38O6/c1-13-11-19(33-25(31)14(13)2)15(3)16-8-9-17-22-18(12-21(30)26(16,17)4)27(5)20(29)7-6-10-28(27,32)24-23(22)34-24/h6-7,15-19,21-24,30,32H,8-12H2,1-5H3/t15-,16+,17-,18-,19+,21+,22-,23-,24-,26+,27-,28-/m0/s1 | NA |
| 101131180 | InChI=1S/C29H42O7/c1-16-12-23(36-26(33)19(16)15-35-4)18(14-30)21-8-7-20-17-13-25(32)29(34)10-5-6-24(31)28(29,3)22(17)9-11-27(20,21)2/h5-6,17-18,20-23,25,30,32,34H,7-15H2,1-4H3/t17-,18-,20-,21+,22-,23+,25+,27-,28-,29-/m0/s1 | (2R)-2-[(1R)-1-[(5R,6R,8S,9S,10R,13S,14S,17R)-5,6-dihydroxy-10,13-dimethyl-1-oxo-6,7,8,9,11,12,14,15,16,17-decahydro-4H-cyclopenta[a]phenanthren-17-yl]-2-hydroxyethyl]-5-(methoxymethyl)-4-methyl-2,3-dihydropyran-6-one |
| 99606234 | InChI=1S/C27H36O7/c1-14(19-5-4-15(13-28)23(31)33-19)16-9-11-26(32)18-12-22-27(34-22)21(30)7-6-20(29)25(27,3)17(18)8-10-24(16,26)2/h4,6-7,14,16-19,21-22,28,30,32H,5,8-13H2,1-3H3/t14-,16+,17-,18+,19+,21-,22+,24+,25-,26+,27+/m0/s1 | NA |
| 90987835 | InChI=1S/C33H46O7/c1-7-14-37-28-11-10-27(35)32(6)25-12-13-31(5)23(8-9-24(31)21(25)16-29-33(28,32)40-29)19(3)26-15-18(2)22(30(36)39-26)17-38-20(4)34/h10-11,19,21,23-26,28-29H,7-9,12-17H2,1-6H3 | NA |
| 90984131 | InChI=1S/C27H38O6/c1-15-12-21(32-25(31)19(15)14-28)16(2)17-6-4-8-18-13-24-27(33-24)23(30)11-10-22(29)26(27,3)20(18)9-5-7-17/h10-11,16-18,20-21,23-24,28,30H,4-9,12-14H2,1-3H3 | NA |
| 85123263 | InChI=1S/C28H40O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,14-18,20-22,30,32-33H,8-13H2,1-5H3 | NA |
| 77987113 | InChI=1S/C28H38O6/c1-13-12-19(33-25(32)14(13)2)15(3)16-6-7-17-22-18(10-11-26(16,17)4)27(5)20(29)8-9-21(30)28(27)24(34-28)23(22)31/h8-9,15-19,21-24,30-31H,6-7,10-12H2,1-5H3 | NA |

TABLE 2-continued

LIST OF WITHAFERIN A ANALOGS AND DERIVATIVES BASED ON SIMILARITY

| | | |
|---|---|---|
| 75072256 | InChI=1S/C28H38O6/c1-15-12-21(33-24(31)16(15)2)17(3)27(32)11-8-19-18-13-23-28(34-23)9-5-6-22(30)26(28,14-29)20(18)7-10-25(19,27)4/h5-6,17-21,23,29,32H,7-14H2,1-4H3 | NA |
| 75072251 | InChI=1S/C28H38O6/c1-13-11-19(33-25(31)14(13)2)15(3)16-8-9-17-22-18(12-21(30)26(16,17)4)27(5)20(29)7-6-10-28(27,32)24-23(22)34-24/h6-7,15-19,21-24,30,32H,8-12H2,1-5H3 | NA |
| 74039187 | InChI=1S/C28H38O7/c1-14-12-21(34-23(31)15(14)2)26(5,32)18-9-11-27(33)17-13-22-28(35-22)20(30)7-6-19(29)25(28,4)16(17)8-10-24(18,27)3/h6-7,16-18,20-22,30,32-33H,8-13H2,1-5H3 | NA |
| 74039185 | InChI=1S/C28H38O7/c1-13-12-20(34-24(32)14(13)2)27(5,33)17-7-6-15-21-16(10-11-25(15,17)3)26(4)18(29)8-9-19(30)28(26)23(35-28)22(21)31/h8-9,15-17,19-23,30-31,33H,6-7,10-12H2,1-5H3 | NA |
| 73123620 | InChI=1S/C30H40O7/c1-16-13-24(36-26(33)17(16)2)28(5,34)22-9-8-21-19-14-25-30(37-25)11-6-7-23(32)27(30,4)20(19)10-12-29(21,22)15-35-18(3)31/h6-7,19-22,24-25,34H,8-15H2,1-5H3 | NA |
| 73021842 | InChI=1S/C27H36O6/c1-13-12-18(32-24(30)14(13)2)21(29)17-8-7-15-20-16(9-11-25(15,17)3)26(4)19(28)6-5-10-27(26,31)23-22(20)33-23/h5-6,15-18,20-23,29,31H,7-12H2,1-4H3 | NA |
| 71481106 | InChI=1S/C28H38O6/c1-13-12-19(33-25(32)14(13)2)15(3)16-6-7-17-22-18(10-11-26(16,17)4)27(5)20(29)8-9-21(30)28(27)24(34-28)23(22)31/h8-9,15-19,21-24,30-31H,6-7,10-12H2,1-5H3/t15-,16+,17-,18-,19+,21-,22-,23+,24+,26+,27-,28+/m0/s1 | NA |
| 58443787 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,24,29H,5-6,9-13H2,1-4H3/t15-,16?,18?,19?,20?,21?,24+,26+,27-,28+/m0/s1 | NA |

TABLE 2-continued

LIST OF WITHAFERIN A ANALOGS AND DERIVATIVES BASED ON SIMILARITY

| | | |
|---|---|---|
| 53398686 | InChI=1S/C27H36O7/c1-14(19-5-4-15(13-28)23(31)33-19)16-9-11-26(32)18-12-22-27(34-22)21(30)7-6-20(29)25(27,3)17(18)8-10-24(16,26)2/h4,6-7,14,16-19,21-22,28,30,32H,5,8-13H2,1-3H3 | NA |
| 45111621 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,24,29H,5-6,9-13H2,1-4H3/t15-,16?,18?,19?,20?,21?,24+,26+,27-,28?/m0/s1 | NA |
| 44566997 | InChI=1S/C28H38O6/c1-15-12-21(33-24(31)16(15)2)17(3)27(32)11-8-19-18-13-23-28(34-23)9-5-6-22(30)26(28,14-29)20(18)7-10-25(19,27)4/h5-6,17-21,23,29,32H,7-14H2,1-4H3/t17-,18+,19+,20+,21-,23-,25+,26+,27+,28-/m1/s1 | NA |
| 44566979 | InChI=1S/C28H38O6/c1-13-11-19(33-25(31)14(13)2)15(3)16-8-9-17-22-18(12-21(30)26(16,17)4)27(5)20(29)7-6-10-28(27,32)24-23(22)34-24/h6-7,15-19,21-24,30,32H,8-12H2,1-5H3/t15-,16+,17-,18-,19+,21-,22-,23-,24-,26+,27-,28-/m0/s1 | NA |
| 44423097 | InChI=1S/C28H40O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,16-18,20-23,30-33H,8-13H2,1-5H3/tl6-,17-,18-,20-,21,22?,23?,24-,25-,26-,27+,28+/m0/s1 | NA |
| 44423090 | InChI=1S/C28H40O6/c1-14-12-20(33-24(31)15(14)2)16(3)27(32)11-9-18-17-13-23-28(34-23)22(30)7-6-21(29)26(28,5)19(17)8-10-25(18,27)4/h6-7,16-20,22-24,30-32H,8-13H2,1-5H3/t16-,17+,18+,19+,20-,22+,23-,24?,25+,26+,27+,28-/m1/s1 | NA |
| 23266162 | InChI=1S/C28H38O7/c1-14-12-21(34-23(31)15(14)2)26(5,32)18-9-11-27(33)17-13-22-28(35-22)20(30)7-6-19(29)25(28,4)16(17)8-10-24(18,27)3/h6-7,16-18,20-22,30,32-33H,8-13H2,1-5H3/t16-,17+,18-,20-,21+,22+,24+,25-,26+,27+,28+/m0/s1 | NA |

TABLE 2-continued

LIST OF WITHAFERIN A ANALOGS AND DERIVATIVES BASED ON SIMILARITY

| | | |
|---|---|---|
| 23266160 | InChI=1S/C28H38O7/c1-13-12-20(34-24(32)14(13)2)27(5,33)17-7-6-15-21-16(10-11-25(15,17)3)26(4)18(29)8-9-19(30)28(26)23(35-28)22(21)31/h8-9,15-17,19-23,30-31,33H,6-7,10-12H2,1-5H3/t15-,16-,17-,19-,20+,21-,22+,23+,25-,26-,27+,28+/m0/s1 | NA |
| 23266158 | InChI=1S/C28H38O6/c1-14-12-20(33-24(31)15(14)2)16(3)17-9-11-27(32)19-13-23-28(34-23)22(30)7-6-21(29)26(28,5)18(19)8-10-25(17,27)4/h6-7,16-20,22-23,30,32H,8-13H2,1-5H3/t16-,17+,18-,19+,20+,22-,23+,25+,26-,27+,28+/m0/s1 | NA |
| 14836386 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,24,29H,5-6,9-13H2,1-4H3 | NA |
| 12070588 | InChI=1S/C28H40O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,14-18,20-22,30,32-33H,8-13H2,1-5H3/t14-,15+,16-,17-,18-,20-,21+,22+,24-,25-,26-,27+,28+/m0/s1 | NA |
| 11844626 | InChI=1S/C30H40O7/c1-16-13-24(36-26(33)17(16)2)28(5,34)22-9-8-21-19-14-25-30(37-25)11-6-7-23(32)27(30,4)20(19)10-12-29(21,22)15-35-18(3)31/h6-7,19-22,24-25,34H,8-15H2,1-5H3/t19-,20+,21+,22-,24-,25-,27+,28+,29-,30-/m1/s1 | NA |
| 11590622 | InChI=1S/C27H36O6/c1-13-12-18(32-24(30)14(13)2)21(29)17-8-7-15-20-16(9-11-25(15,17)3)26(4)19(28)6-5-10-27(26,31)23-22(20)33-23/h5-6,15-18,20-23,29,31H,7-12H2,1-4H3/t15-,16-,17+,18+,20-,21+,22-,23-,25-,26-,27-/m0/s1 | NA |
| 11038269 | InChI=1S/C28H40O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,14-18,20-22,30,32-33H,8-13H2,1-5H3/t14-,15+,16-,17-,18-,20-,21?,22+,24-,25-,26-,27+,28+/m0/s1 | NA |

TABLE 2-continued

LIST OF WITHAFERIN A ANALOGS AND DERIVATIVES BASED ON SIMILARITY

| | | |
|---|---|---|
| 10368236 | InChI=1S/C28H40O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,14-18,20-22,30,32-33H,8-13H2,1-5H3/t14-,15+,16?,17?,18?,20-,21?,22+,24-,25-,26-,27+,28?/m0/s1 | NA |
| 10277878 | InChI=1S/C28H38O7/c1-14-11-20(34-24(32)15(14)2)16(3)17-8-10-27(33)19-12-23-28(35-23)22(31)6-5-21(30)25(28,4)18(19)7-9-26(17,27)13-29/h5-6,16-20,22-23,29,31,33H,7-13H2,1-4H3/t16-,17?,18?,19?,20+,22-,23+,25-,26-,27+,28+/m0/s1 | NA |
| 10228028 | InChI=1S/C28H38O7/c1-14-12-21(34-23(31)15(14)2)26(5,32)18-9-11-27(33)17-13-22-28(35-22)20(30)7-6-19(29)25(28,4)16(17)8-10-24(18,27)3/h6-7,16-18,20-22,30,32-33H,8-13H2,1-5H3/t16?,17?,18?,20-,21?,22+,24+,25-,26+,27+,28?/m0/s1 | NA |
| 10095500 | InChI=1S/C28H38O5/c1-15-13-21(32-24(30)16(15)2)17(3)27(31)12-9-19-18-14-23-28(33-23)10-6-7-22(29)26(28,5)20(18)8-11-25(19,27)4/h6-7,17-21,23,31H,8-14H2,1-5H3/t17-,18+,19+,20+,21-,23-,25+,26+,27+,28-/m1/s1 | NA |
| 321579 | InChI=1S/C28H38O7/c1-14-11-20(34-24(32)16(14)13-29)15(2)17-8-10-27(33)19-12-23-28(35-23)22(31)6-5-21(30)26(28,4)18(19)7-9-25(17,27)3/h5-6,15,17-20,22-23,29,31,33H,7-13H2,1-4H3 | NA |
| 301755 | InChI=1S/C28H38O6/c1-14-12-20(33-24(31)15(14)2)16(3)17-9-11-27(32)19-13-23-28(34-23)22(30)7-6-21(29)26(28,5)18(19)8-10-25(17,27)4/h6-7,16-20,22-23,30,32H,8-13H2,1-5H3 | NA |
| 165541 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,24,29H,5-6,9-13H2,1-4H3/t15-,16-,18+,19-,20-,21+,24+,26+,27-,28+/m0/s1 | NA |

TABLE 2-continued

LIST OF WITHAFERIN A ANALOGS AND DERIVATIVES BASED ON SIMILARITY

| | | |
|---|---|---|
| 102579381 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h7-8,14-21,23-24,29,31H,5-6,9-13H2,1-4H3/t14-,15-,16-,17?,18+,19-,20-,21?,23-,24+,26+,27-,28+/m0/s1 | NA |
| 102357986 | InChI=1S/C32H42O8/c1-16-13-25(39-29(36)21(16)15-37-18(3)33)17(2)22-7-8-23-20-14-28-32(40-28)27(38-19(4)34)10-9-26(35)31(32,6)24(20)11-12-30(22,23)5/h9-10,17,20,22-25,27-28H,7-8,11-15H2,1-6H3/t17-,20-,22+,23-,24-,25?,27+,28+,30+,31-,32+/m0/s1 | NA |
| 102357981 | InChI=1S/C32H42O8/c1-16-13-25(39-29(36)21(16)15-37-18(3)33)17(2)22-7-8-23-20-14-28-32(40-28)27(38-19(4)34)10-9-26(35)31(32,6)24(20)11-12-30(22,23)5/h9-10,17,20,22-25,27-28H,7-8,11-15H2,1-6H3/t17-,20-,22+,23-,24-,25?,27-,28+,30+,31-,32+/m0/s1 | NA |
| 102330662 | InChI=1S/C28H40O7/c1-13-10-21(34-24(32)14(13)2)27(5,33)23-18(29)12-17-15-11-22-28(35-22)20(31)7-6-19(30)26(28,4)16(15)8-9-25(17,23)3/h6-7,13-18,20-23,29,31,33H,8-12H2,1-5H3/t13-,14?,15+,16-,17-,18-,20-,21+,22+,23-,25-,26-,27-,28+/m0/s1 | NA |
| 102065718 | InChI=1S/C30H40O7/c1-15-12-22(36-26(33)16(15)2)17(3)30(34)25(35-18(4)31)14-21-19-13-24-29(37-24)10-7-8-23(32)28(29,6)20(19)9-11-27(21,30)5/h7-8,17,19-22,24-25,34H,9-14H2,1-6H3/t17-,19-,20+,21+,22-,24-,25-,27+,28+,29-,30-/m1/s1 | NA |
| 101911592 | InChI=1S/C28H38O6/c1-14-11-21(34-25(32)15(14)2)16(3)24-20(29)13-19-17-12-23(31)28(33)9-6-7-22(30)27(28,5)18(17)8-10-26(19,24)4/h6-7,16-19,21,23-24,31,33H,8-13H2,1-5H3/t16-,17-,18+,19+,21-,23-,24+,26+,27+,28+/m1/s1 | (5R,6R,8S,9S,10R,13S,14S,17R)-17-[(1S)-1-[(2R)-4,5-dimethyl-6-oxo-2,3-dihydropyran-2-yl]ethyl]-5,6-dihydroxy-10,13-dimethyl-4,6,7,8,9,11,12,14,15,17-decahydrocyclopenta[a]phenanthrene-1,16-dione |
| 101005224 | InChI=1S/C30H40O8/c1-14-13-22(37-26(34)15(14)2)29(6,35)19-8-7-17-23-18(11-12-27(17,19)4)28(5)20(32)9-10-26(35)31(28)... | NA |

TABLE 2-continued

LIST OF WITHAFERIN A ANALOGS AND DERIVATIVES BASED ON SIMILARITY

| | | |
|---|---|---|
| | 10-21(33)30(28)25(38-30)24(23)36-16(3)31/h9-10,17-19,21-25,33,35H,7-8,11-13H2,1-6H3/t17-,18-,19-,21?,22+,23-,24?,25-,27-,28-,29+,30-/m0/s1 | |
| 100990383 | InChI=1S/C28H38O7/c1-13-10-19(34-24(32)14(13)2)15(3)17-11-22(31)27(33)18-12-23-28(35-23)21(30)7-6-20(29)26(28,5)16(18)8-9-25(17,27)4/h6-7,15-19,21-23,30-31,33H,8-12H2,1-5H3/t15-,16+,17-,18-,19-,21+,22+,23-,25-,26+,27-,28-/m1/s1 | NA |
| 99567692 | InChI=1S/C28H38O6/c1-14-13-20(33-24(30)15(14)2)27(5,31)18-9-8-16-21-17(10-12-25(16,18)3)26(4)19(29)7-6-11-28(26,32)23-22(21)34-23/h6-7,16-18,20-23,31-32H,8-13H2,1-5H3/t16-,17-,18-,20+,21-,22+,23+,25-,26-,27-,28-/m0/s1 | NA |
| 99567691 | InChI=1S/C28H38O6/c1-14-13-20(33-24(30)15(14)2)27(5,31)18-9-8-16-21-17(10-12-25(16,18)3)26(4)19(29)7-6-11-28(26,32)23-22(21)34-23/h6-7,16-18,20-23,31-32H,8-13H2,1-5H3/t16-,17-,18-,20-,21-,22+,23+,25-,26-,27-,28-/m0/s1 | NA |
| 99567690 | InChI=1S/C28H38O6/c1-14-13-20(33-24(30)15(14)2)27(5,31)18-9-8-16-21-17(10-12-25(16,18)3)26(4)19(29)7-6-11-28(26,32)23-22(21)34-23/h6-7,16-18,20-23,31-32H,8-13H2,1-5H3/t16-,17-,18-,20+,21-,22+,23+,25-,26-,27+,28-/m0/s1 | NA |
| 99567689 | InChI=1S/C28H38O6/c1-14-13-20(33-24(30)15(14)2)27(5,31)18-9-8-16-21-17(10-12-25(16,18)3)26(4)19(29)7-6-11-28(26,32)23-22(21)34-23/h6-7,16-18,20-23,31-32H,8-13H2,1-5H3/t16-,17-,18-,20-,21-,22+,23+,25-,26-,27+,28-/m0/s1 | NA |
| 90705667 | InChI=1S/C29H42O6/c1-14-10-22(34-26(33)18(14)13-30)16(3)19-6-7-20-17-12-24-29(35-24)25(32)15(2)11-23(31)28(29,5)21(17)8-9-27(19,20)4/h15-17,19-22,24-25,30,32H,6-13H2,1-5H3 | NA |
| 90670456 | InChI=1S/C32H42O8/c1-16-13-25(39-29(36)21(16)15-37-18(3)33)17(2)22-7-8-23-20-14-28-32(40-28)27(38-19(4)34)10-9- | NA |

TABLE 2-continued

LIST OF WITHAFERIN A ANALOGS AND DERIVATIVES BASED ON SIMILARITY

| | | |
|---|---|---|
| | 26(35)31(32,6)24(20)11-12-30(22,23)5/h9-10,17,20,22-25,27-28H,7-8,11-15H2,1-6H3/t17-,20-,22+,23-,24-,25+,27+,28+,30+,31-,32+/m0/s1 | |
| 90670449 | InChI=1S/C32H44O8/c1-17-14-26(40-29(36)22(17)16-38-19(3)33)18(2)23-9-10-24-21-15-28(39-20(4)34)32(37)12-7-8-27(35)31(32,6)25(21)11-13-30(23,24)5/h7-8,18,21,23-26,28,37H,9-16H2,1-6H3/t18-,21-,23+,24-,25-,26+,28+,30+,31-,32-/m0/s1 | [(2R)-2-[(1S)-1-[(5R,6R,8S,9S,10R,13S,14S,17R)-6-acetyloxy-5-hydroxy-10,13-dimethyl-1-oxo-6,7,8,9,11,12,14,15,16,17-decahydro-4H-cyclopenta[a]phenanthren-17-yl]ethyl]-4-methyl-6-oxo-2,3-dihydropyran-5-yl]methyl acetate |
| 90670448 | InChI=1S/C34H46O10/c1-17-14-27(44-31(39)23(17)16-41-19(3)35)18(2)24-8-9-25-22-15-30(43-21(5)37)34(40)29(42-20(4)36)11-10-28(38)33(34,7)26(22)12-13-32(24,25)6/h10-11,18,22,24-27,29-30,40H,8-9,12-16H2,1-7H3/t18-,22-,24+,25-,26-,27+,29-,30-,32+,33-,34+/m0/s1 | [(2R)-2-[(1S)-1-[(4S,5S,6S,8S,9S,10R,13S,14S,17R)-4,6-diacetyloxy-5-hydroxy-10,13-dimethyl-1-oxo-6,7,8,9,11,12,14,15,16,17-decahydro-4H-cyclopenta[a]phenanthren-17-yl]ethyl]-4-methyl-6-oxo-2,3-dihydropyran-5-yl]methyl acetate |
| 90670446 | InChI=1S/C30H40O7/c1-15-13-22(36-27(33)18(15)14-35-17(3)31)16(2)19-8-9-20-24-21(10-12-28(19,20)4)29(5)23(32)7-6-11-30(29,34)26-25(24)37-26/h6-7,16,19-22,24-26,34H,8-14H2,1-5H3/t16-,19+,20-,21-,22+,24-,25-,26-,28+,29-,30-/m0/s1 | NA |
| 90473517 | InChI=1S/C30H40O6/c1-16-13-24(35-27(33)20(16)15-34-18(3)31)17(2)21-8-9-22-19-14-26-30(36-26)11-6-7-25(32)29(30,5)23(19)10-12-28(21,22)4/h6-7,17,19,21-24,26H,8-15H2,1-5H3/t17-,19-,21+,22-,23-,24?,26?,28+,29-,30?/m0/s1 | NA |
| 89092194 | InChI=1S/C31H42O7/c1-6-11-29(5)21(17(3)24-12-16(2)20(28(35)37-24)15-36-18(4)32)7-8-22(29)19-13-27-31(38-27)26(34)10-9-25(33)30(31)14-23(19)30/h9-10,17,19,21-24,26-27,34H,6-8,11-15H2,1-5H3/t17-,19?,21?,22?,23?,24?,26+,27+,29+,30-,31+/m0/s1 | NA |
| 89092040 | InChI=1S/C29H38O6/c1-14-11-21(34-26(33)17(14)13-30)15(2)18-6-7-19-16-12-24-29(35-24)23(32)9-10,17,19,21-24,26-27,34H,6-8,11-15H2,1-5H3/t17-,19?,21?,22?,23?,24?,26+,27+,29+,30-,31+/m0/s1 | NA |

TABLE 2-continued

LIST OF WITHAFERIN A ANALOGS AND DERIVATIVES BASED ON SIMILARITY

| | | |
|---|---|---|
| | 8-22(31)28(29)20(25(16)28)5-4-10-27(18,19)3/h8-9,15-16,18-21,23-25,30,32H,4-7,10-13H2,1-3H3/t15-,16?,18?,19?,20?,21?,23+,24+,25?,27+,28+,29+/m0/s1 | |
| 89092028 | InChI=1S/C29H38O6/c1-14-11-21(34-26(33)17(14)13-30)15(2)18-6-7-19-16-12-24-29(35-24)23(32)9-8-22(31)28(29)20(25(16)28)5-4-10-27(18,19)3/h8-9,15-16,18-21,23-25,30,32H,4-7,10-13H2,1-3H3/t15-,16?,18?,19?,20-,21?,23-,24+,25?,27+,28+,29+/m0/s1 | NA |
| 89064896 | InChI=1S/C29H44O7/c1-14-11-23(35-26(34)19(14)13-30)15(2)20-7-8-21-18-12-24-29(36-24,25(33)16(3)31)28(6,17(4)32)22(18)9-10-27(20,21)5/h15-16,18,20-25,30-31,33H,7-13H2,1-6H3/t15-,16-,18?,20?,21?,22?,23?,24+,25-,27+,28+,29-/m0/s1 | NA |
| 88948989 | InChI=1S/C27H38O6/c1-13-10-21(32-25(31)17(13)12-28)14(2)18-4-5-19-16-11-23-27(33-23)22(30)7-6-20(29)24(27)15(16)8-9-26(18,19)3/h14-16,18-19,21-24,28,30H,4-12H2,1-3H3/t14-,15-,16+,18+,19-,21+,22-,23+,24?,26+,27+/m0/s1 | NA |
| 88858697 | InChI=1S/C33H44O8/c1-7-21-17(2)14-26(40-30(21)37)18(3)23-8-9-24-22-15-29-33(41-29)28(39-20(5)35)11-10-27(36)32(33,16-38-19(4)34)25(22)12-13-31(23,24)6/h10-11,18,22-26,28-29H,7-9,12-16H2,1-6H3/t18-,22-,23?,24-,25-,26+,28-,29+,31+,32-,33+/m0/s1 | NA |
| 85857395 | InChI=1S/C29H44O4/c1-17(2)8-7-9-18(3)21-10-11-22-20-16-26-29(33-26)25(32-19(4)30)13-12-24(31)28(29,6)23(20)14-15-27(21,22)5/h12-13,17-18,20-23,25-26H,7-11,14-16H2,1-6H3 | NA |
| 85836925 | InChI=1S/C27H42O3/c1-16(2)7-6-8-17(3)19-9-10-20-18-15-24-27(30-24)23(29)12-11-22(28)26(27,5)21(18)13-14-25(19,20)4/h11-12,16-21,23-24,29H,6-10,13-15H2,1-5H3 | NA |
| 78384890 | InChI=1S/C28H38O7/c1-13-10-19(34-24(32)14(13)2)15(3)17- | NA |

TABLE 2-continued

LIST OF WITHAFERIN A ANALOGS AND DERIVATIVES BASED ON SIMILARITY

| | | |
|---|---|---|
| | 11-22(31)27(33)18-12-23-28(35-23)21(30)7-6-20(29)26(28,5)16(18)8-9-25(17,27)4/h6-7,15-19,21-23,30-31,33H,8-12H2,1-5H3 | |
| 76385933 | InChI=1S/C32H42O8/c1-16-13-25(39-29(36)17(16)2)18(3)22-7-8-23-21-14-28-32(40-28)27(38-20(5)34)10-9-26(35)31(32,15-37-19(4)33)24(21)11-12-30(22,23)6/h9-10,18,21-25,27-28H,7-8,11-15H2,1-6H3 | NA |
| 76385926 | InChI=1S/C34H44O10/c1-17-13-27(43-31(39)23(17)15-40-19(3)35)18(2)24-7-8-25-22-14-30-34(44-30)29(42-21(5)37)10-9-28(38)33(34,16-41-20(4)36)26(22)11-12-32(24,25)6/h9-10,18,22,24-27,29-30H,7-8,11-16H2,1-6H3 | NA |
| 76328113 | InChI=1S/C37H50O10/c1-7-31(39)43-18-23-20(4)16-27(45-34(23)42)21(5)24-10-11-25-22-17-30-37(47-30)29(46-33(41)9-3)13-12-28(38)36(37,19-44-32(40)8-2)26(22)14-15-35(24,25)6/h12-13,21-22,24-27,29-30H,7-11,14-19H2,1-6H3/t21-,22-,24+,25-,26-,27+,29-,30+,35+,36-,37+/m0/s1 | NA |
| 75072261 | InChI=1S/C28H40O7/c1-13-10-21(34-24(32)14(13)2)27(5,33)23-18(29)12-17-15-11-22-28(35-22)20(31)7-6-19(30)26(28,4)16(15)8-9-25(17,23)3/h6-7,13-18,20-23,29,31,33H,8-12H2,1-5H3 | NA |
| 75072250 | InChI=1S/C28H36O6/c1-13-11-19(33-25(31)14(13)2)15(3)22-18(29)12-17-21-16(8-10-26(17,22)4)27(5)20(30)7-6-9-28(27,32)24-23(21)34-24/h6-7,16-19,21,23-24,29,32H,8-12H2,1-5H3 | NA |
| 73981783 | InChI=1S/C30H40O8/c1-14-13-22(37-26(34)15(14)2)29(6,35)19-8-7-17-23-18(11-12-27(17,19)4)28(5)20(32)9-10-21(33)30(28)25(38-30)24(23)36-16(3)31/h9-10,17-19,21-25,33,35H,7-8,11-13H2,1-6H3 | NA |
| 73797122 | InChI=1S/C28H38O7/c1-14-12-19(34-24(31)16(14)13-29)15(2)27(32)11-8-17-21-18(7-10-25(17,27)3)26(4)20(30)6-5-9-28(26,33)23-22(21)35-23/h5-6,15,17-19,21-23,29,32-33H,7-13H2,1-4H3 | NA |

TABLE 2-continued

LIST OF WITHAFERIN A ANALOGS AND DERIVATIVES BASED ON SIMILARITY

| | | |
|---|---|---|
| 73306655 | InChI=1S/C28H40O7/c1-14-12-20(35-24(32)15(14)2)16(3)27(33)11-9-18-17-13-23(31)28(34)22(30)7-6-21(29)26(28,5)19(17)8-10-25(18,27)4/h6-7,16-20,22-23,30-31,33-34H,8-13H2,1-5H3 | 4,5-dimethyl-2-[1-(4,5,6,17-tetrahydroxy-10,13-dimethyl-1-oxo-4,6,7,8,9,11,12,14,15,16-decahydrocyclopenta[a]phenanthren-17-yl)ethyl]-2,3-dihydropyran-6-one |
| 73306622 | InChI=1S/C28H36O7/c1-12-13(2)24(32)33-23(22(12)31)14(3)27-21(34-27)11-17-15-10-20-28(35-20)19(30)7-6-18(29)26(28,5)16(15)8-9-25(17,27)4/h6-7,14-17,19-23,30-31H,8-11H2,1-5H3 | NA |
| 72835716 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h7-8,14-21,23-24,29,31H,5-6,9-13H2,1-4H3 | NA |
| 72544875 | InChI=1S/C38H48O10/c1-21-17-29(46-35(43)25(21)19-44-23(3)39)22(2)26-11-12-27-24-18-32-38(48-32)31-14-13-30(40)37(38,28(24)15-16-36(26,27)4)20-45-33(41)9-7-5-6-8-10-34(42)47-31/h5-6,13-14,22,24,26-29,31-32H,7-12,15-20H2,1-4H3/b6-5+/t22-,24-,26+,27-,28-,29+,31-,32+,36+,37-,38+/m0/s1 | NA |
| 72544874 | InChI=1S/C40H52O10/c1-7-9-11-35(43)47-22-39-30-17-18-38(6)28(24(4)31-19-23(3)27(37(45)48-31)21-46-25(5)41)13-14-29(38)26(30)20-34-40(39,50-34)33(16-15-32(39)42)49-36(44)12-10-8-2/h7-8,15-16,24,26,28-31,33-34H,1-2,9-14,17-22H2,3-6H3/t24-,26-,28+,29-,30-,31+,33-,34+,38+,39-,40+/m0/s1 | NA |
| 58443796 | InChI=1S/C32H42O8/c1-16-13-25(39-29(36)21(16)15-37-18(3)33)17(2)22-7-8-23-20-14-28-32(40-28)27(38-19(4)34)10-9-26(35)31(32,6)24(20)11-12-30(22,23)5/h9-10,17,20,22-25,27-28H,7-8,11-15H2,1-6H3/t17-,20?,22?,23?,24?,25?,27+,28+,30+,31-,32+/m0/s1 | NA |
| 57523801 | InChI=1S/C34H44O10/c1-17-13-27(43-31(39)23(17)15-40-19(3)35)18(2)24-7-8-25-22-14-30-34(44-30)29(42-21(5)37)10-9- | NA |

TABLE 2-continued

LIST OF WITHAFERIN A ANALOGS AND DERIVATIVES BASED ON SIMILARITY

| | | |
|---|---|---|
| | 28(38)33(34,16-41-20(4)36)26(22)11-12-32(24,25)6/h9-10,18,22,24-27,29-30H,7-8,11-16H2,1-6H3/t18-,22-,24?,25-,26-,27+,29-,30+,32+,33-,34+/m0/s1 | |
| 56649416 | InChI=1S/C32H42O8/c1-16-13-25(39-29(36)17(16)2)18(3)22-7-8-23-21-14-28-32(40-28)27(38-20(5)34)10-9-26(35)31(32,15-37-19(4)33)24(21)11-12-30(22,23)6/h9-10,18,21-25,27-28H,7-8,11-15H2,1-6H3/t18-,21-,22+,23-,24-,25+,27-,28+,30+,31-,32+/m0/s1 | NA |
| 56649399 | InChI=1S/C34H44O10/c1-17-13-27(43-31(39)23(17)15-40-19(3)35)18(2)24-7-8-25-22-14-30-34(44-30)29(42-21(5)37)10-9-28(38)33(34,16-41-20(4)36)26(22)11-12-32(24,25)6/h9-10,18,22,24-27,29-30H,7-8,11-16H2,1-6H3/t18-,22-,24+,25-,26-,27+,29-,30+,32+,33-,34+/m0/s1 | NA |
| 45111623 | InChI=1S/C32H42O8/c1-16-13-25(39-29(36)21(16)15-37-18(3)33)17(2)22-7-8-23-20-14-28-32(40-28)27(38-19(4)34)10-9-26(35)31(32,6)24(20)11-12-30(22,23)5/h9-10,17,20,22-25,27-28H,7-8,11-15H2,1-6H3/t17-,20?,22?,23?,24?,25?,27+,28+,30+,31-,32?/m0/s1 | NA |
| 44567005 | InChI=1S/C28H40O7/c1-13-10-21(34-24(32)14(13)2)27(5,33)23-18(29)12-17-15-11-22-28(35-22)20(31)7-6-19(30)26(28,4)16(15)8-9-25(17,23)3/h6-7,13-18,20-23,29,31,33H,8-12H2,1-5H3/t13-,14+,15+,16-,17-,18-,20-,21+,22+,23-,25-,26-,27-,28+/m0/s1 | NA |
| 44566978 | InChI=1S/C28H36O6/c1-13-11-19(33-25(31)14(13)2)15(3)22-18(29)12-17-21-16(8-10-26(17,22)4)27(5)20(30)7-6-9-28(27,32)24-23(21)34-24/h6-7,16-19,21,23-24,29,32H,8-12H2,1-5H3/b22-15+/t16-,17-,18+,19+,21+,23-,24-,26-,27-,28-/m0/s1 | NA |
| 44566977 | InChI=1S/C28H36O6/c1-13-11-19(33-25(31)14(13)2)15(3)22-18(29)12-17-21-16(8-10-26(17,22)4)27(5)20(30)7-6-9-28(27,32)24-23(21)34-24/h6-7,16- | NA |

TABLE 2-continued

LIST OF WITHAFERIN A ANALOGS AND DERIVATIVES BASED ON SIMILARITY

| | | |
|---|---|---|
| | 19,21,23-24,29,32H,8-12H2,1-5H3/b22-15+/t16-,17-,18-,19+,21+,23-,24-,26-,27-,28-/m0/s1 | |
| 22524628 | InChI=1S/C30H40O8/c1-14-13-22(37-26(34)15(14)2)29(6,35)19-8-7-17-23-18(11-12-27(17,19)4)28(5)20(32)9-10-21(33)30(28)25(38-30)24(23)36-16(3)31/h9-10,17-19,21-25,33,35H,7-8,11-13H2,1-6H3/t17-,18-,19-,21-,22-,23+,24-,25-,27+,28-,29-,30-/m1/s1 | NA |
| 21574483 | InChI=1S/C28H38O7/c1-14-12-19(34-24(31)16(14)13-29)15(2)27(32)11-8-17-21-18(7-10-25(17,27)3)26(4)20(30)6-5-9-28(26,33)23-22(21)35-23/h5-6,15,17-19,21-23,29,32-33H,7-13H2,1-4H3/t15-,17+,18+,19-,21+,22+,23+,25+,26+,27+,28+/m1/s1 | NA |
| 16680446 | InChI=1S/C28H40O7/c1-14-12-20(35-24(32)15(14)2)16(3)27(33)11-9-18-17-13-23(31)28(34)22(30)7-6-21(29)26(28,5)19(17)8-10-25(18,27)4/h6-7,16-20,22-23,30-31,33-34H,8-13H2,1-5H3/t16-,17+,18+,19+,20-,22+,23+,25+,26+,27+,28-/m1/s1 | (2R)-4,5-dimethyl-2-[(1R)-1-[(4S,5S,6S,8S,9S,10R,13S,14S,17S)-4,5,6,17-tetrahydroxy-10,13-dimethyl-1-oxo-4,6,7,8,9,11,12,14,15,16-decahydrocyclopenta[a]phenanthren-17-yl]ethyl]-2,3-dihydropyran-6-one |
| 16680371 | InChI=1S/C28H36O7/c1-12-13(2)24(32)33-23(22(12)31)14(3)27-21(34-27)11-17-15-10-20-28(35-20)19(30)7-6-18(29)26(28,5)16(15)8-9-25(17,27)4/h6-7,14-17,19-23,30-31H,8-11H2,1-5H3/t14-,15-,16+,17+,19+,20-,21-,22+,23+,25+,26+,27-,28-/m1/s1 | NA |
| 16215490 | InChI=1S/C31H46O7/c1-8-37-30-12-9-10-22(32)28(30,6)20-11-13-27(5)26(4,21(20)17-23(30)33)14-15-31(27,36)29(7,35)24-16-18(2)19(3)25(34)38-24/h9-10,20-21,23-24,33,35-36H,8,11-17H2,1-7H3/t20?,21?,23-,24?,26+,27+,28+,29+,30+,31+/m1/s1 | 2-[(1S)-1-[(5R,6R,10R,13S,14S,17S)-5-ethoxy-6,17-dihydroxy-10,13,14-trimethyl-1-oxo-6,7,8,9,11,12,15,16-octahydro-4H-cyclopenta[a]phenanthren-17-yl]-1-hydroxyethyl]-4,5-dimethyl-2,3-dihydropyran-6-one |
| 15411208 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h15-16,18-21,23-24,29,31H,5-13H2,1-4H3/t15-,16-,18+,19-,20-, | NA |

TABLE 2-continued

LIST OF WITHAFERIN A ANALOGS AND DERIVATIVES BASED ON SIMILARITY

| | | |
|---|---|---|
| | 21+,23-,24+,26+,27-,28+/m0/s1 | |
| 14236712 | InChI=1S/C28H38O5/c1-14-13-20(32-25(30)15(14)2)16(3)17-8-9-18-22-19(10-12-26(17,18)4)27(5)21(29)7-6-11-28(27,31)24-23(22)33-24/h6-7,16-20,22-24,31H,8-13H2,1-5H3 | NA |
| 14236711 | InChI=1S/C28H38O5/c1-14-13-20(32-25(30)15(14)2)16(3)17-8-9-18-22-19(10-12-26(17,18)4)27(5)21(29)7-6-11-28(27,31)24-23(22)33-24/h6-7,16-20,22-24,31H,8-13H2,1-5H3/t16-,17+,18-,19-,20+,22-,23-,24-,26+,27-,28-/m0/s1 | NA |
| 14236710 | InChI=1S/C28H38O6/c1-14-13-20(33-24(30)15(14)2)27(5,31)18-9-8-16-21-17(10-12-25(16,18)3)26(4)19(29)7-6-11-28(26,32)23-22(21)34-23/h6-7,16-18,20-23,31-32H,8-13H2,1-5H3 | NA |
| 11408847 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h7-8,14-21,23-24,29,31H,5-6,9-13H2,1-4H3/t14?,15?,16-,17?,18+,19-,20-,21?,23-,24+,26+,27-,28+/m0/s1 | NA |
| 11294368 | InChI=1S/C28H38O6/c1-14-13-20(33-24(30)15(14)2)27(5,31)18-9-8-16-21-17(10-12-25(16,18)3)26(4)19(29)7-6-11-28(26,32)23-22(21)34-23/h6-7,16-18,20-23,31-32H,8-13H2,1-5H3/t16-,17-,18-,20+,21-,22-,23-,25-,26-,27+,28-/m0/s1 | NA |
| 11070744 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h15-16,18-21,23-24,29,31H,5-13H2,1-4H3/t15-,16-,18?,19-,20-,21?,23-,24+,26+,27-,28+/m0/s1 | NA |
| 10814142 | InChI=1S/C28H36O6/c1-13-11-19(33-25(31)14(13)2)15(3)22-18(29)12-17-21-16(8-10-26(17,22)4)27(5)20(30)7-6-9-28(27,32)24-23(21)34-24/h6-7,16-19,21,23-24,29,32H,8-12H2,1-5H3/b22-15+/t16-,17-,18-,19?,21+,23-,24-,26-,27-,28-/m0/s1 | NA |

TABLE 2-continued

LIST OF WITHAFERIN A ANALOGS AND DERIVATIVES BASED ON SIMILARITY

| | | |
|---|---|---|
| 10576254 | InChI=1S/C28H36O6/c1-13-11-19(33-25(31)14(13)2)15(3)22-18(29)12-17-21-16(8-10-26(17,22)4)27(5)20(30)7-6-9-28(27,32)24-23(21)34-24/h6-7,16-19,21,23-24,29,32H,8-12H2,1-5H3/b22-15+/t16-,17-,18+,19?,21+,23-,24-,26-,27-,28-/m0/s1 | NA |
| 10480656 | InChI=1S/C28H40O7/c1-13-10-21(34-24(32)14(13)2)27(5,33)23-18(29)12-17-15-11-22-28(35-22)20(31)7-6-19(30)26(28,4)16(15)8-9-25(17,23)3/h6-7,13-18,20-23,29,31,33H,8-12H2,1-5H3/t13-,14+,15?,16?,17?,18-,20-,21?,22+,23-,25-,26-,27-,28?/m0/s1 | NA |
| 10457436 | InChI=1S/C28H38O6/c1-14-13-20(33-24(30)15(14)2)27(5,31)18-9-8-16-21-17(10-12-25(16,18)3)26(4)19(29)7-6-11-28(26,32)23-22(21)34-23/h6-7,16-18,20-23,31H,8-13H2,1-5H3/t16?,17?,18-,20+,21?,22-,23-,25-,26-,27+,28-/m0/s1 | NA |
| 10434957 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h15-16,18-21,23-24,29,31H,5-13H2,1-4H3/t15-,16?,18?,19?,20?,21?,23-,24+,26+,27-,28+/m0/s1 | NA |
| 10096775 | InChI=1S/C28H34O7/c1-13-11-21(33-23(31)14(13)2)26(4)18-6-5-17-15-12-22-28(34-22)20(30)8-7-19(29)25(28,3)16(15)9-10-27(17,18)24(32)35-26/h7-8,15-18,20-22,30H,5-6,9-12H2,1-4H3/t15-,16+,17+,18-,20+,21-,22-,25+,26-,27-,28-/m1/s1 | NA |
| 5458717 | InChI=1S/C32H42O8/c1-16-13-25(39-29(36)21(16)15-37-18(3)33)17(2)22-7-8-23-20-14-28-32(40-28)27(38-19(4)34)10-9-26(35)31(32,6)24(20)11-12-30(22,23)5/h9-10,17,20,22-25,27-28H,7-8,11-15H2,1-6H3/t17-,20-,22+,23-,24-,25+,27-,28+,30+,31-,32+/m0/s1 | NA |
| 5317154 | InChI=1S/C28H38O7/c1-13-10-19(34-24(32)14(13)2)15(3)17-11-22(31)27(33)18-12-23-28(35-23)21(30)7-6- | NA |

TABLE 2-continued

LIST OF WITHAFERIN A ANALOGS AND DERIVATIVES BASED ON SIMILARITY

| | | |
|---|---|---|
| | 20(29)26(28,5)16(18)8-9-25(17,27)4/h6-7,15-19,21-23,30-31,33H,8-12H2,1-5H3/t15-,16?,17+,18+,19+,21-,22-,23+,25+,26-,27+,28+/m0/s1 | |
| 5315458 | InChI=1S/C30H40O8/c1-14-13-22(37-26(34)15(14)2)29(6,35)19-8-7-17-23-18(11-12-27(17,19)4)28(5)20(32)9-10-21(33)30(28)25(38-30)24(23)36-16(3)31/h9-10,17-19,21-25,33,35H,7-8,11-13H2,1-6H3/t17-,18-,19-,21-,22+,23-,24+,25+,27-,28-,29+,30+/m0/s1 | NA |
| 580587 | InChI=1S/C30H38O7/c1-15-12-23(36-27(34)19(15)14-31)16(2)20-6-7-21-18-13-26-30(37-26)25(35-17(3)32)9-8-24(33)29(30,5)22(18)10-11-28(20,21)4/h8-9,14,16,18,20-23,25-26H,6-7,10-13H2,1-5H3 | NA |
| 433361 | InChI=1S/C32H42O8/c1-16-13-25(39-29(36)21(16)15-37-18(3)33)17(2)22-7-8-23-20-14-28-32(40-28)27(38-19(4)34)10-9-26(35)31(32,6)24(20)11-12-30(22,23)5/h9-10,17,20,22-25,27-28H,7-8,11-15H2,1-6H3 | NA |
| 418033 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h15-16,18-21,23-24,29,31H,5-13H2,1-4H3 | NA |
| 310015 | InChI=1S/C28H40O7/c1-15-13-22(35-23(31)16(15)2)26(5,32)28(34)12-9-18-17-14-21(30)27(33)10-6-7-20(29)25(27,4)19(17)8-11-24(18,28)3/h6-7,17-19,21-22,30,32-34H,8-14H2,1-5H3 | 2-[1-hydroxy-1-(5,6,17-trihydroxy-10,13-dimethyl-1-oxo-4,6,7,8,9,11,12,14,15,16-decahydrocyclopenta[a]phenanthren-17-yl)ethyl]-4,5-dimethyl-2,3-dihydropyran-6-one |
| 193708 | InChI=1S/C28H38O6/c1-14-13-20(33-24(30)15(14)2)27(5,31)18-9-8-16-21-17(10-12-25(16,18)3)26(4)19(29)7-6-11-28(26,32)23-22(21)34-23/h6-7,16-18,20-23,31-32H,8-13H2,1-5H3/t16-,17-,18-,20?,21-,22-,23-,25-,26-,27+,28-/m0/s1 | NA |
| 73056 | InChI=1S/C32H42O8/c1-16-13-25(39-29(36)21(16)15-37-18(3)33)17(2)22-7-8-23-20-14-28-32(40-28)27(38-19(4)34)10-9-26(35)31(32,6)24(20)11-12-30(22,23)5/h9- | NA |

TABLE 2-continued

LIST OF WITHAFERIN A ANALOGS AND DERIVATIVES BASED ON SIMILARITY

| | | |
|---|---|---|
| | 10,17,20,22-25,27-28H,7-8,11-15H2,1-6H3/t17-,20-,22+,23-,24-,25-,27-,28+,30+,31-,32+/m0/s1 | |
| 102064899 | InChI=1S/C28H38O8/c1-15-16(14-29)12-20(35-22(15)31)25(4,32)28(34)11-10-26(33)18-13-21-27(36-21)8-5-6-19(30)24(27,3)17(18)7-9-23(26,28)2/h5-6,17-18,20-21,29,32-34H,7-14H2,1-4H3/t17-,18+,20+,21+,23-,24-,25-,26+,27+,28-/m0/s1 | NA |
| 101958392 | InChI=1S/C28H38O6/c1-14-12-20(33-24(30)15(14)2)27(5,31)19-7-6-17-21-18(9-10-25(17,19)3)26(4)11-8-16(29)13-28(26,32)23-22(21)34-23/h8,11,17-23,31-32H,6-7,9-10,12-13H2,1-5H3/t17-,18-,19-,20+,21-,22-,23-,25-,26+,27+,28-/m0/s1 | NA |
| 101844470 | InChI=1S/C30H38O7/c1-15-13-22(36-27(33)16(15)2)17(3)19-8-9-21-24-20(10-12-29(19,21)14-35-18(4)31)28(5)23(32)7-6-11-30(28,34)26-25(24)37-26/h6-7,20-22,24-26,34H,8-14H2,1-5H3/b19-17+/t20-,21-,22?,24+,25-,26-,28-,29-,30-/m0/s1 | NA |
| 101844370 | InChI=1S/C27H36O7/c1-13-7-8-17(33-23(13)30)14(2)26(31)11-9-15-20-16(12-19(29)24(15,26)3)25(4)18(28)6-5-10-27(25,32)22-21(20)34-22/h5-7,14-17,19-22,29,31-32H,8-12H2,1-4H3/t14-,15+,16+,17?,19+,20+,21+,22+,24-,25+,26+,27+/m1/s1 | NA |
| 101804281 | InChI=1S/C28H38O8/c1-14-12-20(35-22(31)15(14)2)25(5,32)27(34)11-10-26(33)17-13-21-28(36-21)19(30)7-6-18(29)24(28,4)16(17)8-9-23(26,27)3/h6-7,16-17,19-21,30,32-34H,8-13H2,1-5H3/t16-,17+,19-,20+,21+,23-,24-,25-,26-,27-,28+/m0/s1 | NA |
| 101801014 | InChI=1S/C30H42O9/c1-14-25(34)38-23(13-27(14,4)35)29(6,36)24-19(37-15(2)31)12-18-16-11-22-30(39-22)21(33)8-7-20(32)28(30,5)17(16)9-10-26(18,24)3/h7-8,14,16-19,21-24,33,35-36H,9-13H2,1-6H3/t14-,16+,17-,18-,19-,21-,22+,23-,24-,26-,27+,28-,29-,30+/m0/s1 | NA |
| 101664459 | InChI=1S/C32H42O9/c1-14-10-22(40-29(37)15(14)2)16(3)28-23(38-17(4)33)12-20-19- | NA |

TABLE 2-continued

LIST OF WITHAFERIN A ANALOGS AND DERIVATIVES BASED ON SIMILARITY

| | | |
|---|---|---|
| | 11-27-32(41-27)25(36)9-<br>8-<br>24(35)31(32,7)21(19)13-<br>26(30(20,28)6)39-<br>18(5)34/h8-9,16,19-<br>23,25-28,36H,10-13H2,1-<br>7H3/t16-,<br>19+,20+,21+,22-,23-,<br>25+,26-,27-,28+,30-,<br>31+,32-/m1/s1 | |
| 101468625 | InChI=1S/C28H36O7/c1-<br>14-12-21(34-<br>23(31)15(14)2)26(5,32)18-<br>9-11-27(33)17-13-22-<br>28(35-22)20(30)7-6-<br>19(29)25(28,4)16(17)8-<br>10-24(18,27)3/h6-7,9,16-<br>17,20-22,30,32-<br>33H,8,10-13H2,1-<br>5H3/t16-,17+,20-,<br>21?,22+,24+,25-,<br>26+,27+,28+/m0/s1 | NA |
| 101420307 | InChI=1S/C32H42O9/c1-<br>14-10-22(40-<br>29(37)15(14)2)16(3)28-<br>23(38-17(4)33)12-20-19-<br>11-27-32(41-27)25(36)9-<br>8-<br>24(35)31(32,7)21(19)13-<br>26(30(20,28)6)39-<br>18(5)34/h8-9,16,19-<br>23,25-28,36H,10-13H2,1-<br>7H3/t16-,<br>19+,20+,21+,22?,23?,25?,<br>26?,27?,28+,30-,<br>31+,32?/m1/s1 | NA |
| 101317813 | InChI=1S/C30H40O8/c1-<br>14-11-21(37-<br>26(34)15(14)2)16(3)19-<br>12-24(36-<br>17(4)31)29(35)20-13-25-<br>30(38-25)23(33)8-7-<br>22(32)28(30,6)18(20)9-<br>10-27(19,29)5/h7-<br>8,16,18-21,23-<br>25,33,35H,9-13H2,1-<br>6H3/t16-,18-,<br>19+,20+,21+,23-,24-,<br>25+,27+,28-,<br>29+,30+/m0/s1 | NA |
| 101038760 | InChI=1S/C29H40O7/c1-<br>16-14-23(36-<br>24(32)17(16)2)27(5,33)29<br>(34)13-10-19-18-15-<br>22(31)28(35-6)11-7-8-<br>21(30)26(28,4)20(18)9-<br>12-25(19,29)3/h7-<br>8,10,18,20,22-23,31,33-<br>34H,9,11-15H2,1-<br>6H3/t18-,20-,<br>22+,23+,25-,26-,27-,28-,<br>29-/m0/s1 | (2R)-2-[(1S)-1-<br>[(5R,6R,8R,9S,10R,13S,<br>17S)-6,17-<br>dihydroxy-5-<br>methoxy-10,13-<br>dimethyl-1-oxo-<br>4,6,7,8,9,11,12,16-<br>octahydrocyclopenta<br>[a]phenanthren-17-<br>yl]-1-hydroxyethyl]-<br>4,5-dimethyl-2,3-<br>dihydropyran-6-one |
| 99576255 | InChI=1S/C28H38O8/c1-<br>14-12-20(35-<br>22(31)15(14)2)25(5,32)27<br>(34)11-10-26(33)17-13-<br>21-28(36-21)19(30)7-6-<br>18(29)24(28,4)16(17)8-9-<br>23(26,27)3/h6-7,16-<br>17,19-21,30,32-34H,8-<br>13H2,1-5H3/t16-,17+,19-,<br>20+,21+,23-,24-,<br>25+,26+,27-,28-/m0/s1 | NA |
| 99576254 | InChI=1S/C28H38O8/c1-<br>14-12-20(35-<br>22(31)15(14)2)25(5,32)27<br>(34)11-10-26(33)17-13-<br>21-28(36-21)19(30)7-6- | NA |

TABLE 2-continued

LIST OF WITHAFERIN A ANALOGS AND DERIVATIVES BASED ON SIMILARITY

| | | |
|---|---|---|
| | 18(29)24(28,4)16(17)8-9-23(26,27)3/h6-7,16-17,19-21,30,32-34H,8-13H2,1-5H3/t16-,17+,19-,20-,21+,23-,24-,25+,26+,27-,28-/m0/s1 | |
| 99576253 | InChI=1S/C28H38O8/c1-14-12-20(35-22(31)15(14)2)25(5,32)27(34)11-10-26(33)17-13-21-28(36-21)19(30)7-6-18(29)24(28,4)16(17)8-9-23(26,27)3/h6-7,16-17,19-21,30,32-34H,8-13H2,1-5H3/t16-,17+,19-,20+,21+,23-,24-,25-,26+,27-,28-/m0/s1 | NA |
| 99576252 | InChI=1S/C28H38O8/c1-14-12-20(35-22(31)15(14)2)25(5,32)27(34)11-10-26(33)17-13-21-28(36-21)19(30)7-6-18(29)24(28,4)16(17)8-9-23(26,27)3/h6-7,16-17,19-21,30,32-34H,8-13H2,1-5H3/t16-,17+,19-,20-,21+,23-,24-,25-,26+,27-,28-/m0/s1 | NA |
| 89092195 | InChI=1S/C31H40O7/c1-15-12-23(37-28(35)19(15)14-32)16(2)20-7-8-21-18-13-26-31(38-26)25(36-17(3)33)10-9-24(34)30(31)22(27(18)30)6-5-11-29(20,21)4/h9-10,16,18,20-23,25-27,32H,5-8,11-14H2,1-4H3/t16-,18?,20?,21?,22+,23?,25+,26+,27?,29+,30+,31+/m0/s1 | NA |
| 89092046 | InChI=1S/C30H44O9S/c1-6-12-28(5)21(18(4)23-13-17(3)20(27(33)38-23)16-37-40(34,35)36)8-9-22(28)19-14-26-30(39-26)25(32)11-10-24(31)29(30,7-2)15-19/h10-11,18-19,21-23,25-26,32H,6-9,12-16H2,1-5H3,(H,34,35,36)/t18-,19?,21?,22?,23?,25-,26+,28+,29-,30+/m0/s1 | [2-[(1S)-1-[(2S)-3-[(1aR,4aR,8S,8aR)-4a-ethyl-8-hydroxy-5-oxo-2,3,4,8-tetrahydro-1aH-naphtho[1,8a-b]oxiren-3-yl]-2-methyl-2-propylcyclopentyl]ethyl]-4-methyl-6-oxo-2,3-dihydropyran-5-yl]methyl hydrogen sulfate |
| 88949016 | InChI=1S/C27H38O5/c1-13-11-21(31-25(30)14(13)2)15(3)18-5-6-19-17-12-23-27(32-23)22(29)8-7-20(28)24(27)16(17)9-10-26(18,19)4/h15-19,21-24,29H,5-12H2,1-4H3/t15-,16-,17+,18+,19-,21+,22-,23+,24?,26+,27+/m0/s1 | NA |
| 88949015 | InChI=1S/C32H44O8/c1-7-36-37-16-31-24-12-13-30(6)22(19(4)25-14-17(2)18(3)29(35)39-25)8-9-23(30)21(24)15-28-32(31,40-28)27(38-20(5)33)11-10-26(31)34/h10-11,19,21-25,27-28H,7-9,12-16H2,1-6H3/t19-,21-,22+,23-,24-,25?,27-,28+,30+,31-,32+/m0/s1 | NA |

TABLE 2-continued

LIST OF WITHAFERIN A ANALOGS AND DERIVATIVES BASED ON SIMILARITY

| | | |
|---|---|---|
| 88858709 | InChI=1S/C28H40O7/c1-14-10-21(34-25(33)17(14)12-29)15(2)18-4-5-19-16-11-24-28(35-24)23(32)7-6-22(31)27(28,13-30)20(16)8-9-26(18,19)3/h15-16,18-21,23-24,29-30,32H,4-13H2,1-3H3/t15-,16-,18+,19-,20-,21+,23-,24+,26+,27-,28+/m0/s1 | NA |
| 88507988 | InChI=1S/C24H30O6/c1-12-8-16-15-5-4-13-9-14(25)6-7-23(13,3)24(15)18(30-24)11-22(16,2)20(12)21(29)17(26)10-19(27)28/h6-7,9,12,15-18,26,29H,4-5,8,10-11H2,1-3H3,(H,27,28)/t12-,15+,16+,17?,18+,22+,23+,24-/m1/s1 | NA |
| 88507909 | InChI=1S/C24H32O6/c1-12-8-16-15-5-4-13-9-14(25)6-7-23(13,3)24(15)18(30-24)11-22(16,2)20(12)21(29)17(26)10-19(27)28/h9,12,15-18,26,29H,4-8,10-11H2,1-3H3,(H,27,28)/t12-,15+,16+,17?,18+,22+,23+,24-/m1/s1 | NA |
| 85842937 | InChI=1S/C29H46O4/c1-18(2)8-7-9-19(3)22-10-11-23-21-14-17-29(32)26(33-20(4)30)13-12-25(31)28(29,6)24(21)15-16-27(22,23)5/h12-13,18-19,21-24,26,32H,7-11,14-17H2,1-6H3 | [5-hydroxy-10,13-dimethyl-17-(6-methylheptan-2-yl)-1-oxo-6,7,8,9,11,12,14,15,16,17-decahydro-4H-cyclopenta[a]phenanthren-4-yl]acetate |
| 85252359 | InChI=1S/C28H34O6/c1-13-11-19(33-25(31)14(13)2)15(3)22-18(29)12-17-21-16(8-10-26(17,22)4)27(5)20(30)7-6-9-28(27,32)24-23(21)34-24/h6-7,16-17,19,21,23-24,32H,8-12H2,1-5H3 | NA |
| 85172857 | InChI=1S/C28H36O6/c1-13-11-19(33-25(32)14(13)2)15(3)16-8-9-17-22-18(12-21(30)26(16,17)4)27(5)20(29)7-6-10-28(27)24(34-28)23(22)31/h6-7,15-19,22-24,31H,8-12H2,1-5H3 | NA |
| 76787560 | InChI=1S/C29H40O8S/c1-6-17-15(2)13-22(35-26(17)31)16(3)19-7-8-20-18-14-25-29(36-25)24(37-38(32,33)34)10-9-23(30)28(29,5)21(18)11-12-27(19,20)4/h9-10,16,18-22,24-25H,6-8,11-14H2,1-5H3,(H,32,33,34) | NA |

TABLE 2-continued

LIST OF WITHAFERIN A ANALOGS AND DERIVATIVES BASED ON SIMILARITY

| | | |
|---|---|---|
| 76023361 | InChI=1S/C28H40O8/c1-13-23(32)35-21(12-25(13,3)33)27(5,34)22-17(29)11-16-14-10-20-28(36-20)19(31)7-6-18(30)26(28,4)15(14)8-9-24(16,22)2/h6-7,13-17,19-22,29,31,33-34H,8-12H2,1-5H3 | NA |
| 74323736 | InChI=1S/C28H38O7/c1-13-11-18(34-24(31)14(13)2)15(3)27(32)10-8-16-21-17(12-20(30)25(16,27)4)26(5)19(29)7-6-9-28(26,33)23-22(21)35-23/h6-7,15-18,20-23,30,32-33H,8-12H2,1-5H3 | NA |
| 74034727 | InChI=1S/C28H38O5/c1-15-13-24(33-25(31)16(15)2)28(5,32)22-10-9-18-17-14-21(29)20-7-6-8-23(30)27(20,4)19(17)11-12-26(18,22)3/h6-8,17-19,21-22,24,29,32H,9-14H2,1-5H3 | 2-[1-hydroxy-1-(6-hydroxy-10,13-dimethyl-1-oxo-6,7,8,9,11,12,14,15,16,17-decahydrocyclopenta[a]phenanthren-17-yl)ethyl]-4,5-dimethyl-2,3-dihydropyran-6-one |
| 73823419 | InChI=1S/C28H38O7/c1-15-13-22(35-23(31)16(15)2)26(5,32)28(34)12-9-18-17-14-21(30)27(33)10-6-7-20(29)25(27,4)19(17)8-11-24(18,28)3/h6-7,9,17,19,21-22,30,32-34H,8,10-14H2,1-5H3 | 2-[1-hydroxy-1-(5,6,17-trihydroxy-10,13-dimethyl-1-oxo-4,6,7,8,9,11,12,16-octahydrocyclopenta[a]phenanthren-17-yl)ethyl]-4,5-dimethyl-2,3-dihydropyran-6-one |
| 73800765 | InChI=1S/C28H38O9/c1-14-15(13-29)11-20(36-22(14)32)25(4,33)27(35)10-9-26(34)17-12-21-28(37-21)19(31)6-5-18(30)24(28,3)16(17)7-8-23(26,27)2/h5-6,16-17,19-21,29,31,33-35H,7-13H2,1-4H3 | NA |
| 58443798 | InChI=1S/C29H40O8S/c1-6-17-15(2)13-22(35-26(17)31)16(3)19-7-8-20-18-14-25-29(36-25)24(37-38(32,33)34)10-9-23(30)28(29,5)21(18)11-12-27(19,20)4/h9-10,16,18-22,24-25H,6-8,11-14H2,1-5H3,(H,32,33,34)/t16-,18?,19?,20?,21?,22?,24-,25+,27+,28-,29+/m0/s1 | NA |
| 53360900 | InChI=1S/C28H40O8/c1-13-23(32)35-21(12-25(13,3)33)27(5,34)22-17(29)11-16-14-10-20-28(36-20)19(31)7-6-18(30)26(28,4)15(14)8-9-24(16,22)2/h6-7,13-17,19-22,29,31,33-34H,8-12H2,1-5H3/t13-,14+,15-,16-,17-,19-,20+,21+,22-,24-,25+,26-,27-,28+/m0/s1 | NA |
| 49827071 | InChI=1S/C32H42O8/c1-17-13-26(39-29(36)21(17)15-37-18(2)33)22(16-38-19(3)34)24-9-8-23-20-14-28-32(40-28)11-6-7- | NA |

TABLE 2-continued

LIST OF WITHAFERIN A ANALOGS AND DERIVATIVES BASED ON SIMILARITY

| | | |
|---|---|---|
| | 27(35)31(32,5)25(20)10-12-30(23,24)4/h6-7,20,22-26,28H,8-16H2,1-5H3/t20?,22?,23?,24?,25?,26?,28?,30-,31-,32+/m0/s1 | |
| 24814038 | InChI=1S/C28H38O7/c1-13-11-18(34-24(31)14(13)2)15(3)27(32)10-8-16-21-17(12-20(30)25(16,27)4)26(5)19(29)7-6-9-28(26,33)23-22(21)35-23/h6-7,15-18,20-23,30,32-33H,8-12H2,1-5H3/t15-,16+,17+,18?,20+,21+,22+,23+,25-,26+,27+,28+/m1/s1 | NA |
| 23265654 | InChI=1S/C28H38O8/c1-14-12-20(35-22(31)15(14)2)25(5,32)27(34)11-10-26(33)17-13-21-28(36-21)19(30)7-6-18(29)24(28,4)16(17)8-9-23(26,27)3/h6-7,16-17,19-21,30,32-34H,8-13H2,1-5H3/t16-,17+,19-,20?,21+,23-,24-,25-,26+,27-,28+/m0/s1 | NA |
| 23253886 | InChI=1S/C28H38O5/c1-15-13-24(33-25(31)16(15)2)28(5,32)22-10-9-18-17-14-21(29)20-7-6-8-23(30)27(20,4)19(17)11-12-26(18,22)3/h6-8,17-19,21-22,24,29,32H,9-14H2,1-5H3/t17-,18-,19-,21+,22-,24+,26-,27+,28+/m0/s1 | (2R)-2-[(1R)-1-hydroxy-1-[(6R,8S,9S,10R,13S,14S,17S)-6-hydroxy-10,13-dimethyl-1-oxo-6,7,8,9,11,12,14,15,16,17-decahydrocyclopenta[a]phenanthren-17-yl]ethyl]-4,5-dimethyl-2,3-dihydropyran-6-one |
| 21679037 | InChI=1S/C28H38O7/c1-15-13-22(35-23(31)16(15)2)26(5,32)28(34)12-9-18-17-14-21(30)27(33)10-6-7-20(29)25(27,4)19(17)8-11-24(18,28)3/h6-7,9,17,19,21-22,30,32-34H,8,10-14H2,1-5H3/t17-,19-,21+,22+,24-,25-,26-,27-,28-/m0/s1 | (2R)-2-[(1S)-1-hydroxy-1-[(5R,6R,8R,9S,10R,13S,17S)-5,6,17-trihydroxy-10,13-dimethyl-1-oxo-4,6,7,8,9,11,12,16-octahydrocyclopenta[a]phenanthren-17-yl]ethyl]-4,5-dimethyl-2,3-dihydropyran-6-one |
| 21607725 | InChI=1S/C28H38O9/c1-14-15(13-29)11-20(36-22(14)32)25(4,33)27(35)10-9-26(34)17-12-21-28(37-21)19(31)6-5-18(30)24(28,3)16(17)7-8-23(26,27)2/h5-6,16-17,19-21,29,31,33-35H,7-13H2,1-4H3/t16-,17+,19-,20+,21+,23-,24-,25-,26+,27-,28+/m0/s1 | NA |
| 21595082 | InChI=1S/C30H40O8/c1-14-11-21(37-26(34)15(14)2)16(3)19-12-24(36-17(4)31)29(35)20-13-25-30(38-25)23(33)8-7-22(32)28(30,6)18(20)9-10-27(19,29)5/h7-8,16,18-21,23-25,33,35H,9-13H2,1-6H3/t16-,18-,19+,20+,21+,23-,24-, | NA |

US 10,729,703 B2

TABLE 2-continued

LIST OF WITHAFERIN A ANALOGS AND DERIVATIVES BASED ON SIMILARITY

| | | | |
|---|---|---|---|
| | | 25+,27+,28-,29-,<br>30+/m0/s1 | |
| | 10742847 | InChI=1S/C28H34O6/c1-<br>13-11-19(33-<br>25(31)14(13)2)15(3)22-<br>18(29)12-17-21-16(8-10-<br>26(17,22)4)27(5)20(30)7-<br>6-9-28(27,32)24-<br>23(21)34-24/h6-7,16-<br>17,19,21,23-24,32H,8-<br>12H2,1-5H3/b22-<br>15+/t16-,17-,19?,21+,23-,<br>24-,26-,27-,28-/m0/s1 | NA |
| | 10528283 | InChI=1S/C28H36O6/c1-<br>13-11-19(33-<br>25(32)14(13)2)15(3)16-<br>8-9-17-22-18(12-<br>21(30)26(16,17)4)27(5)20<br>(29)7-6-10-<br>28(27)24(34-<br>28)23(22)31/h6-7,15-<br>19,22-24,31H,8-12H2,1-<br>5H3/t15-,16+,17-,18-,<br>19+,22-,23-,24-,26+,27-,<br>28-/m0/s1 | NA |
| | 10141855 | InChI=1S/C28H38O8/c1-<br>14-12-22(36-<br>23(32)15(14)2)26(5,33)27<br>(34)11-9-17-16-13-<br>21(31)28(35)20(30)7-6-<br>19(29)25(28,4)18(16)8-<br>10-24(17,27)3/h6-<br>7,9,16,18,20-22,30-<br>31,33-35H,8,10-13H2,1-<br>5H3/t16?,18?,20-,21-,<br>22+,24-,25-,26-,27-,<br>28+/m0/s1 | (2R)-2-[(1S)-1-<br>hydroxy-1-<br>[(4S,5S,6S,10R,13S,17S)-<br>4,5,6,17-<br>tetrahydroxy-10,13-<br>dimethyl-1-oxo-<br>4,6,7,8,9,11,12,16-<br>octahydrocyclopenta<br>[a]phenanthren-17-<br>yl]ethyl]-4,5-<br>dimethyl-2,3-<br>dihydropyran-6-one |
| | 3836120 | InChI=1S/C28H38O8/c1-<br>14-12-20(35-<br>22(31)15(14)2)25(5,32)27<br>(34)11-10-26(33)17-13-<br>21-28(36-21)19(30)7-6-<br>18(29)24(28,4)16(17)8-9-<br>23(26,27)3/h6-7,16-<br>17,19-21,30,32-34H,8-<br>13H2,1-5H3 | NA |
| | 592382 | InChI=1S/C28H38O7/c1-<br>14-13-19(34-<br>23(31)15(14)2)26(5,32)28<br>(33)12-9-16-20-17(8-<br>11-<br>24(16,28)3)25(4)18(29)7-<br>6-10-27(25)22(35-<br>27)21(20)30/h6-7,16-<br>17,19-22,30,32-33H,8-<br>13H2,1-5H3 | NA |
| | 496243 | InChI=1S/C32H42O8/c1-<br>17-13-26(39-<br>29(36)21(17)15-37-<br>18(2)33)22(16-38-<br>19(3)34)24-9-8-23-20-<br>14-28-32(40-28)11-6-7-<br>27(35)31(32,5)25(20)10-<br>12-30(23,24)4/h6-<br>7,20,22-26,28H,8-<br>16H2,1-5H3 | NA |
| | 435365 | InChI=1S/C30H40O8/c1-<br>14-11-21(37-<br>26(34)15(14)2)16(3)19-<br>12-24(36-<br>17(4)31)29(35)20-13-25-<br>30(38-25)23(33)8-7-<br>22(32)28(30,6)18(20)9-<br>10-27(19,29)5/h7-<br>8,16,18-21,23-<br>25,33,35H,9-13H2,1-6H3 | NA |
| | 435219 | InChI=1S/C28H38O8/c1-<br>14-12-22(36- | 2-[1-hydroxy-1-<br>(4,5,6,17- |

TABLE 2-continued

LIST OF WITHAFERIN A ANALOGS AND DERIVATIVES BASED ON SIMILARITY

| | | |
|---|---|---|
| | 23(32)15(14)2)26(5,33)27(34)11-9-17-16-13-21(31)28(35)20(30)7-6-19(29)25(28,4)18(16)8-10-24(17,27)3/h6-7,9,16,18,20-22,30-31,33-35H,8,10-13H2,1-5H3 | tetrahydroxy-10,13-dimethyl-1-oxo-4,6,7,8,9,11,12,16-octahydrocyclopenta[a]phenanthren-17-yl)ethyl]-4,5-dimethyl-2,3-dihydropyran-6-one |
| 388300 | InChI=1S/C32H42O8/c1-17-13-26(39-29(36)21(17)15-37-18(2)33)22(16-38-19(3)34)24-9-8-23-20-14-28-32(40-28)11-6-7-27(35)31(32,5)25(20)10-12-30(23,24)4/h6-7,20,22-26,28H,8-16H2,1-5H3/t20?,22-,23?,24?,25?26+,28+,30-,31-,32+/m0/s1 | NA |
| 263436 | InChI=1S/C28H40O5/c1-14-12-21(32-25(31)15(14)2)16(3)18-6-7-19-17-13-24-28(33-24)23(30)9-8-22(29)27(28,5)20(17)10-11-26(18,19)4/h16-21,23-24,30H,6-13H2,1-5H3 | NA |
| 73621 | InChI=1S/C28H38O8/c1-14-12-20(35-22(31)15(14)2)25(5,32)27(34)11-10-26(33)17-13-21-28(36-21)19(30)7-6-18(29)24(28,4)16(17)8-9-23(26,27)3/h6-7,16-17,19-21,30,32-34H,8-13H2,1-5H3/t16-,17+,19-,20+,21+,23-,24-,25-,26+,27-,28+/m0/s1 | NA |
| 102471217 | InChI=1S/C28H38O9/c1-13-10-20(36-22(32)14(13)2)25(5,33)26(34)12-19(31)27(35)16-11-21-28(37-21)18(30)7-6-17(29)24(28,4)15(16)8-9-23(26,27)3/h6-7,15-16,18-21,30-31,33-35H,8-12H2,1-5H3/t15-,16+,18-,19-,20+,21+,23-,24-,25-,26-,27-,28+/m0/s1 | NA |
| 102066413 | InChI=1S/C28H38O6/c1-14-13-18(33-24(30)15(14)2)16(3)17-8-9-19-25(17,4)12-10-20-26(5)21(29)7-6-11-27(26,31)22-23(34-22)28(19,20)32/h6-7,16-20,22-23,31-32H,8-13H2,1-5H3/t16-,17+,18+,19+,20+,22+,23-,25+,26-,27-,28+/m0/s1 | NA |
| 101942518 | InChI=1S/C28H38O6/c1-14-13-19(33-24(30)15(14)2)16(3)27(31)12-9-17-21-18(8-11-25(17,27)4)26(5)20(29)7-6-10-28(26,32)23-22(21)34-23/h6-7,16-19,21-23,31-32H,8-13H2,1-5H3/t16-,17+,18+,19-,21+,22+,23+,25+,26+,27-,28+/m1/s1 | NA |
| 101713202 | InChI=1S/C28H38O7/c1-13-11-18(34-24(31)14(13)2)15(3)28(33) | NA |

TABLE 2-continued

LIST OF WITHAFERIN A ANALOGS AND DERIVATIVES BASED ON SIMILARITY

| | | |
|---|---|---|
| | 20(30)12-17-21-16(8-10-25(17,28)4)26(5)19(29)7-6-9-27(26,32)23-22(21)35-23/h6-7,15-18,20-23,30,32-33H,8-12H2,1-5H3/t15-,16+,17+,18-,20-,21-,22+,23+,25+,26+,27+,28-/m1/s1 | |
| 101403752 | InChI=1S/C29H42O7/c1-16-13-23(36-24(33)17(16)2)27(5,34)20-9-11-25(3)19-14-22(32)29(35)10-6-7-21(31)26(29,4)18(19)8-12-28(20,25)15-30/h6-7,13,17-20,22-23,30,32,34-35H,8-12,14-15H2,1-5H3/t17?18-,19+,20+,22+,23+,25-,26-,27+,28-,29-/m0/s1 | (2R)-2-[(1R)-1-[(5R,6R,8R,9S,10R,13S,14S,17S)-5,6-dihydroxy-13-(hydroxymethyl)-10,14-dimethyl-1-oxo-4,6,7,8,9,11,12,15,16,17-decahydrocyclopenta[a]phenanthren-17-yl]-1-hydroxyethyl]-4,5-dimethyl-2,5-dihydropyran-6-one |
| 101130899 | InChI=1S/C28H40O8/c1-23-11-10-16-14(12-20-28(36-20)19(30)9-8-18(29)25(16,28)3)15(23)6-7-17(23)26(4,33)21-13-24(2,32)27(5,34)22(31)35-21/h8-9,14-17,19-21,30,32-34H,6-7,10-13H2,1-5H3/t14-,15-,16-,17-,19-,20+,21+,23-,24-,25-,26+,27-,28+/m0/s1 | NA |
| 101005225 | InChI=1S/C32H42O10/c1-14-12-23(41-28(37)15(14)2)31(7,38)20-13-19(39-16(3)33)25-24-18(10-11-29(20,25)5)30(6)21(35)8-9-22(36)32(30)27(42-32)26(24)40-17(4)34/h8-9,18-20,22-27,36,38H,10-13H2,1-7H3/t18-,19?20-,22?23+,24+,25-,26?27-,29+,30-,31+,32-/m0/s1 | NA |
| 99576247 | InChI=1S/C28H38O7/c1-15-13-20(34-22(30)16(15)2)25(5,31)28(33)12-11-26(32)18-14-21-27(35-21)9-6-7-19(29)24(27,4)17(18)8-10-23(26,28)3/h6-7,17-18,20-21,31-33H,8-14H2,1-5H3/t17-,18+,20+,21+,23-,24-,25+,26-,27-,28-/m0/s1 | NA |
| 99576246 | InChI=1S/C28H38O7/c1-15-13-20(34-22(30)16(15)2)25(5,31)28(33)12-11-26(32)18-14-21-27(35-21)9-6-7-19(29)24(27,4)17(18)8-10-23(26,28)3/h6-7,17-18,20-21,31-33H,8-14H2,1-5H3/t17-,18+,20-,21+,23-,24-,25+,26+,27-,28-/m0/s1 | NA |
| 99576245 | InChI=1S/C28H38O7/c1-15-13-20(34-22(30)16(15)2)25(5,31)28(33)12-11-26(32)18-14-21-27(35-21)9-6-7-19(29)24(27,4)17(18)8-10-23(26,28)3/h6-7,17-18,20-21,31-33H,8- | NA |

TABLE 2-continued

LIST OF WITHAFERIN A ANALOGS AND DERIVATIVES BASED ON SIMILARITY

| | | |
|---|---|---|
| | 14H2,1-5H3/t17-,<br>18+,20+,21+,23-,24-,25-,<br>26+,27-,28-/m0/s1 | |
| 99576244 | InChI=1S/C28H38O7/c1-<br>15-13-20(34-<br>22(30)16(15)2)25(5,31)28<br>(33)12-11-26(32)18-14-<br>21-27(35-21)9-6-7-<br>19(29)24(27,4)17(18)8-<br>10-23(26,28)3/h6-7,17-<br>18,20-21,31-33H,8-<br>14H2,1-5H3/t17-,18+,20-,<br>21+,23-,24-,25-,26+,27-,<br>28-/m0/s1 | NA |
| 99575095 | InChI=1S/C28H38O6/c1-<br>13-11-19(33-<br>25(31)14(13)2)15(3)22-<br>18(29)12-17-21-16(8-10-<br>26(17,22)4)27(5)20(30)7-<br>6-9-28(27,32)24-<br>23(21)34-24/h6-7,15-<br>19,21-24,29,32H,8-<br>12H2,1-5H3/t15-,<br>16+,17+,18+,19-,21-,<br>22+,23+,24+,26+,27+,28+/<br>m1/s1 | NA |
| 99575094 | InChI=1S/C28H38O6/c1-<br>13-11-19(33-<br>25(31)14(13)2)15(3)22-<br>18(29)12-17-21-16(8-10-<br>26(17,22)4)27(5)20(30)7-<br>6-9-28(27,32)24-<br>23(21)34-24/h6-7,15-<br>19,21-24,29,32H,8-<br>12H2,1-5H3/t15-,<br>16+,17+,18+,19+,21-,<br>22+,23+,24+,26+,27+,28+/<br>m1/s1 | NA |
| 99575093 | InChI=1S/C28H38O6/c1-<br>13-11-19(33-<br>25(31)14(13)2)15(3)22-<br>18(29)12-17-21-16(8-10-<br>26(17,22)4)27(5)20(30)7-<br>6-9-28(27,32)24-<br>23(21)34-24/h6-7,15-<br>19,21-24,29,32H,8-<br>12H2,1-5H3/t15-,16-,17-,<br>18-,19+,21+,22-,23-,24-,<br>26-,27-,28-/m0/s1 | NA |
| 99575092 | InChI=1S/C28H38O6/c1-<br>13-11-19(33-<br>25(31)14(13)2)15(3)22-<br>18(29)12-17-21-16(8-10-<br>26(17,22)4)27(5)20(30)7-<br>6-9-28(27,32)24-<br>23(21)34-24/h6-7,15-<br>19,21-24,29,32H,8-<br>12H2,1-5H3/t15-,16-,17-,<br>18-,19-,21+,22-,23-,24-,<br>26-,27-,28-/m0/s1 | NA |
| 99571105 | InChI=1S/C28H38O5/c1-<br>15-12-24(33-<br>26(32)18(15)14-<br>29)16(2)19-8-9-20-17-<br>13-23(30)22-6-5-7-<br>25(31)28(22,4)21(17)10-<br>11-27(19,20)3/h5-7,16-<br>17,19-21,23-24,29-<br>30H,8-14H2,1-4H3/t16-,<br>17+,19-,20+,21+,23+,24-,<br>27-,28-/m1/s1 | (2R)-2-[(1R)-1-<br>[(6S,8S,9S,10R,13S,14S,<br>17R)-6-hydroxy-<br>10,13-dimethyl-1-<br>oxo-<br>6,7,8,9,11,12,14,15,16,<br>17-<br>decahydrocyclopenta<br>[a]phenanthren-17-<br>yl]ethyl]-5-<br>(hydroxymethyl)-4-<br>methyl-2,3-<br>dihydropyran-6-one |
| 99571104 | InChI=1S/C28H38O5/c1-<br>15-12-24(33-<br>26(32)18(15)14-<br>29)16(2)19-8-9-20-17-<br>13-23(30)22-6-5-7- | (2S)-2-[(1R)-1-<br>[(6S,8S,9S,10R,13S,14S,<br>17R)-6-hydroxy-<br>10,13-dimethyl-1-<br>oxo- |

TABLE 2-continued

LIST OF WITHAFERIN A ANALOGS AND DERIVATIVES BASED ON SIMILARITY

| | | |
|---|---|---|
| | 25(31)28(22,4)21(17)10-11-27(19,20)3/h5-7,16-17,19-21,23-24,29-30H,8-14H2,1-4H3/t16-,17+,19-,20+,21+,23+,24+,27-,28-/m1/s1 | 6,7,8,9,11,12,14,15,16,17-decahydrocyclopenta[a]phenanthren-17-yl]ethyl]-5-(hydroxymethyl)-4-methyl-2,3-dihydropyran-6-one |
| 99571103 | InChI=1S/C28H38O5/c1-15-12-24(33-26(32)18(15)14-29)16(2)19-8-9-20-17-13-23(30)22-6-5-7-25(31)28(22,4)21(17)10-11-27(19,20)3/h5-7,16-17,19-21,23-24,29-30H,8-14H2,1-4H3/t16-,17-,19+,20-,21-,23-,24+,27+,28+/m0/s1 | (2R)-2-[(1S)-1-[(6S,8S,9S,10R,13S,14S,17R)-6-hydroxy-10,13-dimethyl-1-oxo-6,7,8,9,11,12,14,15,16,17-decahydrocyclopenta[a]phenanthren-17-yl]ethyl]-5-(hydroxymethyl)-4-methyl-2,3-dihydropyran-6-one |
| 99571102 | InChI=1S/C28H38O5/c1-15-12-24(33-26(32)18(15)14-29)16(2)19-8-9-20-17-13-23(30)22-6-5-7-25(31)28(22,4)21(17)10-11-27(19,20)3/h5-7,16-17,19-21,23-24,29-30H,8-14H2,1-4H3/t16-,17-,19+,20-,21-,23-,24-,27+,28+/m0/s1 | (2S)-2-[(1S)-1-[(6S,8S,9S,10R,13S,14S,17R)-6-hydroxy-10,13-dimethyl-1-oxo-6,7,8,9,11,12,14,15,16,17-decahydrocyclopenta[a]phenanthren-17-yl]ethyl]-5-(hydroxymethyl)-4-methyl-2,3-dihydropyran-6-one |
| 99567961 | InChI=1S/C28H38O6/c1-13-11-19(33-25(31)14(13)2)15(3)22-18(29)12-17-21-16(8-10-26(17,22)4)27(5)20(30)7-6-9-28(27,32)24-23(21)34-24/h6-7,15-19,21-24,29,32H,8-12H2,1-5H3/t15-,16-,17-,18+,19+,21+,22-,23+,24+,26-,27-,28-/m0/s1 | NA |
| 99567960 | InChI=1S/C28H38O6/c1-13-11-19(33-25(31)14(13)2)15(3)22-18(29)12-17-21-16(8-10-26(17,22)4)27(5)20(30)7-6-9-28(27,32)24-23(21)34-24/h6-7,15-19,21-24,29,32H,8-12H2,1-5H3/t15-,16-,17-,18+,19-,21+,22-,23+,24+,26-,27-,28-/m0/s1 | NA |
| 99567959 | InChI=1S/C28H38O6/c1-13-11-19(33-25(31)14(13)2)15(3)22-18(29)12-17-21-16(8-10-26(17,22)4)27(5)20(30)7-6-9-28(27,32)24-23(21)34-24/h6-7,15-19,21-24,29,32H,8-12H2,1-5H3/t15-,16+,17+,18-,19-,21-,22+,23-,24-,26+,27+,28+/m1/s1 | NA |
| 99567958 | InChI=1S/C28H38O6/c1-13-11-19(33-25(31)14(13)2)15(3)22-18(29)12-17-21-16(8-10-26(17,22)4)27(5)20(30)7-6-9-28(27,32)24-23(21)34-24/h6-7,15-19,21-24,29,32H,8- | NA |

TABLE 2-continued

LIST OF WITHAFERIN A ANALOGS AND DERIVATIVES BASED ON SIMILARITY

| | | |
|---|---|---|
| | 12H2,1-5H3/t15-,16+,17+,18-,19+,21-,22+,23-,24-,26+,27+,28+/m1/s1 | |
| 91809632 | InChI=1S/C28H36O6/c1-13-11-19(33-25(31)14(13)2)15(3)16-8-9-17-22-18(12-21(30)26(16,17)4)27(5)20(29)7-6-10-28(27,32)24-23(22)34-24/h6-7,15-19,22-24,32H,8-12H2,1-5H3/t15-,16+,17-,18-,19-,22-,23-,24-,26+,27-,28-/m0/s1 | NA |
| 91535074 | InChI=1S/C30H42O5/c1-7-19-16(2)14-23(35-26(19)33)17(3)20-8-9-21-22-15-34-28(6)24(31)10-11-25(32)30(28)18(4)29(22,30)13-12-27(20,21)5/h10-11,17-18,20-24,31H,7-9,12-15H2,1-6H3 | NA |
| 90670443 | InChI=1S/C28H38O12S2/c1-14-11-21(38-25(30)17(14)13-37-41(31,32)33)15(2)18-5-6-19-16-12-24-28(39-24)23(40-42(34,35)36)8-7-22(29)27(28,4)20(16)9-10-26(18,19)3/h7-8,15-16,18-21,23-24H,5-6,9-13H2,1-4H3,(H,31,32,33)(H,34,35,36)/t15-,16-,18+,19-,20-,21+,23-,24+,26+,27-,28+/m0/s1 | NA |
| 89255534 | InChI=1S/C28H40O5/c1-15-13-22(32-24(30)16(15)2)27(5,31)20-9-8-18-17-14-23-28(33-23)11-6-7-21(29)26(28,4)19(17)10-12-25(18,20)3/h6-7,15-20,22-23,31H,8-14H2,1-5H3/t15-,16+,17?,18?,19?,20?,22?,23+,25-,26-,27+,28+/m0/s1 | NA |
| 89245302 | InChI=1S/C28H40O5/c1-15-13-22(32-24(30)16(15)2)27(5,31)20-9-8-18-17-14-23-28(33-23)11-6-7-21(29)26(28,4)19(17)10-12-25(18,20)3/h6-7,15-20,22-23,31H,8-14H2,1-5H3/t15-,16+,17?,18?,19?,20-,22?,23+,25-,26-,27+,28+/m0/s1 | NA |
| 88858705 | InChI=1S/C28H40O6/c1-14-11-21(33-25(32)15(14)2)16(3)18-5-6-19-17-12-24-28(34-24)23(31)8-7-22(30)27(28,13-29)20(17)9-10-26(18,19)4/h16-21,23-24,29,31H,5-13H2,1-4H3/t16-,17-,18+,19-,20-,21+,23-,24+,26+,27-,28+/m0/s1 | NA |
| 85244687 | InChI=1S/C30H38O7/c1-14-12-20(36-27(33)15(14)2)16(3)24- | NA |

TABLE 2-continued

LIST OF WITHAFERIN A ANALOGS AND DERIVATIVES BASED ON SIMILARITY

| | | |
|---|---|---|
| | 21(35-17(4)31)13-19-23-18(9-11-28(19,24)5)29(6)22(32)8-7-10-30(29,34)26-25(23)37-26/h7-8,18-21,23,25-26,34H,9-13H2,1-6H3 | |
| 85191725 | InChI=1S/C28H32O7/c1-13-14(2)28(35-23(13)32)22(31)16(12-29)18-8-7-17,15-10-21-26(34-21)9-5-6-20(30)25(26,4)19(15)11-27(28,33)24(17,18)3/h5-6,15,17,19,21,29,33H,7-12H2,1-4H3 | NA |
| 85182572 | InChI=1S/C28H38O7/c1-13-11-18(34-24(31)14(13)2)15(3)28(33)20(30)12-17-21-16(8-10-25(17,28)4)26(5)19(29)7-6-9-27(26,32)23-22(21)35-23/h6-7,15-18,20-23,30,32-33H,8-12H2,1-5H3 | NA |
| 78200674 | InChI=1S/C32H42O10/c1-14-12-23(41-28(37)15(14)2)31(7,38)26-20(39-16(3)33)13-19-24-18(10-11-29(19,26)5)30(6)21(35)8-9-22(36)32(30)27(42-32)25(24)40-17(4)34/h8-9,18-20,22-27,36,38H,10-13H2,1-7H3 | NA |
| 78019496 | InChI=1S/C30H44O5/c1-16-13-24(35-27(34)20(16)15-31)18(3)21-7-8-22-19-14-17(2)29(5)25(32)9-10-26(33)30(29,6)23(19)11-12-28(21,22)4/h9-10,17-19,21-25,31-32H,7-8,11-15H2,1-6H3 | 5-(hydroxymethyl)-2-[1-(4-hydroxy-5,6,10,13-tetramethyl-1-oxo-6,7,8,9,11,12,14,15,16,17-decahydro-4H-cyclopenta[a]phenanthren-17-yl)ethyl]-4-methyl-2,3-dihydropyran-6-one |
| 77846436 | InChI=1S/C28H38O6/c1-14-13-18(33-24(30)15(14)2)16(3)17-8-9-19-25(17,4)12-10-20-26(5)21(29)7-6-11-27(26,31)22-23(34-22)28(19,20)32/h6-7,16-20,22-23,31-32H,8-13H2,1-5H3/t16-,17+,18+,19+,20?,22+,23-,25+,26-,27-,28+/m0/s1 | NA |
| 75093297 | InChI=1S/C28H38O12S2/c1-14-11-21(38-25(30)17(14)13-37-41(31,32)33)15(2)18-5-6-19-16-12-24-28(39-24)23(40-42(34,35)36)8-7-22(29)27(28,4)20(16)9-10-26(18,19)3/h7-8,15-16,18-21,23-24H,5-6,9-13H2,1-4H3,(H,31,32,33)(H,34,35,36) | NA |
| 75072260 | InChI=1S/C32H42O9/c1-15-14-24(40-28(36)16(15)2)31(7,37)21-9-8-19-25-20(12-13-29(19,21)5)30(6)22(35)10-11-23(38-17(3)33)32(30)27(41-32)26(25)39-32)26(25)39- | NA |

TABLE 2-continued

LIST OF WITHAFERIN A ANALOGS AND DERIVATIVES BASED ON SIMILARITY

| | | |
|---|---|---|
| | 18(4)34/h10-11,19-21,23-27,37H,8-9,12-14H2,1-7H3 | |
| 74110113 | InChI=1S/C28H38O7/c1-12-9-18(34-25(32)13(12)2)14(3)15-10-17(29)22-21-16(11-20(31)26(15,22)4)27(5)19(30)7-6-8-28(27,33)24-23(21)35-24/h6-7,14-18,20-24,29,31,33H,8-11H2,1-5H3 | NA |
| 74039536 | InChI=1S/C28H38O7/c1-15-14-22(35-23(31)16(15)2)26(5,32)28(34)13-10-18-17-8-12-27(33)21(30)7-6-20(29)25(27,4)19(17)9-11-24(18,28)3/h6-7,19,21-22,30,32-34H,8-14H2,1-5H3 | 2-[1-hydroxy-1-(4,5,17-trihydroxy-10,13-dimethyl-1-oxo-4,6,7,9,11,12,15,16-octahydrocyclopenta[a]phenanthren-17-yl)ethyl]-4,5-dimethyl-2,3-dihydropyran-6-one |
| 74034725 | InChI=1S/C30H40O6/c1-16-13-26(36-28(34)20(16)15-35-18(3)31)17(2)21-9-10-22-19-14-25(32)24-7-6-8-27(33)30(24,5)23(19)11-12-29(21,22)4/h6-8,17,19,21-23,25-26,32H,9-15H2,1-5H3 | [2-[1-(6-hydroxy-10,13-dimethyl-1-oxo-6,7,8,9,11,12,14,15,16,17-decahydrocyclopenta[a]phenanthren-17-yl)ethyl]-4-methyl-6-oxo-2,3-dihydropyran-5-yl]methyl acetate |
| 73823416 | InChI=1S/C30H40O9/c1-15-13-22(38-24(33)16(15)2)27(6,34)29(36)12-11-28(35)19-14-23-30(39-23)21(37-17(3)31)8-7-20(32)26(30,5)18(19)9-10-25(28,29)4/h7-8,18-19,21-23,34-36H,9-14H2,1-6H3 | NA |
| 73823410 | InChI=1S/C30H40O8/c1-15-13-23(37-25(33)16(15)2)28(6,34)20-10-12-29(35)19-14-24-30(38-24)22(36-17(3)31)8-7-21(32)27(30,5)18(19)9-11-26(20,29)4/h7-8,18-20,22-24,34-35H,9-14H2,1-6H3 | NA |
| 73802223 | InChI=1S/C28H44O4/c1-15(2)16(3)7-8-17(4)19-9-10-20-18-13-23(31)28-24(32-28)12-11-22(30)27(28,6)25(18)21(29)14-26(19,20)5/h11-12,15-21,23-25,29,31H,7-10,13-14H2,1-6H3 | NA |
| 73802222 | InChI=1S/C28H42O4/c1-15(2)16(3)7-8-17(4)19-9-10-20-18-13-23(31)28-24(32-28)12-11-22(30)27(28,6)25(18)21(29)14-26(19,20)5/h7-8,11-12,15-21,23-25,29,31H,9-10,13-14H2,1-6H3 | NA |
| 73800707 | InChI=1S/C32H42O9/c1-15-12-23(40-29(36)19(15)14-38-17(3)33)16(2)20-9-10-21-26-22(13-25(30(20,21)5)39- | NA |

TABLE 2-continued

LIST OF WITHAFERIN A ANALOGS AND DERIVATIVES BASED ON SIMILARITY

| | | |
|---|---|---|
| | 18(4)34)31(6)24(35)8-7-11-32(31,37)28-27(26)41-28/h7-8,16,20-23,25-28,37H,9-14H2,1-6H3 | |
| 73800270 | InChI=1S/C28H36O7/c1-13-11-21(33-23(31)14(13)2)26(4)18-6-5-17-15-12-22-28(34-22)20(30)8-7-19(29)25(28,3)16(15)9-10-27(17,18)24(32)35-26/h7-8,15-18,20-22,24,30,32H,5-6,9-12H2,1-4H3 | NA |
| 73353768 | InChI=1S/C28H38O7/c1-14-13-20(34-23(30)15(14)2)26(5,31)16-8-9-17-24(16,3)12-10-18-25(4)19(29)7-6-11-27(25,32)21-22(35-21)28(17,18)33/h6-7,16-18,20-22,31-33H,8-13H2,1-5H3/t16-,17+,18+,20+,21+,22-,24+,25-,26+,27-,28+/m0/s1 | NA |
| 73324216 | InChI=1S/C28H38O9/c1-13-10-20(36-22(32)14(13)2)25(5,33)26(34)12-19(31)27(35)16-11-21-28(37-21)18(30)7-6-17(29)24(28,4)15(16)8-9-23(26,27)3/h6-7,15-16,18-21,30-31,33-35H,8-12H2,1-5H3 | NA |
| 73211836 | InChI=1S/C32H42O8/c1-17-13-26(39-29(36)22(17)15-37-19(3)33)18(2)23-8-9-24-21-14-28-32(40-28)11-6-7-27(35)31(32,16-38-20(4)34)25(21)10-12-30(23,24)5/h6-7,18,21,23-26,28H,8-16H2,1-5H3/t18-,21-,23+,24-,25-,26+,28+,30+,31-,32+/m0/s1 | NA |
| 73123619 | InChI=1S/C28H40O7/c1-15-12-23(35-24(32)16(15)2)26(4,33)20-8-7-19-17-13-22(31)28(34)10-5-6-21(30)25(28,3)18(17)9-11-27(19,20)14-29/h5-6,17-20,22-23,29,31,33-34H,7-14H2,1-4H3 | 2-[1-[5,6-dihydroxy-13-(hydroxymethyl)-10-methyl-1-oxo-6,7,8,9,11,12,14,15,16,17-decahydro-4H-cyclopenta[a]phenanthren-17-yl]-1-hydroxyethyl]-4,5-dimethyl-2,3-dihydropyran-6-one |
| 73100450 | InChI=1S/C28H40O7/c1-14-11-20(34-24(32)17(14)13-29)15(2)27(33)10-8-18-16-12-23-28(35-23)22(31)6-5-21(30)26(28,4)19(16)7-9-25(18,27)3/h15-16,18-20,22-23,29,31,33H,5-13H2,1-4H3 | NA |
| 73077149 | InChI=1S/C28H40O8/c1-14-22(31)35-21(13-24(14,3)32)26(5,33)27(34)11-9-16-15-12-20-28(36-20)19(30)7-6-18(29)25(28,4)17(15)8-10-23(16,27)2/h6-7,14-17,19-21,30,32-34H,8-13H2,1-5H3 | NA |

TABLE 2-continued

LIST OF WITHAFERIN A ANALOGS AND DERIVATIVES BASED ON SIMILARITY

| | | |
|---|---|---|
| 72544433 | InChI=1S/C31H43NO8/c1-16-12-23(38-27(36)19(16)14-33)17(2)20-6-7-21-18-13-26-31(40-26)25(39-28(37)32(4)5)9-8-24(35)30(31,15-34)22(18)10-11-29(20,21)3/h8-9,17-18,20-23,25-26,33-34H,6-7,10-15H2,1-5H3/t17-,18-,20+,21-,22-,23+,25-,26+,29+,30-,31+/m0/s1 | NA |
| 71167047 | InChI=1S/C30H44O5/c1-16-13-24(35-27(34)20(16)15-31)18(3)21-7-8-22-19-14-17(2)29(5)25(32)9-10-26(33)30(29,6)23(19)11-12-28(21,22)4/h9-10,17-19,21-25,31-32H,7-8,11-15H2,1-6H3/t17-,18+,19?,21?,22?,23?,24?,25+,28-,29-,30+/m1/s1 | 5-(hydroxymethyl)-2-[(1S)-1-[(4S,5S,6R,10R,13S)-4-hydroxy-5,6,10,13-tetramethyl-1-oxo-6,7,8,9,11,12,14,15,16,17-decahydro-4H-cyclopenta[a]phenanthren-17-yl]ethyl]-4-methyl-2,3-dihydropyran-6-one |
| 52931499 | InChI=1S/C28H38O7/c1-12-9-18(34-25(32)13(12)2)14(3)15-10-17(29)22-21-16(11-20(31)26(15,22)4)27(5)19(30)7-6-8-28(27,33)24-23(21)35-24/h6-7,14-18,20-24,29,31,33H,8-11H2,1-5H3/t14-,15+,16-,17+,18?,20-,21+,22-,23-,24-,26-,27-,28-/m0/s1 | NA |
| 50909326 | InChI=1S/C28H36O6/c1-13-11-19(33-25(31)14(13)2)15(3)16-8-9-17-22-18(12-21(30)26(16,17)4)27(5)20(29)7-6-10-28(27,32)24-23(22)34-24/h6-7,15-19,22-24,32H,8-12H2,1-5H3/t15-,16+,17?,18?,19?,22?,23?,24-,26+,27-,28-/m0/s1 | NA |
| 45359706 | InChI=1S/C28H38O6/c1-13-11-19(33-25(31)14(13)2)15(3)22-18(29)12-17-21-16(8-10-26(17,22)4)27(5)20(30)7-6-9-28(27,32)24-23(21)34-24/h6-7,15-19,21-24,29,32H,8-12H2,1-5H3 | NA |
| 45111620 | InChI=1S/C28H38O12S2/c1-14-11-21(38-25(30)17(14)13-37-41(31,32)33)15(2)18-5-6-19-16-12-24-28(39-24)23(40-42(34,35)36)8-7-22(29)27(28,4)20(16)9-10-26(18,19)3/h7-8,15-16,18-21,23-24H,5-6,9-13H2,1-4H3,(H,31,32,33)(H,34,35,36)/t15-,16?,18?,19?,20?,21?,23-,24+,26+,27-,28?/m0/s1 | NA |
| 44567004 | InChI=1S/C32H42O9/c1-15-14-24(40-28(36)16(15)2)31(7,37)21-9-8-19-25-20(12-13-29(19,21)5)30(6)22(35)10-11-23(38-17(3)33)32(30)27(41- | NA |

TABLE 2-continued

LIST OF WITHAFERIN A ANALOGS AND DERIVATIVES BASED ON SIMILARITY

| | | |
|---|---|---|
| | 32)26(25)39-18(4)34/h10-11,19-21,23-27,37H,8-9,12-14H2,1-7H3/t19-,20-,21-,23-,24+,25-,26+,27+,29-,30-,31+,32+/m0/s1 | |
| 44566968 | InChI=1S/C28H36O7/c1-13-11-21(33-23(31)14(13)2)26(4)18-6-5-17-15-12-22-28(34-22)20(30)8-7-19(29)25(28,3)16(15)9-10-27(17,18)24(32)35-26/h7-8,15-18,20-22,24,30,32H,5-6,9-12H2,1-4H3/t15-,16+,17+,18-,20+,21-,22-,24?,25+,26-,27-,28-/m1/s1 | NA |
| 42610658 | InChI=1S/C30H38O8/c1-14-11-21(37-26(34)15(14)2)16(3)19-12-24(36-17(4)31)29(35)20-13-25-30(38-25)23(33)8-7-22(32)28(30,6)18(20)9-10-27(19,29)5/h7-8,12,16,18,20-21,23-25,33,35H,9-11,13H2,1-6H3/t16-,18?,20?,21+,23-,24-,25+,27+,28-,29-,30+/m0/s1 | NA |
| 23727871 | InChI=1S/C28H38O7/c1-12-9-18(34-25(32)13(12)2)14(3)15-10-17(29)22-21-16(11-20(31)26(15,22)4)27(5)19(30)7-6-8-28(27,33)24-23(21)35-24/h6-7,14-18,20-24,29,31,33H,8-11H2,1-5H3/t14?,15?,16?,17?,18?,20?,21?,22?,23?,24?,26?,27?,28-/m0/s1 | NA |
| 23267120 | InChI=1S/C28H38O7/c1-15-14-22(35-23(31)16(15)2)26(5,32)28(34)13-10-18-17-8-12-27(33)21(30)7-6-20(29)25(27,4)19(17)9-11-24(18,28)3/h6-7,19,21-22,30,32-34H,8-14H2,1-5H3/t19?,21-,22?,24-,25-,26-,27+,28-/m0/s1 | 2-[(1S)-1-hydroxy-1-[(4S,5S,10R,13S,17S)-4,5,17-trihydroxy-10,13-dimethyl-1-oxo-4,6,7,9,11,12,15,16-octahydrocyclopenta[a]phenanthren-17-yl]ethyl]-4,5-dimethyl-2,3-dihydropyran-6-one |
| 23265672 | InChI=1S/C30H40O9/c1-15-13-22(38-24(33)16(15)2)27(6,34)29(36)12-11-28(35)19-14-23-30(39-23)21(37-17(3)31)8-7-20(32)26(30,5)18(19)9-10-25(28,29)4/h7-8,18-19,21-23,34-36H,9-14H2,1-6H3/t18?,19?,21-,22?,23+,25-,26-,27-,28-,29-,30+/m0/s1 | NA |
| 23253884 | InChI=1S/C30H40O6/c1-16-13-26(36-28(34)20(16)15-35-18(3)31)17(2)21-9-10-22-19-14-25(32)24-7-6-8-27(33)30(24,5)23(19)11-12-29(21,22)4/h6-8,17,19,21-23,25- | [(2R)-2-[(1S)-1-[(6R,8S,9S,10R,13S,14S,17R)-6-hydroxy-10,13-dimethyl-1-oxo-6,7,8,9,11,12,14,15,16,17-decahydrocyclopenta[a]phenanthren-17- |

TABLE 2-continued

LIST OF WITHAFERIN A ANALOGS AND DERIVATIVES BASED ON SIMILARITY

| | | |
|---|---|---|
| | 26,32H,9-15H2,1-5H3/t17-,19-,21+,22-,23-,25+,26+,29+,30+/m0/s1 | yl]ethyl]-4-methyl-6-oxo-2,3-dihydropyran-5-yl]methyl acetate |
| 21679035 | InChI=1S/C28H38O7/c1-14-13-19(34-23(30)15(14)2)26(5,31)28(33)12-9-16-20-17(8-11-24(16,28)3)25(4)18(29)7-6-10-27(25,32)22-21(20)35-22/h6-7,16-17,19-22,31-33H,8-13H2,1-5H3/t16-,17-,19+,20-,21-,22-,24-,25-,26-,27-,28+/m0/s1 | NA |
| 21679033 | InChI=1S/C30H40O9/c1-15-13-22(38-24(33)16(15)2)27(6,34)29(36)12-11-28(35)19-14-23-30(39-23)21(37-17(3)31)8-7-20(32)26(30,5)18(19)9-10-25(28,29)4/h7-8,18-19,21-23,34-36H,9-14H2,1-6H3/t18-,19+,21-,22+,23+,25-,26-,27-,28+,29-,30+/m0/s1 | NA |
| 21679027 | InChI=1S/C28H38O6/c1-14-13-19(33-24(30)15(14)2)16(3)27(31)12-9-17-21-18(8-11-25(17,27)4)26(5)20(29)7-6-10-28(26,32)23-22(21)34-23/h6-7,16-19,21-23,31-32H,8-13H2,1-5H3/t16-,17+,18+,19-,21+,22+,23+,25+,26+,27+,28+/m1/s1 | NA |
| 21679024 | InChI=1S/C28H38O7/c1-15-13-20(34-22(30)16(15)2)25(5,31)28(33)12-11-26(32)18-14-21-27(35-21)9-6-7-19(29)24(27,4)17(18)8-10-23(26,28)3/h6-7,17-18,20-21,31-33H,8-14H2,1-5H3/t17-,18+,20+,21+,23-,24-,25-,26+,27+,28+/m0/s1 | NA |
| 21679018 | InChI=1S/C30H40O8/c1-15-13-23(37-25(33)16(15)2)28(6,34)20-10-12-29(35)19-14-24-30(38-24)22(36-17(3)31)8-7-21(32)27(30,5)18(19)9-11-26(20,29)4/h7-8,18-20,22-24,34-35H,9-14H2,1-6H3/t18-,19+,20-,22-,23+,24+,26+,27-,28+,29+,30+/m0/s1 | NA |
| 21607603 | InChI=1S/C32H42O9/c1-15-12-23(40-29(36)19(15)14-38-17(3)33)16(2)20-9-10-21-26-22(13-25(30(20,21)5)39-18(4)34)31(6)24(35)8-7-11-32(31,37)28-27(26)41-28/h7-8,16,20-23,25-28,37H,9-14H2,1-6H3/t16-,20+,21-,22-,23+,25-,26-,27-,28-,30+,31-,32-/m0/s1 | NA |
| 21606679 | InChI=1S/C28H36O7/c1-13-11-21(33- | NA |

TABLE 2-continued

LIST OF WITHAFERIN A ANALOGS AND DERIVATIVES BASED ON SIMILARITY

| | | |
|---|---|---|
| | 23(31)14(13)2)26(4)18-6-5-17-15-12-22-28(34-22)20(30)8-7-19(29)25(28,3)16(15)9-10-27(17,18)24(32)35-26/h7-8,15-18,20-22,24,30,32H,5-6,9-12H2,1-4H3/t15-,16+,17+,18-,20+,21-,22-,24+,25+,26-,27-,28-/m1/s1 | |
| 21606678 | InChI=1S/C28H36O7/c1-13-11-21(33-23(31)14(13)2)26(4)18-6-5-17-15-12-22-28(34-22)20(30)8-7-19(29)25(28,3)16(15)9-10-27(17,18)24(32)35-26/h7-8,15-18,20-22,24,30,32H,5-6,9-12H2,1-4H3/t15-,16+,17+,18-,20+,21-,22-,24-,25+,26-,27-,28-/m1/s1 | NA |
| 21575410 | InChI=1S/C28H44O4/c1-15(2)16(3)7-8-17(4)19-9-10-20-18-13-23(31)28-24(32-28)12-11-22(30)27(28,6)25(18)21(29)14-26(19,20)5/h11-12,15-21,23-25,29,31H,7-10,13-14H2,1-6H3/t16-,17+,18-,19+,20-,21+,23+,24-,25+,26+,27+,28-/m0/s1 | NA |
| 21575409 | InChI=1S/C28H42O4/c1-15(2)16(3)7-8-17(4)19-9-10-20-18-13-23(31)28-24(32-28)12-11-22(30)27(28,6)25(18)21(29)14-26(19,20)5/h7-8,11-12,15-21,23-25,29,31H,9-10,13-14H2,1-6H3/b8-7+/t16-,17+,18-,19+,20-,21+,23+,24-,25+,26+,27+,28-/m0/s1 | NA |
| 16757497 | InChI=1S/C28H38O9/c1-13-10-20(36-22(32)14(13)2)25(5,33)26(34)12-19(31)27(35)16-11-21-28(37-21)18(30)7-6-17(29)24(28,4)15(16)8-9-23(26,27)3/h6-7,15-16,18-21,30-31,33-35H,8-12H2,1-5H3/t15-,16+,18-,19-,20?,21+,23+,24-,25-,26-,27-,28+/m0/s1 | NA |
| 14779030 | InChI=1S/C30H38O8/c1-14-11-21(37-26(34)15(14)2)16(3)19-12-24(36-17(4)31)29(35)20-13-25-30(38-25)23(33)8-7-22(32)28(30,6)18(20)9-10-27(19,29)5/h7-8,12,16,18,20-21,23-25,33,35H,9-11,13H2,1-6H3 | NA |
| 14605180 | InChI=1S/C28H38O7/c1-14-13-19(34-23(30)15(14)2)26(5,31)28(33)12-9-16-20-17(8-11-24(16,28)3)25(4)18(29)7-6-10-27(25,32)22-21(20)35-22/h6-7,16- | NA |

TABLE 2-continued

LIST OF WITHAFERIN A ANALOGS AND DERIVATIVES BASED ON SIMILARITY

| | | |
|---|---|---|
| | 17,19-22,31-33H,8-13H2,1-5H3 | |
| 12444955 | InChI=1S/C28H36O6/c1-13-11-19(33-25(31)14(13)2)15(3)16-8-9-17-22-18(12-21(30)26(16,17)4)27(5)20(29)7-6-10-28(27,32)24-23(22)34-24/h6-7,15-19,22-24,32H,8-12H2,1-5H3/t15-,16+,17-,18-,19+,22-,23-,24-,26+,27-,28-/m0/s1 | NA |
| 12444953 | InChI=1S/C28H36O6/c1-13-11-19(33-25(31)14(13)2)15(3)16-8-9-17-22-18(12-21(30)26(16,17)4)27(5)20(29)7-6-10-28(27,32)24-23(22)34-24/h6-7,15-19,22-24,32H,8-12H2,1-5H3 | NA |
| 12304664 | InChI=1S/C28H40O7/c1-14-10-21(35-25(33)17(14)13-29)15(2)18-7-8-19-16-11-24(32)28(34)9-5-6-22(30)27(28,4)20(16)12-23(31)26(18,19)3/h5-6,15-16,18-21,23-24,29,31-32,34H,7-13H2,1-4H3/t15-,16-,18+,19-,20-,21+,23-,24+,26+,27-,28-/m0/s1 | (2R)-5-(hydroxymethyl)-4-methyl-2-[(1S)-1-[(5R,6R,8S,9S,10R,12S,13S,14S,17R)-5,6,12-trihydroxy-10,13-dimethyl-1-oxo-6,7,8,9,11,12,14,15,16,17-decahydro-4H-cyclopenta[a]phenanthren-17-yl]ethyl]-2,3-dihydropyran-6-one |
| 12070589 | InChI=1S/C28H40O8/c1-14-22(31)35-21(13-24(14,3)32)26(5,33)27(34)11-9-16-15-12-20-28(36-20)19(30)7-6-18(29)25(28,4)17(15)8-10-23(16,27)2/h6-7,14-17,19-21,30,32-34H,8-13H2,1-5H3/t14-,15-,16-,17-,19-,20+,21+,23-,24+,25-,26-,27+,28+/m0/s1 | NA |
| 11844625 | InChI=1S/C28H40O7/c1-15-12-23(35-24(32)16(15)2)26(4,33)20-8-7-19-17-13-22(31)28(34)10-5-6-21(30)25(28,3)18(17)9-11-27(19,20)14-29/h5-6,17-20,22-23,29,31,33-34H,7-14H2,1-4H3/t17-,18+,19+,20-,22-,23-,25+,26-,27-,28+/m1/s1 | (2R)-2-[(1R)-1-[(5R,6R,8S,9S,10R,13R,14S,17S)-5,6-dihydroxy-13-(hydroxymethyl)-10-methyl-1-oxo-6,7,8,9,11,12,14,15,16,17-decahydro-4H-cyclopenta[a]phenanthren-17-yl]-1-hydroxyethyl]-4,5-dimethyl-2,3-dihydropyran-6-one |
| 11785089 | InChI=1S/C28H40O7/c1-14-11-20(34-24(32)17(14)13-29)15(2)27(33)10-8-18-16-12-23-28(35-23)22(31)6-5-21(30)26(28,4)19(16)7-9-25(18,27)3/h15-16,18-20,22-23,29,31,33H,5-13H2,1-4H3/t15-,16+,18+,19-,20-,22+,23-,25+,26+,27+,28-/m1/s1 | NA |
| 11730849 | InChI=1S/C28H40O8/c1-14-22(31)35-21(13-24(14,3)32)26(5,33)27(34)11-9-16-15-12-20-28(36-20)19(30)7-6- | NA |

TABLE 2-continued

LIST OF WITHAFERIN A ANALOGS AND DERIVATIVES BASED ON SIMILARITY

| | | |
|---|---|---|
| | 18(29)25(28,4)17(15)8-10-23(16,27)2/h6-7,14-17,19-21,30,32-34H,8-13H2,1-5H3/t14-,15-,16-,17-,19-,20+,21?,23-,24+,25-,26-,27+,28+/m0/s1 | |
| 11408805 | InChI=1S/C28H38O6/c1-14-13-19(33-24(30)15(14)2)16(3)27(31)12-9-17-21-18(8-11-25(17,27)4)26(5)20(29)7-6-10-28(26,32)23-22(21)34-23/h6-7,16-19,21-23,31-32H,8-13H2,1-5H3/t16-,17?,18?,19?,21?,22+,23+,25+,26-,27+,28+/m1/s1 | NA |
| 10791040 | InChI=1S/C28H36O7/c1-13-11-21(33-23(31)14(13)2)26(4)18-6-5-17-15-12-22-28(34-22)20(30)8-7-19(29)25(28,3)16(15)9-10-27(17,18)24(32)35-26/h7-8,15-18,20-22,24,30,32H,5-6,9-12H2,1-4H3/t15-,16+,17+,18-,20+,21?,22-,24?,25+,26-,27-,28-/m1/s1 | NA |
| 10720495 | InChI=1S/C30H38O7/c1-14-12-20(36-27(33)15(14)2)16(3)24-21(35-17(4)31)13-19-23-18(9-11-28(19,24)5)29(6)22(32)8-7-10-30(29,34)26-25(23)37-26/h7-8,18-21,23,25-26,34H,9-13H2,1-6H3/b24-16+/t18-,19-,20?,21-,23+,25-,26-,28-,29-,30-/m0/s1 | NA |
| 10576702 | InChI=1S/C28H32O7/c1-13-14(2)28(35-23(13)32)22(31)16(12-29)18-8-7-17-15-10-21-26(34-21)9-5-6-20(30)25(26,4)19(15)11-27(28,33)24(17,18)3/h5-6,15,17,19,21,29,33H,7-12H2,1-4H3/t15-,17-,19-,21+,24-,25-,26+,27+,28-/m0/s1 | NA |
| 10552958 | InChI=1S/C28H38O7/c1-13-11-18(34-24(31)14(13)2)15(3)28(33)20(30)12-17-21-16(8-10-25(17,28)4)26(5)19(29)7-6-9-27(26,32)23-22(21)35-23/h6-7,15-18,20-23,30,32-33H,8-12H2,1-5H3/t15-,16+,17+,18?,20-,21-,22+,23+,25+,26+,27+,28-/m1/s1 | NA |
| 10413803 | InChI=1S/C28H40O8/c1-14-22(31)35-21(13-24(14,3)32)26(5,33)27(34)11-9-16-15-12-20-28(36-20)19(30)7-6-18(29)25(28,4)17(15)8-10-23(16,27)2/h6-7,14-17,19-21,30,32-34H,8-13H2,1-5H3/t14-, | NA |

TABLE 2-continued

LIST OF WITHAFERIN A ANALOGS AND DERIVATIVES BASED ON SIMILARITY

| | | |
|---|---|---|
| | 15?,16?,17?,19-,<br>20+,21?,23-,24+,25-,26-,<br>27+,28?/m0/s1 | |
| 10413139 | InChI=1S/C28H38O7/c1-<br>15-13-20(34-<br>22(30)16(15)2)25(5,31)28<br>(33)12-11-26(32)18-14-<br>21-27(35-21)9-6-7-<br>19(29)24(27,4)17(18)8-<br>10-23(26,28)3/h6-7,17-<br>18,20-21,31-33H,8-<br>14H2,1-5H3/t17-,<br>18+,20?,21+,23-,24-,25-,<br>26+,27+,28-/m0/s1 | NA |
| 10301870 | InChI=1S/C30H38O8/c1-<br>14-11-21(37-<br>26(34)15(14)2)16(3)19-<br>12-24(36-<br>17(4)31)29(35)20-13-25-<br>30(38-25)23(33)8-7-<br>22(32)28(30,6)18(20)9-<br>10-27(19,29)5/h7-<br>8,12,16,18,20-21,23-<br>25,33,35H,9-11,13H2,1-<br>6H3/t16-<br>18?,20?,21+,23-,24-,<br>25+,27+,28-,<br>29+,30+/m0/s1 | NA |
| 9806892 | InChI=1S/C30H38O8/c1-<br>14-11-21(37-<br>26(34)15(14)2)16(3)19-<br>12-24(36-<br>17(4)31)29(35)20-13-25-<br>30(38-25)23(33)8-7-<br>22(32)28(30,6)18(20)9-<br>10-27(19,29)5/h7-<br>8,12,16,18,20-21,23-<br>25,33,35H,9-11,13H2,1-<br>6H3/t16?,18?,20?,21-,<br>23+,24+,25-,27-,<br>28+,29+,30-/m1/s1 | NA |
| 5315322 | InChI=1S/C28H36O6/c1-<br>13-11-19(33-<br>25(31)14(13)2)15(3)16-<br>8-9-17-22-18(12-<br>21(30)26(16,17)4)27(5)20<br>(29)7-6-10-28(27,32)24-<br>23(22)34-24/h6-7,15-<br>19,22-24,32H,8-12H2,1-<br>5H3/t15-,<br>16?,17?,18?,19?,22?,23?,<br>24?,26+,27-,28?/m0/s1 | NA |
| 3935211 | InChI=1S/C28H38O5/c1-<br>15-12-24(33-<br>26(32)18(15)14-<br>29)16(2)19-8-9-20-17-<br>13-23(30)22-6-5-7-<br>25(31)28(22,4)21(17)10-<br>11-27(19,20)3/h5-7,16-<br>17,19-21,23-24,29-<br>30H,8-14H2,1-4H3 | 2-[1-(6-hydroxy-<br>10,13-dimethyl-1-<br>oxo-<br>6,7,8,9,11,12,14,15,16,<br>17-<br>decahydrocyclopenta<br>[a]phenanthren-17-<br>yl)ethyl]-5-<br>(hydroxymethyl)-4-<br>methyl-2,3-<br>dihydropyran-6-one |
| 3372729 | InChI=1S/C28H38O7/c1-<br>15-13-20(34-<br>22(30)16(15)2)25(5,31)28<br>(33)12-11-26(32)18-14-<br>21-27(35-21)9-6-7-<br>19(29)24(27,4)17(18)8-<br>10-23(26,28)3/h6-7,17-<br>18,20-21,31-33H,8-<br>14H2,1-5H3 | NA |
| 3084736 | InChI=1S/C28H36O6/c1-<br>13-11-19(33-<br>25(31)14(13)2)15(3)16-<br>8-9-17-22-18(12-<br>21(30)26(16,17)4)27(5)20<br>(29)7-6-10-28(27,32)24- | NA |

TABLE 2-continued

LIST OF WITHAFERIN A ANALOGS AND DERIVATIVES BASED ON SIMILARITY

| | | |
|---|---|---|
| | 23(22)34-24/h6-7,15-19,22-24,32H,8-12H2,1-5H3/t15-,16+,17?,18?,19?,22?,23-,24-,26+,27-,28-/m0/s1 | |
| 3034071 | InChI=1S/C28H38O7/c1-15-13-20(34-22(30)16(15)2)25(5,31)28(33)12-11-26(32)18-14-21-27(35-21)9-6-7-19(29)24(27,4)17(18)8-10-23(26,28)3/h6-7,17-18,20-21,31-33H,8-14H2,1-5H3/t17-,18+,20-,21+,23-,24-,25-,26+,27+,28-/m0/s1 | NA |
| 636567 | InChI=1S/C32H42O10/c1-14-12-23(41-28(37)15(14)2)31(7,38)26-20(39-16(3)33)13-19-24-18(10-11-29(19,26)5)30(6)21(35)8-9-22(36)32(30)27(42-32)25(24)40-17(4)34/h8-9,18-20,22-27,36,38H,10-13H2,1-7H3/t18-,19-,20+,22-,23+,24+,25+,26-,27+,29-,30-,31-,32+/m0/s1 | NA |
| 301757 | InChI=1S/C28H38O6/c1-14-13-19(33-24(30)15(14)2)16(3)27(31)12-9-17-21-18(8-11-25(17,27)4)26(5)20(29)7-6-10-28(26,32)23-22(21)34-23/h6-7,16-19,21-23,31-32H,8-13H2,1-5H3 | NA |
| 301751 | InChI=1S/C28H38O7/c1-15-13-20(34-22(30)16(15)2)25(5,31)28(33)12-11-26(32)18-14-21-27(35-21)9-6-7-19(29)24(27,4)17(18)8-10-23(26,28)3/h6-7,17-18,20-21,31-33H,8-14H2,1-5H3/t17-,18+,20+,21+,23-,24-,25-,26+,27+,28-/m0/s1 | |
| 268946 | InChI=1S/C28H38O5/c1-15-12-24(33-26(32)18(15)14-29)16(2)19-8-9-20-17-13-23(30)22-6-5-7-25(31)28(22,4)21(17)10-11-27(19,20)3/h5-7,16-17,19-21,23-24,29-30H,8-14H2,1-4H3/t16-,17-,19+,20-,21-,23+,24+,27+,28+/m0/s1 | (2R)-2-[(1S)-1-[(6R,8S,9S,10R,13S,14S,17R)-6-hydroxy-10,13-dimethyl-1-oxo-6,7,8,9,11,12,14,15,16,17-decahydrocyclopenta[a]phenanthren-17-yl]ethyl]-5-(hydroxymethyl)-4-methyl-2,3-dihydropyran-6-one |
| 147647 | InChI=1S/C30H38O8/c1-14-11-21(37-26(34)15(14)2)16(3)19-12-24(36-17(4)31)29(35)20-13-25-30(38-25)23(33)8-7-22(32)28(30,6)18(20)9-10-27(19,29)5/h7-8,12,16,18,20-21,23-25,33,35H,9-11,13H2,1-6H3/t16-,18-,20+,21+,23-,24-,25+,27+,28-,29-,30+/m0/s1 | NA |
| 265237 | InChI=1S/C28H38O6/c1-14-11-21(33- | NA |

TABLE 2-continued

LIST OF WITHAFERIN A ANALOGS AND DERIVATIVES BASED ON SIMILARITY

| | | |
|---|---|---|
| | 25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-,21+,23-,24+,26+,27-,28+/m0/s1 | |
| 9825988 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15?,16-,18+,19-,20-,21?,23-,24+,26+,27-,28+/m0/s1 | NA |
| 15411208 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h15-16,18-21,23-24,29,31H,5-13H2,1-4H3/t15-,16-,18+,19-,20-,21+,23-,24+,26+,27-,28+/m0/s1 | NA |
| 11070744 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h15-16,18-21,23-24,29,31H,5-13H2,1-4H3/t15-,16-,18?,19-,20-,21?,23-,24+,26+,27-,28+/m0/s1 | NA |
| 50907377 | InChI=1S/C28H36O7/c1-13-9-19(33-24(32)15(13)12-29)14(2)17-10-22-27(34-22)18-11-23-28(35-23)21(31)6-5-20(30)26(28,4)16(18)7-8-25(17,27)3/h5-6,14,16-19,21-23,29,31H,7-12H2,1-4H3/t14-,16-,17+,18+,19+,21-,22-,23+,25+,26-,27-,28+/m0/s1 | NA |
| 10141001 | InChI=1S/C28H38O7/c1-13-9-20(34-25(33)16(13)12-29)14(2)17-5-6-18-15-10-24-28(35-24)22(31)8-7-21(30)27(28,4)19(15)11-23(32)26(17,18)3/h7-8,14-15,17-20,22-24,29,31-32H,5-6,9-12H2,1-4H3/t14?,15-,17+,18-,19-,20?,22-,23-,24+,26+,27-,28+/m0/s1 | NA |
| 10161347 | InChI=1S/C28H38O5/c1-14-12-21(32-25(31)15(14)2)16(3)18-6-7-19-17-13-24-28(33-24)23(30)9-8-22(29)27(28,5)20(17)10- | NA |

TABLE 2-continued

LIST OF WITHAFERIN A ANALOGS AND DERIVATIVES BASED ON SIMILARITY

| | | |
|---|---|---|
| | 11-26(18,19)4/h8-9,16-21,23-24,30H,6-7,10-13H2,1-5H3/t16?,17-,18+,19-,20-,21?,23-,24+,26+,27-,28+/m0/s1 | |
| 165541 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,24,29H,5-6,9-13H2,1-4H3/t15-,16-,18+,19-,20-,21+,24+,26+,27-,28+/m0/s1 | NA |
| 50990201 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-,21?,23-,24+,26+,27-,28+/m0/s1 | NA |
| 11785089 | InChI=1S/C28H40O7/c1-14-11-20(34-24(32)17(14)13-29)15(2)27(33)10-8-18-16-12-23-28(35-23)22(31)6-5-21(30)26(28,4)19(16)7-9-25(18,27)3/h15-16,18-20,22-23,29,31,33H,5-13H2,1-4H3/t15-,16+,18+,19-,20-,22+,23-,25+,26+,27+,28-/m1/s1 | NA |
| 23266163 | InChI=1S/C28H38O7/c1-14-11-22(34-24(32)16(14)13-29)27(4,33)19-6-5-17-15-12-23-28(35-23)21(31)8-7-20(30)26(28,3)18(15)9-10-25(17,19)2/h7-8,15,17-19,21-23,29,31,33H,5-6,9-13H2,1-4H3/t15-,17-,18-,19-,21-,22+,23+,25+,26-,27+,28+/m0/s1 | NA |
| 11408847 | InChI=1S/C28H40O6/c1-14-11-21(33-25(32)17(14)13-29)15(2)18-5-6-19-16-12-24-28(34-24)23(31)8-7-22(30)27(28,4)20(16)9-10-26(18,19)3/h7-8,14-21,23-24,29,31H,5-6,9-13H2,1-4H3/t14?,15?,16-,17?,18+,19-,20-,21?,23-,24+,26+,27-,28+/m0/s1 | NA |
| 5315320 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18?,19?,20?,21?,23?,24+,26+,27-,28+/m0/s1 | NA |

TABLE 2-continued

LIST OF WITHAFERIN A ANALOGS AND DERIVATIVES BASED ON SIMILARITY

| | | |
|---|---|---|
| 176114 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h7-8,13,15-16,18-21,23-24,31H,5-6,9-12H2,1-4H3/t15-,16-,18+,19-,20-,21+,23-,24+,26+,27-,28+/m0/s1 | NA |
| 56926114 | InChI=1S/C28H38O7/c1-13-9-20(34-25(33)16(13)12-29)14(2)17-5-6-18-15-10-23-28(35-23)22(32)8-7-21(31)27(28,4)24(15)19(30)11-26(17,18)3/h7-8,14-15,17-20,22-24,29-30,32H,5-6,9-12H2,1-4H3/t14-,15-,17+,18-,19-,20+,22-,23+,24+,26+,27+,28+/m0/s1 | NA |
| 88948989 | InChI=1S/C27H38O6/c1-13-10-21(32-25(31)17(13)12-28)14(2)18-4-5-19-16-11-23-27(33-23)22(30)7-6-20(29)24(27)15(16)8-9-26(18,19)3/h14-16,18-19,21-24,28,30H,4-12H2,1-3H3/t14-,15-,16+,18+,19-,21+,22-,23+,24?,26+,27+/m0/s1 | NA |
| 71772576 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18?,19-,20-,21+,23-,24+,26+,27-,28+/m0/s1 | NA |
| 11798584 | InChI=1S/C28H38O6/c1-14-11-21(33-25(32)15(14)2)16(3)18-5-6-20-17-12-24-28(34-24)23(31)8-7-22(30)26(28,4)19(17)9-10-27(18,20)13-29/h7-8,16-21,23-24,29,31H,5-6,9-13H2,1-4H3/t16-,17+,18+,19-,20-,21?,23-,24+,26-,27-,28+/m0/s1 | NA |
| 11145377 | InChI=1S/C28H40O7/c1-13-9-21(34-25(33)16(13)12-29)14(2)17-5-6-18-15-10-23-28(35-23)24(32)20(30)11-22(31)27(28,4)19(15)7-8-26(17,18)3/h14-15,17-21,23-24,29-30,32H,5-12H2,1-4H3/t14-,15-,17?,18-,19-,20-,21?,23+,24-,26+,27-,28-/m0/s1 | NA |
| 5458778 | InChI=1S/C30H41NO6/c1-15-11-23(36-27(35)18(15)14-32)16(2)19-5-6-20-17-12-25-30(37-25)26(34)22(31-9-10- | NA |

TABLE 2-continued

LIST OF WITHAFERIN A ANALOGS AND DERIVATIVES BASED ON SIMILARITY

| | | |
|---|---|---|
| | 31)13-24(33)29(30,4)21(17)7-8-28(19,20)3/h13,16-17,19-21,23,25-26,32,34H,5-12,14H2,1-4H3/t16-,17-,19+,20-,21-,23+,25+,26-,28+,29?,30-/m0/s1 | |
| 5287384 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18?,19?,20-,21+,23-,24+,26+,27-,28+/m0/s1 | NA |
| 90670439 | InChI=1S/C28H38O5/c1-15-13-24(33-26(32)18(15)14-29)16(2)19-7-8-20-17-5-6-22-23(30)9-10-25(31)28(22,4)21(17)11-12-27(19,20)3/h6,9-10,16-17,19-21,23-24,29-30H,5,7-8,11-14H2,1-4H3/t16-,17-,19+,20-,21-,23-,24+,27+,28+/m0/s1 | (2R)-2-[(1S)-1-[(4S,8S,9S,10R,13S,14S,17R)-4-hydroxy-10,13-dimethyl-1-oxo-4,7,8,9,11,12,14,15,16,17-decahydrocyclopenta[a]phenanthren-17-yl]ethyl]-5-(hydroxymethyl)-4-methyl-2,3-dihydropyran-6-one |
| 45489105 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20?,21+,23-,24+,26+,27-,28+/m0/s1 | NA |
| 46939432 | InChI=1S/C28H36O6/c1-14-11-23(34-26(33)17(14)13-29)15(2)25-22(31)12-20-16-5-6-19-21(30)7-8-24(32)28(19,4)18(16)9-10-27(20,25)3/h6-8,16,18,20-23,29-31H,5,9-13H2,1-4H3/b25-15+/t16-,18+,20+,21+,22+,23-,27+,28-/m1/s1 | (2R)-2-[(1Z)-1-[(4S,8S,9S,10R,13S,14S,16S)-4,16-dihydroxy-10,13-dimethyl-1-oxo-7,8,9,11,12,14,15,16-octahydro-4H-cyclopenta[a]phenanthren-17-ylidene]ethyl]-5-(hydroxymethyl)-4-methyl-2,3-dihydropyran-6-one |
| 23266155 | InChI=1S/C28H38O5/c1-14-12-21(32-25(31)15(14)2)16(3)18-6-7-19-17-13-24(33-24)23(30)9-8-22(29)27(28,5)20(17)10-11-26(18,19)4/h8-9,16-21,23-24,30H,6-7,10-13H2,1-5H3/t16-,17-,18+,19-,20-,21+,23-,24+,26+,27-,28+/m0/s1 | NA |
| 16760705 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1- | NA |

TABLE 2-continued

LIST OF WITHAFERIN A ANALOGS AND DERIVATIVES BASED ON SIMILARITY

| | | |
|---|---|---|
| | 4H3/t15-,16-,18+,19?,20?,21+,23-,24+,26+,27-,28+/m0/s1 | |
| 16745397 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16?,18?,19-,20?,21?,23-,24+,26+,27-,28+/m0/s1 | NA |
| 10648050 | InChI=1S/C28H38O6/c1-15-11-22(33-25(32)18(15)13-29)16(2)19-6-7-20-17-12-24-28(34-24)9-4-5-23(31)27(28,14-30)21(17)8-10-26(19,20)3/h4-5,16-17,19-22,24,29-30H,6-14H2,1-3H3/t16-,17-,19+,20-,21-,22?,24+,26+,27-,28+/m0/s1 | NA |
| 88858700 | InChI=1S/C28H38O7/c1-14-10-21(34-25(33)17(14)12-29)15(2)18-4-5-19-16-11-24-28(35-24)23(32)7-6-22(31)27(28,13-30)20(16)8-9-26(18,19)3/h6-7,15-16,18-21,23-24,29-30,32H,4-5,8-13H2,1-3H3/t15-,16-,18?,19-,20-,21+,23-,24+,26+,27-,28+/m0/s1 | NA |
| 70690365 | InChI=1S/C28H36O5/c1-14-12-21(32-25(31)15(14)2)16(3)18-6-7-19-17-13-24-28(33-24)23(30)9-8-22(29)27(28,5)20(17)10-11-26(18,19)4/h7-9,16-18,20-21,23-24,30H,6,10-13H2,1-5H3/t16-,17-,18+,20-,21+,23-,24+,26+,27-,28+/m0/s1 | NA |
| 23266158 | InChI=1S/C28H38O6/c1-14-12-20(33-24(31)15(14)2)16(3)17-9-11-27(32)19-13-23-28(34-23)22(30)7-6-21(29)26(28,5)18(19)8-10-25(17,27)4/h6-7,16-20,22-23,30,32H,8-13H2,1-5H3/t16-,17+,18-,19+,20+,22-,23-,25+,26-,27+,28+/m0/s1 | NA |
| 66572429 | InChI=1S/C28H36O7/c1-13-9-20(34-25(33)16(13)12-29)14(2)24-19(30)11-18-15-10-23-28(35-23)22(32)6-5-21(31)27(28,4)17(15)7-8-26(18,24)3/h5-6,15,17-20,22-23,29-30,32H,7-12H2,1-4H3/b24-14+/t15-,17+,18+,19+,20-,22+,23-,26+,27+,28-/m1/s1 | NA |

TABLE 2-continued

LIST OF WITHAFERIN A ANALOGS AND DERIVATIVES BASED ON SIMILARITY

| | | |
|---|---|---|
| 90670452 | InChI=1S/C28H38O7/c1-13-9-20(34-25(33)16(13)12-29)14(2)18-11-19(30)24-15-10-23-28(35-23)22(32)6-5-21(31)27(28,4)17(15)7-8-26(18,24)3/h5-6,14-15,17-20,22-24,29-30,32H,7-12H2,1-4H3/t14-,15+,17-,18+,19+,20+,22-,23+,24+,26+,27-,28+/m0/s1 | NA |
| 53477765 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16-,17-,18-,19-,21-,22+,23+,25-,26-,27+,28?/m0/s1 | NA |
| 11134251 | InChI=1S/C28H40O5/c1-14-12-21(32-25(31)15(14)2)16(3)18-6-7-19-17-13-24-28(33-24)23(30)9-8-22(29)27(28,5)20(17)10-11-26(18,19)4/h8-9,14-21,23-24,30H,6-7,10-13H2,1-5H3/t14-,15+,16+,17+,18?,19+,20+,21?,23+,24-,26-,27+,28-/m1/s1 | NA |
| 10814731 | InChI=1S/C28H36O7/c1-13-9-20(34-25(33)14(13)2)15(3)24-19(30)11-18-16-10-23-28(35-23)22(32)6-5-21(31)26(28,4)17(16)7-8-27(18,24)12-29/h5-6,12,15-20,22-24,30,32H,7-11H2,1-4H3/t15-,16-,17+,18+,19-,20?,22+,23-,24+,26+,27-,28-/m1/s1 | NA |
| 10028564 | InChI=1S/C28H39ClO5/c1-15-12-22(34-25(33)18(15)14-30)16(2)19-7-8-20-17-13-24(32)28(29)10-5-6-23(31)27(28,4)21(17)9-11-26(19,20)3/h5-6,16-17,19-22,24,30,32H,7-14H2,1-4H3/t16?,17?,19-,20?,21?,22?,24-,26-,27+,28+/m1/s1 | 2-[1-[(5R,6R,10S,13S,17R)-5-chloro-6-hydroxy-10,13-dimethyl-1-oxo-6,7,8,9,11,12,14,15,16,17-decahydro-4H-cyclopenta[a]phenanthren-17-yl]ethyl]-5-(hydroxymethyl)-4-methyl-2,3-dihydropyran-6-one |
| 56649372 | InChI=1S/C28H38O8/c1-13-8-20(35-25(34)16(13)11-29)14(2)17-4-5-18-15-9-23-28(36-23)22(33)7-6-21(32)27(28,12-30)24(15)19(31)10-26(17,18)3/h6-7,14-15,17-20,22-24,29-31,33H,4-5,8-12H2,1-3H3/t14-,15-,17+,18-,19-,20+,22-,23+,24+,26+,27+,28+/m0/s1 | NA |
| 21670295 | InChI=1S/C28H36O7/c1-13-9-20(34-25(33)14(13)2)15(3)24- | NA |

TABLE 2-continued

LIST OF WITHAFERIN A ANALOGS AND DERIVATIVES BASED ON SIMILARITY

| CID | InChI | |
|---|---|---|
| | 19(30)11-18-16-10-23-28(35-23)22(32)6-5-21(31)26(28,4)17(16)7-8-27(18,24)12-29/h5-6,12,15-20,22-24,30,32H,7-11H2,1-4H3/t15-,16-,17+,18+,19-,20-,22+,23-,24+,26+,27-,28-/m1/s1 | |
| 10814230 | InChI=1S/C28H38O6/c1-13-10-20(33-25(32)14(13)2)15(3)24-19(29)12-18-16-11-23-28(34-23)22(31)7-6-21(30)27(28,5)17(16)8-9-26(18,24)4/h6-7,15-20,22-24,29,31H,8-12H2,1-5H3/t15-,16-,17+,18+,19-,20?,22+,23-,24+,26+,27-,28-/m1/s1 | NA |
| 5287385 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16-,17?,18-,19?,21-,22+,23+,25-,26-,27+,28+/m0/s1 | NA |
| 161671 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16-,17-,18-,19-,21-,22+,23+,25-,26-,27+,28+/m0/s1 | NA |
| 91799372 | InChI=1S/C29H40O6/c1-15-12-22(34-26(32)18(15)14-30)16(2)19-6-7-20-17-13-25-29(35-25)24(33-5)9-8-23(31)28(29,4)21(17)10-11-27(19,20)3/h8-9,16-17,19-22,24-25,30H,6-7,10-14H2,1-5H3/t16-,17-,19-,20-,21-,22+,24-,25+,27+,28-,29+/m0/s1 | NA |
| 90670450 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-,21+,23+,24+,26+,27-,28+/m0/s1 | NA |
| 23266167 | InChI=1S/C28H40O6/c1-14-12-22(33-24(31)15(14)2)27(5,32)19-7-6-17-16-13-23-28(34-23)21(30)9-8-20(29)26(28,4)18(16)10-11-25(17,19)3/h8-9,14-19,21-23,30,32H,6-7,10-13H2,1-5H3/t14-,15+,16-,17-,18-,19-,21-,22+,23+,25-,26-,27+,28+/m0/s1 | NA |

TABLE 2-continued

LIST OF WITHAFERIN A ANALOGS AND DERIVATIVES BASED ON SIMILARITY

| | | |
|---|---|---|
| 56649343 | InChI=1S/C28H38O7/c1-14-10-21(34-25(33)17(14)12-29)15(2)18-4-5-19-16-11-24-28(35-24)23(32)7-6-22(31)27(28,13-30)20(16)8-9-26(18,19)3/h6-7,15-16,18-21,23-24,29-30,32H,4-5,8-13H2,1-3H3/t15-,16-,18+,19-,20-,21+,23-,24+,26+,27-,28+/m0/s1 | NA |
| 44566999 | InChI=1S/C28H38O6/c1-13-10-20(33-25(32)14(13)2)15(3)24-19(29)12-18-16-11-23-28(34-23)22(31)7-6-21(30)27(28,5)17(16)8-9-26(18,24)4/h6-7,15-20,22-24,29,31H,8-12H2,1-5H3/t15-,16-,17+,18+,19+,20-,22+,23-,24+,26+,27+,28-/m1/s1 | NA |
| 10277878 | InChI=1S/C28H38O7/c1-14-11-20(34-24(32)15(14)2)16(3)17-8-10-27(33)19-12-23-28(35-23)22(31)6-5-21(30)25(28,4)18(19)7-9-26(17,27)13-29/h5-6,16-20,22-23,29,31,33H,7-13H2,1-4H3/t16-,17?,18?,19?,20+,22-,23+,25-,26-,27+,28+/m0/s1 | NA |
| 88949016 | InChI=1S/C27H38O5/c1-13-11-21(31-25(30)14(13)2)15(3)18-5-6-19-17-12-23-27(32-23)22(29)8-7-20(28)24(27)16(17)9-10-26(18,19)4/h15-19,21-24,29H,5-12H2,1-4H3/t15-,16-,17+,18+,19-,21+,22-,23+,24?,26+,27+/m0/s1 | NA |
| 57403080 | InChI=1S/C28H40O7/c1-13-9-21(34-25(33)16(13)12-29)14(2)17-5-6-18-15-10-23-28(35-23)24(32)20(30)11-22(31)27(28,4)19(15)7-8-26(17,18)3/h14-15,17-21,23-24,29-30,32H,5-12H2,1-4H3/t14-,15-,17+,18-,19-,20-,21+,23+,24+,26+,27-,28-/m0/s1 | NA |
| 49864510 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20-,21-,23-,24+,26+,27-,28+/m0/s1 | NA |
| 23266166 | InChI=1S/C28H40O5/c1-14-12-21(32-25(31)15(14)2)16(3)18-6-7-19-17-13-24-28(33-24)23(30)9-8-22(29)27(28,5)20(17)10- | NA |

TABLE 2-continued

LIST OF WITHAFERIN A ANALOGS AND DERIVATIVES BASED ON SIMILARITY

| | | |
|---|---|---|
| | 11-26(18,19)4/h8-9,14-21,23-24,30H,6-7,10-13H2,1-5H3/t14-,15+,16-,17-,18+,19-,20-,21+,23-,24+,26+,27-,28+/m0/s1 | |
| 90670451 | InChI=1S/C28H38O7/c1-13-9-20(34-25(33)16(13)12-29)14(2)17-5-6-18-15-10-24-28(35-24)22(31)8-7-21(30)27(28,4)19(15)11-23(32)26(17,18)3/h7-8,14-15,17-20,22-24,29,31-32H,5-6,9-12H2,1-4H3/t14-,15-,17+,18-,19-,20+,22-,23+,24+,26+,27-,28+/m0/s1 | NA |
| 88858703 | InChI=1S/C29H42O7/c1-13-8-21(35-26(34)17(13)12-30)15(3)18-6-7-19-16-10-23-29(36-23)25(33)14(2)9-22(32)28(29,5)24(16)20(31)11-27(18,19)4/h14-16,18-21,23-25,30-31,33H,6-12H2,1-5H3/t14-,15-,16-,18+,19-,20-,21+,23+,24+,25-,27+,28+,29-/m0/s1 | NA |
| 12304656 | InChI=1S/C28H38O5/c1-15-12-22(32-25(31)18(15)14-29)16(2)19-7-8-20-17-13-24-28(33-24)10-5-6-23(30)27(28,4)21(17)9-11-26(19,20)3/h5-6,16-17,19-22,24,29H,7-14H2,1-4H3/t16-,17-,19+,20-,21-,22+,24+,26+,27-,28+/m0/s1 | NA |
| 12147447 | InChI=1S/C28H38O7/c1-14-11-20(34-24(32)17(14)13-29)15(2)27(33)10-8-18-16-12-23-28(35-23)22(31)6-5-21(30)26(28,4)19(16)7-9-25(18,27)3/h5-6,15-16,18-20,22-23,29,31,33H,7-13H2,1-4H3/t15-,16+,18+,19+,20-,22+,23-,25+,26+,27+,28-/m1/s1 | NA |
| 57519534 | InChI=1S/C28H38O6/c1-14-11-21(33-25(32)17(14)13-29)15(2)18-5-6-19-16-12-24-28(34-24)23(31)8-7-22(30)27(28,4)20(16)9-10-26(18,19)3/h7-8,15-16,18-21,23-24,29,31H,5-6,9-13H2,1-4H3/t15-,16-,18+,19-,20+,21-,23+,24+,26+,27-,28+/m0/s1 | NA |
| 21670293 | InChI=1S/C28H38O6/c1-13-10-20(33-25(32)14(13)2)15(3)24-19(29)12-18-16-11-23-28(34-23)22(31)7-6-21(30)27(28,5)17(16)8-9-26(18,24)4/h6-7,15-20,22-24,29,31H,8-12H2,1-5H3/t15-,16-, | |

TABLE 2-continued

LIST OF WITHAFERIN A ANALOGS AND DERIVATIVES BASED ON SIMILARITY

| | | |
|---|---|---|
| | 17+,18+,19-,20-,22+,23-,24+,26+,27+,28-/m1/s1 | |
| 10005030 | InChI=1S/C28H40O6/c1-14-12-22(33-24(31)15(14)2)27(5,32)19-7-6-17-16-13-23-28(34-23)21(30)9-8-20(29)26(28,4)18(16)10-11-25(17,19)3/h8-9,14-19,21-23,30,32H,6-7,10-13H2,1-5H3/t14-,15+,16?,17?,18?,19?,21-,22?,23+,25-,26-,27+,28+/m0/s1 | NA |
| 88949008 | InChI=1S/C27H36O6/c1-13-10-21(32-25(31)17(13)12-28)14(2)18-4-5-19-16-11-23-27(33-23)22(30)7-6-20(29)24(27)15(16)8-9-26(18,19)3/h6-7,14-16,18-19,21-24,28,30H,4-5,8-12H2,1-3H3/t14-,15-,16+,18+,19-,21+,22-,23+,24?,26+,27+/m0/s1 | NA |
| 50925597 | InChI=1S/C28H36O7/c1-13-9-19(33-24(32)15(13)12-29)14(2)17-10-22-27(34-22)18-11-23-28(35-23)21(31)6-5-20(30)26(28,4)16(18)7-8-25(17,27)3/h5-6,14,16-19,21-23,29,31H,7-12H2,1-4H3/t14-,16-,17+,18+,19+,21-,22-,23+,25+,26-,27+,28+/m0/s1 | NA |
| 46939433 | InChI=1S/C28H36O5/c1-15-12-23(33-26(32)19(15)14-29)16(2)25-22(30)13-21-18-9-8-17-6-5-7-24(31)28(17,4)20(18)10-11-27(21,25)3/h5,7-8,18,20-23,29-30H,6,9-14H3/b25-16+/t18-,20+,21+,22+,23-,27+,28+/m1/s1 | (2R)-2-[(1Z)-1-[(8S,9S,10R,13S,14S,16S)-16-hydroxy-10,13-dimethyl-1-oxo-7,8,9,11,12,14,15,16-octahydro-4H-cyclopenta[a]phenanthren-17-ylidene]ethyl]-5-(hydroxymethyl)-4-methyl-2,3-dihydropyran-6-one |
| 46872824 | InChI=1S/C28H38O7/c1-13-10-22(34-24(32)14(13)2)27(5,33)18-7-6-16-15-11-23-28(35-23)20(30)9-8-19(29)26(28,4)17(15)12-21(31)25(16,18)3/h8-9,15-18,20-23,30-31,33H,6-7,10-12H2,1-5H3/t15-,16-,17-,18-,20-,21+,22+,23+,25-,26-,27+,28+/m0/s1 | NA |
| 10095500 | InChI=1S/C28H38O5/c1-15-13-21(32-24(30)16(15)2)17(3)27(31)12-9-19-18-14-23-28(33-23)10-6-7-22(29)26(28,5)20(18)8-11-25(19,27)4/h6,7,17-21,23,31H,8-14H2,1-5H3/t17-,18+,19+,20+,21-,23-,25+,26+,27+,28-/m1/s1 | NA |
| 88949017 | InChI=1S/C27H38O7/c1-12-8-21(33-25(32)16(12)11- | NA |

TABLE 2-continued

LIST OF WITHAFERIN A ANALOGS AND DERIVATIVES BASED ON SIMILARITY

| | | |
|---|---|---|
| | 28)13(2)17-4-5-18-15-9-22-27(34-22)23(14(15)6-7-26(17,18)3)19(29)10-20(30)24(27)31/h13-15,17-18,20-24,28,30-31H,4-11H2,1-3H3/t13-,14-,15+,17+,18-,20-,21+,22+,23?,24-,26+,27+/m0/s1 | |
| 46198373 | InChI=1S/C28H40O6/c1-14(19-13-25(3)27(5,34-25)23(31)32-19)16-6-7-17-15-12-22-28(33-22)21(30)9-8-20(29)26(28,4)18(15)10-11-24(16,17)2/h8-9,14-19,21-23,30-31H,6-7,10-13H2,1-5H3/t14-,15-,16+,17-,18-,19+,21-,22+,23+,24+,25-,26-,27+,28+/m0/s1 | NA |
| 21606687 | InChI=1S/C28H38O7/c1-14-11-22(34-24(32)15(14)2)26(4,33)19-6-5-18-16-12-23-28(35-23)21(31)8-7-20(30)25(28,3)17(16)9-10-27(18,19)13-29/h7-8,16-19,21-23,29,31,33H,5-6,9-13H2,1-4H3/t16-,17+,18+,19-,21+,22-,23-,25+,26-,27-,28-/m1/s1 | NA |
| 16680447 | InChI=1S/C28H38O6/c1-14-12-20(33-24(31)15(14)2)16(3)27(32)11-9-18-17-13-23-28(34-23)22(30)7-6-21(29)26(28,5)19(17)8-10-25(18,27)4/h6-7,16-20,22-23,30,32H,8-13H2,1-5H3/t16-,17+,18+,19+,20-,22+,23-,25+,26+,27+,28-/m1/s1 | NA |
| 10321754 | InChI=1S/C28H38O5/c1-15-12-22(32-25(31)18(15)14-29)16(2)19-7-8-20-17-13-24-28(33-24)10-5-6-23(30)27(28,4)21(17)9-11-26(19,20)3/h5-6,16-17,19-22,24,29H,7-14H2,1-4H3/t16?,17-,19+,20-,21-,22?,24+,26+,27-,28+/m0/s1 | NA |
| 10163221 | InChI=1S/C28H38O7/c1-13-9-20(34-25(33)16(13)12-29)14(2)18-11-19(30)24-15-10-23-28(35-23)22(32)6-5-21(31)27(28,4)17(15)7-8-26(18,24)3/h5-6,14-15,17-20,22-24,29-30,32H,7-12H2,1-4H3/t14?,15-,17+,18-,19+,20?,22+,23-,24-,26-,27+,28-/m1/s1 | NA |
| 88949019 | InChI=1S/C27H36O5/c1-13-11-21(31-25(30)14(13)2)15(3)18-5-6-19-17-12-23-27(32-23)22(29)8-7-20(28)24(27)16(17)9-10-26(18,19)4/h7-8,15-19,21-24,29H,5-6,9-12H2,1-4H3/t15-, | NA |

TABLE 2-continued

LIST OF WITHAFERIN A ANALOGS AND DERIVATIVES BASED ON SIMILARITY

| | | |
|---|---|---|
| | 16?,17+,18+,19-,21+,22-,23+,24?,26+,27+/m0/s1 | |
| 88948987 | InChI=1S/C27H36O5/c1-13-11-21(31-25(30)14(13)2)15(3)18-5-6-19-17-12-23-27(32-23)22(29)8-7-20(28)24(27)16(17)9-10-26(18,19)4/h7-8,15-19,21-24,29H,5-6,9-12H2,1-4H3/t15-,16-,17+,18?,19-,21+,22-,23+,24?,26+,27+/m0/s1 | NA |
| 60148726 | InChI=1S/C28H38O7/c1-14-10-21(34-25(33)17(14)12-29)15(2)18-4-5-19-16-11-24-28(35-24)23(32)7-6-22(31)27(28,13-30)20(16)8-9-26(18,19)3/h6-7,15-16,18-21,23-24,29-30,32H,4-5,8-13H2,1-3H3/t15?,16-,18+,19-,20-,21?,23-,24+,26+,27-,28+/m0/s1 | NA |
| 23266162 | InChI=1S/C28H38O7/c1-14-12-21(34-23(31)15(14)2)26(5,32)18-9-11-27(33)17-13-22-28(35-22)20(30)7-6-19(29)25(28,4)16(17)8-10-24(18,27)3/h6-7,16-18,20-22,30,32-33H,8-13H2,1-5H3/t16-,17+,18-,20-,21+,22+,24+,25-,26+,27+,28+/m0/s1 | NA |
| 15519705 | InChI=1S/C30H40O8/c1-15-12-24(37-26(34)16(15)2)28(5,35)21-7-6-20-18-13-25-30(38-25)23(33)9-8-22(32)27(30,4)19(18)10-11-29(20,21)14-36-17(3)31/h8-9,18-21,23-25,33,35H,6-7,10-14H2,1-5H3/t18-,19+,20+,21-,23+,24-,25-,27+,28-,29-,30-/m1/s1 | NA |
| 10767272 | InChI=1S/C28H38O7/c1-14-11-22(34-24(32)15(14)2)26(4,33)19-6-5-18-16-12-23-28(35-23)21(31)8-7-20(30)25(28,3)17(16)9-10-27(18,19)13-29/h7-8,16-19,21-23,29,31,33H,5-6,9-13H2,1-4H3/t16-,17+,18+,19-,21+,22?,23-,25+,26-,27-,28-/m1/s1 | NA |
| 10228028 | InChI=1S/C28H38O7/c1-14-12-21(34-23(31)15(14)2)26(5,32)18-9-11-27(33)17-13-22-28(35-22)20(30)7-6-19(29)25(28,4)16(17)8-10-24(18,27)3/h6-7,16-18,20-22,30,32-33H,8-13H2,1-5H3/t16?,17?,18?,20-,21?,22+,24+,25-,26+,27+,28?/m0/s1 | NA |
| 88858709 | InChI=1S/C28H40O7/c1-14-10-21(34-25(33)17(14)12-29)15(2)18-4-5-19-16-11-24-28(35-24)23(32)7- | NA |

TABLE 2-continued

LIST OF WITHAFERIN A ANALOGS AND DERIVATIVES BASED ON SIMILARITY

| | | |
|---|---|---|
| | 6-22(31)27(28,13-30)20(16)8-9-26(18,19)3/h15-16,18-21,23-24,29-30,32H,4-13H2,1-3H3/t15-,16-,18+,19-,20-,21+,23-,24+,26+,27-,28+/m0/s1 | |
| 70686221 | InChI=1S/C28H40O6/c1-15-11-22(34-25(33)18(15)13-29)16(2)19-5-6-20-17-12-24(32)28(14-30)10-8-23(31)27(28,4)21(17)7-9-26(19,20)3/h14,16-17,19-22,24,29,32H,5-13H2,1-4H3/t16-,17-,19+,20-,21-,22+,24+,26+,27-,28+/m0/s1 | (3aR,3bS,5aS,6R,8aS,8bS,10R,10aS)-10-hydroxy-6-[(1S)-1-[(2R)-5-(hydroxymethyl)-4-methyl-6-oxo-2,3-dihydropyran-2-yl]ethyl]-3a,5a-dimethyl-3-oxo-1,2,3b,4,5,6,7,8,8a,8b,9,10-dodecahydroindeno[6,7-e]indene-10a-carbaldehyde |
| 56649344 | InChI=1S/C28H38O6/c1-14-11-21(33-25(32)15(14)2)16(3)18-5-6-19-17-12-24-28(34-24)23(31)8-7-22(30)27(28,13-29)20(17)9-10-26(18,19)4/h7-8,16-21,23-24,29,31H,5-6,9-13H2,1-4H3/t16-,17-,18+,19-,20-,21+,23-,24+,26+,27-,28+/m0/s1 | NA |
| 49864537 | InChI=1S/C28H38O6/c1-14-12-22(33-24(31)15(14)2)27(5,32)19-7-6-17-16-13-23-28(34-23)21(30)9-8-20(29)26(28,4)18(16)10-11-25(17,19)3/h8-9,16-19,21-23,30,32H,6-7,10-13H2,1-5H3/t16-,17-,18-,19-,21-,22-,23+,25-,26-,27+,28+/m0/s1 | NA |
| 10458125 | InChI=1S/C28H38O7/c1-14-11-22(34-24(32)15(14)2)26(4,33)19-6-5-18-16-12-23-28(35-23)21(31)8-7-20(30)25(28,3)17(16)9-10-27(18,19)13-29/h7-8,16-19,21-23,29,31,33H,5-6,9-13H2,1-4H3/t16?,17?,18?,19-,21+,22?,23-,25+,26-,27-,28?/m1/s1 | NA |
| 66572354 | InChI=1S/C28H38O6/c1-15-11-22(34-25(33)18(15)13-29)16(2)19-5-6-20-17-12-24(32)28(14-30)10-8-23(31)27(28,4)21(17)7-9-26(19,20)3/h8,10,14,16-17,19-22,24,29,32H,5-7,9,11-13H2,1-4H3/t16-,17-,19+,20-,21-,22+,24+,26+,27-,28+/m0/s1 | (3aR,3bS,5aS,6R,8aS,8bS,10R,10aS)-10-hydroxy-6-[(1S)-1-[(2R)-5-(hydroxymethyl)-4-methyl-6-oxo-2,3-dihydropyran-2-yl]ethyl]-3a,5a-dimethyl-3-oxo-3b,4,5,6,7,8,8a,8b,9,10-decahydroindeno[6,7-e]indene-10a-carbaldehyde |
| 56926115 | InChI=1S/C29H42O8/c1-14-9-21(36-26(34)17(14)12-30)15(2)18-5-6-19-16-10-24-29(37-24)25(33)22(35-4)11-23(32)28(29,13- | NA |

TABLE 2-continued

LIST OF WITHAFERIN A ANALOGS AND DERIVATIVES BASED ON SIMILARITY

| | | |
|---|---|---|
| | 31)20(16)7-8-27(18,19)3/h15-16,18-22,24-25,30-31,33H,5-13H2,1-4H3/t15-,16-,18+,19-,20-,21+,22-,24+,25-,27+,28-,29-/m0/s1 | |
| 46939434 | InChI=1S/C28H34O6/c1-14-11-23(34-26(33)17(14)13-29)15(2)25-22(31)12-20-16-5-6-19-21(30)7-8-24(32)28(19,4)18(16)9-10-27(20,25)3/h6-8,16,18,20,22-23,29,31H,5,9-13H2,1-4H3/b25-15+/t16-,18+,20+,22+,23-,27+,28-/m1/s1 | (8S,9S,10R,13S,14S,16S,17Z)-16-hydroxy-17-[1-[(2R)-5-(hydroxymethyl)-4-methyl-6-oxo-2,3-dihydropyran-2-yl]ethylidene]-10,13-dimethyl-7,8,9,11,12,14,15,16-octahydrocyclopenta[a]phenanthrene-1,4-dione |
| 23266161 | InChI=1S/C28H38O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,16-18,20-22,30,32-33H,8-13H2,1-5H3/t16-,17-,18-,20-,21+,22+,24-,25-,26-,27+,28+/m0/s1 | NA |
| 21670294 | InChI=1S/C28H38O6/c1-14-11-21(33-25(32)15(14)2)16(3)18-5-6-20-17-12-24-28(34-24)23(31)8-7-22(30)26(28,4)19(17)9-10-27(18,20)13-29/h7-8,16-21,23-24,29,31H,5-6,9-13H2,1-4H3/t16-,17+,18+,19-,20-,21+,23-,24+,26-,27-,28+/m0/s1 | NA |
| 16680715 | InChI=1S/C29H42O7/c1-14-11-22(35-25(32)15(14)2)28(5,33)20-8-7-17-16-12-23-29(36-23)24(31)19(34-6)13-21(30)27(29,4)18(16)9-10-26(17,20)3/h16-20,22-24,31,33H,7-13H2,1-6H3/t16-,17-,18-,19-,20-,22+,23+,24-,26-,27-,28+,29-/m0/s1 | NA |
| 12070588 | InChI=1S/C28H40O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,14-18,20-22,30,32-33H,8-13H2,1-5H3/t14-,15+,16-,17-,18-,20-,21+,22+,24-,25-,26-,27+,28+/m0/s1 | NA |
| 11038269 | InChI=1S/C28H40O7/c1-14-12-21(34-23(31)15(14)2)26(5,32)27(33)11-9-17-16-13-22-28(35-22)20(30)7-6-19(29)25(28,4)18(16)8-10-24(17,27)3/h6-7,14-18,20-22,30,32-33H,8-13H2,1-5H3/t14-,15+,16-,17-,18-,20-,21?,22+,24-,25-,26-,27+,28+/m0/s1 | NA |
| 54606507 | InChI=1S/C30H40O7/c1-15-12-23(36-27(34)16(15)2)17(3)20- | NA |

TABLE 2-continued

LIST OF WITHAFERIN A ANALOGS AND DERIVATIVES BASED ON SIMILARITY

| | | |
|---|---|---|
| | 6-7-22-19-13-26-30(37-26)25(33)9-8-24(32)28(30,5)21(19)10-11-29(20,22)14-35-18(4)31/h8-9,17,19-23,25-26,33H,6-7,10-14H2,1-5H3/t17-,19+,20+,21-,22-,23+,25-,26+,28-,29-,30+/m0/s1 | |
| 44567005 | InChI=1S/C28H40O7/c1-13-10-21(34-24(32)14(13)2)27(5,33)23-18(29)12-17-15-11-22-28(35-22)20(31)7-6-19(30)26(28,4)16(15)8-9-25(17,23)3/h6-7,13-18,20-23,29,31,33H,8-12H2,1-5H3/t13-,14+,15+,16-,17-,18-,20-,21+,22+,23-,25-,26-,27-,28+/m0/s1 | NA |
| 10767792 | InChI=1S/C29H42O7/c1-14-10-21(35-26(33)17(14)13-30)15(2)18-6-7-19-16-11-24-29(36-24)25(32)22(34-5)12-23(31)28(29,4)20(16)8-9-27(18,19)3/h15-16,18-22,24-25,30,32H,6-13H2,1-5H3/t15-,16-,18+,19-,20-,21+,22-,24+,25-,27+,28-,29-/m0/s1 | NA |
| 476483 | InChI=1S/C28H46O3/c1-16-15-25(31-26(30)17(16)2)18(3)20-10-11-21-19-8-9-23-24(29)7-6-13-27(23,4)22(19)12-14-28(20,21)5/h16-25,29H,6-15H2,1-5H3/t16?,17?,18?,19-,20?,21-,22-,23?,24-,25+,27+,28+/m0/s1 | (6R)-6-[1-[(4S,8S,9S,10R,13S,14S)-4-hydroxy-10,13-dimethyl-2,3,4,5,6,7,8,9,11,12,14,15,16,17-tetradecahydro-1H-cyclopenta[a]phenanthren-17-yl]ethyl]-3,4-dimethyloxan-2-one |
| 268946 | InChI=1S/C28H38O5/c1-15-12-24(33-26(32)18(15)14-29)16(2)19-8-9-20-17-13-23(30)22-6-5-7-25(31)28(22,4)21(17)10-11-27(19,20)3/h5-7,16-17,19-21,23-24,29-30H,8-14H2,1-4H3/t16-,17-,19+,20-,21-,23+,24+,27+,28+/m0/s1 | (2R)-2-[(1S)-1-[(6R,8S,9S,10R,13S,14S,17R)-6-hydroxy-10,13-dimethyl-1-oxo-6,7,8,9,11,12,14,15,16,17-decahydrocyclopenta[a]phenanthren-17-yl]ethyl]-5-(hydroxymethyl)-4-methyl-2,3-dihydropyran-6-one |
| 23266164 | InChI=1S/C28H39ClO5/c1-15-12-22(34-25(33)18(15)14-30)16(2)19-7-8-20-17-13-24(32)28(29)10-5-6-23(31)27(28,4)21(17)9-11-26(19,20)3/h5-6,16-17,19-22,24,30,32H,7-14H2,1-4H3/t16-,17-,19+,20-,21-,22?,24+,26+,27-,28-/m0/s1 | 2-[(1S)-1-[(5R,6R,8S,9S,10S,13S,14S,17R)-5-chloro-6-hydroxy-10,13-dimethyl-1-oxo-6,7,8,9,11,12,14,15,16,17-decahydro-4H-cyclopenta[a]phenanthren-17-yl]ethyl]-5-(hydroxymethyl)-4-methyl-2,3-dihydropyran-6-one |
| 12304664 | InChI=1S/C28H40O7/c1-14-10-21(35-25(33)17(14)13-29)15(2)18-7-8-19-16-11-24(32)28(34)9-5-6-22(30)27(28,4)20(16)12-23(31)26(18,19)3/h5-6,15-16,18-21,23- | (2R)-5-(hydroxymethyl)-4-methyl-2-[(1S)-1-[(5R,6R,8S,9S,10R,12S,13S,14S,17R)-5,6,12-trihydroxy-10,13-dimethyl-1-oxo- |

TABLE 2-continued

LIST OF WITHAFERIN A ANALOGS AND DERIVATIVES BASED ON SIMILARITY

| | | |
|---|---|---|
| | 24,29,31-32,34H,7-13H2,1-4H3/t15-,16-,18+,19-,20-,21+,23-,24+,26+,27-,28-/m0/s1 | 6,7,8,9,11,12,14,15,16,17-decahydro-4H-cyclopenta[a]phenanthren-17-yl]ethyl]-2,3-dihydropyran-6-one |
| 10528446 | InChI=1S/C28H40O6/c1-15-11-22(33-25(32)18(15)13-29)16(2)19-6-7-20-17-12-24-28(34-24)9-4-5-23(31)27(28,14-30)21(17)8-10-26(19,20)3/h16-17,19-22,24,29-30H,4-14H2,1-3H3/t16-,17-,19+,20-,21-,22?,24+,26+,27-,28+/m0/s1 | NA |
| 5458717 | InChI=1S/C32H42O8/c1-16-13-25(39-29(36)21(16)15-37-18(3)33)17(2)22-7-8-23-20-14-28-32(40-28)27(38-19(4)34)10-9-26(35)31(32,6)24(20)11-12-30(22,23)5/h9-10,17,20,22-25,27-28H,7-8,11-15H2,1-6H3/t17-,20-,22+,23-,24-,25+,27-,28+,30+,31-,32+/m0/s1 | NA |
| 88948978 | InChI=1S/C27H40O5/c1-13-11-21(31-25(30)14(13)2)15(3)18-5-6-19-17-12-23-27(32-23)22(29)8-7-20(28)24(27)16(17)9-10-26(18,19)4/h13-19,21-24,29H,5-12H2,1-4H3/t13-,14+,15-,16-,17+,18+,19-,21+,22-,23+,24?,26+,27+/m0/s1 | NA |
| 16720560 | InChI=1S/C29H38O8/c1-14-11-21(36-25(32)15(14)2)16(3)18-5-6-20-17-12-24-29(37-24)23(31)8-7-22(30)27(29,4)19(17)9-10-28(18,20)13-35-26(33)34/h7-8,16-21,23-24,31H,5-6,9-13H2,1-4H3,(H,33,34)/t16-,17+,18+,19-,20-,21+,23-,24+,27-,28-,29+/m0/s1 | NA |
| 88949005 | InChI=1S/C27H36O6/c1-13-10-21(32-25(31)17(13)12-28)14(2)18-4-5-19-16-11-23-27(33-23)22(30)7-6-20(29)24(27)15(16)8-9-26(18,19)3/h6-7,14-16,18-19,21-24,28,30H,4-5,8-12H2,1-3H3/t14-,15-,16+,18?,19-,21+,22-,23+,24?,26+,27+/m0/s1 | NA |
| 72945677 | InChI=1S/C28H38O7/c1-13-8-20(34-25(32)16(13)11-29)14(2)17-4-5-18-15-9-23-28(35-23)24(31)21-10-22(30)27(28,12-33-21)19(15)6-7-26(17,18)3/h14-15,17-21,23-24,29,31H,4-12H2,1-3H3/t14-,15-,17+,18-,19-,20+,21-, | NA |

TABLE 2-continued

LIST OF WITHAFERIN A ANALOGS AND DERIVATIVES BASED ON SIMILARITY

| | | |
|---|---|---|
| | 23+,24-,26+,27-,28-/ m0/s1 | |
| 88858695 | InChI=1S/C29H40O6/c1-5-17-15(2)12-22(34-26(17)33)16(3)19-6-7-20-18-13-25-29(35-25)24(32)9-8-23(31)28(29,14-30)21(18)10-11-27(19,20)4/h8-9,16,18-22,24-25,30,32H,5-7,10-14H2,1-4H3/t16-,18-,19?,20-,21-,22+,24-,25+,27+,28-,29+/m0/s1 | NA |
| 21679032 | InChI=1S/C28H38O6/c1-16-14-23(34-24(31)18(16)15-29)27(4,32)21-11-13-28(33)20-9-8-17-6-5-7-22(30)26(17,3)19(20)10-12-25(21,28)2/h5,7-8,19-21,23,29,32-33H,6,9-15H2,1-4H3/t19-,20+,21-,23+,25+,26-,27+,28+/m0/s1 | (2R)-2-[(1R)-1-hydroxy-1-[(8R,9S,10R,13R,14R, 17S)-14-hydroxy-10,13-dimethyl-1-oxo-7,8,9,11,12,15,16,17-octahydro-4H-cyclopenta[a]phenanthren-17-yl]ethyl]-5-(hydroxymethyl)-4-methyl-2,3-dihydropyran-6-one |
| 14605183 | InChI=1S/C28H38O7/c1-23-11-10-16-14(12-20-28(34-20)19(30)9-8-18(29)25(16,28)3)15(23)6-7-17(23)26(4,32)21-13-24(2)27(5,35-24)22(31)33-21/h8-9,14-17,19-21,30,32H,6-7,10-13H2,1-5H3/t14-,15-,16-,17-,19-,20+,21+,23-,24-,25-,26+,27+,28+/m0/s1 | NA |
| 11512113 | InChI=1S/C29H40O9/c1-13-15(12-30)9-20(37-25(13)33)14(2)17-5-6-18-16-10-23-29(38-23)24(32)21(36-4)11-22(31)28(29,26(34)35)19(16)7-8-27(17,18)3/h14,16-21,23-24,30,32H,5-12H2,1-4H3,(H,34,35)/t14-,16-,17+,18-,19-,20+,21-,23+,24-,27+,28-,29-/m0/s1 | NA |
| 71481106 | InChI=1S/C28H38O6/c1-13-12-19(33-25(32)14(13)2)15(3)16-6-7-17-22-18(10-11-26(16,17)4)27(5)20(29)8-9-21(30)28(27)24(34-28)23(22)31/h8-9,15-19,21-24,30-31H,6-7,10-12H2,1-5H3/t15-,16+,17-,18-,19+,21-,22-,23+,24+,26+,27-,28+/m0/s1 | NA |
| 70690364 | InChI=1S/C28H36O6/c1-14-11-21(33-25(32)17(14)13-29)15(2)18-5-6-19-16-12-24-28(34-24)23(31)8-7-22(30)27(28,4)20(16)9-10-26(18,19)3/h5,7-8,15-16,19-21,23-24,29,31H,6,9-13H2,1-4H3/t15-,16-,19-,20-,21+,23-,24+,26+,27-,28+/m0/s1 | NA |
| 56649416 | InChI=1S/C32H42O8/c1-16-13-25(39- | NA |

TABLE 2-continued

LIST OF WITHAFERIN A ANALOGS AND DERIVATIVES BASED ON SIMILARITY

| | | |
|---|---|---|
| | 29(36)17(16)2)18(3)22-7-8-23-21-14-28-32(40-28)27(38-20(5)34)10-9-26(35)31(32,15-37-19(4)33)24(21)11-12-30(22,23)6/h9-10,18,21-25,27-28H,7-8,11-15H2,1-6H3/t18-,21-,22+,23-,24-,25+,27-,28+,30+,31-,32+/m0/s1 | |
| 12070589 | InChI=1S/C28H40O8/c1-14-22(31)35-21(13-24(14,3)32)26(5,33)27(34)11-9-16-15-12-20-28(36-20)19(30)7-6-18(29)25(28,4)17(15)8-10-23(16,27)2/h6-7,14-17,19-21,30,32-34H,8-13H2,1-5H3/t14-,15-,16-,17-,19-,20+,21+,23-,24+,25-,26-,27+,28+/m0/s1 | NA |
| 10720368 | InChI=1S/C28H42O8/c1-14-10-21(36-25(34)17(14)12-29)15(2)18-4-5-19-16-11-24(33)28(35)23(32)7-6-22(31)27(28,13-30)20(16)8-9-26(18,19)3/h15-16,18-21,23-24,29-30,32-33,35H,4-13H2,1-3H3/t15-,16-,18+,19-,20-,21?,23-,24+,26+,27-,28-/m0/s1 | 5-(hydroxymethyl)-4-methyl-2-[(1S)-1-[(4S,5S,6R,8S,9S,10S,13S,14S,17R)-4,5,6-trihydroxy-10-(hydroxymethyl)-13-methyl-1-oxo-3,4,6,7,8,9,11,12,14,15,16,17-dodecahydro-2H-cyclopenta[a]phenanthren-17-yl]ethyl]-2,3-dihydropyran-6-one |
| 5315323 | InChI=1S/C28H38O5/c1-14-12-21(32-25(31)15(14)2)16(3)18-6-7-19-17-13-24-28(33-24)23(30)9-8-22(29)27(28,5)20(17)10-11-26(18,19)4/h8-9,16-21,23-24,30H,6-7,10-13H2,1-5H3/t16-,17-,18?,19?,20?,21?,23?,24+,26+,27-,28+/m0/s1 | NA |
| 88858705 | InChI=1S/C28H40O6/c1-14-11-21(33-25(32)15(14)2)16(3)18-5-6-19-17-12-24-28(34-24)23(31)8-7-22(30)27(28,13-29)20(17)9-10-26(18,19)4/h16-21,23-24,29,31H,5-13H2,1-4H3/t16-,17-,18+,19-,20-,21+,23-,24+,26+,27-,28+/m0/s1 | NA |
| 53495499 | InChI=1S/C28H39N3O6/c1-13-9-21(36-25(35)16(13)12-32)14(2)17-5-6-18-15-10-23-28(37-23)24(34)20(30-31-29)11-22(33)27(28,4)19(15)7-8-26(17,18)3/h14-15,17-21,23-24,32,34H,5-12H2,1-4H3/t14-,15-,17+,18-,19-,20-,21+,23-,24-,26+,27-,28-/m0/s1 | NA |
| 15747012 | InChI=1S/C29H44O3/c1-16-13-24(32-26(30)17(16)2)18(3)21-7-8-22-20-14-25(31-6)29-15-19(29)9-12- | NA |

TABLE 2-continued

LIST OF WITHAFERIN A ANALOGS AND DERIVATIVES BASED ON SIMILARITY

| | | |
|---|---|---|
| | 28(29,5)23(20)10-11-27(21,22)4/h18-25H,7-15H2,1-6H3/t18-,19+,20-,21+,22-,23-,24+,25+,27+,28+,29-/m0/s1 | |
| 56926117 | InChI=1S/C27H36O4/c1-15-13-23(31-25(30)19(15)14-28)16(2)20-8-9-21-18-7-5-17-6-10-24(29)27(17,4)22(18)11-12-26(20,21)3/h5-6,10,16,18,20-23,28H,7-9,11-14H2,1-4H3/t16-,18-,20+,21-,22-,23+,26+,27-/m0/s1 | (2R)-2-[(1S)-1-[(3aR,3bS,5aS,6R,8aS,8bS)-3a,5a-dimethyl-3-oxo-4,5,6,7,8,8a,8b,9-octahydro-3bH-indeno[5,4-e]inden-6-yl]ethyl]-5-(hydroxymethyl)-4-methyl-2,3-dihydropyran-6-one |
| 46198372 | InChI=1S/C30H42O8/c1-14(20-13-27(4)29(6,38-27)25(34)36-20)24-19(35-15(2)31)12-18-16-11-23-30(37-23)22(33)8-7-21(32)28(30,5)17(16)9-10-26(18,24)3/h7-8,14,16-20,22-25,33-34H,9-13H2,1-6H3/t14-,16-,17+,18+,19-,20-,22+,23-,24+,25-,26+,27+,28+,29-,30-/m1/s1 | NA |
| 21679019 | InChI=1S/C30H40O7/c1-15-13-24(36-26(33)16(15)2)29(6,34)21-8-7-19-18-14-25-30(37-25)23(35-17(3)31)10-9-22(32)28(30,5)20(18)11-12-27(19,21)4/h9-10,18-21,23-25,34H,7-8,11-14H2,1-6H3/t18-,19-,20-,21-,23-,24+,25+,27-,28-,29+,30+/m0/s1 | NA |
| 16680631 | InChI=1S/C32H46O7/c1-7-8-11-36-23-15-24(33)30(6)20-9-10-29(5)21(19(20)13-25-32(30,39-25)27(23)34)14-26-31(29,38-26)18(4)22-12-16(2)17(3)28(35)37-22/h18-23,25-27,34H,7-15H2,1-6H3/t18-,19-,20+,21+,22-,23+,25-,26-,27+,29+,30+,31?,32+/m1/s1 | NA |
| 88949020 | InChI=1S/C27H36O6/c1-13-11-20(32-24(30)14(13)2)15(3)17-5-6-18-16-12-23-27(33-23)22(29)8-7-21(28)26(27,31)19(16)9-10-25(17,18)4/h7-8,15-20,22-23,29,31H,5-6,9-12H2,1-4H3/t15-,16-,17?,18-,19-,20+,22-,23+,25+,26?,27+/m0/s1 | NA |
| 53495632 | InChI=1S/C33H44O7S/c1-17-12-25(39-30(37)21(17)15-34)18(2)22-7-8-23-20-13-28-33(40-28)29(36)26(41-16-19-6-5-11-38-19)14-27(35)32(33,4)24(20)9-10-31(22,23)3/h5-6,11,18,20,22-26,28-29,34,36H,7-10,12-16H2,1-4H3/t18-,20-, | NA |

TABLE 2-continued

LIST OF WITHAFERIN A ANALOGS AND DERIVATIVES BASED ON SIMILARITY

| | | |
|---|---|---|
| | 22+,23-,24-,25+,26-,28+,29-,31+,32-,33-/m0/s1 | |
| 44631487 | InChI=1S/C28H39ClO5/c1-15-12-22(34-25(33)18(15)14-30)16(2)19-7-8-20-17-13-24(32)28(29)10-5-6-23(31)27(28,4)21(17)9-11-26(19,20)3/h5-6,16-17,19-22,24,30,32H,7-14H2,1-4H3/t16-,17?,19+,20?,21?,22?,24+,26+,27-,28-/m0/s1 | 2-[(1S)-1-[(5R,6R,10S,13S,17R)-5-chloro-6-hydroxy-10,13-dimethyl-1-oxo-6,7,8,9,11,12,14,15,16,17-decahydro-4H-cyclopenta[a]phenanthren-17-yl]ethyl]-5-(hydroxymethyl)-4-methyl-2,3-dihydropyran-6-one |
| 15251339 | InChI=1S/C28H44O3/c1-16-6-9-23(31-25(16)29)17(2)20-7-8-21-19-14-24(30-5)28-15-18(28)10-13-27(28,4)22(19)11-12-26(20,21)3/h16-24H,6-15H2,1-5H3/t16?,17-,18+,19-,20+,21-,22-,23+,24+,26+,27+,28-/m0/s1 | NA |
| 11038270 | InChI=1S/C28H40O7/c1-13-9-20(35-25(32)16(13)12-29)14(2)17-5-6-18-15-10-23-28(33)24(31)21(34-23)11-22(30)27(28,4)19(15)7-8-26(17,18)3/h14-15,17-21,23-24,29,31,33H,5-12H2,1-4H3/t14-,15-,17+,18-,19-,20+,21+,23-,24-,26+,27-,28-/m0/s1 | NA |
| 88949018 | InChI=1S/C27H36O7/c1-13-10-20(33-24(31)16(13)12-28)14(2)17-4-5-18-15-11-23-27(34-23)22(30)7-6-21(29)26(27,32)19(15)8-9-25(17,18)3/h6-7,14-15,17-20,22-23,28,30,32H,4-5,8-12H2,1-3H3/t14-,15-,17?,18-,19?,20+,22-,23+,25+,26?,27+/m0/s1 | NA |
| 10984509 | InChI=1S/C33H46O7/c1-16-13-23(38-29(37)19(16)15-34)17(2)20-7-8-21-18-14-26-33(40-26)25(39-28-27(36)30(28,3)4)10-9-24(35)32(33,6)22(18)11-12-31(20,21)5/h17-18,20-23,25-26,28,34H,7-15H2,1-6H3/t17-,18-,20+,21-,22-,23?,25-,26+,28?,31+,32-,33+/m0/s1 | NA |
| 21574482 | InChI=1S/C28H36O5/c1-14-12-21(32-25(31)15(14)2)16(3)18-6-7-19-17-13-24-28(33-24)23(30)9-8-22(29)27(28,5)20(17)10-11-26(18,19)4/h6,8-9,16-17,19-21,23-24,30H,7,10-13H2,1-5H3/t16-,17-,19-,20-,21+,23-,24+,26+,27-,28+/m0/s1 | NA |

TABLE 2-continued

LIST OF WITHAFERIN A ANALOGS AND DERIVATIVES BASED ON SIMILARITY

| | | |
|---|---|---|
| 15519706 | InChI=1S/C30H40O7/c1-16-14-26(37-27(34)17(16)2)29(5,35)24-10-8-21-19-6-7-22-23(32)9-11-25(33)28(22,4)20(19)12-13-30(21,24)15-36-18(3)31/h7,9,11,19-21,23-24,26,32,35H,6,8,10,12-15H2,1-5H3/t19-,20+,21+,23+,24-,26-,28-,29-,30-/m1/s1 | [(4S,8S,9S,10R,13R,14S,16S,17S)-17-[(1R)-1-[(2R)-4,5-dimethyl-6-oxo-2,3-dihydropyran-2-yl]-1-hydroxyethyl]-4-hydroxy-10-methyl-1-oxo-4,7,8,9,11,12,14,15,16,17-decahydrocyclopenta[a]phenanthren-13-yl]methyl acetate |
| 15251338 | InChI=1S/C27H42O3/c1-16(22-6-5-7-24(28)30-22)19-8-9-20-18-14-23(29-4)27-15-17(27)10-13-26(27,3)21(18)11-12-25(19,20)2/h16-23H,5-15H2,1-4H3/t16-,17+,18-,19+,20-,21-,22+,23+,25+,26+,27-/m0/s1 | NA |
| 462178 | InChI=1S/C30H41NO6/c1-15-11-23(36-27(35)18(15)14-32)16(2)19-5-6-20-17-12-25-30(37-25)26(34)22(31-9-10-31)13-24(33)29(30,4)21(17)7-8-28(19,20)3/h13,16-17,19-21,23,25-26,32,34H,5-12,14H2,1-4H3/t16-,17-,19+,20-,21-,23-,25+,26+,28+,29?,30-/m0/s1 | NA |
| 89333022 | InChI=1S/C28H40O5/c1-14-12-21(32-25(31)15(14)2)16(3)18-6-7-19-17-13-24(33-24)23(30)9-8-22(29)27(28,5)20(17)10-11-26(18,19)4/h8-9,14-21,23-24,30H,6-7,10-13H2,1-5H3/t14-,15+,16+,17?,18?,19?,20?,21?,23+,24-,26-,27+,28-/m1/s1 | NA |
| 50899672 | InChI=1S/C26H34O4/c1-15(24-10-4-17(14-27)25(29)30-24)22-8-9-23-21-6-3-16-13-18(28)5-7-19(16)20(21)11-12-26(22,23)2/h4-5,7,13,15,20-24,27-28H,3,6,8-12,14H2,1-2H3/t15-,20+,21+,22+,23-,24-,26+/m0/s1 | (2R)-5-(hydroxymethyl)-2-[(1S)-1-[(8S,9S,13S,14S,17R)-3-hydroxy-13-methyl-6,7,8,9,11,12,14,15,16,17-decahydrocyclopenta[a]phenanthren-17-yl]ethyl]-2,3-dihydropyran-6-one |
| 23266165 | InChI=1S/C28H39ClO5/c1-15-12-22(34-25(32)18(15)14-30)16(2)19-7-8-20-17-13-23(29)28(33)10-5-6-24(31)27(28,4)21(17)9-11-26(19,20)3/h5-6,16-17,19-23,30,33H,7-14H2,1-4H3/t16-,17-,19+,20-,21-,22?,23-,26+,27-,28+/m0/s1 | 2-[(1S)-1-[(5S,6S,8S,9S,10R,13S,14S,17R)-6-chloro-5-hydroxy-10,13-dimethyl-1-oxo-6,7,8,9,11,12,14,15,16,17-decahydro-4H-cyclopenta[a]phenanthren-17-yl]ethyl]-5-(hydroxymethyl)-4-methyl-2,3-dihydropyran-6-one |
| 16680369 | InChI=1S/C28H36O6/c1-13-10-19(32-24(31)14(13)2)15(3)27-23(33-27)12-18-16-11-22-28(34-22)21(30)7-6- | NA |

TABLE 2-continued

LIST OF WITHAFERIN A ANALOGS AND DERIVATIVES BASED ON SIMILARITY

| | | |
|---|---|---|
| | 20(29)26(28,5)17(16)8-9-25(18,27)4/h6-7,15-19,21-23,30H,8-12H2,1-5H3/t15-,16-,17+,18+,19-,21+,22-,23-,25+,26+,27-,28-/m1/s1 | |
| 21628725 | InChI=1S/C35H45NO5/c1-20-17-29(40-31(38)21(20)2)34(5,39)26-12-11-24-23-18-30-35(41-30)27(36-19-22-9-7-6-8-10-22)13-14-28(37)33(35,4)25(23)15-16-32(24,26)3/h6-10,13-14,23-27,29-30,36,39H,11-12,15-19H2,1-5H3/t23-,24-,25-,26-,27-,29+,30+,32-,33-,34+,35+/m0/s1 | NA |

The invention claimed is:

1. A method of protecting an elderly subject from aging-associated changes, the method comprising:
   providing a gero-protective pharmaceutical composition having at least two senolytic agents in a pharmaceutically acceptable carrier;
   administering the gero-protective pharmaceutical composition to the elderly subject to provide a therapeutically effective amount of the at least two senolytic agents in order to inhibit cellular senescence; and
   inhibiting the cellular senescence in the elderly subject sufficient to inhibit aging-associated changes,
   wherein the at least two senolytic agents include a Withaferin A analog and at least one of: Withaferin A, coumestrol, a ginsenoside, quinidine, silymarin, lico-chalcone A, lipoic acid or apigenin, wherein the Withaferin A analog is selected from one of:
   (2E)-3-[4-(carbamoylmethoxy)-3-hydroxyphenyl]-N-methyl-N-[1-(4-sulfamoylphenyl)ethyl]prop-2-enamide;
   N-[5-(5-amino-4-cyano-1H-pyrazol-3-yl)pentyl]-3-(6-methyl-4-oxo-2-sulfanyl-1,4-dihydropyrimidin-5-yl) propanamide;
   N'-[(1E)-(2,4-dihydroxyphenyl)methylidene]-2-{[6-hydroxy-3-methyl-2-oxo-7-(2-phenylethyl)-3,7-dihydro-2H-purin-8-yl]sulfanyl}acetohydrazide;
   1-(3-cyclopropaneamidobenzoyl)-N-(4-sulfamoylphenyl)piperidine-4-carboxamide;
   (4E)-10-acetyl-11,13-dihydroxy-4-[1-({2-[(2-hydroxyethylsulfanyl]ethyl}amino)ethylidene]-2,12-dimethyl-8-oxatricyclo[7.4.0.0$^{2,7}$]trideca-1(9),6,10,12-tetraene-3,5-dione;
   2-oxo-N-(3-{[2-(4-sulfamoylpheny)ethyl]carbamoyl}phenyl)-1,2-dihydroquinoline-4-carboxamide;
   (1S,2R,6S,7R,9R,11S,12S,15R,16R)-6-hydroxy-15-[(1R)-1-[(1R,6R)-4-(hydroxymethyl)-3,6-dimethyl-5-oxocyclohex-3-en-1-yl]ethyl]-2,16-dimethyl-8-oxapentacyclo[9.7.0.0$^{2,7}$.0$^{7,9}$.0$^{12,16}$]octadec-4-en-3-one;
   (1S,2R,7R,9R,11S,12S,15R,16R)-6-hydroxy-15-[(1R)-1-[(1R)-4-(hydroxymethyl)-3,5-dimethylcyclohex-3-en-1-yl]ethyl]-2,16-dimethyl-8-oxapentacyclo[9.7.0.0$^{2,7}$.0$^{7,9}$.0$^{12,16}$]octadec-4-en-3-one;
   (1S,2R,7R,9R,11S,12S,15S,16S)-6-hydroxy-15-[(S)-hydroxy[(2R)-4-(hydroxyl-5-(hydroxymethyl)-6-oxo-3,6-dihydro-2H-pyran-2-yl]methyl]-2,16-dimethyl-8-oxapentacyclo[9.7.0.0$^{2,7}$.0$^{7,9}$.0$^{12,16}$]octadec-4-en-3-one;
   (1S,2R,6S,7S,9R,11S,12S,15R,16S)-6-ethyl-15-[(1S)-1-[(2R)-5-(hydroxymethyl)-4-methyl-6-oxo-3,6-dihydro-2H-pyran-2-yl]ethyl]-2,16-dimethyl-8-oxapentacyclo[9.7.0.0$^{2,7}$.0$^{7,9}$.0$^{12,16}$]octadec-4-en-3-one;
   (6R)-6-[(1S)-1-[(1S,2R,6S,7R,9S,11S,12S,15R,16S)-6-ethyl-2,6,16-trimethyl-3-oxopentacyclo[9.7.0.0$^{2,7}$.0$^{7,9}$.0$^{12,16}$]octadec-4-en-15-yl]ethyl]-3-(hydroxymethyl)-4-methyl-5,6-dihydro-2H-pyran-2-one;
   3-methyl-2-{4-[2-({4-methyl-6-oxo-6H,7H,8H,9H,10H-cyclohexa[c]chromen-3-yl}oxy)acetamido]butanamidol butanoic acid;
   2-(1[(7E)-1-hydroxy-1,9a,11a-trimethyl-1H,2H,3H,3aH,3bH,4H, 5H,7H,8H,9H,9aH,9bH,10H,11H,11aH-cyclopenta[a]phenanthren-7-ylidene]amino}oxy)-N-[(pyridin-2-yl)methyl]acetamide;
   (2E)-2-(hydroxymethyl)-6-{7,7,12,16-tetramethyl-6-oxopentacyclo[9.7.0.0$^{1,3}$.0$^{3,8}$.0$^{12,16}$]octaddecan-5-yl}hept-2-enoic acid;
   methyl 1-[2-({[(7Z)-1-ethynyl-1-hydroxy-9a,11a-dimethyl-1H,2H,3H,3aH,3bH,4H,5H,7H,8H,9H,9aH,9bH, 10H,11H,11aH-cyclopenta[a]phenanthren-7-ylidene]amino}oxy)acetyl]pyrrolidine-2-carboxylate;
   (2E)-6-{7-hydroxy-3a,6,6,9a,11a-pentamethyl-1H,2H,3H,3aH,5H,5aH,6H,7H,8H,9H,9aH,11H,11aH-cyclopenta[a]phenanthren-1-yl}-2-methylhept-2-enoic acid;
   7-ethoxy-5-hydroxy-3-(4-{[3,4,5-trihydroxy-6-(hydroxymethyl)oxan-2-yl]oxylphenyl)-4H-chromen-4-one; or
   N'1,N'12-bis[(1E)-(2,4-dihydroxyphenyl)methylidene]dodecanedihydrazide.

2. The method of claim 1, wherein the pharmaceutical composition includes at least one of the Withaferin A analogs based on target-wise screening and at least one of coumestrol, a ginsenoside, silymarin, lipoic acid and apigenin.

3. The method of 1, wherein the pharmaceutical composition includes at least one of the Withaferin A analogs based on target-wise screening and at least one of a ginsenoside, silymarin, lipoic acid and apigenin.

4. The method of claim 1, further comprising at least one of:
   enhancing cell metabolism in the elderly subject;
   enhancing cell survival in the elderly subject;

vitalizing cells in the elderly subject; or mimicking a metformin-associated response and blood glucose lowering in the elderly subject.

5. The method of claim 1, further comprising at least one of:

inhibiting aging-associated changes in skin of the elderly subject;

inhibiting aging-associated changes in a liver of the elderly subject;

inhibiting aging-associated changes in neural tissue of the elderly subject;

inhibiting the neural tissue from age-related diseases;

inhibiting aging-associated changes in adipocytes of the elderly subject; or inhibiting aging-associated changes in mesenchymal stem cells of the elderly subject.

6. The method of claim 1, wherein the gero-protective pharmaceutical composition modulates one or more of the following in the elderly subject: NF-kB; AP-1; or HSP90.

7. A method of treating or ameliorating symptoms of a disease or disorder associated with aging-associated changes in a subject, the method comprising:

providing a gero-protective pharmaceutical composition having at least two senolytic agents in a pharmaceutically acceptable carrier;

administering the gero-protective pharmaceutical composition to the elderly subject to provide a therapeutically effective amount of the at least two senolytic agents in order to inhibit cellular senescence; and inhibiting the cellular senescence in the elderly subject sufficient to treat or ameliorate symptoms of the disease or disorder associated with aging-associated changes in the subject, wherein the at least two senolytic agents include a Withaferin A analog and at least one of: Withaferin A, coumestrol, a ginsenoside, quinidine, silymarin, licochalcone A, lipoic acid and apigenin, wherein the Withaferin A analog is selected from one of:

(2E)-3-[4-(carbamoylmethoxy)-3-hydroxyphenyl]-N-methyl-N-[1-(4-sulfamoylphenyl)ethyl]prop-2-enamide;

N-[5-(5-amino-4-cyano-1H-pyrazol-3-yl)pentyl]-3-(6-methyl-4-oxo-2-sulfanyl-1,4-dihydropyrimidin-5-yl) propanamide;

N'-[(1E)-(2,4-dihydroxyphenyl)methylidene]-2-{[6-hydroxy-3-methyl-2-oxo-7-(2-phenylethyl)-3,7-dihydro-2H-purin-8-yl]sulfanyl}acetohydrazide;

1-(3-cyclopropaneamidobenzoyl)-N-(4-sulfamoylphenyl) piperidine-4-carboxamide;

(4E)-10-acetyl-11,13-dihydroxy-4-[1-({2-[(2-hydroxyethyl)sulfanyl]ethyl}amino)ethylidene]-2,12-dimethyl-8-oxatricyclo[7.4.0.0$^{2,7}$]trideca-1(9),6,10,12-tetraene-3,5-dione;

2-oxo-N-(3-{[2-(4-sulfamoylpheny)ethyl]carbamoyl}phenyl)-1,2-dihydroquinoline-4-carboxamide;

(1S,2R,6S,7R,9R,11S,12S,15R,16R)-6-hydroxy-15-[(1R)-1-[(1R,6R)-4-(hydroxymethyl)-3,6-dimethyl-5-oxocyclohex-3-en-1-yl]ethyl]-2,16-dimethyl-8-oxapentacyclo[9.7.0.0$^{2,7}$.0$^{7,9}$.0$^{12,16}$]octadec-4-en-3-one;

(1S,2R,7R,9R,11S,12S,15R,16R)-6-hydroxy-15-[(1R)-1-[(1R)-4-(hydroxymethyl)-3,5-dimethylcyclohex-3-en-11-yl]ethyl]-2,16-dimethyl-8-oxapentacyclo[9.7.0.0$^{2,7}$.0$^{7,9}$.0$^{12,16}$]octadec-4-en-3-one;

(1S,2R,7R,9R,11S,12S,15S,16S)-6-hydroxy-15-[(S)-hydroxy[(2R)-4-(hydroxyl-5-(hydroxymethyl)-6-oxo-3,6-dihydro-2H-pyran-2-yl]methyl]-2,16-dimethyl-8-oxapentacyclo[9.7.0.0$^{2,7}$.0$^{7,9}$.0$^{12,16}$]octadec-4-en-3-one;

(1S,2R,6S,7S,9R,11S,12S,15R,16S)-6-ethyl-15-[(1S)-1-[(2R)-5-(hydroxymethyl)-4-methyl-6-oxo-3,6-dihydro-2H-pyran-2-yl]ethyl]-2,16-dimethyl-8-oxapentacyclo[9.7.0.0$^{2,7}$.0$^{7,9}$.0$^{12,16}$]octadec-4-en-3-one;

(6R)-6-[(1S)-1-[(1S,2R,6S,7R,9S,11S,12S,15R,16S)-6-ethyl-2,6,16-trimethyl-3-oxopentacyclo[9.7.0.0$^{2,7}$.0$^{7,9}$.0$^{12,16}$]octadec-4-en-15-yl]ethyl]-3-(hydroxymethyl)-4-methyl-5,6-dihydro-2H-pyran-2-one;

3-methyl-2-{4-[2-({4-methyl-6-oxo-6H,7H,8H,9H,10H-cyclohexa[c]chromen-3-yl}oxy)acetamido]butanamido] butanoic acid;

2-(1 [(7E)-1-hydroxy-1,9a,11a-trimethyl-1H,2H,3H,3aH,3bH,4H,5H,7H,8H,9H,9aH,9bH,10H,11H,11aH-cyclopenta[a]phenanthren-7-ylidene]amino}oxy)-N-[(pyridin-2-yl)methyl]acetamide;

(2E)-2-(hydroxymethyl)-6-{7,7,12,16-tetramethyl-6-oxopentacyclo[9.7.0.0$^{1,3}$.0$^{3,8}$.0$^{12,16}$]octaddecan-5-yl}hept-2-enoic acid;

methyl 1-[2-({[(7Z)-1-ethynyl-1-hydroxy-9a,11a-dimethyl-1H,2H,3H,3aH,3bH,4H,5H,7H,8H,9H,9aH,9bH,10H,11H,11aH-cyclopenta[a]phenanthren-7-ylidene]amino}oxy)acetyl]pyrrolidine-2-carboxylate;

(2E)-6-{7-hydroxy-3a,6,6,9a,11a-pentamethyl-1H,2H,3H,3aH,5H,5aH,6H,7H,8H,9H,9aH,11H,11aH-cyclopenta[a]phenanthren-1-yl}-2-methylhept-2-enoic acid;

7-ethoxy-5-hydroxy-3-(4-{[3,4,5-trihydroxy-6-(hydroxymethyl)oxan-2-yl]oxy]phenyl)-4H-chromen-4-one; or N'1,N'12-bis[(1E)-(2,4-dihydroxyphenyl)methylidene] dodecanedihydrazide.

8. The method of claim 7, wherein the disease or disorder associated with the aging-associated changes in the subject includes a neurological disease.

9. The method of claim 7, wherein the neurological disease is dementia or Alzheimer's disease.

* * * * *